United States Patent
Weikart et al.

(10) Patent No.: US 10,201,660 B2
(45) Date of Patent: Feb. 12, 2019

(54) CONTROLLING THE UNIFORMITY OF PECVD DEPOSITION ON MEDICAL SYRINGES, CARTRIDGES, AND THE LIKE

(71) Applicant: SiO2 Medical Products, Inc., Auburn, AL (US)

(72) Inventors: Christopher Weikart, Auburn, AL (US); Becky L. Clark, Auburn, AL (US); Adam Stevenson, Opelika, AL (US); Robert S. Abrams, Albany, NY (US); John Belfance, Phenix City, AL (US); Joseph A. Jones, Birmingham, AL (US); Thomas E. Fisk, Green Valley, AL (US)

(73) Assignee: SiO2 Medical Products, Inc., Auburn, AL (US)

( * ) Notice: Subject to any disclaimer, the term of this patent is extended or adjusted under 35 U.S.C. 154(b) by 523 days.

(21) Appl. No.: 14/647,189

(22) PCT Filed: Nov. 25, 2013

(86) PCT No.: PCT/US2013/071752
§ 371 (c)(1),
(2) Date: May 26, 2015

(87) PCT Pub. No.: WO2014/085348
PCT Pub. Date: Jun. 5, 2014

(65) Prior Publication Data
US 2015/0335823 A1    Nov. 26, 2015

Related U.S. Application Data

(60) Provisional application No. 61/732,180, filed on Nov. 30, 2012, provisional application No. 61/747,584,
(Continued)

(51) Int. Cl.
*A61M 5/31* (2006.01)
*C23C 16/52* (2006.01)
(Continued)

(52) U.S. Cl.
CPC ...... *A61M 5/3129* (2013.01); *A61M 5/31513* (2013.01); *C23C 16/045* (2013.01);
(Continued)

(58) Field of Classification Search
None
See application file for complete search history.

(56) References Cited

U.S. PATENT DOCUMENTS 3,274,267 A  9/1966  Chow
3,297,465 A  1/1967  Connell
(Continued)

FOREIGN PATENT DOCUMENTS

AT    414209 B    10/2006
AT    504533 A1    6/2008
(Continued)

OTHER PUBLICATIONS

US 5,645,643, 07/1997, Thomas (withdrawn)
(Continued)

*Primary Examiner* — Cachet I Sellman
(74) *Attorney, Agent, or Firm* — McAndrews, Held & Malloy, Ltd.

(57) ABSTRACT

A method and apparatus for plasma modifying a workpiece such as a medical barrel, medical barrel, vial, or blood tube is described. Plasma is provided within the lumen of the workpiece. The plasma is provided under conditions effective for plasma modification of a surface of the workpiece. A magnetic field is provided in at least a portion of the lumen. The magnetic field has an orientation and field strength effective to improve the uniformity of plasma
(Continued)

modification of the generally cylindrical interior surface 16 of the generally cylindrical interior surface 16.

26 Claims, 44 Drawing Sheets

Related U.S. Application Data filed on Dec. 31, 2012, provisional application No. 61/800,660, filed on Mar. 15, 2013, provisional application No. 61/872,481, filed on Aug. 30, 2013.

(51) Int. Cl.
*C23C 16/505* (2006.01)
*C23C 16/04* (2006.01)
*C23C 16/40* (2006.01)
*A61M 5/315* (2006.01)

(52) U.S. Cl.
CPC .......... *C23C 16/401* (2013.01); *C23C 16/505* (2013.01); *C23C 16/52* (2013.01); *A61M 2005/3131* (2013.01); *A61M 2205/0222* (2013.01); *A61M 2205/0238* (2013.01); *A61M 2207/00* (2013.01); *A61M 2207/10* (2013.01)

(56) References Cited

U.S. PATENT DOCUMENTS

| | | |
|---|---|---|
| 3,355,947 A | 12/1967 | Karlby |
| 3,442,686 A | 5/1969 | Jones |
| 3,448,614 A | 6/1969 | Muger |
| 3,590,634 A | 7/1971 | Pasternak |
| 3,838,598 A | 10/1974 | Tomkins |
| 3,957,653 A | 5/1976 | Blecher |
| 4,111,326 A | 9/1978 | Percarpio |
| 4,118,972 A | 10/1978 | Goeppner |
| 4,134,832 A | 1/1979 | Heimreid |
| 4,136,794 A | 1/1979 | Percapio |
| 4,162,528 A | 7/1979 | Maldonado |
| 4,168,330 A | 9/1979 | Kaganowicz |
| 4,186,840 A | 2/1980 | Percarpio |
| 4,187,952 A | 2/1980 | Percarpio |
| 4,226,333 A | 10/1980 | Percarpio |
| 4,289,726 A | 9/1981 | Potoczky |
| 4,290,534 A | 9/1981 | Percarpio |
| 4,293,078 A | 10/1981 | Percarpio |
| 4,338,764 A | 7/1982 | Percarpio |
| 4,391,128 A | 7/1983 | McWorter |
| 4,392,218 A | 7/1983 | Plunkett, Jr. |
| 4,422,896 A | 12/1983 | Class |
| 4,452,679 A | 6/1984 | Dunn |
| 4,478,873 A | 10/1984 | Masso |
| 4,481,229 A | 11/1984 | Suzuki |
| 4,483,737 A | 11/1984 | Mantei |
| 4,484,479 A | 11/1984 | Eckhardt |
| 4,486,378 A | 12/1984 | Hirata |
| 4,522,510 A | 6/1985 | Rosencwaig |
| 4,524,089 A | 6/1985 | Haque |
| 4,524,616 A | 6/1985 | Drexel |
| 4,552,791 A | 11/1985 | Hahn |
| 4,576,204 A | 3/1986 | Smallborn |
| 4,609,428 A | 9/1986 | Fujimura |
| 4,610,770 A | 9/1986 | Saito |
| 4,648,107 A | 3/1987 | Latter |
| 4,648,281 A | 3/1987 | Morita |
| 4,652,429 A | 3/1987 | Konrad |
| 4,664,279 A | 5/1987 | Obrist |
| 4,667,620 A | 5/1987 | White |
| 4,668,365 A | 5/1987 | Foster |
| 4,668,368 A * | 5/1987 | Ferro .................. C22B 11/10 204/212 |
| 4,683,838 A | 8/1987 | Kimura |
| 4,697,717 A | 10/1987 | Grippi |
| 4,703,187 A | 10/1987 | Hofling |
| 4,716,491 A | 12/1987 | Ohno |
| 4,721,553 A | 1/1988 | Saito |
| 4,725,481 A | 2/1988 | Ostapchenko |
| 4,741,446 A | 5/1988 | Miller |
| 4,756,964 A | 7/1988 | Kincaid |
| 4,767,414 A | 8/1988 | Williams |
| 4,778,721 A | 10/1988 | Sliemers |
| 4,799,246 A | 1/1989 | Fischer |
| 4,808,453 A | 2/1989 | Romberg |
| 4,809,876 A | 3/1989 | Tomaswick |
| 4,810,752 A | 3/1989 | Bayan |
| 4,824,444 A | 4/1989 | Nomura |
| 4,841,776 A | 6/1989 | Kawachi |
| 4,842,704 A | 6/1989 | Collins |
| 4,844,986 A | 7/1989 | Karakelle |
| 4,846,101 A | 7/1989 | Montgomery |
| 4,853,102 A | 8/1989 | Tateishi |
| 4,869,203 A | 9/1989 | Pinkhasov |
| 4,872,758 A | 10/1989 | Miyazaki |
| 4,874,497 A | 10/1989 | Matsuoka |
| 4,880,675 A | 11/1989 | Mehta |
| 4,883,686 A | 11/1989 | Doehler |
| 4,886,086 A | 12/1989 | Etchells |
| 4,894,256 A | 1/1990 | Gartner |
| 4,894,510 A | 1/1990 | Nakanishi |
| 4,897,285 A | 1/1990 | Wilhelm |
| 4,926,791 A | 5/1990 | Hirose |
| 4,948,628 A | 8/1990 | Montgomery |
| 4,973,504 A | 11/1990 | Romberg |
| 4,978,714 A | 12/1990 | Bayan |
| 4,991,104 A | 2/1991 | Miller |
| 4,999,014 A | 3/1991 | Gold |
| 5,000,994 A | 3/1991 | Romberg |
| 5,009,646 A | 4/1991 | Sudo |
| 5,016,564 A | 5/1991 | Nakamura |
| 5,021,114 A | 6/1991 | Saito |
| 5,028,566 A | 7/1991 | Lagendijk |
| 5,030,475 A | 7/1991 | Ackermann |
| 5,032,202 A | 7/1991 | Tsai |
| 5,039,548 A | 8/1991 | Hirose |
| 5,041,303 A | 8/1991 | Wertheimer |
| 5,042,951 A | 8/1991 | Gold |
| 5,044,199 A | 9/1991 | Drexel |
| 5,064,083 A | 11/1991 | Alexander |
| 5,067,491 A | 11/1991 | Taylor |
| 5,079,481 A * | 1/1992 | Moslehi .............. H01J 37/3266 118/723 E |
| 5,082,542 A | 1/1992 | Moslehi |
| 5,084,356 A | 1/1992 | Deak |
| 5,085,904 A | 2/1992 | Deak |
| 5,099,881 A | 3/1992 | Nakajima |
| 5,113,790 A | 5/1992 | Geisler |
| 5,120,966 A | 6/1992 | Kondo |
| 5,131,752 A | 7/1992 | Yu |
| 5,144,196 A | 9/1992 | Gegenwart |
| 5,147,678 A | 9/1992 | Foerch |
| 5,154,943 A | 10/1992 | Etzkorn |
| 5,189,446 A | 2/1993 | Barnes |
| 5,192,849 A | 3/1993 | Moslehi |
| 5,198,725 A | 3/1993 | Chen |
| 5,203,959 A | 4/1993 | Hirose |
| 5,204,141 A | 4/1993 | Roberts |
| 5,209,882 A | 5/1993 | Hattori |
| 5,216,329 A | 6/1993 | Pelleteir |
| 5,224,441 A | 7/1993 | Felts |
| 5,225,024 A | 7/1993 | Hanley |
| 5,232,111 A | 8/1993 | Burns |
| 5,252,178 A | 10/1993 | Moslehi |
| 5,260,095 A | 11/1993 | Affinito |
| 5,266,398 A | 11/1993 | Hioki |
| 5,271,274 A | 12/1993 | Khuri-Yakub |
| 5,272,417 A | 12/1993 | Ohmi |
| 5,272,735 A | 12/1993 | Bryan |
| 5,275,299 A | 1/1994 | Konrad |
| 5,286,297 A | 2/1994 | Moslehi |
| 5,288,560 A | 2/1994 | Sudo |
| 5,292,370 A | 3/1994 | Tsai |
| 5,294,011 A | 3/1994 | Konrad |

(56) References Cited

U.S. PATENT DOCUMENTS

| | | |
|---|---|---|
| 5,294,464 A | 3/1994 | Geisler |
| 5,297,561 A | 3/1994 | Hulon |
| 5,298,587 A | 3/1994 | Hu |
| 5,300,901 A | 4/1994 | Krummel |
| 5,302,266 A | 4/1994 | Grabarz |
| 5,308,649 A | 5/1994 | Babacz |
| 5,314,561 A | 5/1994 | Komiya |
| 5,320,875 A | 6/1994 | Hu |
| 5,321,634 A | 6/1994 | Obata |
| 5,330,578 A | 7/1994 | Sakama |
| 5,333,049 A | 7/1994 | Ledger |
| 5,338,579 A | 8/1994 | Ogawa et al. |
| 5,346,579 A | 9/1994 | Cook |
| 5,354,286 A | 10/1994 | Mesa |
| 5,356,029 A | 10/1994 | Hogan |
| 5,361,921 A | 11/1994 | Burns |
| 5,364,665 A | 11/1994 | Felts |
| 5,364,666 A | 11/1994 | Williams |
| 5,372,851 A | 12/1994 | Ogawa et al. |
| 5,374,314 A | 12/1994 | Babacz |
| 5,378,510 A | 1/1995 | Thomas |
| 5,381,228 A | 1/1995 | Brace |
| 5,395,644 A | 3/1995 | Affinito |
| 5,396,080 A | 3/1995 | Hannotiau |
| 5,397,956 A | 3/1995 | Araki |
| 5,409,782 A | 4/1995 | Murayama |
| 5,413,813 A | 5/1995 | Cruse |
| 5,423,915 A | 6/1995 | Murata |
| 5,429,070 A | 7/1995 | Campbell |
| 5,433,786 A | 7/1995 | Hu |
| 5,434,008 A | 7/1995 | Felts |
| 5,439,736 A | 8/1995 | Nomura |
| 5,440,446 A | 8/1995 | Shaw |
| 5,443,645 A | 8/1995 | Otoshi |
| 5,444,207 A | 8/1995 | Sekine |
| 5,449,432 A | 9/1995 | Hanawa |
| 5,452,082 A | 9/1995 | Sanger |
| 5,468,520 A | 11/1995 | Williams |
| 5,470,388 A | 11/1995 | Goedicke |
| 5,472,660 A | 12/1995 | Fortin |
| 5,485,091 A | 1/1996 | Verkuil |
| 5,486,701 A | 1/1996 | Norton |
| 5,494,170 A | 2/1996 | Burns |
| 5,494,712 A | 2/1996 | Hu |
| 5,495,958 A | 3/1996 | Konrad |
| 5,508,075 A | 4/1996 | Roulin |
| 5,510,155 A | 4/1996 | Williams |
| 5,513,515 A | 5/1996 | Mayer |
| 5,514,276 A * | 5/1996 | Babcock .............. B01D 67/009 210/490 |
| 5,521,351 A | 5/1996 | Mahoney |
| 5,522,518 A | 6/1996 | Konrad |
| 5,531,060 A | 7/1996 | Fayet |
| 5,531,683 A | 7/1996 | Kriesel |
| 5,536,253 A | 7/1996 | Haber |
| 5,543,919 A | 8/1996 | Mumola |
| 5,545,375 A | 8/1996 | Tropsha |
| 5,547,508 A | 8/1996 | Affinito |
| 5,547,723 A | 8/1996 | Williams |
| 5,554,223 A | 9/1996 | Imahashi |
| 5,555,471 A | 9/1996 | Xu |
| 5,565,248 A | 10/1996 | Piester |
| 5,569,810 A | 10/1996 | Tsuji |
| 5,571,366 A | 11/1996 | Ishii |
| 5,578,103 A | 11/1996 | Araujo |
| 5,591,898 A | 1/1997 | Mayer |
| 5,593,550 A | 1/1997 | Stewart |
| 5,597,456 A | 1/1997 | Maruyama |
| 5,616,369 A | 4/1997 | Williams |
| 5,620,523 A | 4/1997 | Maeda |
| 5,632,396 A | 5/1997 | Burns |
| 5,633,711 A | 5/1997 | Nelson |
| 5,643,638 A | 7/1997 | Otto |
| 5,652,030 A | 7/1997 | Delperier |
| 5,654,054 A | 8/1997 | Tropsha |
| 5,656,141 A | 8/1997 | Betz |
| 5,658,438 A | 8/1997 | Givens |
| 5,665,280 A | 9/1997 | Tropsha |
| 5,667,840 A | 9/1997 | Tingey |
| 5,674,321 A | 10/1997 | Pu |
| 5,677,010 A | 10/1997 | Esser |
| 5,679,412 A | 10/1997 | Kuehnle |
| 5,679,413 A | 10/1997 | Petrmichl |
| 5,683,771 A | 11/1997 | Tropsha |
| 5,686,157 A | 11/1997 | Harvey |
| 5,690,745 A | 11/1997 | Grunwald |
| 5,691,007 A | 11/1997 | Montgomery |
| 5,693,196 A | 12/1997 | Stewart |
| 5,699,923 A | 12/1997 | Burns |
| 5,702,770 A | 12/1997 | Martin |
| 5,704,983 A | 1/1998 | Thomas et al. |
| 5,716,683 A | 2/1998 | Harvey |
| 5,718,967 A | 2/1998 | Hu |
| 5,725,909 A | 3/1998 | Shaw |
| 5,733,405 A | 3/1998 | Taki |
| 5,736,207 A | 4/1998 | Walther |
| 5,737,179 A | 4/1998 | Shaw |
| 5,738,233 A | 4/1998 | Burns |
| 5,738,920 A | 4/1998 | Knors |
| 5,744,360 A | 4/1998 | Hu |
| 5,750,892 A | 5/1998 | Huang |
| 5,763,033 A | 6/1998 | Tropsha |
| 5,766,362 A | 6/1998 | Montgomery |
| 5,769,273 A | 6/1998 | Sasaki |
| 5,779,074 A | 7/1998 | Burns |
| 5,779,716 A | 7/1998 | Cano |
| 5,779,802 A | 7/1998 | Borghs |
| 5,779,849 A | 7/1998 | Blalock |
| 5,788,670 A | 8/1998 | Reinhard |
| 5,792,550 A | 8/1998 | Phillips |
| 5,792,940 A | 8/1998 | Ghandhi |
| 5,798,027 A | 8/1998 | Lefebvre |
| 5,800,880 A | 9/1998 | Laurent |
| 5,807,343 A | 9/1998 | Tucker |
| 5,807,605 A | 9/1998 | Tingey |
| 5,812,261 A | 9/1998 | Nelson |
| 5,814,257 A | 9/1998 | Kawata |
| 5,814,738 A | 9/1998 | Pinkerton |
| 5,820,603 A | 10/1998 | Tucker |
| 5,823,373 A | 10/1998 | Sudo |
| 5,824,198 A | 10/1998 | Williams |
| 5,824,607 A | 10/1998 | Trow |
| 5,833,752 A | 11/1998 | Martin |
| 5,837,888 A | 11/1998 | Mayer |
| 5,837,903 A | 11/1998 | Weingand |
| 5,840,167 A | 11/1998 | Kim |
| 5,849,368 A | 12/1998 | Hostettler |
| 5,853,833 A | 12/1998 | Sudo |
| 5,855,686 A | 1/1999 | Rust |
| 5,861,546 A | 1/1999 | Sagi |
| 5,871,700 A | 2/1999 | Konrad |
| 5,877,895 A | 3/1999 | Shaw |
| 5,880,034 A | 3/1999 | Keller |
| 5,888,414 A | 3/1999 | Collins |
| 5,888,591 A | 3/1999 | Gleason |
| 5,897,508 A | 4/1999 | Konrad |
| 5,900,284 A | 5/1999 | Hu |
| 5,900,285 A | 5/1999 | Walther |
| 5,902,461 A | 5/1999 | Xu |
| 5,904,952 A | 5/1999 | Lopata |
| 5,913,140 A | 6/1999 | Roche |
| 5,914,189 A | 6/1999 | Hasz |
| 5,919,328 A | 7/1999 | Tropsha |
| 5,919,420 A | 7/1999 | Niermann |
| 5,935,391 A | 8/1999 | Nakahigashi |
| 5,945,187 A | 8/1999 | Buch-Rasmussen |
| 5,951,527 A | 9/1999 | Sudo |
| 5,952,069 A | 9/1999 | Tropsha |
| 5,955,161 A | 9/1999 | Tropsha |
| 5,961,911 A | 10/1999 | Hwang |
| 5,968,620 A | 10/1999 | Harvey |
| 5,972,297 A | 10/1999 | Niermann |
| 5,972,436 A | 10/1999 | Walther |
| 5,985,103 A | 11/1999 | Givens |

(56) References Cited

U.S. PATENT DOCUMENTS

| | | |
|---|---|---|
| 6,001,429 A | 12/1999 | Martin |
| 6,009,743 A | 1/2000 | Mayer |
| 6,013,337 A | 1/2000 | Knors |
| 6,017,317 A | 1/2000 | Newby |
| 6,018,987 A | 2/2000 | Mayer |
| 6,020,196 A | 2/2000 | Hu |
| 6,027,619 A | 2/2000 | Cathey |
| 6,032,813 A | 3/2000 | Niermann |
| 6,035,717 A | 3/2000 | Carodiskey |
| 6,050,400 A | 4/2000 | Taskis |
| 6,051,151 A | 4/2000 | Keller |
| 6,054,016 A | 4/2000 | Tuda |
| 6,054,188 A | 4/2000 | Tropsha |
| 6,068,884 A | 5/2000 | Rose |
| 6,077,403 A | 6/2000 | Kobayashi |
| 6,081,330 A | 6/2000 | Nelson |
| 6,082,295 A | 7/2000 | Lee |
| 6,083,313 A | 7/2000 | Venkatraman et al. |
| 6,085,927 A | 7/2000 | Kusz |
| 6,090,081 A | 7/2000 | Sudo |
| 6,093,175 A | 7/2000 | Gyure |
| 6,106,678 A | 8/2000 | Shufflebotham |
| 6,110,395 A | 8/2000 | Gibson, Jr. |
| 6,110,544 A | 8/2000 | Yang |
| 6,112,695 A | 9/2000 | Felts |
| 6,116,081 A | 9/2000 | Ghandhi |
| 6,117,243 A | 9/2000 | Walther |
| 6,118,844 A | 9/2000 | Fischer |
| 6,124,212 A | 9/2000 | Fan |
| 6,125,687 A | 10/2000 | McClelland |
| 6,126,640 A | 10/2000 | Tucker |
| 6,129,712 A | 10/2000 | Sudo |
| 6,136,275 A | 10/2000 | Niermann |
| 6,139,802 A | 10/2000 | Niermann |
| 6,143,140 A | 11/2000 | Wang |
| 6,149,982 A | 11/2000 | Plester |
| 6,153,269 A | 11/2000 | Gleason |
| 6,156,152 A | 12/2000 | Ogino |
| 6,156,399 A | 12/2000 | Spallek |
| 6,156,435 A | 12/2000 | Gleason |
| 6,160,350 A | 12/2000 | Sakemi |
| 6,161,712 A | 12/2000 | Savitz |
| 6,163,006 A | 12/2000 | Doughty |
| 6,165,138 A | 12/2000 | Miller |
| 6,165,542 A | 12/2000 | Jaworowski |
| 6,165,566 A | 12/2000 | Tropsha |
| 6,171,670 B1 | 1/2001 | Sudo |
| 6,175,612 B1 | 1/2001 | Sato |
| 6,177,142 B1 | 1/2001 | Felts |
| 6,180,185 B1 | 1/2001 | Felts |
| 6,180,191 B1 | 1/2001 | Felts |
| 6,188,079 B1 | 2/2001 | Juvinall |
| 6,189,484 B1 | 2/2001 | Yin |
| 6,190,992 B1 | 2/2001 | Sandhu |
| 6,193,853 B1 | 2/2001 | Yumshtyk |
| 6,196,155 B1 | 3/2001 | Setoyama |
| 6,197,166 B1 | 3/2001 | Moslehi |
| 6,200,658 B1 | 3/2001 | Walther |
| 6,200,675 B1 | 3/2001 | Neerinck |
| 6,204,922 B1 | 3/2001 | Chalmers |
| 6,210,791 B1 | 4/2001 | Skoog |
| 6,214,422 B1 | 4/2001 | Yializis |
| 6,217,716 B1 | 4/2001 | Fai Lai |
| 6,223,683 B1 | 5/2001 | Plester |
| 6,236,459 B1 | 5/2001 | Negahdaripour |
| 6,245,190 B1 | 6/2001 | Masuda |
| 6,248,219 B1 | 6/2001 | Wellerdieck |
| 6,248,397 B1 | 6/2001 | Ye |
| 6,251,792 B1 | 6/2001 | Collins |
| 6,254,983 B1 | 7/2001 | Namiki |
| 6,261,643 B1 | 7/2001 | Hasz |
| 6,263,249 B1 | 7/2001 | Stewart |
| 6,271,047 B1 | 8/2001 | Ushio |
| 6,276,296 B1 | 8/2001 | Plester |
| 6,277,331 B1 | 8/2001 | Konrad |
| 6,279,505 B1 | 8/2001 | Plester |
| 6,284,986 B1 | 9/2001 | Dietze |
| 6,306,132 B1 | 10/2001 | Moorman |
| 6,308,556 B1 | 10/2001 | Sagi |
| 6,322,661 B1 | 11/2001 | Bailey, III |
| 6,331,174 B1 | 12/2001 | Reinhard et al. |
| 6,344,034 B1 | 2/2002 | Sudo |
| 6,346,596 B1 | 2/2002 | Mallen |
| 6,348,967 B1 | 2/2002 | Nelson |
| 6,350,415 B1 | 2/2002 | Niermann |
| 6,351,075 B1 | 2/2002 | Barankova |
| 6,352,629 B1 | 3/2002 | Wang |
| 6,354,452 B1 | 3/2002 | DeSalvo |
| 6,355,033 B1 | 3/2002 | Moorman |
| 6,365,013 B1 | 4/2002 | Beele |
| 6,375,022 B1 | 4/2002 | Zurcher |
| 6,376,028 B1 | 4/2002 | Laurent |
| 6,379,757 B1 | 4/2002 | Iacovangelo |
| 6,382,441 B1 | 5/2002 | Carano |
| 6,394,979 B1 | 5/2002 | Sharp |
| 6,396,024 B1 | 5/2002 | Doughty |
| 6,399,944 B1 | 6/2002 | Vasilyev |
| 6,402,885 B2 | 6/2002 | Loewenhardt |
| 6,410,926 B1 | 6/2002 | Munro |
| 6,413,645 B1 | 7/2002 | Graff |
| 6,432,494 B1 | 8/2002 | Yang |
| 6,432,510 B1 | 8/2002 | Kim |
| 6,470,650 B1 | 10/2002 | Lohwasser |
| 6,471,822 B1 | 10/2002 | Yin |
| 6,475,622 B2 | 11/2002 | Namiki |
| 6,482,509 B2 | 11/2002 | Buch-Rasmussen et al. |
| 6,486,081 B1 | 11/2002 | Ishikawa |
| 6,500,500 B1 | 12/2002 | Okamura |
| 6,503,579 B1 | 1/2003 | Murakami |
| 6,518,195 B1 | 2/2003 | Collins |
| 6,524,282 B1 | 2/2003 | Sudo |
| 6,524,448 B2 | 2/2003 | Brinkmann |
| 6,539,890 B1 | 4/2003 | Felts |
| 6,544,610 B1 | 4/2003 | Minami |
| 6,551,267 B1 | 4/2003 | Cohen |
| 6,558,679 B2 | 5/2003 | Flament-Garcia et al. |
| 6,562,010 B1 | 5/2003 | Gyure |
| 6,562,189 B1 | 5/2003 | Quiles |
| 6,565,791 B1 | 5/2003 | Laurent |
| 6,582,426 B2 | 6/2003 | Moorman |
| 6,582,823 B1 | 6/2003 | Sakhrani et al. |
| 6,584,828 B2 | 7/2003 | Sagi |
| 6,595,961 B2 | 7/2003 | Hetzler |
| 6,597,193 B2 | 7/2003 | Lagowski |
| 6,599,569 B1 | 7/2003 | Humele |
| 6,599,594 B1 | 7/2003 | Walther |
| 6,602,206 B1 | 8/2003 | Niermann |
| 6,616,632 B2 | 9/2003 | Sharp |
| 6,620,139 B1 | 9/2003 | Plicchi |
| 6,620,334 B2 | 9/2003 | Kanno |
| 6,623,861 B2 | 9/2003 | Martin |
| 6,638,403 B1 | 10/2003 | Inaba |
| 6,638,876 B2 | 10/2003 | Levy |
| 6,645,354 B1 | 11/2003 | Gorokhovsky |
| 6,645,635 B2 | 11/2003 | Muraki |
| 6,651,835 B2 | 11/2003 | Iskra |
| 6,652,520 B2 | 11/2003 | Moorman |
| 6,656,540 B2 | 12/2003 | Sakamoto |
| 6,658,919 B2 | 12/2003 | Chatard |
| 6,662,957 B2 | 12/2003 | Zurcher |
| 6,663,601 B2 | 12/2003 | Hetzler |
| 6,663,603 B1 | 12/2003 | Gyure |
| 6,670,200 B2 | 12/2003 | Ushio |
| 6,673,199 B1 | 1/2004 | Yamartino |
| 6,680,091 B2 | 1/2004 | Buch-Rasmussen et al. |
| 6,680,621 B2 | 1/2004 | Savtchouk |
| 6,683,308 B2 | 1/2004 | Itagaki |
| 6,684,683 B2 | 2/2004 | Potyrailo |
| 6,702,898 B2 | 3/2004 | Hosoi |
| 6,706,412 B2 | 3/2004 | Yializis |
| 6,746,430 B2 | 6/2004 | Lubrecht |
| 6,749,078 B2 | 6/2004 | Iskra |
| 6,752,899 B1 | 6/2004 | Singh |
| 6,753,972 B1 | 6/2004 | Hirose |

(56) References Cited

U.S. PATENT DOCUMENTS

| | | |
|---|---|---|
| 6,757,056 B1 | 6/2004 | Meeks |
| 6,764,714 B2 | 7/2004 | Wei |
| 6,765,466 B2 | 7/2004 | Miyata |
| 6,766,682 B2 | 7/2004 | Engle |
| 6,774,018 B2 | 8/2004 | Mikhael |
| 6,796,780 B1 | 9/2004 | Chatard |
| 6,800,852 B2 | 10/2004 | Larson |
| 6,808,753 B2 | 10/2004 | Rule |
| 6,810,106 B2 | 10/2004 | Sato |
| 6,815,014 B2 | 11/2004 | Gabelnick |
| 6,818,310 B2 | 11/2004 | Namiki |
| 6,822,015 B2 | 11/2004 | Muraki |
| 6,827,972 B2 | 12/2004 | Darras |
| 6,837,954 B2 | 1/2005 | Carano |
| 6,844,075 B1 | 1/2005 | Saak |
| 6,853,141 B2 | 2/2005 | Hoffman |
| 6,858,259 B2 | 2/2005 | Affinito |
| 6,863,731 B2 | 3/2005 | Elsayed-Ali |
| 6,864,773 B2 | 3/2005 | Perrin |
| 6,866,656 B2 | 3/2005 | Tingey |
| 6,872,428 B2 | 3/2005 | Yang |
| 6,876,154 B2 | 4/2005 | Appleyard |
| 6,885,727 B2 | 4/2005 | Tamura |
| 6,887,578 B2 | 5/2005 | Gleason |
| 6,891,158 B2 | 5/2005 | Larson |
| 6,892,567 B1 | 5/2005 | Morrow |
| 6,899,054 B1 | 5/2005 | Bardos |
| 6,905,769 B2 | 6/2005 | Komada |
| 6,910,597 B2 | 6/2005 | Iskra |
| 6,911,779 B2 | 6/2005 | Madocks |
| 6,919,107 B2 | 7/2005 | Schwarzenbach |
| 6,919,114 B1 | 7/2005 | Darras |
| 6,933,460 B2 | 8/2005 | Vanden Brande |
| 6,946,164 B2 | 9/2005 | Huang |
| 6,952,949 B2 | 10/2005 | Moore |
| 6,960,393 B2 | 11/2005 | Yializis |
| 6,962,671 B2 | 11/2005 | Martin |
| 6,965,221 B2 | 11/2005 | Lipcsei |
| 6,981,403 B2 | 1/2006 | Ascheman |
| 6,989,675 B2 | 1/2006 | Kesil |
| 6,995,377 B2 | 2/2006 | Darr |
| 7,029,755 B2 | 4/2006 | Terry |
| 7,029,803 B2 | 4/2006 | Becker |
| 7,039,158 B1 | 5/2006 | Janik |
| 7,052,736 B2 | 5/2006 | Wei |
| 7,052,920 B2 | 5/2006 | Ushio |
| 7,059,268 B2 | 6/2006 | Russell |
| 7,067,034 B2 | 6/2006 | Bailey, III |
| 7,074,501 B2 | 7/2006 | Czeremuszkin |
| 7,098,453 B2 | 8/2006 | Ando |
| 7,109,070 B2 | 9/2006 | Behle |
| 7,112,352 B2 | 9/2006 | Schaepkens |
| 7,112,541 B2 | 9/2006 | Xia |
| 7,115,310 B2 | 10/2006 | Jacoud |
| 7,118,538 B2 | 10/2006 | Konrad |
| 7,119,908 B2 | 10/2006 | Nomoto |
| 7,121,135 B2 | 10/2006 | Moore |
| 7,130,373 B2 | 10/2006 | Omote |
| 7,150,299 B2 | 12/2006 | Hertzler |
| 7,160,292 B2 | 1/2007 | Moorman |
| 7,180,849 B2 | 2/2007 | Hirokane |
| 7,183,197 B2 | 2/2007 | Won |
| 7,186,242 B2 | 3/2007 | Gyure |
| 7,188,734 B2 | 3/2007 | Konrad |
| 7,189,290 B2 | 3/2007 | Hama |
| 7,193,724 B2 | 3/2007 | Isei |
| 7,198,685 B2 | 4/2007 | Hetzler |
| 7,206,074 B2 | 4/2007 | Fujimoto |
| 7,214,214 B2 | 5/2007 | Sudo |
| 7,244,381 B2 | 7/2007 | Chatard |
| 7,253,892 B2 | 8/2007 | Semersky |
| 7,286,242 B2 | 10/2007 | Kim |
| 7,288,293 B2 | 10/2007 | Koulik |
| 7,297,216 B2 | 11/2007 | Hetzler |
| 7,297,640 B2 | 11/2007 | Xie |
| 7,300,684 B2 | 11/2007 | Boardman |
| 7,303,789 B2 | 12/2007 | Saito |
| 7,303,790 B2 | 12/2007 | Delaunay |
| 7,306,852 B2 | 12/2007 | Komada |
| 7,332,227 B2 | 2/2008 | Hardman |
| 7,338,576 B2 | 3/2008 | Ono |
| 7,339,682 B2 | 3/2008 | Aiyer |
| 7,344,766 B1 | 3/2008 | Sorensen |
| 7,348,055 B2 | 3/2008 | Chappa |
| 7,348,192 B2 | 3/2008 | Mikami |
| 7,362,425 B2 | 4/2008 | Meeks |
| 7,381,469 B2 | 6/2008 | Moelle |
| 7,390,573 B2 | 6/2008 | Korevaar |
| 7,399,500 B2 | 7/2008 | Bicker |
| 7,405,008 B2 | 7/2008 | Domine |
| 7,409,313 B2 | 8/2008 | Ringermacher |
| 7,411,685 B2 | 8/2008 | Takashima |
| RE40,531 E | 10/2008 | Graff |
| 7,431,989 B2 | 10/2008 | Sakhrani |
| 7,438,783 B2 | 10/2008 | Miyata |
| 7,444,955 B2 | 11/2008 | Boardman |
| 7,455,892 B2 | 11/2008 | Goodwin |
| 7,480,363 B2 | 1/2009 | Lasiuk |
| 7,488,683 B2 | 2/2009 | Kobayashi |
| 7,494,941 B2 | 2/2009 | Kasahara |
| 7,507,378 B2 | 3/2009 | Reichenbach |
| 7,513,953 B1 | 4/2009 | Felts |
| 7,520,965 B2 | 4/2009 | Wei |
| 7,521,022 B2 | 4/2009 | Konrad |
| 7,534,615 B2 | 5/2009 | Havens |
| 7,534,733 B2 | 5/2009 | Bookbinder |
| RE40,787 E | 6/2009 | Martin |
| 7,541,069 B2 | 6/2009 | Tudhope |
| 7,547,297 B2 | 6/2009 | Brinkhues |
| 7,552,620 B2 | 6/2009 | DeRoos |
| 7,553,529 B2 | 6/2009 | Sakhrani |
| 7,555,934 B2 | 7/2009 | DeRoos |
| 7,569,035 B1 | 8/2009 | Wilmot |
| 7,579,056 B2 | 8/2009 | Brown |
| 7,586,824 B2 | 8/2009 | Hirokane |
| 7,582,868 B2 | 9/2009 | Jiang |
| 7,595,097 B2 | 9/2009 | Iacovangelo |
| 7,608,151 B2 | 10/2009 | Tudhope |
| 7,609,605 B2 | 10/2009 | Hirokane |
| 7,618,686 B2 | 11/2009 | Colpo |
| 7,624,622 B1 | 12/2009 | Mayer |
| 7,625,494 B2 | 12/2009 | Honda |
| 7,641,636 B2 | 1/2010 | Moesli |
| 7,645,696 B1 | 1/2010 | Dulkin |
| 7,648,481 B2 | 1/2010 | Geiger |
| 7,682,816 B2 | 3/2010 | Kim |
| 7,691,308 B2 | 4/2010 | Brinkhues |
| 7,694,403 B2 | 4/2010 | Moulton |
| 7,699,933 B2 | 4/2010 | Lizenberg |
| 7,704,683 B2 | 4/2010 | Wittenberg |
| 7,713,638 B2 | 5/2010 | Moelle |
| 7,736,689 B2 | 6/2010 | Chappa |
| 7,740,610 B2 | 6/2010 | Moh |
| 7,744,567 B2 | 6/2010 | Glowacki |
| 7,744,790 B2 | 6/2010 | Behle |
| 7,745,228 B2 | 6/2010 | Schwind |
| 7,745,547 B1 | 6/2010 | Auerbach |
| 7,749,202 B2 | 7/2010 | Miller |
| 7,749,914 B2 | 7/2010 | Honda |
| 7,754,302 B2 | 7/2010 | Yamaski |
| 7,766,882 B2 | 8/2010 | Sudo |
| 7,780,866 B2 | 8/2010 | Miller |
| 7,785,862 B2 | 8/2010 | Kim |
| 7,790,475 B2 | 9/2010 | Galbraith |
| 7,798,993 B2 | 9/2010 | Lim |
| 7,803,305 B2 | 9/2010 | Ahern |
| 7,807,242 B2 | 10/2010 | Sorensen |
| 7,815,922 B2 | 10/2010 | Chaney |
| 7,846,293 B2 | 12/2010 | Iwasaki |
| 7,854,889 B2 | 12/2010 | Perot |
| 7,867,366 B1 | 1/2011 | McFarland |
| 7,901,783 B2 | 3/2011 | Rose |
| 7,905,866 B2 | 3/2011 | Haider |
| 7,922,880 B1 | 4/2011 | Pradhan |

(56) References Cited

U.S. PATENT DOCUMENTS

| | | | |
|---|---|---|---|
| 7,922,958 B2 | 4/2011 | D'Arrigo | |
| 7,927,315 B2 | 4/2011 | Sudo | |
| 7,931,955 B2 | 4/2011 | Behle | |
| 7,932,678 B2 | 4/2011 | Madocks | |
| 7,934,613 B2 | 5/2011 | Sudo | |
| 7,943,205 B2 | 5/2011 | Schaepkens | |
| 7,947,337 B2 | 5/2011 | Kuepper | |
| 7,955,986 B2 | 6/2011 | Hoffman | |
| 7,960,043 B2 | 6/2011 | Harris | |
| 7,964,438 B2 | 6/2011 | Roca I Cabarrocas | |
| 7,967,945 B2 | 6/2011 | Glukhoy | |
| 7,975,646 B2 | 7/2011 | Rius | |
| 7,985,188 B2 | 7/2011 | Felts | |
| 8,002,754 B2 | 8/2011 | Kawamura | |
| 8,025,915 B2 | 9/2011 | Haines | |
| 8,038,858 B1 | 10/2011 | Bures | |
| 8,039,524 B2 | 10/2011 | Chappa | |
| 8,056,719 B2 | 11/2011 | Porret | |
| 8,062,266 B2 | 11/2011 | McKinnon | |
| 8,066,663 B2 | 11/2011 | Sudo | |
| 8,066,854 B2 | 11/2011 | Storey | |
| 8,067,070 B2 * | 11/2011 | Klein | C23C 16/30 428/34.6 |
| 8,070,917 B2 | 12/2011 | Tsukamoto | |
| 8,075,995 B2 | 12/2011 | Zhao | |
| 8,092,605 B2 | 1/2012 | Shannon | |
| 8,101,246 B2 | 1/2012 | Fayet | |
| 8,101,674 B2 | 1/2012 | Kawauchi | |
| 8,105,294 B2 | 1/2012 | Araki | |
| 8,197,452 B2 | 6/2012 | Harding | |
| 8,227,025 B2 | 7/2012 | Lewis | |
| 8,258,486 B2 | 9/2012 | Avnery | |
| 8,268,410 B2 | 9/2012 | Moelle | |
| 8,273,222 B2 | 9/2012 | Wei | |
| 8,277,025 B2 | 10/2012 | Nakazawa et al. | |
| 8,313,455 B2 | 11/2012 | DiGregorio | |
| 8,323,166 B2 | 12/2012 | Haines | |
| 8,389,958 B2 | 3/2013 | Vo-Dinh | |
| 8,397,667 B2 | 3/2013 | Behle | |
| 8,409,441 B2 | 4/2013 | Wilt | |
| 8,418,650 B2 | 4/2013 | Goto | |
| 8,435,605 B2 | 5/2013 | Aitken et al. | |
| 8,475,886 B2 | 7/2013 | Chen et al. | |
| 8,512,796 B2 | 8/2013 | Felts | |
| 8,524,331 B2 | 9/2013 | Honda | |
| 8,592,015 B2 | 11/2013 | Bicker | |
| 8,603,638 B2 | 12/2013 | Liu | |
| 8,618,509 B2 | 12/2013 | Vo-Dinh | |
| 8,623,324 B2 | 1/2014 | Diwu | |
| 8,633,034 B2 | 1/2014 | Trotter | |
| 8,747,962 B2 | 6/2014 | Bicker | |
| 8,802,603 B2 | 8/2014 | D'Souza | |
| 8,816,022 B2 | 8/2014 | Zhao | |
| 9,068,565 B2 | 6/2015 | Alarcon | |
| 2001/0000279 A1 | 4/2001 | Daniels | |
| 2001/0021356 A1 | 9/2001 | Konrad | |
| 2001/0038894 A1 | 11/2001 | Komada | |
| 2001/0042510 A1 | 11/2001 | Plester | |
| 2001/0043997 A1 | 11/2001 | Uddin | |
| 2002/0006487 A1 | 1/2002 | O'Connor | |
| 2002/0007796 A1 | 1/2002 | Gorokhovsky | |
| 2002/0070647 A1 | 6/2002 | Ginovker | |
| 2002/0117114 A1 | 8/2002 | Ikenaga | |
| 2002/0125900 A1 | 9/2002 | Savtchouk | |
| 2002/0130674 A1 | 9/2002 | Logowski | |
| 2002/0141477 A1 | 10/2002 | Akahori | |
| 2002/0153103 A1 | 10/2002 | Madocks | |
| 2002/0155218 A1 | 10/2002 | Meyer | |
| 2002/0170495 A1 | 11/2002 | Nakamura | |
| 2002/0176947 A1 | 11/2002 | Darras | |
| 2002/0182101 A1 | 12/2002 | Koulik | |
| 2002/0185226 A1 | 12/2002 | Lea | |
| 2002/0190207 A1 | 12/2002 | Levy | |
| 2003/0010454 A1 | 1/2003 | Bailey, III | |
| 2003/0013818 A1 | 1/2003 | Hakuta | |
| 2003/0029837 A1 | 2/2003 | Trow | |
| 2003/0031806 A1 | 2/2003 | Jinks | |
| 2003/0046982 A1 | 3/2003 | Chartard | |
| 2000/3119193 | 6/2003 | Hess | |
| 2003/0102087 A1 | 6/2003 | Ito | |
| 2003/0159654 A1 | 8/2003 | Arnold | |
| 2003/0215652 A1 | 11/2003 | O'Connor | |
| 2003/0219547 A1 | 11/2003 | Arnold | |
| 2003/0232150 A1 | 12/2003 | Arnold | |
| 2004/0024371 A1 | 2/2004 | Plicchi | |
| 2004/0039401 A1 | 2/2004 | Chow | |
| 2004/0040372 A1 | 3/2004 | Plester | |
| 2004/0045811 A1 | 3/2004 | Wang | |
| 2004/0050744 A1 | 3/2004 | Hama | |
| 2004/0055538 A1 | 3/2004 | Gorokhovsky | |
| 2004/0071960 A1 | 4/2004 | Weber | |
| 2004/0082917 A1 | 4/2004 | Hetzler | |
| 2004/0084151 A1 | 5/2004 | Kim | |
| 2004/0125913 A1 | 7/2004 | Larson | |
| 2004/0135081 A1 | 7/2004 | Larson | |
| 2004/0149225 A1 | 8/2004 | Weikart | |
| 2004/0175961 A1 | 9/2004 | Olsen | |
| 2004/0177676 A1 | 9/2004 | Moore | |
| 2004/0195960 A1 | 10/2004 | Czeremuszkin | |
| 2004/0206309 A1 | 10/2004 | Bera | |
| 2004/0217081 A1 | 11/2004 | Konrad | |
| 2004/0247948 A1 | 12/2004 | Behle | |
| 2004/0267194 A1 | 12/2004 | Sano | |
| 2005/0000962 A1 | 1/2005 | Crawford | |
| 2005/0010175 A1 | 1/2005 | Beedon | |
| 2005/0019503 A1 | 1/2005 | Komada | |
| 2005/0037165 A1 | 2/2005 | Ahern | |
| 2005/0039854 A1 | 2/2005 | Matsuyama | |
| 2005/0045472 A1 | 3/2005 | Nagata | |
| 2005/0057754 A1 | 3/2005 | Smith | |
| 2005/0073323 A1 | 4/2005 | Kohno | |
| 2005/0075611 A1 | 4/2005 | Heltzer | |
| 2005/0075612 A1 | 4/2005 | Lee | |
| 2005/0161149 A1 | 7/2005 | Yokota | |
| 2005/0169803 A1 | 8/2005 | Betz | |
| 2005/0190450 A1 | 9/2005 | Becker | |
| 2005/0194619 A1 * | 9/2005 | Edelstein | H01L 31/103 257/232 |
| 2005/0196629 A1 | 9/2005 | Bariatinsky | |
| 2005/0199571 A1 | 9/2005 | Geisler | |
| 2005/0206907 A1 | 9/2005 | Fujimoto | |
| 2005/0211383 A1 | 9/2005 | Miyata | |
| 2005/0223988 A1 | 10/2005 | Behle | |
| 2005/0227002 A1 | 10/2005 | Lizenberg | |
| 2005/0227022 A1 | 10/2005 | Domine | |
| 2005/0229850 A1 | 10/2005 | Behle | |
| 2005/0233077 A1 | 10/2005 | Lizenberg | |
| 2005/0233091 A1 | 10/2005 | Kumar | |
| 2005/0236346 A1 | 10/2005 | Whitney | |
| 2005/0260504 A1 | 11/2005 | Becker | |
| 2005/0284550 A1 | 12/2005 | Bicker | |
| 2006/0005608 A1 | 1/2006 | Kitzhoffer | |
| 2006/0013997 A1 | 1/2006 | Kuepper | |
| 2006/0014309 A1 | 1/2006 | Sachdev | |
| 2006/0024849 A1 | 2/2006 | Zhu | |
| 2006/0042755 A1 | 3/2006 | Holmberg | |
| 2006/0046006 A1 | 3/2006 | Bastion | |
| 2006/0051252 A1 | 3/2006 | Yuan | |
| 2006/0051520 A1 | 3/2006 | Behle | |
| 2006/0076231 A1 | 4/2006 | Wei | |
| 2006/0086320 A1 | 4/2006 | Lizenberg | |
| 2006/0099340 A1 | 5/2006 | Behle | |
| 2006/0121222 A1 | 6/2006 | Audrich | |
| 2006/0121613 A1 | 6/2006 | Havens | |
| 2006/0121623 A1 | 6/2006 | He | |
| 2006/0127699 A1 | 6/2006 | Moelle | |
| 2006/0135945 A1 | 6/2006 | Bankiewicz | |
| 2006/0138326 A1 | 6/2006 | Jiang | |
| 2006/0150909 A1 | 7/2006 | Behle | |
| 2006/0169026 A1 | 8/2006 | Kage | |
| 2006/0178627 A1 | 8/2006 | Geiger | |
| 2006/0183345 A1 | 8/2006 | Nguyen | |
| 2006/0192973 A1 | 8/2006 | Aiyer | |
| 2006/0196419 A1 | 9/2006 | Tudhope | |

(56) References Cited

U.S. PATENT DOCUMENTS

| | | |
|---|---|---|
| 2006/0198903 A1 | 9/2006 | Storey |
| 2006/0198965 A1 | 9/2006 | Tudhope |
| 2006/0200078 A1 | 9/2006 | Konrad |
| 2006/0200084 A1 | 9/2006 | Ito |
| 2006/0210425 A1 | 9/2006 | Mirkarimi |
| 2006/0228497 A1 | 10/2006 | Kumar |
| 2006/0260360 A1 | 11/2006 | Dick |
| 2007/0003441 A1 | 1/2007 | Wohleb |
| 2007/0009673 A1 | 1/2007 | Fukazawa et al. |
| 2007/0017870 A1 | 1/2007 | Belay |
| 2007/0048456 A1 | 3/2007 | Keshner |
| 2007/0049048 A1 | 3/2007 | Rauf |
| 2007/0051629 A1 | 3/2007 | Donlik |
| 2007/0065680 A1 | 3/2007 | Schultheis |
| 2007/0076833 A1 | 4/2007 | Becker |
| 2007/0102344 A1 | 5/2007 | Konrad |
| 2007/0123920 A1 | 5/2007 | Inokuti |
| 2007/0148326 A1 | 6/2007 | Hatings |
| 2007/0166187 A1 | 7/2007 | Song |
| 2007/0184657 A1 | 8/2007 | Iijima |
| 2007/0187229 A1 | 8/2007 | Aksenov |
| 2007/0187280 A1 | 8/2007 | Haines |
| 2007/0205096 A1 | 9/2007 | Nagashima |
| 2007/0215009 A1 | 9/2007 | Shimazu |
| 2007/0215046 A1 | 9/2007 | Lupke |
| 2007/0218265 A1 | 9/2007 | Harris |
| 2007/0224236 A1 | 9/2007 | Boden |
| 2007/0229844 A1 | 10/2007 | Holz |
| 2007/0231655 A1 | 10/2007 | Ha |
| 2007/0232066 A1 | 10/2007 | Bicker |
| 2007/0235890 A1 | 10/2007 | Lewis |
| 2007/0243618 A1 | 10/2007 | Hatchett |
| 2007/0251458 A1 | 11/2007 | Mund |
| 2007/0258894 A1 | 11/2007 | Melker et al. |
| 2007/0259184 A1 | 11/2007 | Martin |
| 2007/0281108 A1 | 12/2007 | Weikart |
| 2007/0281117 A1 | 12/2007 | Kaplan |
| 2007/0287950 A1 | 12/2007 | Kjeken |
| 2007/0287954 A1 | 12/2007 | Zhao |
| 2007/0298189 A1 | 12/2007 | Straemke |
| 2008/0011232 A1 | 1/2008 | Ruis |
| 2008/0017113 A1 | 1/2008 | Goto |
| 2008/0023414 A1 | 1/2008 | Konrad |
| 2008/0027400 A1 | 1/2008 | Harding |
| 2008/0045880 A1 | 2/2008 | Kjeken |
| 2008/0050567 A1 | 2/2008 | Kawashima |
| 2008/0050932 A1 | 2/2008 | Lakshmanan |
| 2008/0053373 A1 | 3/2008 | Mund |
| 2008/0069970 A1 | 3/2008 | Wu |
| 2008/0071228 A1 | 3/2008 | Wu |
| 2008/0210550 A1 | 3/2008 | Mund |
| 2008/0081184 A1 | 4/2008 | Kubo |
| 2008/0090039 A1 | 4/2008 | Klein |
| 2008/0093245 A1 | 4/2008 | Periasamy |
| 2008/0102206 A1 | 5/2008 | Wagner |
| 2008/0109017 A1 | 5/2008 | Herweck |
| 2008/0110852 A1 | 5/2008 | Kuroda |
| 2008/0113109 A1 | 5/2008 | Moelle |
| 2008/0118734 A1 | 5/2008 | Goodwin |
| 2008/0131628 A1 | 6/2008 | Abensour |
| 2008/0131638 A1 | 6/2008 | Hutton |
| 2008/0139003 A1 | 6/2008 | Pirzada |
| 2008/0145271 A1 | 6/2008 | Kidambi |
| 2008/0187681 A1 | 8/2008 | Hofrichter |
| 2008/0195059 A1 | 8/2008 | Sudo |
| 2008/0202414 A1 | 8/2008 | Yan |
| 2008/0206477 A1 | 8/2008 | Leontaris |
| 2008/0220164 A1 | 9/2008 | Bauch |
| 2008/0223815 A1 | 9/2008 | Konrad |
| 2008/0233355 A1 | 9/2008 | Henze |
| 2008/0260966 A1 | 10/2008 | Hanawa |
| 2008/0268252 A1 | 10/2008 | Garces |
| 2008/0277332 A1 | 11/2008 | Liu |
| 2008/0289957 A1 | 11/2008 | Takigawa |
| 2008/0292806 A1 | 11/2008 | Wei |
| 2008/0295772 A1 | 12/2008 | Park |
| 2008/0303131 A1 | 12/2008 | Mcelerea |
| 2008/0312607 A1 | 12/2008 | Delmotte |
| 2008/0314318 A1 | 12/2008 | Han |
| 2009/0004091 A1 | 1/2009 | Kang |
| 2009/0004363 A1 | 1/2009 | Keshner |
| 2009/0017217 A1 | 1/2009 | Hass |
| 2009/0022981 A1 | 1/2009 | Yoshida |
| 2009/0029402 A1 | 1/2009 | Papkovsky |
| 2009/0031953 A1 | 2/2009 | Ingle |
| 2009/0032393 A1 | 2/2009 | Madocks |
| 2009/0039240 A1 | 2/2009 | Van Nijnatten |
| 2009/0053491 A1 | 2/2009 | Laboda |
| 2009/0061237 A1 | 3/2009 | Gates |
| 2009/0065485 A1 | 3/2009 | O'Neill |
| 2009/0069790 A1 | 3/2009 | Yokley |
| 2009/0081797 A1 | 3/2009 | Fadeev |
| 2009/0099512 A1 | 4/2009 | Digregorio |
| 2009/0104392 A1 | 4/2009 | Takada |
| 2009/0117268 A1 | 5/2009 | Lewis |
| 2009/0117389 A1 | 5/2009 | Amberg-Schwab |
| 2009/0122832 A1 | 5/2009 | Feist |
| 2009/0134884 A1 | 5/2009 | Bosselmann |
| 2009/0137966 A1 | 5/2009 | Rueckert |
| 2009/0142227 A1 | 6/2009 | Fuchs |
| 2009/0142514 A1 | 6/2009 | O'Neill |
| 2009/0147719 A1 | 6/2009 | Rak |
| 2009/0149816 A1 | 6/2009 | Hetzler |
| 2009/0155490 A1 | 6/2009 | Bicker |
| 2009/0162571 A1 | 6/2009 | Haines |
| 2009/0166312 A1 | 7/2009 | Giraud |
| 2009/0176031 A1 | 7/2009 | Armellin |
| 2009/0214801 A1 | 8/2009 | Higashi |
| 2009/0220948 A1 | 9/2009 | Oviso et al. |
| 2009/0263668 A1 | 10/2009 | David |
| 2009/0274851 A1 | 11/2009 | Goudar |
| 2009/0280268 A1 | 11/2009 | Glukhoy |
| 2009/0297730 A1 | 12/2009 | Glukhoy |
| 2009/0306595 A1 | 12/2009 | Shih |
| 2009/0326517 A1 | 12/2009 | Bork |
| 2010/0021998 A1 | 1/2010 | Sanyal |
| 2010/0028238 A1 | 2/2010 | Maschwitz |
| 2010/0034985 A1 | 2/2010 | Krueger |
| 2010/0042055 A1 | 2/2010 | Sudo |
| 2010/0075077 A1 | 3/2010 | Bicker |
| 2010/0086808 A1 | 4/2010 | Nagata |
| 2010/0089097 A1 | 4/2010 | Brack |
| 2010/0104770 A1 | 4/2010 | Goudar |
| 2010/0105208 A1 | 4/2010 | Winniczek |
| 2010/0132762 A1 | 6/2010 | Graham, Jr. |
| 2010/0145284 A1 | 6/2010 | Togashi |
| 2010/0149540 A1 | 6/2010 | Boukherroub |
| 2010/0174239 A1 | 7/2010 | Yodfat |
| 2010/0174245 A1 | 7/2010 | Halverson |
| 2010/0178490 A1 | 7/2010 | Cerny |
| 2010/0185157 A1 | 7/2010 | Kawamura |
| 2010/0186740 A1 | 7/2010 | Lewis |
| 2010/0190036 A1 | 7/2010 | Komvopoulos |
| 2010/0193461 A1 | 8/2010 | Boutroy |
| 2010/0195471 A1 | 8/2010 | Hirokane |
| 2010/0198554 A1 | 8/2010 | Skliar |
| 2010/0204648 A1 | 8/2010 | Stout |
| 2010/0230281 A1 | 9/2010 | Park |
| 2010/0231194 A1 | 9/2010 | Bauch |
| 2010/0237545 A1 | 9/2010 | Haury |
| 2010/0264139 A1 | 10/2010 | Kawachi |
| 2010/0273261 A1 | 10/2010 | Chen |
| 2010/0275847 A1 | 11/2010 | Yamasaki |
| 2010/0279397 A1 | 11/2010 | Crawford |
| 2010/0298738 A1* | 11/2010 | Felts .................. B05D 1/62 600/576 |
| 2010/0298779 A1 | 11/2010 | Hetzler |
| 2011/0037159 A1 | 2/2011 | Mcelerea |
| 2011/0046570 A1 | 2/2011 | Stout |
| 2011/0056912 A1 | 3/2011 | Magsuyama |
| 2011/0062047 A1 | 3/2011 | Haines |
| 2011/0065798 A1 | 3/2011 | Hoang |
| 2011/0079582 A1 | 4/2011 | Yonesu |
| 2011/0093056 A1 | 4/2011 | Kaplan |

(56) References Cited

U.S. PATENT DOCUMENTS

| | | |
|---|---|---|
| 2011/0111132 A1 | 5/2011 | Wei |
| 2011/0117202 A1 | 5/2011 | Bourke, Jr. |
| 2011/0117288 A1 | 5/2011 | Honda |
| 2011/0137263 A1 | 6/2011 | Ashmead |
| 2011/0152820 A1 | 6/2011 | Chattaraj |
| 2011/0159101 A1 | 6/2011 | Kurdyumov et al. |
| 2011/0160662 A1 | 6/2011 | Stout |
| 2011/0160663 A1 | 6/2011 | Stout |
| 2011/0174220 A1 | 7/2011 | Laure |
| 2011/0186537 A1 | 8/2011 | Rodriguez San Juan et al. |
| 2011/0220490 A1 | 9/2011 | Wei |
| 2011/0252899 A1 | 10/2011 | Felts |
| 2011/0253674 A1 | 10/2011 | Chung |
| 2011/0313363 A1 | 12/2011 | D'Souza |
| 2011/0319758 A1 | 12/2011 | Wang |
| 2011/0319813 A1 | 12/2011 | Kamen |
| 2012/0003497 A1 | 1/2012 | Handy |
| 2012/0004339 A1 | 1/2012 | Chappa |
| 2012/0021136 A1 | 1/2012 | Dzengeleski |
| 2012/0031070 A1 | 2/2012 | Slough |
| 2012/0035543 A1 | 2/2012 | Kamen |
| 2012/0052123 A9 | 3/2012 | Kurdyumov et al. |
| 2012/0053530 A1 | 3/2012 | Zhao |
| 2012/0058351 A1 | 3/2012 | Zhao |
| 2012/0065612 A1 | 3/2012 | Stout |
| 2012/0097527 A1 | 4/2012 | Kodaira |
| 2012/0097870 A1 | 4/2012 | Leray |
| 2012/0108058 A1 | 5/2012 | Ha |
| 2012/0109076 A1 | 5/2012 | Kawamura |
| 2012/0123345 A1 | 5/2012 | Felts |
| 2012/0149871 A1 | 5/2012 | Saxena |
| 2012/0141913 A1 | 6/2012 | Lee |
| 2012/0143148 A1 | 6/2012 | Zhao |
| 2012/0171386 A1 | 7/2012 | Bicker |
| 2012/0174239 A1 | 7/2012 | Anderson et al. |
| 2012/0175384 A1 | 7/2012 | Greter |
| 2012/0183954 A1 | 7/2012 | Diwu |
| 2012/0205374 A1 | 8/2012 | Klumpen |
| 2012/0231182 A1 | 9/2012 | Stevens |
| 2012/0234720 A1 | 9/2012 | Digregorio |
| 2012/0252709 A1* | 10/2012 | Felts ............... A61M 5/3129 508/100 |
| 2013/0041241 A1 | 2/2013 | Felts |
| 2013/0046375 A1 | 2/2013 | Chen |
| 2013/0057677 A1 | 3/2013 | Weil |
| 2013/0072025 A1 | 3/2013 | Singh |
| 2013/0081953 A1 | 4/2013 | Bruna et al. |
| 2013/0190695 A1 | 7/2013 | Wu |
| 2013/0209704 A1 | 8/2013 | Krueger |
| 2013/0264303 A1 | 10/2013 | Andersen |
| 2013/0296235 A1 | 11/2013 | Alarcon |
| 2014/0010969 A1 | 1/2014 | Bicker |
| 2014/0052076 A1 | 2/2014 | Zhao |
| 2014/0054803 A1 | 2/2014 | Chen |
| 2014/0099455 A1 | 4/2014 | Stanley |
| 2014/0110297 A1 | 4/2014 | Trotter |
| 2014/0147654 A1 | 5/2014 | Walther |
| 2014/0151320 A1 | 6/2014 | Chang |
| 2014/0151370 A1 | 6/2014 | Chang |
| 2014/0187666 A1 | 7/2014 | Aizenberg |
| 2014/0190846 A1 | 7/2014 | Belt |
| 2014/0221934 A1 | 8/2014 | Janvier |
| 2014/0251856 A1 | 9/2014 | Larsson |
| 2014/0251859 A1 | 9/2014 | Weikart |
| 2014/0305830 A1 | 10/2014 | Bicker |
| 2015/0165125 A1 | 6/2015 | Foucher |
| 2015/0224263 A1 | 8/2015 | Dugand |

FOREIGN PATENT DOCUMENTS

| | | |
|---|---|---|
| AU | 2002354470 B2 | 5/2007 |
| CA | 2085805 | 12/1992 |
| CA | 2277679 A1 | 7/1997 |
| CA | 2355681 | 7/2000 |
| CA | 2571380 A1 | 7/2006 |
| CA | 2718253 | 9/2009 |
| CA | 2268719 C | 8/2010 |
| CN | 2546041 Y | 4/2003 |
| CN | 1711310 A | 12/2005 |
| CN | 2766863 Y | 3/2006 |
| CN | 1898172 A | 1/2007 |
| CN | 201002786 Y | 1/2008 |
| CN | 101147813 A | 3/2008 |
| CN | 201056331 Y | 5/2008 |
| CN | 102581274 A | 7/2012 |
| DE | 1147836 | 4/1969 |
| DE | 1147838 | 4/1969 |
| DE | 3632748 A1 | 4/1988 |
| DE | 3908418 A1 | 9/1990 |
| DE | 4214401 C1 | 3/1993 |
| DE | 4204082 A1 | 8/1993 |
| DE | 4316349 A1 | 11/1994 |
| DE | 4438359 | 5/1996 |
| DE | 19707645 A1 | 8/1998 |
| DE | 19830794 A1 | 1/2000 |
| DE | 19912737 A1 | 6/2000 |
| DE | 10010831 A1 | 9/2001 |
| DE | 10154404 C1 | 6/2003 |
| DE | 10201110 A1 | 10/2003 |
| DE | 10242698 | 3/2004 |
| DE | 10246181 A1 | 4/2004 |
| DE | 10353540 A1 | 5/2004 |
| DE | 102004017236 A1 | 10/2005 |
| DE | 102006061585 A1 | 2/2008 |
| DE | 102008023027 A1 | 11/2009 |
| EP | 0121340 A2 | 10/1984 |
| EP | 0251812 A2 | 1/1988 |
| EP | 0275965 A2 | 7/1988 |
| EP | 0284867 A2 | 10/1988 |
| EP | 0306307 | 3/1989 |
| EP | 0329041 A2 | 8/1989 |
| EP | 0343017 A2 | 11/1989 |
| EP | 0396919 A2 | 11/1990 |
| EP | 0482613 A1 | 10/1991 |
| EP | 0484746 A2 | 10/1991 |
| EP | 0495447 A1 | 7/1992 |
| EP | 0520519 A1 | 12/1992 |
| EP | 0535810 A1 | 4/1993 |
| EP | 0375778 B1 | 9/1993 |
| EP | 0571116 A1 | 11/1993 |
| EP | 0580094 A1 | 1/1994 |
| EP | 0603717 A2 | 6/1994 |
| EP | 0619178 | 10/1994 |
| EP | 0645470 A1 | 3/1995 |
| EP | 0697378 A2 | 2/1996 |
| EP | 0709485 B1 | 5/1996 |
| EP | 0719877 A1 | 7/1996 |
| EP | 0728676 A1 | 8/1996 |
| EP | 0787824 A2 | 8/1997 |
| EP | 0787828 A2 | 8/1997 |
| EP | 0814114 A1 | 12/1997 |
| EP | 0833366 A2 | 4/1998 |
| EP | 0879611 A2 | 11/1998 |
| EP | 0940183 A2 | 9/1999 |
| EP | 0962229 A2 | 12/1999 |
| EP | 0992610 A2 | 4/2000 |
| EP | 1119034 A1 | 7/2001 |
| EP | 0954272 B1 | 3/2002 |
| EP | 1245694 A1 | 10/2002 |
| EP | 1388594 B1 | 1/2003 |
| EP | 1317937 A1 | 6/2003 |
| EP | 1365043 A1 | 11/2003 |
| EP | 1367145 | 12/2003 |
| EP | 1388593 A1 | 2/2004 |
| EP | 1439241 A2 | 7/2004 |
| EP | 1447459 A2 | 8/2004 |
| EP | 1990639 A1 | 2/2005 |
| EP | 1510595 A1 | 3/2005 |
| EP | 1522403 A2 | 4/2005 |
| EP | 1901067 A2 | 8/2005 |
| EP | 1507894 | 12/2005 |
| EP | 1507723 | 3/2006 |
| EP | 1653192 A1 | 5/2006 |

(56) References Cited

FOREIGN PATENT DOCUMENTS

| | | |
|---|---|---|
| EP | 1810758 A1 | 7/2007 |
| EP | 1356260 B1 | 12/2007 |
| EP | 1870117 A2 | 12/2007 |
| EP | 1881088 A1 | 1/2008 |
| EP | 1507887 | 7/2008 |
| EP | 1415018 | 10/2008 |
| EP | 2199264 A1 | 11/2009 |
| EP | 1388594 B1 | 1/2010 |
| EP | 2178109 A1 | 4/2010 |
| EP | 1507895 | 7/2010 |
| EP | 2218465 A1 | 8/2010 |
| EP | 2243751 A1 | 10/2010 |
| EP | 2251671 | 11/2010 |
| EP | 2261185 | 12/2010 |
| EP | 2369038 A2 | 9/2011 |
| EP | 1960279 B1 | 10/2011 |
| EP | 2602354 A1 | 6/2013 |
| EP | 2639330 A1 | 9/2013 |
| FR | 891892 A | 11/1942 |
| GB | 752822 | 7/1956 |
| GB | 1363762 | 8/1974 |
| GB | 1513426 A | 6/1978 |
| GB | 1566251 | 4/1980 |
| GB | 2210826 A | 6/1989 |
| GB | 2231197 A | 11/1990 |
| GB | 2246794 A | 2/1992 |
| GB | 2246795 A | 2/1992 |
| GB | 2387964 A | 10/2003 |
| JP | 56027330 A | 3/1981 |
| JP | 58154602 A | 9/1983 |
| JP | 59087307 A | 5/1984 |
| JP | 59154029 | 9/1984 |
| JP | S61183462 A | 8/1986 |
| JP | S62180069 A | 8/1987 |
| JP | S62290866 A | 12/1987 |
| JP | 63124521 A2 | 5/1988 |
| JP | 1023105 A | 1/1989 |
| JP | H01225775 A | 9/1989 |
| JP | 1279745 | 11/1989 |
| JP | 2501490 | 5/1990 |
| JP | 3183759 A2 | 8/1991 |
| JP | H03260065 A | 11/1991 |
| JP | H03271374 A | 12/1991 |
| JP | 4000373 A | 1/1992 |
| JP | 4000374 A | 1/1992 |
| JP | 4000375 A | 1/1992 |
| JP | 4014440 A | 1/1992 |
| JP | H04124273 A | 4/1992 |
| JP | H0578844 A | 3/1993 |
| JP | 05-006688 A | 4/1993 |
| JP | H05263223 A | 10/1993 |
| JP | 6010132 A | 1/1994 |
| JP | 6289401 | 10/1994 |
| JP | 7041579 A | 2/1995 |
| JP | 7068614 A | 3/1995 |
| JP | 7126419 A | 5/1995 |
| JP | 7-304127 | 11/1995 |
| JP | 8025244 A | 1/1996 |
| JP | 8084773 A | 4/1996 |
| JP | H08296038 A | 11/1996 |
| JP | 9005038 A | 1/1997 |
| JP | 10008254 A | 1/1998 |
| JP | 10-130844 | 5/1998 |
| JP | 11-108833 A | 4/1999 |
| JP | 11106920 | 4/1999 |
| JP | H11256331 A | 9/1999 |
| JP | 11344316 A | 12/1999 |
| JP | 2000064040 A | 2/2000 |
| JP | 2000109076 A | 4/2000 |
| JP | 2001033398 A | 2/2001 |
| JP | 2001231841 A | 8/2001 |
| JP | 2002177364 A | 6/2002 |
| JP | 2002206167 A | 7/2002 |
| JP | 2002371364 A | 12/2002 |
| JP | 2003171771 A | 6/2003 |
| JP | 2003-268550 A | 9/2003 |
| JP | 2003294431 A | 10/2003 |
| JP | 2003305121 A | 10/2003 |
| JP | 2004002928 A | 1/2004 |
| JP | 2004008509 A | 1/2004 |
| JP | 2004043789 A | 2/2004 |
| JP | 2004100036 A | 4/2004 |
| JP | 2004156444 A | 6/2004 |
| JP | 2004168359 A | 6/2004 |
| JP | 2004169087 A | 6/2004 |
| JP | 2004203682 A | 7/2004 |
| JP | 2004-253683 A | 9/2004 |
| JP | 2004307935 A | 11/2004 |
| JP | 2005035597 A | 2/2005 |
| JP | 2005043285 A | 2/2005 |
| JP | 2005132416 A | 5/2005 |
| JP | 2005160888 A | 6/2005 |
| JP | 2005-200044 | 7/2005 |
| JP | 2005200044 A | 7/2005 |
| JP | 2005-241524 A | 9/2005 |
| JP | 2005-290560 A | 10/2005 |
| JP | 2005271997 A | 10/2005 |
| JP | 2005290561 A | 10/2005 |
| JP | 2006-064416 A | 3/2006 |
| JP | 2006111967 A | 4/2006 |
| JP | 2006160268 A | 6/2006 |
| JP | 2006-224992 A | 8/2006 |
| JP | 2006249577 A | 9/2006 |
| JP | 2007050898 A | 3/2007 |
| JP | 2007231386 A | 9/2007 |
| JP | 2007246974 A | 9/2007 |
| JP | 2008-132766 A | 6/2008 |
| JP | 2008174793 A | 7/2008 |
| JP | 2009-062620 A | 3/2009 |
| JP | 2009062620 A | 3/2009 |
| JP | 2009079298 A | 4/2009 |
| JP | 2009084203 A | 4/2009 |
| JP | 2009185330 A | 8/2009 |
| JP | 2010155134 A | 7/2010 |
| JP | 2012210315 A | 11/2012 |
| JP | 5362941 B2 | 12/2013 |
| KR | 10-2005-0100367 A | 10/2005 |
| KR | 10-2006-0029694 | 4/2006 |
| KR | 10-0685594 B1 | 2/2007 |
| SU | 1530913 | 12/1989 |
| TW | 200703536 A | 1/2007 |
| WO | WO9324243 A1 | 12/1993 |
| WO | WO9400247 A1 | 1/1994 |
| WO | WO9426497 A1 | 11/1994 |
| WO | WO95/24275 | 9/1995 |
| WO | WO97/11482 | 3/1997 |
| WO | WO97/13802 | 4/1997 |
| WO | WO98-27926 | 7/1998 |
| WO | WO98/45871 | 10/1998 |
| WO | WO9917334 A1 | 4/1999 |
| WO | WO99/41425 | 8/1999 |
| WO | WO99/50471 | 10/1999 |
| WO | WO0038566 A2 | 7/2000 |
| WO | WO0104668 A1 | 1/2001 |
| WO | WO0125788 | 4/2001 |
| WO | WO0154816 A1 | 8/2001 |
| WO | WO0156706 A1 | 8/2001 |
| WO | WO0170403 A1 | 9/2001 |
| WO | WO02/43116 A2 | 5/2002 |
| WO | WO0249925 A1 | 6/2002 |
| WO | WO02/056333 A1 | 7/2002 |
| WO | WO02072914 | 9/2002 |
| WO | WO03033426 | 9/2002 |
| WO | WO02076709 A1 | 10/2002 |
| WO | WO03014415 A1 | 2/2003 |
| WO | WO03038143 | 5/2003 |
| WO | WO03040649 A1 | 5/2003 |
| WO | WO03044240 A1 | 5/2003 |
| WO | 03080259 | 10/2003 |
| WO | WO2005035147 A1 | 4/2005 |
| WO | WO2005/052555 A1 | 6/2005 |
| WO | WO2005051525 A1 | 6/2005 |
| WO | WO2005103605 A1 | 11/2005 |
| WO | WO2006012281 A1 | 2/2006 |

(56) References Cited

FOREIGN PATENT DOCUMENTS

| | | |
|---|---|---|
| WO | WO2006027568 A1 | 3/2006 |
| WO | WO2006029743 A1 | 3/2006 |
| WO | WO2006044254 A1 | 4/2006 |
| WO | WO2006/048650 | 5/2006 |
| WO | WO2006048276 | 5/2006 |
| WO | WO2006048277 A1 | 5/2006 |
| WO | WO2006069774 A1 | 7/2006 |
| WO | WO2006135755 A2 | 12/2006 |
| WO | WO2007028061 A2 | 3/2007 |
| WO | WO2007035741 A2 | 3/2007 |
| WO | WO2007036544 A1 | 4/2007 |
| WO | WO2007/081814 | 7/2007 |
| WO | WO2007/089216 A1 | 8/2007 |
| WO | WO2007112328 A2 | 10/2007 |
| WO | WO2007120507 A2 | 10/2007 |
| WO | WO2007133378 A1 | 11/2007 |
| WO | WO2007134347 A2 | 11/2007 |
| WO | WO2008014438 A2 | 1/2008 |
| WO | WO2008024566 A2 | 2/2008 |
| WO | WO2008040531 A1 | 4/2008 |
| WO | WO2008047541 A1 | 4/2008 |
| WO | WO2008067574 A1 | 6/2008 |
| WO | WO2008071458 A1 | 6/2008 |
| WO | WO2008093335 A2 | 8/2008 |
| WO | 2008/121478 A2 | 10/2008 |
| WO | WO2009/015862 A1 | 2/2009 |
| WO | WO2009020550 A2 | 2/2009 |
| WO | WO2009021257 A1 | 2/2009 |
| WO | WO2009030974 | 3/2009 |
| WO | WO2009030975 A1 | 3/2009 |
| WO | WO2009030976 A1 | 3/2009 |
| WO | WO2009031838 A1 | 3/2009 |
| WO | WO2009040109 | 4/2009 |
| WO | WO2009053947 A2 | 4/2009 |
| WO | WO2009112053 A1 | 9/2009 |
| WO | WO2009117032 | 9/2009 |
| WO | WO2009118361 A1 | 10/2009 |
| WO | WO2009158613 | 12/2009 |
| WO | WO2010047825 A1 | 4/2010 |
| WO | WO2010095011 A1 | 8/2010 |
| WO | WO2010/132579 | 11/2010 |
| WO | WO2010/132581 | 11/2010 |
| WO | WO2010/132584 | 11/2010 |
| WO | WO2010/132585 | 11/2010 |
| WO | WO2010/132589 | 11/2010 |
| WO | WO2010/132591 | 11/2010 |
| WO | WO2010034004 A1 | 11/2010 |
| WO | WO2010132579 | 11/2010 |
| WO | WO2010132579 A2 | 11/2010 |
| WO | WO2010132589 | 11/2010 |
| WO | WO2010132591 | 11/2010 |
| WO | WO2011029628 | 3/2011 |
| WO | WO2011007055 A1 | 6/2011 |
| WO | WO2011080543 A1 | 7/2011 |
| WO | WO2011082296 A1 | 7/2011 |
| WO | WO2011090717 A1 | 7/2011 |
| WO | WO2011/143329 | 11/2011 |
| WO | WO2011/143509 | 11/2011 |
| WO | WO2011/143509 A1 | 11/2011 |
| WO | WO2011137437 | 11/2011 |
| WO | WO2011143329 | 11/2011 |
| WO | WO2011159975 A1 | 12/2011 |
| WO | WO2012003221 | 1/2012 |
| WO | WO2012009653 | 1/2012 |
| WO | WO2013045671 A1 | 4/2013 |
| WO | WO2013/071138 | 5/2013 |
| WO | WO2013/071138 A1 | 5/2013 |
| WO | WO2013/170044 | 11/2013 |
| WO | WO2013/170052 | 11/2013 |
| WO | WO2014/008138 | 1/2014 |
| WO | WO2014/059012 | 4/2014 |
| WO | WO2014/071061 | 5/2014 |
| WO | WO2014/078666 | 5/2014 |
| WO | WO2014/085346 | 6/2014 |
| WO | WO2014/085348 | 6/2014 |
| WO | WO2014/134577 | 9/2014 |
| WO | WO2014/144926 | 9/2014 |
| WO | WO2014/164928 | 10/2014 |

OTHER PUBLICATIONS

PCT, Notification of Transmittal of the International Search Report and the Written Opinion of the International Searching Authority, or the Declaration, in International application No. PCT/US2014/029531, dated Jun. 20, 2014 (12 pages).

State Intellectual Property Office of the People's Republic of China, Notification of the Third Office Action, with translation, in Application No. 201080029199.0, dated Jun. 27, 2014 (19 pages).

Intellectual Property Office of Singapore, Invitation to Respond to Written Opinion, in Application No. 2012083077, dated Jun. 30, 2014 (12 pages).

PCT, Notification of Transmittal of International Preliminary Report on Patentability, in International application No. PCT/US13/40368, dated Jul. 16, 2014 (6 pages).

Australian Government, IP Australia, Patent Examination Report No. 1, in Application No. 2011252925, dated Sep. 6, 2013 (3 pages).

State Intellectual Property Office of the People's Republic of China, Notification of the Third Office Action, in Application No. 201080029201.4, dated Jul. 7, 2014 (15 pages).

Australian Government, IP Australia, Patent Examination Report No. 1, in Application No. 2010249031, dated Mar. 13, 2014. (4 pages).

Australian Government, IP Australia, Patent Examination Report No. 1, in Application No. 2013202893, dated Mar. 13, 2014. (4 pages).

European Patent Office, Communication pursuant to Article 93(3) EPC, in Application No. 11 731 554.9 dated Apr. 15, 2014. (7 pages).

PCT, Notification Concerning Transmittal of International Preliminary Report on Patentability, in International application No. PCT/US2012/064489, dated May 22, 2014. (10 pages).

PCT, Notification of Transmittal of the International Search Report and the Written Opinion of the International Searching Authority, or the Declaration, in International application No. PCT/US2013/071750, dated Apr. 4, 2014. (13 pages).

PCT, Notification of Transmittal of the International Search Report and the Written Opinion of the International Searching Authority, or the Declaration, in International application No. PCT/US2014/019684, dated May 23, 2014. (16 pages).

PCT, Notification of Transmittal of the International Search Report and the Written Opinion of the International Searching Authority, or the Declaration, in International application No. PCT/US2014/023813, dated May 22, 2014. (11 pages).

European Patent Office, Communication pursuant to Article 94(3) EPC, in Application No. 11 736 511.4, dated Mar. 28, 2014.

PCT, Notification Concerning Transmittal of International Preliminary Report on Patentability, in International application No. PCT/US2011/042387, dated Jan. 17, 2013. (7 pages).

State Intellectual Property Office of the People's Republic of China, Notification of the First Office Action, in Application No. 201180032145.4, dated Jan. 30, 2014. (16 pages).

PCT, Notification Concerning Transmittal of International Preliminary Report on Patentability, in International application No. PCT/US2011/044215, dated Jan. 31, 2013. (14 pages).

Da Silva Sobrinho A S et al., "Transparent barrier coatings on polyethylene terephthalate by single-and dual-frequency plasma-enhanced chemical vapor deposition", Journal of Vacuum Science and Technology; Part A, AVS/AIP, Melville, NY, US, vol. 16, No. 6, Nov. 1, 1998 (Nov. 1, 1998), pp. 3190-3198, XP01200471, ISSN: 0734-2101, DOI: 10.1116/1.581519 (9 pages).

Australian Government, IP Australia, Patent Examination Report No. 1, in Application No. 2012318242, dated Apr. 30, 2014. (6 pages).

State Intellectual Property Office of the People's Republic of China, Notification of the First Office Action, in Application No. 201180023461.5, dated May 21, 2014. (25 pages).

(56) References Cited

OTHER PUBLICATIONS

European Patent Office, Communication pursuant to Article 94(3) EPC, in Application No. 10162758.6 dated May 27, 2014. (7 pages).
Japanese Patent Office, Notice of Reasons for Refusal, Patent Application No. 2013-510276, dated Mar. 8, 2016 (15 pages).
European Patent Office, Communication pursuant to Article 94(3) EPC, in Application No. 13 726 337.2, dated Dec. 2, 2016 (6 pages).
Patent Cooperation Treaty, International Preliminary Examining Authority, Notification of Transmittal of International Preliminary Report on Patentability, in international application No. PCT/US2010/034571, dated Jun. 13, 2011.
Patent Cooperation Treaty, International Preliminary Examining Authority, Written Opinion of the International Preliminary Examining Authority, in international application No. PCT/US2010/034586, dated Aug. 23, 2011.
Patent Cooperation Treaty, International Preliminary Examining Authority, Written Opinion of the International Preliminary Examining Authority, in international application No. PCT/US2010/034568, dated May 30, 2011.
Coating Syringes, http://www.triboglide.com/syringes.htm, printed Aug. 31, 2009.
Coating/Production Process, http://www.triboglide.com/process.htm, printed Aug. 31, 2009.
Munich Exp, Materialica 2005: Fundierte Einblicke in den Werkstofsektor, Seite 1, von 4, ME095-6.
Schott Developing Syringe Production in United States, Apr. 14, 2009, http://www.schott.com/pharmaceutical_packaging, printed Aug. 31, 2009.
Sterile Prefillable Glass and Polymer Syringes, Schott forma vitrum, http://www.schott.com/pharmaceutical_packaging.
Transparent und recyclingfähig, neue verpackung, Dec. 2002, pp. 54-57.
European Patent Office, Communication with European Search Report, in Application No. 10162758.6, dated Aug. 19, 2010.
Griesser, Hans J., et al., Elimination of Stick-Slip of Elastomeric Sutures by Radiofrequency Glow Discharge Deposited Coatings, Biomed Mater. Res. Appl Biomater, 2000, vol. 53, 235-243, John Wiley & Sons, Inc.
European Patent Office, Communication with extended Search Report, in Application No. EP 10162761.0, dated Feb. 10, 2011.
European Patent Office, Communication with partial Search Report, in Application No. EP 10162758.6, dated Aug. 19, 2010.
European Patent Office, Communication with extended Search Report, in Application No. EP 10162758.6, dated Dec. 21, 2010.
Yang, et al., Microstructure and tribological properties of SiOx/DLC films grown by PECVD, Surface and Coatings Technology, vol. 194 (2005), Apr. 20, 2005, pp. 128-135.
European Patent Office, Communication with extended European search report, in Application No. EP10162756.0, dated Nov. 17, 2010.
Prasad, G.R. et al., "Biocompatible Coatings with Silicon and Titanium Oxides Deposited by PECVD", 3rd Mikkeli International Industrial Coating Seminar, Mikkeli, Finland, Mar. 16-18, 2006.
European Patent Office, Communication with extended European search report, in Application No. EP10162757.8, dated Nov. 10, 2010.
Patent Cooperation Treaty, Notification of Transmittal of the International Search Report and the Written Opinion of the International Searching Authority, in PCT/US2010/034568, dated Jan. 21, 2011.
Patent Cooperation Treaty, Notification of Transmittal of the International Search Report and the Written Opinion of the International Searching Authority, in PCT/US2010/034571, dated Jan. 26, 2011.
Patent Cooperation Treaty, Notification of Transmittal of the International Search Report and the Written Opinion of the International Searching Authority, in PCT/US2010/034576, dated Jan. 25, 2011.
Patent Cooperation Treaty, Notification of Transmittal of the International Search Report and the Written Opinion of the International Searching Authority, in PCT/US2010/034577, dated Jan. 21, 2011.
Patent Cooperation Treaty, Notification of Transmittal of the International Search Report and the Written Opinion of the International Searching Authority, in PCT/US2010/034582, dated Jan. 24, 2011.
European Patent Office, Communication with Extended Search Report, in Application No. EP 10162755.2, dated Nov. 9, 2010.
European Patent Office, Communication with Extended Search Report, in Application No. EP 10162760.2, dated Nov. 12, 2010.
PCT, Written Opinion of the International Searching Authority with International Search Report in Application No. PCT/US2010/034586, dated Mar. 15, 2011.
Shimojima, Atsushi et al., Structure and Properties of Multilayered Siloxane-Organic Hybrid Films Prepared Using Long-Chain Organotrialkoxysilanes Containing C=C Double Bonds, Journal of Materials Chemistry, 2007, vol. 17, pp. 658-663, ©The Royal Society of Chemistry, 2007.
Sone, Hayato et al., Picogram Mass Sensor Using Resonance Frequency Shift of Cantilever, Japanese Journal of Applied Physics, vol. 43, No. 6A, 2004, pp. 3648-3651, © The Japan Society of Applied Physics.
Sone, Hayato et al., Femtogram Mass Sensor Using Self-Sensing Cantilever for Allergy Check, Japanese Journal of Applied Physics, vol. 45, No. 3B, 2006, pp. 2301-2304, © The Japan Society of Applied Physics.
Mallikarjunan, Anupama et al, The Effect of Interfacial Chemistry on Metal Ion Penetration into Polymeric Films, Mat. Res. Soc. Symp. Proc. vol. 734, 2003, © Materials Research Society.
Schonher, H., et al., Friction and Surface Dynamics of Polymers on the Nanoscale by AFM, STM and AFM Studies on (Bio)molecular Systems: Unravelling the Nanoworld. Topics in Current Chemistry, 2008, vol. 285, pp. 103-156, ® Springer-Verlag Berlin Heidelberg.
Lang, H.P., Gerber, C., Microcantilever Sensors, STM and AFM Studies on (Bio)molecular Systems: Unravelling the Nanoworld. Topics in Current Chemistry, 2008, vol. 285, pp. 1-28, © Springer-Verlag Berlin Heidelberg.
Allison, H.L., The Real Markets for Transparent Barrier Films, 37th Annual Technical Conference Proceedings, 1994, ISBN 1-878068-13-X, pp. 458.
Bailey, R. et al., Thin-Film Multilayer Capacitors Using Pyrolytically Deposited Silicon Dioxide, IEEE Transactions on Parts, Hybrids, and Packaging, vol. PHP-12, No. 4, Dec. 1976, pp. 361-364.
Banks, B.A., et al., Fluoropolymer Filled SiO2 Coatings; Properties and Potential Applications, Society of Vacuum Coaters, 35th Annual Technical Conference Proceedings, 1992, ISBN 1-878068-11-3, pp. 89-93.
Baouchi, W., X-Ray Photoelectron Spectroscopy Study of Sodium Ion Migration through Thin Films of SiO2 Deposited on Sodalime Glass, 37th Annual Technical Conference Proceedings, 1994, ISBN 1-878068-13-X, pp. 419-422.
Boebel, F. et al., Simultaneous In Situ Measurement of Film Thickness and Temperature by Using Multiple Wavelengths Pyrometric Interferometry (MWPI), IEEE Transaction on Semiconductor Manufacturing, vol. 6, No. 2, May 1993, pp. 112-118.
Bush, V. et al., The Evolution of Evacuated Blood Collection Tubes, BD Diagnostics—Preanalytical Systems Newsletter, vol. 19, No. 1, 2009.
Chahroudi, D., Deposition Technology for Glass Barriers, 33rd Annual Technical Conference Proceedings, 1990, ISBN 1-878068-09-1, pp. 212-220.
Chahroudi, D., et al., Transparent Glass Barrier Coatings for Flexible Film Packaging, Society of Vacuum Coaters, 34th Annual Technical Conference Proceedings, 1991, ISBN 1-878068-10-5, pp. 130-133.
Chahroudi, D., Glassy Barriers from Electron Beam Web Coaters, 32nd Annual Technical Conference Proceedings, 1989, pp. 29-39.
Czeremuszkin, G. et al., Ultrathin Silicon-Compound Barrier Coatings for Polymeric Packaging Materials: An Industrial Perspective, Plasmas and Polymers, vol. 6, Nos. 1/2, Jun. 2001, pp. 107-120.
Ebihara, K. et al., Application of the Dielectric Barrier Discharge to Detect Defects in a Teflon Coated Metal Surface, 2003 J. Phys. D: Appl. Phys. 36 2883-2886, doi: 10.1088/0022-3727/36/23/003, IOP Electronic Journals, http://www.iop.org/EJ/abstract/0022-3727/36/23/003, printed Jul. 14, 2009.

(56) References Cited

OTHER PUBLICATIONS

Egitto, F.D., et al., Plasma Modification of Polymer Surfaces, Society of Vacuum Coaters, 36th Annual Technical Conference Proceedings, 1993, ISBN 1-878068-12-1, pp. 10-21.

Erlat, A.G. et al., SIOx Gas Barrier Coatings on Polymer Substrates: Morphology and Gas Transport Considerations, ACS Publications, Journal of Physical Chemistry, published Jul. 2, 1999, http://pubs.acs.org/doi/abs/10.1021/jp990737e, printed Jul. 14, 2009.

Fayet, P., et al., Commercialism of Plasma Deposited Barrier Coatings for Liquid Food Packaging, 37th Annual Technical Conference Proceedings, 1995, ISBN 1-878068-13-X, pp. 15-16.

Felts, J., Hollow Cathode Based Multi-Component Depositions, Vacuum Technology & Coating, Mar. 2004, pp. 48-55.

Felts, J.T., Thickness Effects on Thin Film Gas Barriers: Silicon-Based Coatings, Society of Vacuum Coaters, 34th Annual Technical Conference Proceedings, 1991, ISBN 1-878068-10-5, pp. 99-104.

Felts, J.T., Transparent Barrier Coatings Update: Flexible Substrates, Society of Vacuum Coaters, 36th Annual Technical Conference Proceedings, 1993, ISBN 1-878068-12-1, pp. 324-331.

Felts, J.T., Transparent Gas Barrier Technologies, 33rd Annual Technical Conference Proceedings, 1990, ISBN 1-878068-09-1, pp. 184-193.

Finson, E., et al., Transparent SiO2 Barrier Coatings: Conversion and Production Status, 37th Annual Technical Conference Proceedings, 1994, ISBN 1-878068-13-X, pp. 139-143.

Flaherty, T. et al., Application of Spectral Reflectivity to the Measurement of Thin-Film Thickness, Opto-Ireland 2002: Optics and Photonics Technologies and Applications, Proceedings of SPIE vol. 4876, 2003, pp. 976-983.

Hora, R., et al., Plasma Polymerization: A New Technology for Functional Coatings on Plastics, 36th Annual Technical Conference Proceedings, 1993, ISBN 1-878068-12-1, pp. 51-55.

Izu, M., et al., High Performance Clear CoatTM Barrier Film, 36th Annual Technical Conference Proceedings, 1993, ISBN 1-878068-12-1, pp. 333-340.

Jost, S., Plasma Polymerized Organosilicon Thin Films on Reflective Coatings, 33rd Annual Technical Conference Proceedings, 1990, ISBN 1-878068-09-1, pp. 344-346.

Kaganowicz, G., et al., Plasma-Deposited Coatings—Properties and Applications, 23rd Annual Technical Conference Proceedings, 1980, pp. 24-30.

Kamineni, V. et al., Thickness Measurement of Thin Metal Films by Optical Metrology, College of Nanoscale Science and Engineering, University of Albany, Albany, NY.

Klemberg-Sapieha, J.E., et al., Transparent Gas Barrier Coatings Produced by Dual Frequency PECVD, 36th Annual Technical Conference Proceedings, 1993, ISBN 1-878068-12-1, pp. 445-449.

Krug, T., et al., New Developments in Transparent Barrier Coatings, 36th Annual Technical Conference Proceedings, 1993, ISBN 1-878068-12-1, pp. 302-305.

Kuhr, M. et al., Multifunktionsbeschichtungen für innovative Applikationen von Kunststoff-Substraten, HiCotec Smart Coating Solutions.

Kulshreshtha, D.S., Specifications of a Spectroscopic Ellipsometer, Department of Physics & Astrophysics, University of Delhi, Delhi-110007, Jan. 16, 2009.

Krug, T.G., Transparent Barriers for Food Packaging, 33rd Annual Technical Conference Proceedings, 1990, ISBN 1-878068-09-1, pp. 163-169.

Lee, K. et al., The Ellipsometric Measurements of a Curved Surface, Japanese Journal of Applied Physics, vol. 44, No. 32, 2005, pp. L1015-L1018.

Lelait, L. et al., Microstructural Investigations of EBPVD Thermal Barrier Coatings, Journal De Physique IV, Colloque C9, supplément au Journal de Physique III, vol. 3, Dec. 1993, pp. 645-654.

Masso, J.D., Evaluation of Scratch Resistant and Antireflective Coatings for Plastic Lenses, 32nd Annual Technical Conference Proceedings, 1989, p. 237-240.

Misiano, C., et al., New Colourless Barrier Coatings (Oxygen & Water Vapor Transmission Rate) on Plastic Substrates, 35th Annual Technical Conference Proceedings, 1992, ISBN 1-878068-11-3, pp. 28-40.

Misiano, C., et al., Silicon Oxide Barrier Improvements on Plastic Substrate, Society of Vacuum Coaters, 34th Annual Technical Conference Proceedings, 1991, ISBN 1-878068-10-5, pp. 105-112.

Mount, E., Measuring Pinhole Resistance of Packaging, Corotec Corporation website, http://www.convertingmagazine.com, printed Jul. 13, 2009.

Murray, L. et al., The Impact of Foil Pinholes and Flex Cracks on the Moisture and Oxygen Barrier of Flexible Packaging.

Nelson, R.J., et al., Double-Sided QLF® Coatings for Gas Barriers, Society of Vacuum Coaters, 34th Annual Technical Conference Proceedings, 1991, ISBN 1-878068-10-5, pp. 113-117.

Nelson, R.J., Scale-Up of Plasma Deposited SiOx Gas Diffusion Barrier Coatings, 35th Annual Technical Conference Proceedings, 1992, ISBN 1-878068-11-3, pp. 75-78.

Novotny, V. J., Ultrafast Ellipsometric Mapping of Thin Films, IBM Technical Disclosure Bulletin, vol. 37, No. 02A, Feb. 1994, pp. 187-188.

Rüger, M., Die Pulse Sind das Plus, PICVD-Beschichtungsverfahren.

Schultz, A. et al., Detection and Identification of Pinholes in Plasma-Polymerised Thin Film Barrier Coatings on Metal Foils, Surface & Coatings Technology 200, 2005, pp. 213-217.

Stchakovsky, M. et al., Characterization of Barrier Layers by Spectroscopic Ellipsometry for Packaging Applications, Horiba Jobin Yvon, Application Note, Spectroscopic Ellipsometry, SE 14, Nov. 2005.

Teboul, E., Thi-Film Metrology: Spectroscopic Ellipsometer Becomes Industrial Thin-Film Tool, LaserFocusWorld, http://www.laserfocusworld.com/display_article, printed Jul. 14, 2009.

Teyssedre, G. et al., Temperature Dependence of the Photoluminescence in Poly(Ethylene Terephthalate) Films, Polymer 42, 2001, pp. 8207-8216.

Tsung, L. et al., Development of Fast CCD Cameras for In-Situ Electron Microscopy, Microsc Microanal 14(Supp 2), 2008.

Wood, L. et al., A Comparison of SiO2 Barrier Coated Polypropylene to Other Coated Flexible Substrates, 35th Annual Technical Conference Proceedings, 1992, ISBN 1-878068-11-3, pp. 59-62.

Yang, et al., Microstructure and tribological properties of SiOx/DLC films grown by PECVD, Surface and Coatings Technology, vol. 194, Issue 1, Apr. 20, 2005, pp. 128-135.

AN 451, Accurate Thin Film Measurements by High-Resoluiton Transmission Electron Microscopy (HRTEM), Evans Alalytical Group, Version 1.0, Jun. 12, 2008, pp. 1-2.

Benefits of TriboGlide, TriboGlide Silicone-Free Lubrication Systems, http://www.triboglide.com/benfits.htm, printed Aug. 31, 2009.

PCT, Written Opinion of the International Preliminary Examining Authority, in International application No. PCT/US2013/071750, dated Jan. 20, 2015 (9 pages).

PCT, Written Opinion of the International Preliminary Examining Authority, in International application No. PCT/US2013/064121, dated Nov. 21, 2014 (7 pages).

Japanese Patent Office, Decision of Rejection in Application No. 2012-510983, dated Jan. 20, 2015 (4 pages).

Australian Government, IP Australia, Patent Examination Report No. 1, in Application No. 2010249033, dated Dec. 19, 2014 (7 pages).

Australian Government, IP Australia, Patent Examination Report No. 1, in Application No. 2011252925, dated Dec. 2, 2014 (3 pages).

PCT, Written Opinion of the International Preliminary Examining Authority, in International application No. PCT/USUS13/048709, dated Sep. 30, 2014 (4 pages).

PCT, Notification of Transmittal of the International Preliminary Report on Patentability, in International application No. PCT/USUS13/048709, dated Oct. 15, 2014 (7 pages).

PCT, Written Opinion of the International Preliminary Examining Authority, in International application No. PCT/USUS13/064121, dated Nov. 19, 2014 (8 pages).

(56) References Cited

OTHER PUBLICATIONS

PCT, Written Opinion of the International Preliminary Examining Authority, in International application No. PCT/USUS13/064121, dated Nov. 21, 2014 (7 pages).
Intellectual Property Corporation of Malaysia, Substantive Examintion Adverse Report (section 30(1)/30(2)), in Application No. PI 2011005486, dated Oct. 31, 2014 (3 pages).
Patent Office of the Russian Federation, Official Action, in Application No. 2011150499, dated Sep. 25, 2014 (4 pages).
Instituto Mexicano de la Propiedad Indutrial, Official Action, in Appilcation No. MX/a/2012/013129, dated Sep. 22, 2014 (5 pages).
Sahagian, Khoren; Larner, Mikki; Kaplan, Stephen L., "Altering Biological Interfaces with Gas Plasma: Example Applications", Plasma Technology Systems, Belmont, CA, In SurFACTS in Biomaterials, Surfaces in Biomaterials Foundation, Summer 2013, 18(3), p. 1-5.
Daikyo Cyrystal Zenith Insert Needle Syringe System, West Delivering Innovative Services, West Pharmaceutical Services, Inc., 2010.
Daikyo Crystal Zenigh Syringes, West Pharmaceutical Services, Inc., www. WestPFSsolutions.com, #5659, 2011.
Zhang, Yongchao and Heller, Adam, Reduction of the Nonspecific Binding of a Target Antibody and of Its Enzyme-Labeled Detection Probe Enabling Electrochemical Immunoassay of Antibody through the 7 pg/mL-100 ng/mL (40 fM-400 pM) Range, Department of Chemical Engineering and Texas Materials Institute, University of Texas at Austin, Anal. Chem. 2005, 7, 7758-7762. (6 pages).
Principles and Applications of Liquid Scintillation Counting, LSC Concepts—Fundamentals of Liquid Scintillation Counting, National Diagnostics, 2004, pp. 1-15.
Chikkaveeraiah, Bhaskara V. and Rusling, Dr. James, Non Specific Binding (NSB) in Antigen-Antibody Assays, University of Connecticut, Spring 2007. (13 pages).
Sahagian, Khoren; Larner, Mikki; Kaplan, Stephen L., "Cold Gas Plasma in Surface Modification of Medical Plastics", Plasma Technology Systems, Belmont, CA, Publication pending. Presented at SPE Antec Medical Plastics Division, Apr. 23, 2013, Ohio.
Lipman, Melissa, "Jury Orders Becton to Pay $114M in Syringe Antitrust Case", © 2003-2013, Portfolio Media, Inc., Law360, New York (Sep. 20, 2013, 2:53 PM ET), http://www.law360.com/articles/474334/print?section=ip, [retrieved Sep. 23, 2013].
Wikipedia, the free encyclopedia, http://en.wikipedia.org/wiki/Birefringence, page last modified Sep. 18, 2013 at 11:39. [retrieved on Oct. 8, 2013]. (5 pages).
Wikipedia, the free encyclopedia, http://en.wikipedia.org/wiki/Confocal_microscopy, page last modified Aug. 28, 2013 at 11:12. [retrieved on Oct. 8, 2013]. (4 pages).
Wang, Jun et al., "Fluorocarbon thin film with superhydrophobic property prepared by pyrolysis of hexafluoropropylene oxide", Applied Surface Science, vol. 258, 2012, pp. 9782-9784 (4 pages).
Wang, Hong et al., "Ozone-Initiated Secondary Emission Rates of Aldehydes from Indoor surfaces in Four Homes", American Chemical Society, Environmental Science & Technology, vol. 40, No. 17, 2006, pp. 5263-5268 (6 pages).
Lewis, Hilton G. Pryce, et al., "HWCVD of Polymers: Commercialization and Scale-Up", Thin Solid Films 517, 2009, pp. 3551-3554.
Wolgemuth, Lonny, "Challenges With Prefilled Syringes: The Parylene Solution", Frederick Furness Publishing, www.ongrugdelivery.com, 2012, pp. 44-45.
History of Parylene (12 pages).
SCS Parylene HTX brochure, Stratamet Thin Film Corporation, Fremont, CA, 2012, retrieved from the Internet Feb. 13, 2013, http://www.stratametthinfilm.com/parylenes/htx. (2 pages).
SCS Parylene Properties, Specialty Coating Systems, Inc., Indianapolis, IN, 2011. (12 pages).
Werthheimer, M.R., Studies of the earliest stages of plasma-enhanced chemical vapor deposition of SiO2 on polymeric substrates, Thin Solid Films 382 (2001) 1-3, and references therein, United States Pharmacopeia 34. In General Chapters <1>, 2001.

Gibbins, Bruce and Warner, Lenna, The Role of Antimicrobial Silver Nanotechnology, Medical Device & Diagnostic Industry, Aug. 205, pp. 2-6.
MTI CVD Tube Furnace w Gas Delivery & Vacuum Pump, http://mtixtl.com/MiniCVDTubeFurnace2ChannelsGasVacuum-OTF-1200X-S50-2F.aspx (2 pages).
Lab-Built HFPO CVD Coater, HFPO Decomp to Give Thin Fluorocarbon Films, Applied Surface Science 2012 258 (24) 9782.
Technical Report No. 10, Journal of Parenteral Science and Technology, 42, Supplement 1988, Parenteral Formulation of Proteins and Peptides: Stability and Stabilizers, Parenteral Drug Association, 1988.
Technical Report No. 12, Journal of Parenteral Science and Technology, 42, Supplement 1988, Siliconization of Parenteral Drug Packaging Components, Parenteral Drug Association, 1988.
European Patent Office, Communication under Rule 71(3) EPC, in Application No. 10 162 760.2-1353, dated Oct. 25, 2013. (366 pages).
Wikipedia, the free encyclopedia, http://en.wikipedia.org/wiki/Difluorocarbene, page last modified Feb. 20, 2012 at 14:41. [retrieved on Sep. 7, 2012]. (4 pages).
O'Shaughnessy, W.S., et al., "Initiated Chemical Vapor Deposition of a Siloxane Coating for Insulation of Neutral Probes", Thin Solid Films 517 (2008) 3612-3614. (3 pages).
Denler, et al., Investigations of SiOx-polymer "interphases" by glancing angle RBS with Li+ and Be+ ions, Nuclear Instruments and Methods in Physical Research B 208 (2003) 176-180, United States Pharmacopeia 34. In General Chapters <1>, 2003.
PCT, Invitation to Pay Additional Fees and Annex to Form PCT/ISA/206 Communication relating to the results of the partial international search in International application No. PCT/US2013/071750, dated Feb. 14, 2014. (6 pages).
PCT, Notification of Transmittal of the International Search Report and the Written Opinion of the International Searching Authority, or the Declaration, in International application No. PCT/US2013/62247, dated Dec. 30, 2013. (13 pages).
PCT, Notification of Transmittal of the International Search Report and the Written Opinion of the International Searching Authority, or the Declaration, in International application No. PCT/US2013/043642, dated Dec. 5, 2013. (21 pages).
PCT, Notification of Transmittal of the International Search Report and the Written Opinion of the International Searching Authority, or the Declaration, in International application No. PCT/US2013/064121, dated Mar. 24, 2014. (8 pages).
PCT, Notification of Transmittal of the International Search Report and the Written Opinion of the International Searching Authority, or the Declaration, in International application No. PCT/US2013/070325, dated Mar. 24, 2014. (16 pages).
Japanese Patent Office, Notice of Reason(s) for Rejection in Patent application No. 2012-510983, dated Jan. 7, 2014. (6 pages).
Chinese Patent Office, Notification of the Second Office Action in Application No. 201080029199.0, dated Jan. 6, 2014. (26 pages).
Chinese Patent Office, Notification of the First Office Action in Application No. 201180023474.2, dated Dec. 23, 2013. (18 pages).
PCT, Notification of Transmittal of the International Search Report and the Written Opinion of the International Searching Authority, or the Declaration, in International application No. PCT/US2013/067852, dated Jan. 22, 2014. (9 pages).
Australian Government, Patent Examination Report No. 2 in Application No. 2010249031 dated Apr. 21, 2015.
Japanese Patent Office, Notice of Reasons for Refusal in application No. 2013-510276, dated Mar. 31, 2015.
State Intellectual Property Office of the People's Republic of China, Notification of the Fourth Office Action in Application No. 201080029199.0, dated Mar. 18, 2015 (15 pages).
Hlobik, Plastic Pre-Fillable Syringe Systems (http://www.healthcarepackaging.com/package-type/Containers/plastic-prefillablesyringe-systems, Jun. 8, 2010).
PCT, Written Opinion of the International Preliminary Examining Authority, International application No. PCT/SU2013/071752, dated May 6, 2015.

(56) References Cited

OTHER PUBLICATIONS

Hopwood J Ed—CRC Press: "Plasma-assisted deposition", Aug. 17, 1997 (Aug. 17, 1997), Handbook of Nanophase Materials, Chapter 6, pp. 141-197, XP008107730, ISBN: 978-0-8247-9469-9.
Bose, Sagarika and Constable, Kevin, Advanced Delivery Devices, Design & Evaluation of a Polymer-Based Prefillable Syringe for Biopharmaceuticals With Improved Functionality & Performance, JR Automation Technologies, May 2015.
PCT, Notification of Transmittal of the International Search Report and the Written Opinion of the International Searching Authority, or the Declaration, in International application No. PCT/US2013/040380, dated Sep. 3, 2013. (13 pages).
PCT, Notification of Transmittal of the International Search Report and the Written Opinion of the International Searching Authority, or the Declaration, in International application No. PCT/US2013/040368, dated Oct. 21, 2013. (21 pages).
PCT, Notification of Transmittal of the International Search Report and the Written Opinion of the International Searching Authority, or the Declaration, in International application No. PCT/US2013/048709, dated Oct. 2, 2013. (7 pages).
Coclite A.M. et al., "On the relationship between the structure and the barrier performance of plasma deposited silicon dioxide-like films", Surface and Coatings Technology, Elsevier, Amsterdam, NL, vol. 204, No. 24, Sep. 15, 2010 (Sep. 15, 2010), pp. 4012-4017, XPO27113381, ISSN: 0257-8972 [retrieved on Jun. 16, 2010] abstract, p. 4014, right-hand column-p. 4015, figures 2, 3.
Brunet-Bruneau A. et al., "Microstructural characterization of ion assisted Sio2 thin films by visible and infrared ellipsometry", Journal of Vacuum Science and Technology: Part A, AVS/AIP, Melville, NY, US, vol. 16, No. 4, Jul. 1, 1998 (Jul. 1, 1998), pp. 2281-2286, XPO12004127, ISSN: 0734-2101, DOI: 10.1116/1.581341, p. 2283, right-hand column-p. 2284, left-hand column, figures 2, 4.
Patent Cooperation Treaty, Written Opinion of the International Searching Authority with International Search Report in Application No. PCT/US2012/064489, dated Jan. 25, 2013.
Danish Patent and Trademark Office, Singapore Written Opinion, in Application No. 201108308-6, dated Dec. 6, 2012.
Danish Patent and Trademark Office, Singapore Search Report, in Application No. 201108308-6, dated Dec. 12, 2012.
Arganguren, Mirta I., Macosko, Christopher W., Thakkar, Bimal, and Tirrel, Matthew, "Interfacial Interactions in Silica Reinforced Silicones," Materials Research Society Symposium Proceedings, vol. 170, 1990, pp. 303-308.
Patent Cooperation Treaty, International Preliminary Examining Authority, Notification of Transmittal of International Preliminary Report on Patentability, in international application No. PCT/US2011/036097, dated Nov. 13, 2012.
Hanlon, Adriene Lepiane, Pak, Chung K., Pawlikowski, Beverly A., Decision on Appeal, Appeal No. 2005-1693, U.S. Appl. No. 10/192,333, dated Sep. 30, 2005.
European Patent Office, Communication pursuant to Article 94(3) EPC, in Application No. 10 162 758.6-1234, dated May 8, 2012 (6 pages).
Tao, Ran et al., Condensationand Polymerization of Supersaturated Monomer Vapor, ACS Publications, 2012 American Chemical Society, ex.doi.org/10.1021/la303462q/Langmuir 2012, 28, 16580-16587.
State Intellectual Property Office of Teh People's Republic of China, Notification of First Office Action in Application No. 201080029201.4, dated Mar. 37, 2013. (15 pages).

Silicone Oil Layer, Contract Testing, webpage, http://www.siliconization.com/downloads/siliconeoillayercontracttesting.pdf, retrieved from the internet Oct. 28, 2011.
Patent Cooperation Treaty, Notification of Transmittal of International Preliminary Report on Patentability, in PCT/US2010/034577, dated Nov. 24, 2011.
Patent Cooperation Treaty, Notification of Transmittal of International Preliminary Report on Patentability, in PCT/US2010/034582, dated Nov. 24, 2011.
Patent Cooperation Treaty, Notification of Transmittal of International Preliminary Report on Patentability, in PCT/US2010/034586, dated Dec. 20, 2011.
Patent Cooperation Treaty, Notification of Transmittal of the International Search Report and the Written Opinion of the International Searching Authority, in PCT/US2011/036097, dated Dec. 29, 2011.
"Oxford instruments plasmalab 80plus", XP55015205, retrieved from the Internet on Dec. 20, 2011, URL:http://www.oxfordplasma.de/pdf_inst/plas_80.pdf.
Patent Cooperation Treaty, Notification of Transmittal of the International Search Report and the Written Opinion of the International Searching Authority, in PCT/US2011/044215, dated Dec. 29, 2011.
Patent Cooperation Treaty, Notification of Transmittal of International Preliminary Report on Patentability, in Application No. PCT/US2010/034576, dated Sep. 14, 2011.
Patent Cooperation Treaty, Notification of Transmittal of International Preliminary Report on Patentability, in Application No. PCT/US2010/034568, dated Sep. 14, 2011.
Patent Cooperation Treaty, International Search Report and Written Opinion, in Application No. PCT/US2011/036358, dated Sep. 9, 2011.
Patent Cooperation Treaty, International Search Report and Written Opinion, in Application No. PCT/US2011/036340, dated Aug. 1, 2011.
MacDonald, Gareth, "West and Daikyo Seiko Launch Ready Pack", http://www.in-pharmatechnologist.com/Packaging/West-and-Daikyo-Seiko-launch-Ready-Pack, 2 pages, retrieved from the internet Sep. 22, 2011.
Kumer, Vijai, "Development of Terminal Sterilization Cycle for Pre-Filled Cyclic Olefin Polymer (COP) Syringes", http://abstracts.aapspharmaceutica.com/ExpoAAPS09/CC/forms/attendee/index.aspx?content=sessionInfo&sessionId=401, 1 page, retrieved from the internet Sep. 22, 2011.
Quinn, F.J., "Biotech Lights Up the Glass Packaging Picture", http://www.pharmaceuticalcommerce.com/frontEnd/main.php?idSeccion=840, 4 pages, retrieved from the Internet Sep. 21, 2011.
Wen, Zai-Qing et al., Distribution of Silicone Oil in Prefilled Glass Syringes Probed with Optical and Spectroscopic Methods, PDA Journal of Pharmaceutical Science and Technology 2009, 63, pp. 149-158.
ZebraSci—Intelligent Inspection Products, webpage, http://zebrasci.com/index.html, retrieved from the internet Sep. 30, 2011.
Google search re "cyclic olefin polymer resin" syringe OR vial, http://www.google.com/search?sclient=psy-ab&hl=en&lr=&source=hp&q=%22cyclic+olefin+polymer+resin%22+syringe+OR+vial&btnG=Search&pbx=1&oq=%22cyclic+olefin+polymer+resin%22+syringe+OR+vial&aq, 1 page, retrieved from the internet Sep. 22, 2011.
Taylor, Nick, "West to Add CZ Vials as Glass QC Issues Drive Interest", ttp://twitter.com/WestPharma/status/98804071674281986, 2 pages, retrieved from the internet Sep. 22, 2011.

* cited by examiner

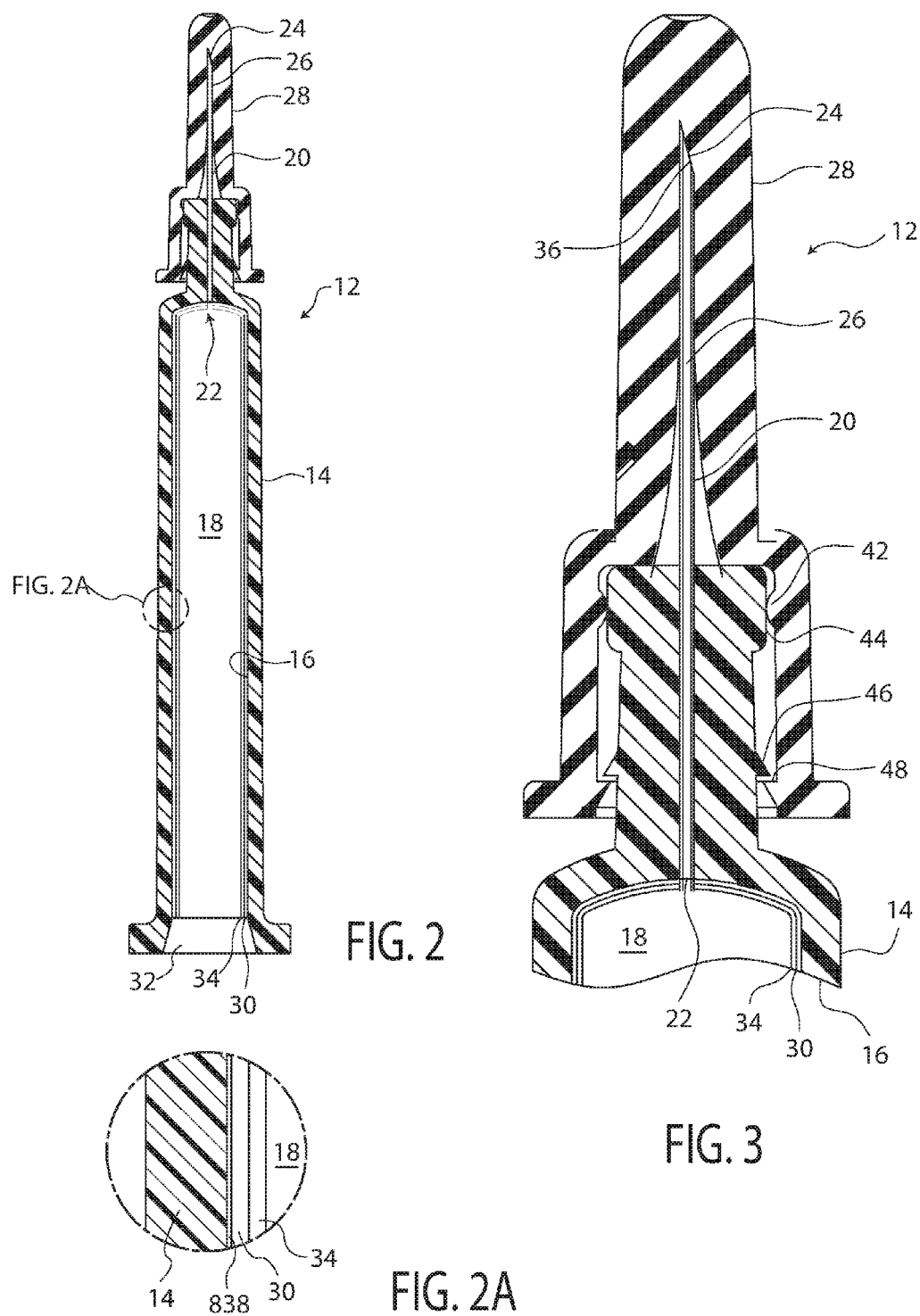

CONTROLLING THE UNIFORMITY OF PECVD DEPOSITION ON MEDICAL SYRINGES, CARTRIDGES, AND THE LIKE

The priority of the following U.S. Provisional Patent Applications is claimed: Ser. No. 61/872,481, filed Aug. 30, 2013; Ser. No. 61/800,660, filed Mar. 15, 2013; Ser. No. 61/747,584, filed Dec. 31, 2012; Ser. No. 61/732,180, filed Nov. 30, 2012. These priority applications are all incorporated here by reference in their entirety to provide continuity of disclosure.

Patent application Ser. No. 12/779,007, filed May 12, 2010, now U.S. Pat. No. 7,985,188; PCT/US11/36097, filed May 11, 2011; PCT/US12/64489, filed Nov. 9, 2012; 61/558,885, filed Nov. 11, 2011; 61/636,377, filed Apr. 20, 2012; 61/645,003, filed May 9, 2012; 61/713,435, filed Oct. 12, 2012; 61/716,381, filed Oct. 19, 2012 are all incorporated here by reference in their entirety.

FIELD OF THE INVENTION

The present invention relates to the technical field of coated surfaces, for example generally cylindrical interior surfaces of pharmaceutical packages or other vessels for storing or other contact with fluids. Examples of suitable fluids include foods or biologically active compounds, for example pharmaceutical compositions, body fluids, for example blood, or other types of compositions, for example diagnostic and analytical reagents or compositions. The present invention also relates to a pharmaceutical package or other fluid filled vessel having a coated generally cylindrical interior surface. The present invention also relates more generally to medical devices, including devices other than packages or vessels, for example catheters.

The present disclosure also relates to improved methods for processing pharmaceutical packages or other vessels, for example multiple identical pharmaceutical packages or other vessels used for pharmaceutical preparation storage and delivery, sample collection tubes (e.g. blood collection tubes for venipuncture) and other medical sample collection, and other purposes. Such pharmaceutical packages or other vessels are used in large numbers for these purposes, and must be relatively economical to manufacture and yet highly reliable in storage and use.

BACKGROUND OF THE INVENTION

One important consideration in manufacturing pharmaceutical packages or other vessels for storing or other contact with fluids, for example vials and pre-filled syringes, is that the contents of the pharmaceutical package or other vessel desirably will have a substantial shelf life. During this shelf life, it can be important to isolate the material filling the pharmaceutical package or other vessel from the external environment. Also, it can be important to isolate the material filling the pharmaceutical package or other vessel from the vessel wall containing it, to avoid leaching material from the pharmaceutical package or other vessel wall, barrier coating or layer, or other functional coatings or layers into the prefilled contents or vice versa.

Since many of these pharmaceutical packages or other vessels are inexpensive and used in large quantities, for certain applications it will be useful to reliably obtain the necessary shelf life without increasing the manufacturing cost to a prohibitive level.

For decades, most parenteral therapeutics have been delivered to end users in Type I medical grade borosilicate glass vessels such as vials or pre-filled syringes. The relatively strong, impermeable and inert surface of borosilicate glass has performed adequately for most drug products. However, the recent advent of costly, complex and sensitive biologics as well as such advanced delivery systems as auto injectors has exposed the physical and chemical shortcomings of glass pharmaceutical packages or other vessels, including possible contamination from metals, flaking, delamination, and breakage, among other problems. Moreover, glass contains several components which can leach out during storage and cause damage to the stored material.

In more detail, borosilicate pharmaceutical packages or other vessels exhibit a number of drawbacks.

Glass is manufactured from sand containing a heterogeneous mixture of many elements (silicon, oxygen, boron, aluminum, sodium, calcium) with trace levels of other alkali and earth metals. Type I borosilicate glass consists of approximately 76% $SiO_2$, 10.5% $B_2O_3$, 5% $A_{l2}O_3$, 7% $Na_2O$ and 1.5% CaO and often contains trace metals such as iron, magnesium, zinc, copper and others. The heterogeneous nature of borosilicate glass creates a non-uniform surface chemistry at the molecular level. Glass forming processes used to create glass vessels expose some portions of the vessels to temperatures as great as 1200° C. Under such high temperatures alkali ions migrate to the local surface and form oxides. The presence of ions extracted from borosilicate glass devices may be involved in degradation, aggregation and denaturation of some biologics. Many proteins and other biologics must be lyophilized (freeze dried), because they are not sufficiently stable in solution in glass vials or syringes.

In glass syringes, silicone oil is typically used as a lubricant to allow the plunger tip, piston, stopper, or seal to slide in the barrel. Silicone oil has been implicated in the precipitation of protein solutions such as insulin and some other biologics. Additionally, the silicone oil coating or layer is often non-uniform, resulting in syringe failures in the market.

Glass pharmaceutical packages or other vessels are prone to breakage or degradation during manufacture, filling operations, shipping and use, which means that glass particulates may enter the drug. The presence of glass particles has led to many FDA Warning Letters and to product recalls. Glass-forming processes do not yield the tight dimensional tolerances required for some of the newer auto-injectors and delivery systems.

As a result, some companies have turned to plastic pharmaceutical packages or other vessels, which provide tighter dimensional tolerances and less breakage than glass.

Although plastic is superior to glass with respect to breakage, dimensional tolerances and surface uniformity, its use for primary pharmaceutical packaging remains limited due to the following shortcomings:

Gas (oxygen) permeability: Plastic allows small molecule gases to permeate into (or out of) the device. The permeability of plastics to gases can be significantly greater than that of glass and, in many cases (as with oxygen-sensitive drugs such as epinephrine), plastics previously have been unacceptable for that reason.

Water vapor transmission: Plastics allow water vapor to pass through devices to a greater degree than glass. This can be detrimental to the shelf life of a solid (lyophilized) drug. Alternatively, a liquid product may lose water in an arid environment.

Leachables and extractables: Plastic pharmaceutical packages or other vessels contain organic compounds that can leach out or be extracted into the drug product. These compounds can contaminate the drug and/or negatively impact the drug's stability.

Clearly, while plastic and glass pharmaceutical packages or other vessels each offer certain advantages in pharmaceutical primary packaging, neither is optimal for all drugs, biologics or other therapeutics. Thus, there is a desire for plastic pharmaceutical packages or other vessels, in particular plastic syringes, with gas and solute barrier properties which approach the properties of glass. Moreover, there is a need for plastic syringes with sufficient lubricity and/or passivation or protective properties and a lubricity and/or passivation layer or pH protective coating or layer which is compatible with the syringe contents. There also can be a need for glass vessels with surfaces that do not tend to delaminate or dissolve or leach constituents when in contact with the vessel contents.

There are additional considerations to be taken into account when manufacturing a prefilled syringe. Prefilled syringes are commonly prepared and sold so the syringe does not need to be filled before use, and can be disposed of after use. The syringe can be prefilled with saline solution, a dye for injection, or a pharmaceutically active preparation, for some examples.

Commonly, the prefilled syringe can be capped at the distal end, as with a cap (or, if the hypodermic needle is preinstalled, a needle shield that can also be a cap), and can be closed at the proximal end by its drawn plunger tip, piston, stopper, or seal. The prefilled syringe can be wrapped in a sterile package before use. To use the prefilled syringe, any packaging and cap are removed, optionally a hypodermic needle or another delivery conduit can be attached to the distal end of the barrel, the delivery conduit or syringe can be moved to a use position (such as by inserting the hypodermic needle into a patient's blood vessel or into apparatus to be rinsed with the contents of the syringe), and the plunger tip, piston, stopper, or seal can be advanced in the barrel to inject the contents of the barrel.

A syringe or auto-injector cartridge generally contains a plunger tip, piston, stopper, or seal, or other movable part in sliding contact with the coated surface to dispense the contents. The movable part is prevented from moving easily and smoothly by frictional resistance. A common need for syringes, auto-injector cartridges, and similar devices is lubrication or a lubricity coating or layer to reduce frictional resistance and adhesion between the barrel and the movable part, allowing it to slide in the barrel more easily when dispensing a pharmaceutical composition or other material from the device. The frictional resistance has two main aspects—breakout force and plunger sliding force.

The breakout force is the force required to start a stationary plunger moving within a barrel, or the comparable force required to unseat a seated, stationary closure and begin its movement. (A "barrel" refers either to a medical syringe barrel or to a medical cartridge barrel, both more generally known as a medical barrel.) The breakout force tends to increase with storage of a syringe, after the prefilled syringe plunger has pushed away the intervening lubricant or adhered to the medical barrel due to decomposition of the lubricant between the plunger and the medical barrel. The breakout force is the force needed to overcome "sticktion," an industry term for the adhesion between the plunger and medical barrel that needs to be overcome to break out the plunger and allow it to begin moving.

The plunger sliding force is the force required to continue moving the plunger or closure within the medical barrel or other package after it has "broken out" and begun moving.

In syringes, auto-injector cartridges, or similar devices, whether prefilled or sold separately, silicone oil or polydimethylsiloxane (PDMS) is typically used as a lubricant to reduce the breakout and sliding forces. One of the concerns with the use of PDMS in parenteral drug storage/delivery devices is the introduction of foreign material from the device to the drug solution. PDMS-based lubricant systems are known to present with a measurable extractable profile in pre-filled syringes, which provides the potential for adverse interaction with the drug formulation and results in the bolus injection of silicone oil. FIGS. 52-54 are diagrammatic views showing the drawbacks of silicon oil (or any other oil) as a lubricant. Non-uniformity of silicone oil occurs because it is not covalently bound to the surface and flows. FIG. 52 shows that silicone oil is pushed off the medical barrel wall by the plunger following insertion of the plunger. FIG. 53 shows that silicone oil is forced out of the area between the plunger and syringe wall leading to high break loose forces. FIG. 54 shows that silicone oil flows over time due to gravitational forces.

U.S. Pat. No. 7,985,188 refers to a medical barrel or other device "coated with a lubricity coating or layer configured to provide a lower piston sliding force or breakout force than the uncoated substrate. The lubricity coating or layer has one of the following atomic ratios, measured by X-ray photo-electron spectroscopy (XPS), $SiO_xC_y$ or $SiN_xC_y$, where w is 1, x in this formula is from about 0.5 to 2.4, and y is from about 0.6 to about 3." "The lubricity layer is deposited by plasma enhanced chemical vapor deposition (PECVD) under conditions effective to form a coating." "The lubricity layer is configured to provide a lower piston sliding force or breakout force than the uncoated substrate." This PECVD lubricity coating or layer addresses some of the issues with PDMS, as it lubricates the device with a coating or layer that is more securely anchored to the wall of the medical barrel or other lubricated part. The lubricity coating or layer also can be far thinner and more uniform than PDMS, reducing the amount of lubricant used.

SUMMARY OF THE INVENTION

An aspect of the invention is a method of making a medical barrel for a medical cartridge or syringe. A medical barrel is provided comprising a wall having a generally cylindrical inner surface defining at least a portion of a lumen. The generally cylindrical inner surface has a diameter in the range from 4 to 15 mm. An inner electrode is provided having an outer surface including a portion located within the lumen and coaxial with and radially spaced from 1.2 to 6.9 mm. from the generally cylindrical inner surface. The inner electrode has an internal passage having at least one outlet. An outer electrode is also provided.

A gaseous PECVD precursor is introduced into the lumen via at least one outlet of the internal passage.

Electromagnetic energy is applied to the outer electrode under conditions effective to form a plasma enhanced chemical vapor deposition (PECVD) gas barrier coating on at least a portion of the generally cylindrical inner surface. The barrier coating or layer has a mean thickness.

A magnetic field is applied adjacent to the medical barrel while applying the electromagnetic energy, optionally for the entire applying step. The magnetic field is applied under conditions effective to reduce the standard deviation of the mean thickness of the gas barrier coating on the generally cylindrical inner surface.

A further aspect of the invention is an apparatus for applying a magnetic field within the generally cylindrical wall of the medical barrel described above. The apparatus includes a medical barrel holder, a feeder, and one or more magnetic field generators.

The medical barrel holder comprises a seat sized and positioned for seating the medical barrel to establish the location of the axis of the generally cylindrical inner surface.

The feeder is associated with the holder and configured to feed a PECVD precursor to the lumen of a medical barrel when seated on the seat.

The one or more magnetic field generators associated with the holder apply a magnetic field within the lumen of a medical barrel when seated on the seat.

Even another aspect of the invention is an apparatus for coating a medical barrel for a medical cartridge or syringe. The apparatus comprises a barrel holder, an inner electrode, an outer electrode, a feeder, and one or more magnetic field generators.

The barrel holder comprises a seat sized and positioned for seating a medical barrel of the type comprising a wall having a generally cylindrical inner surface defining at least a portion of a lumen, optionally the entire lumen, having a diameter in the range from 4 to 15 mm.

The inner electrode has an outer surface including a portion positioned to be located within a lumen of a medical barrel when seated on the seat. The inner electrode is coaxial with and radially spaced from 1.2 to 6.9 mm. from the generally cylindrical inner surface when a medical barrel of suitable proportions is seated on the seat. The inner electrode has an internal passage having at least one outlet. An outer electrode is also provided.

The feeder associated with the holder, and is configured to feed a PECVD precursor to the lumen of a medical barrel when seated on the seat.

The one or more magnetic field generators are associated with the holder for applying a magnetic field within the lumen of a medical barrel when seated on the seat.

Other aspects of the invention are identified or apparent from the present specification and claims.

BRIEF DESCRIPTION OF THE DRAWING FIGURES

FIG. 2 is a longitudinal section of the capped assembly of FIG. 1, showing in an enlargement a trilayer PECVD set.

FIG. 3 is an enlarged fragmentary view of the capped assembly of FIG. 1.

Figure 38:
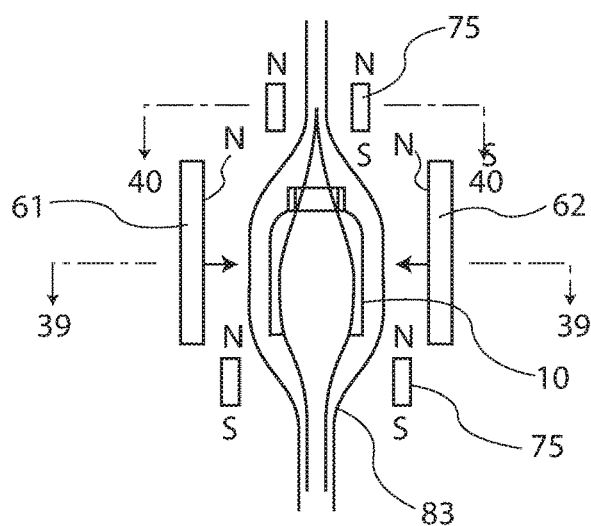
FIG. 38 is a schematic longitudinal section of plasma treatment apparatus including an electronic bottle. The plasma generation, material feed, and exhaust systems are omitted to better show the construction of the electronic bottle.
Figure 40:
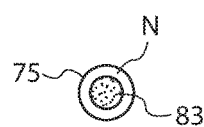

FIG. 40 is a partial section of FIG. 38 taken along section lines 40-40, showing cross sections of the ring magnet 75 and closely spaced magnetic lines 83.

Figure 41:
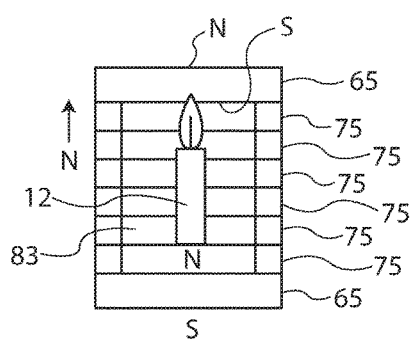

FIG. 41 is a schematic section of an alternative electron bottle made of a stack of ring magnets 75 to provide radial confinement of electrons, capped on each end by a bar magnet 65 to provide axial confinement of electrons. The plasma generation, material feed, and exhaust systems are omitted to better show the construction of the electronic bottle.

Figure 42:
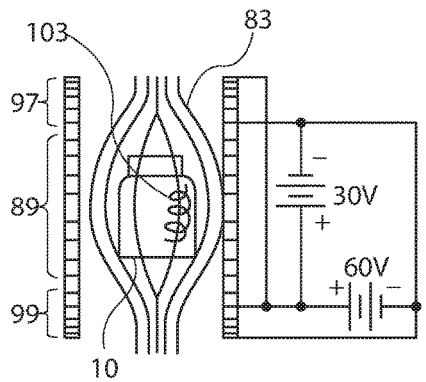

FIG. 42 is a schematic section of an alternative electron bottle made of a solenoid coil to provide radial and axial confinement of electrons. The plasma generation, material feed, and exhaust systems are omitted to better show the construction of the electronic bottle.

Figure 43:
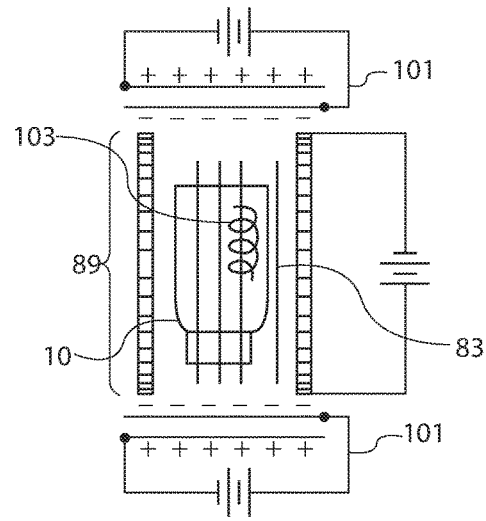

FIG. 43 is a schematic section of yet another alternative electron bottle made of a solenoid to provide radial confinement of electrons and electrostatic electron mirrors to provide axial confinement of electrons. The plasma generation, material feed, and exhaust systems are omitted to better show the construction of the electronic bottle.

Figure 44:
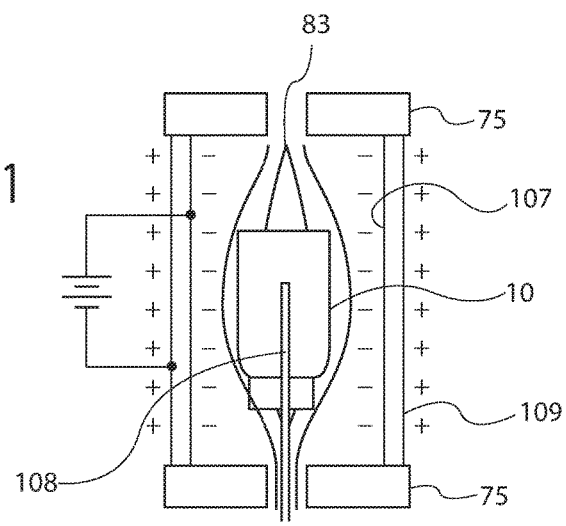

FIG. 44 is a schematic section of even another alternative electron bottle made of a cylindrical electrostatic mirror providing radial confinement of electrons and magnetic electron mirrors to provide axial confinement of electrons. The plasma generation, material feed, and exhaust systems are omitted to better show the construction of the electronic bottle.

Figure 45:
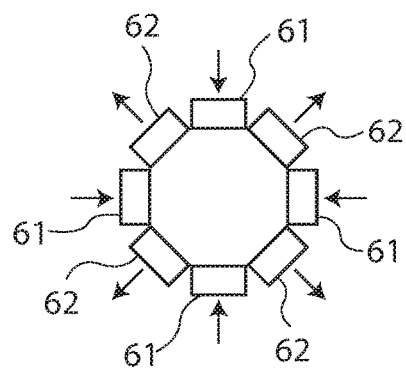

FIG. 45 is a detail of an eight-magnet quadrupole analog made up of alternating bar magnets 61 and 62 having radially extending polar axes. The magnets 61 have the north pole oriented inward and the alternating magnets 62 have the north pole oriented outward.

Figure 46:
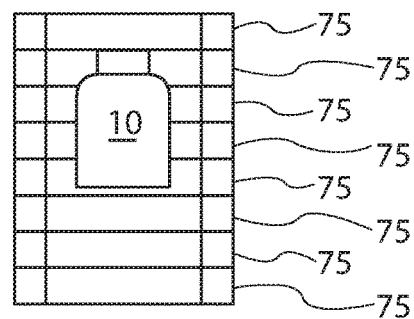

FIG. 46 is a detail of a stack of eight ring magnets with their pole axes directed axially, as their annular faces define their poles. In one embodiment all eight have the same field strength, providing only radial confinement. In another embodiment the ring magnets on each end of the stack have a higher field strength, providing axial confinement too.

Figure 47:
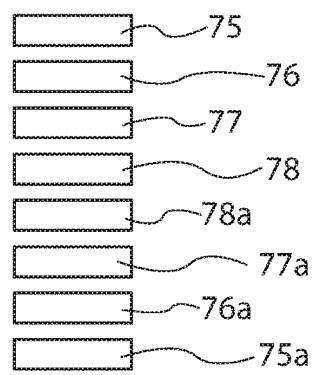

FIG. 47 is a schematic side view of a magnet array contemplated for use in certain aspects of the present invention.

Figure 48:
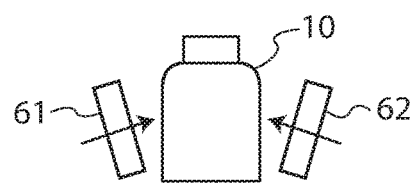

FIG. 48 is a schematic side view of a vial in PECVD apparatus including a tilted quadrupole magnet array.

Figure 49:
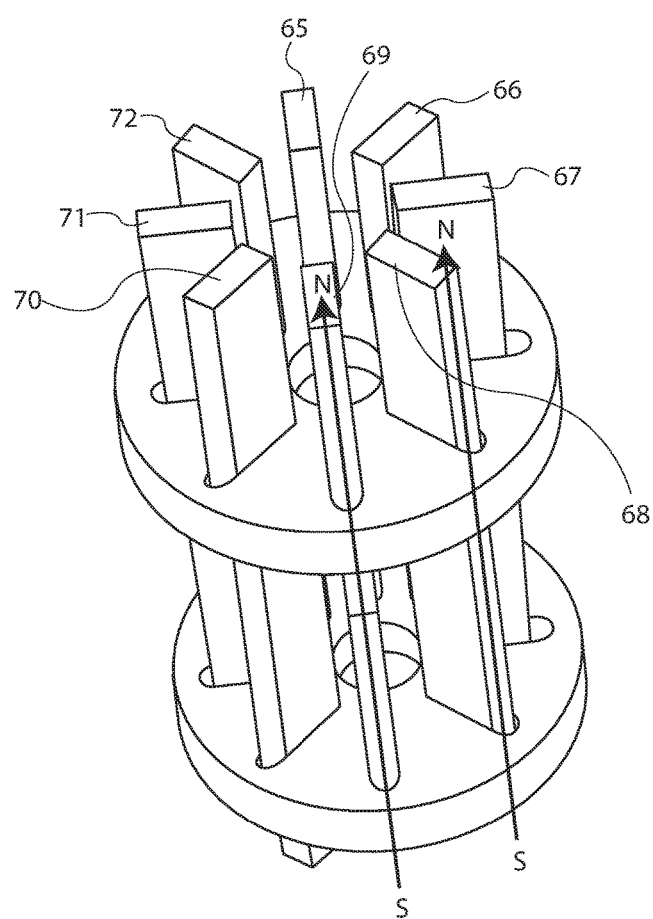

FIG. 49 is a perspective view of an axial magnet array contemplated for use in certain aspects of the present invention.

Figure 1:
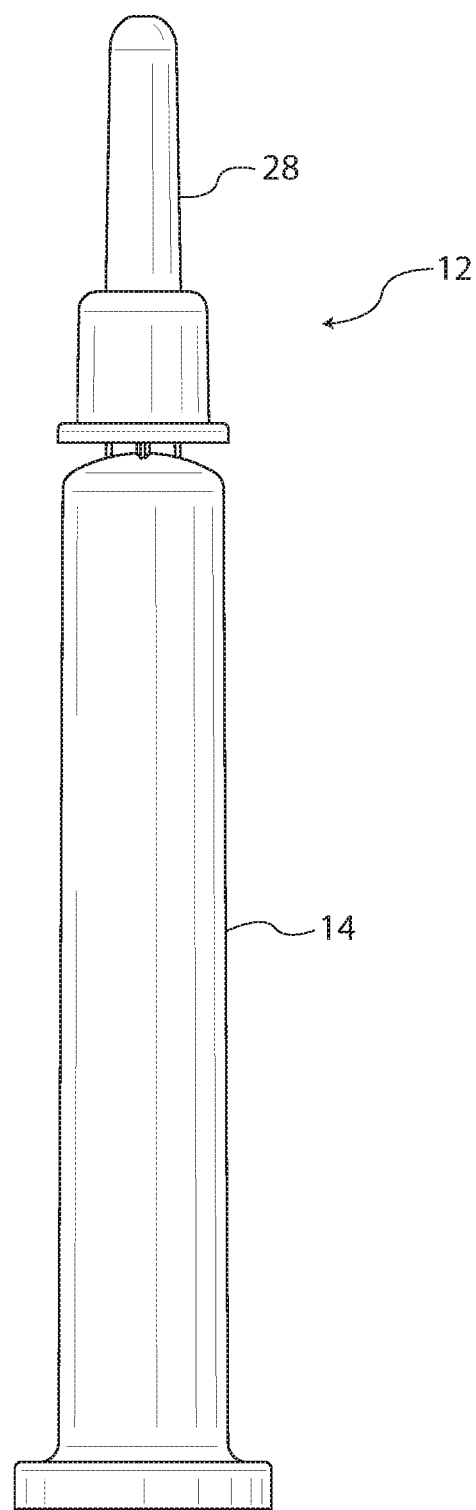
FIG. 1 is an elevation view of a capped assembly of a medical barrel, hypodermic needle, and cap, also known as a capped assembly, according to an embodiment of the disclosure.
Figure 50:
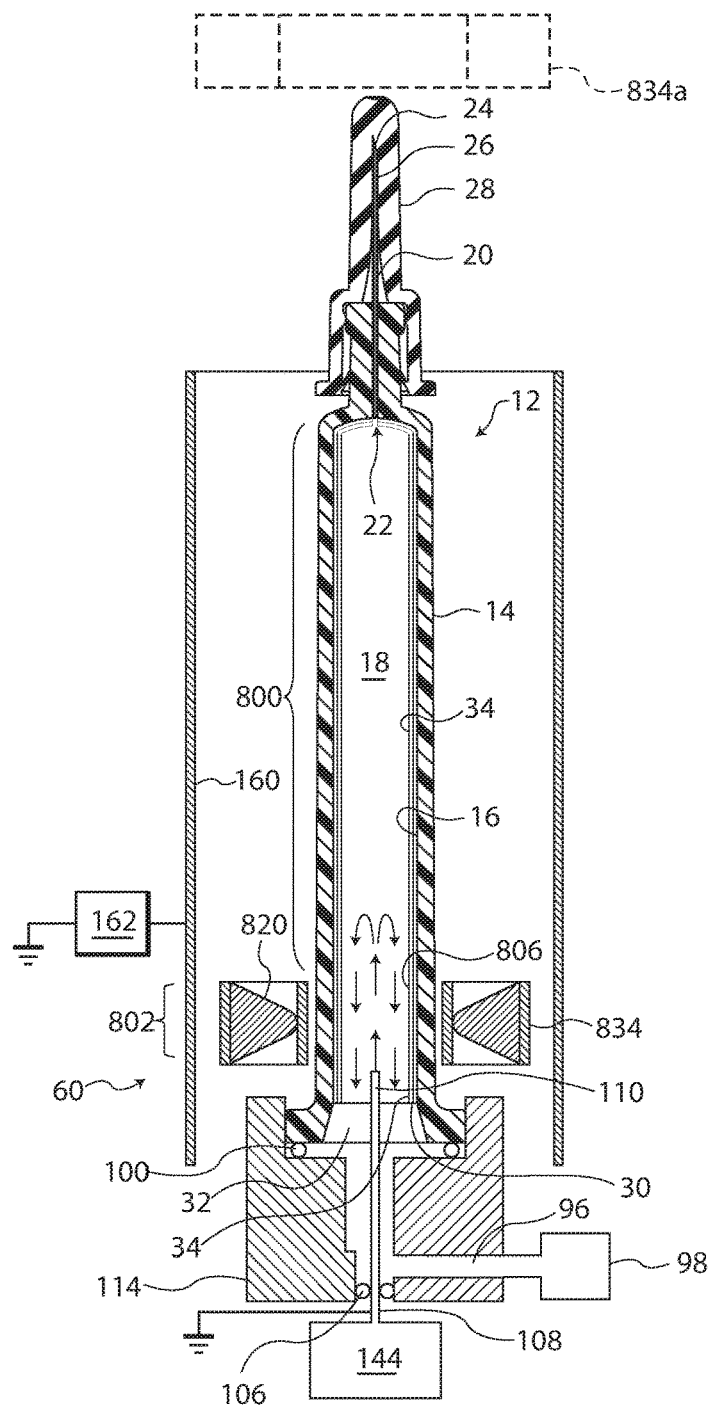

FIG. 50 is a longitudinal section of an alternative coating station for localized coating or layer of the capped assembly of FIG. 1.

Figure 5:
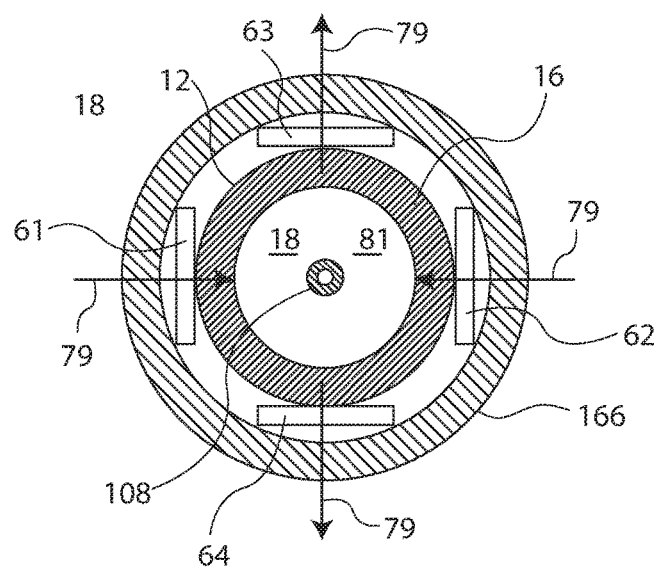
FIG. 5 is a section taken along section lines A-A of FIG. 4, showing a quadrupole magnet array.
Figure 6:
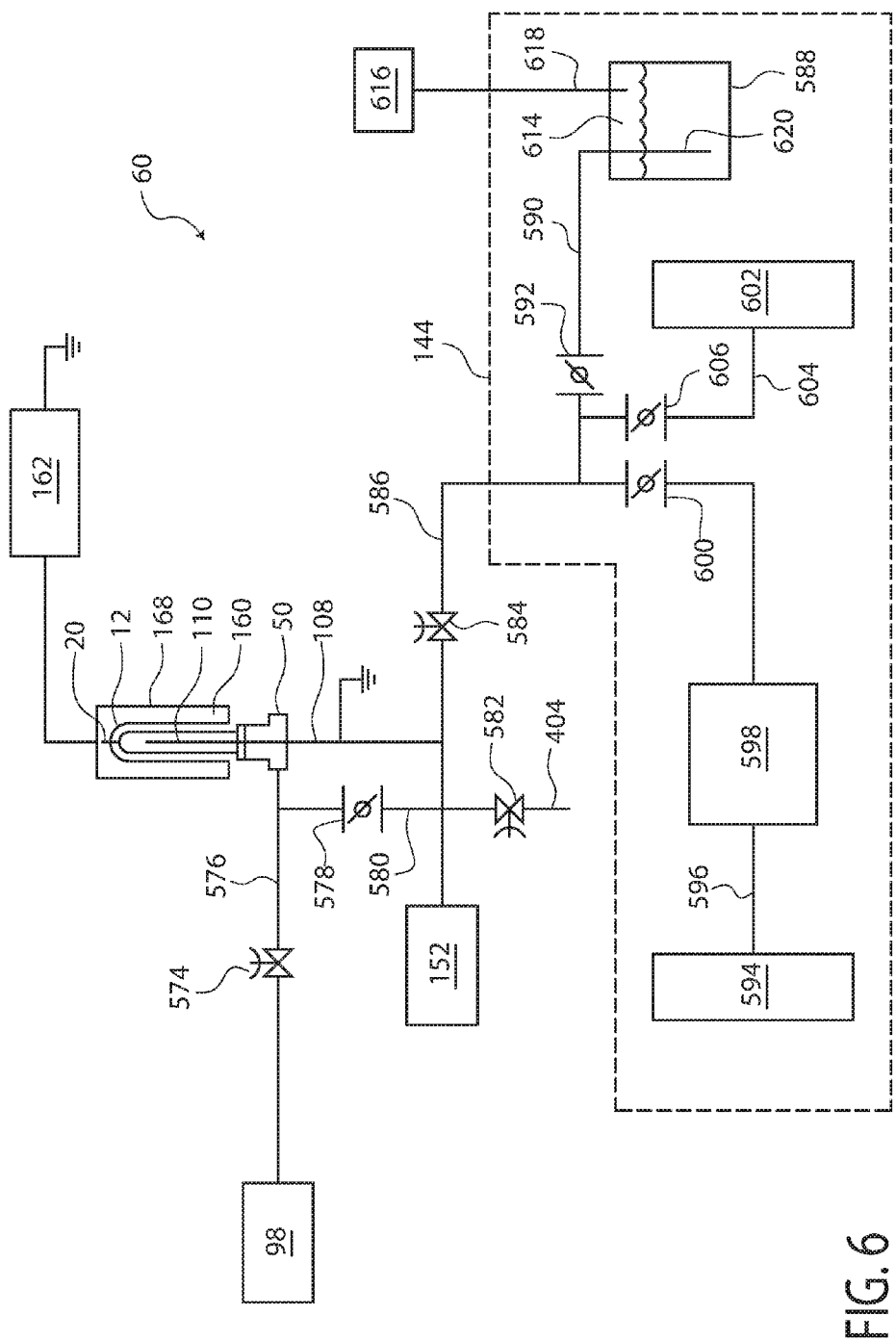
FIG. 6 is a schematic view showing more details of the chemical vapor deposition coating station shown in FIGS. 4 and 5.
Figure 7:
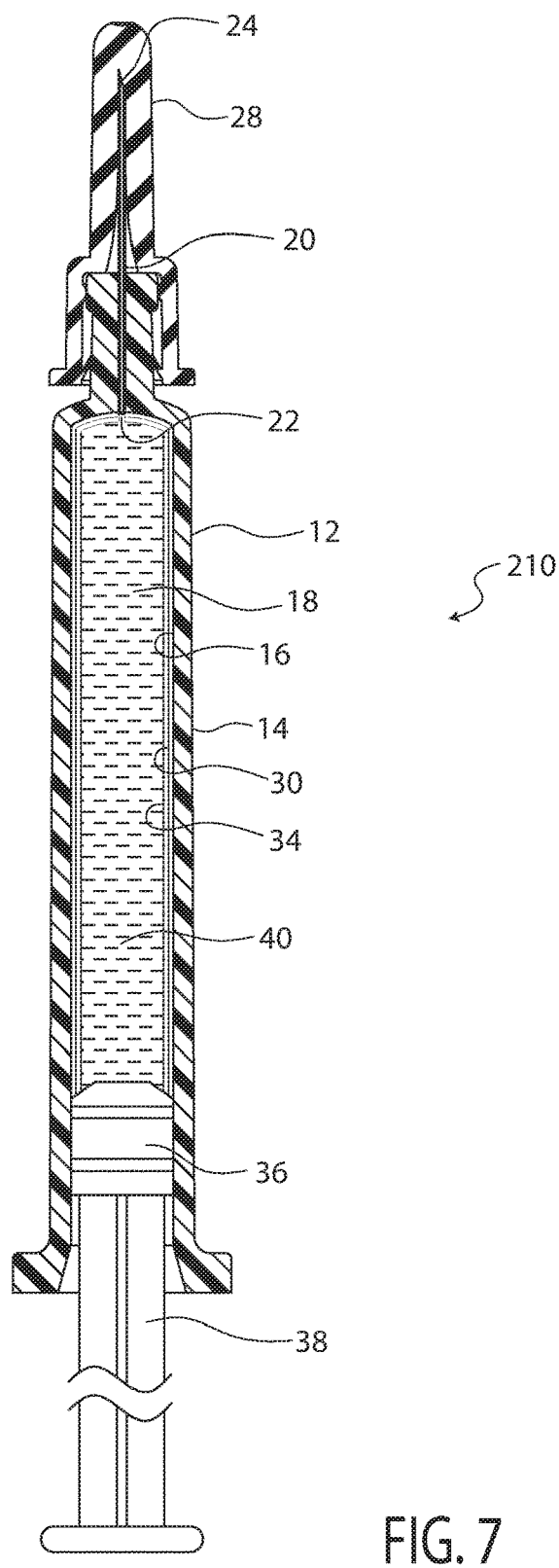
FIG. 7 is a view similar to FIG. 2 of the capped assembly of FIGS. 1-6, filled with a pharmaceutical preparation and fitted with a plunger tip, piston, stopper, or seal to define a pre-filled syringe. In the option shown, a plunger tip, piston, stopper, or seal and plunger push rod are installed.
Figure 51:
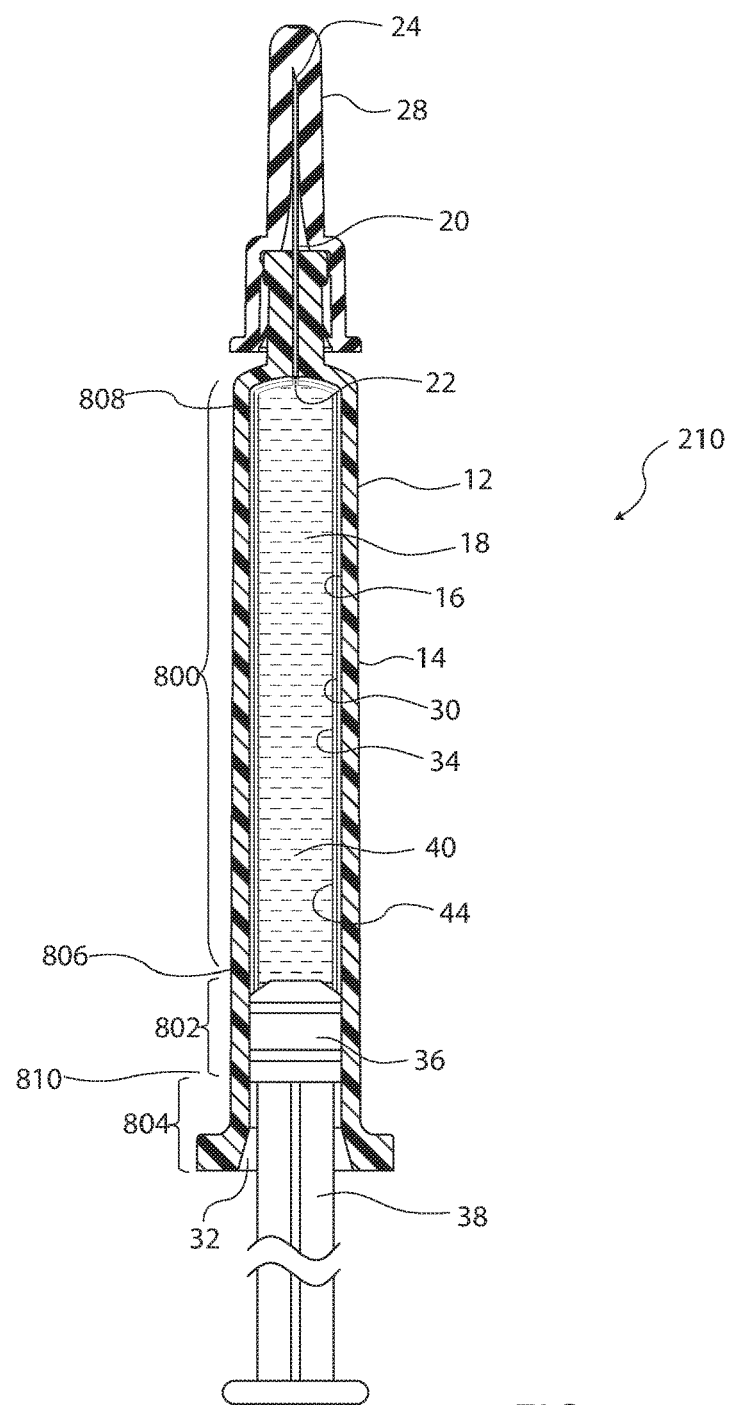

FIG. 51 is a view similar to FIG. 7 of the capped assembly of FIGS. 1-6, illustrating an optional localized lubricity coating.

Figure 52:
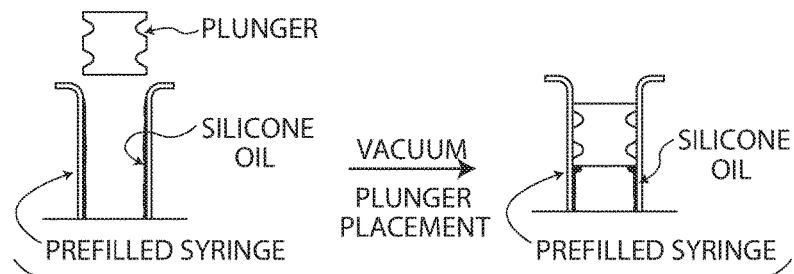
Figure 53:
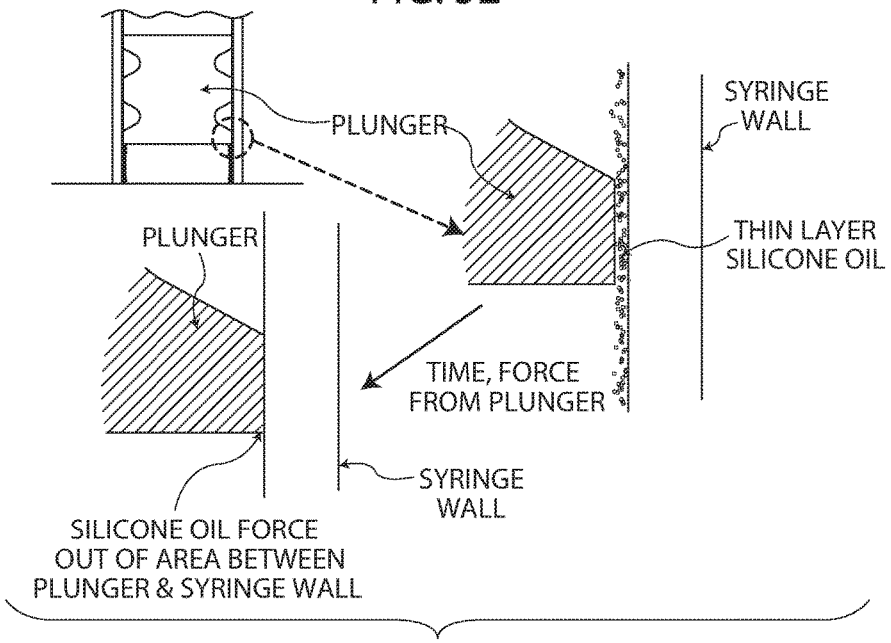
Figure 54:
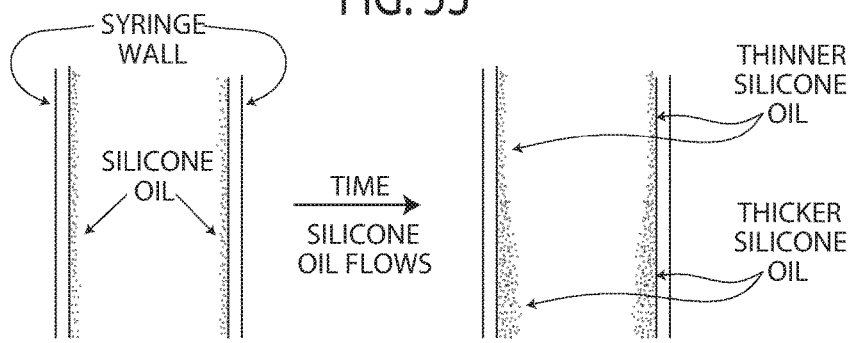

FIGS. 52 to 54 are diagrammatic views showing the drawbacks of silicon oil (or any other oil) as lubricant.

Figure 55:
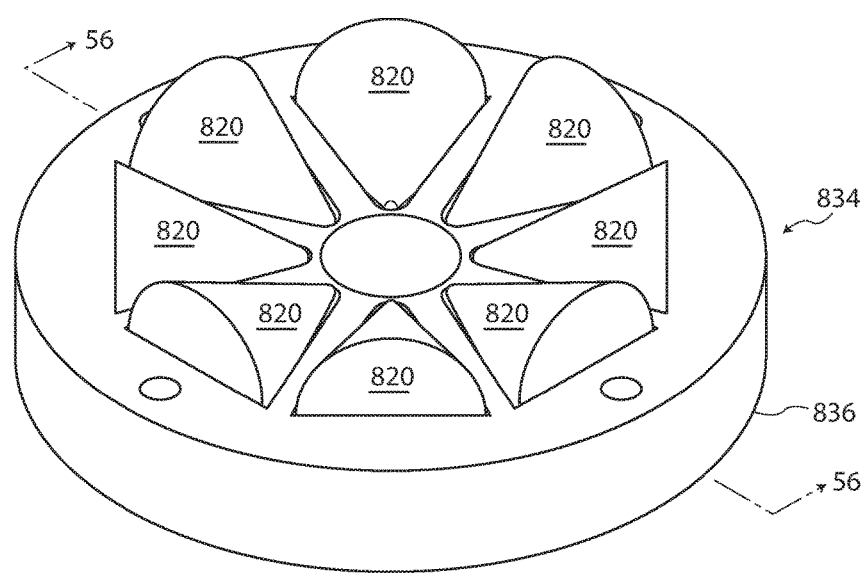

FIG. 55 is a perspective view of a ring shaped array of conical magnets supported in a lower shell support 836, with the identical upper shell support removed.

Figure 56:
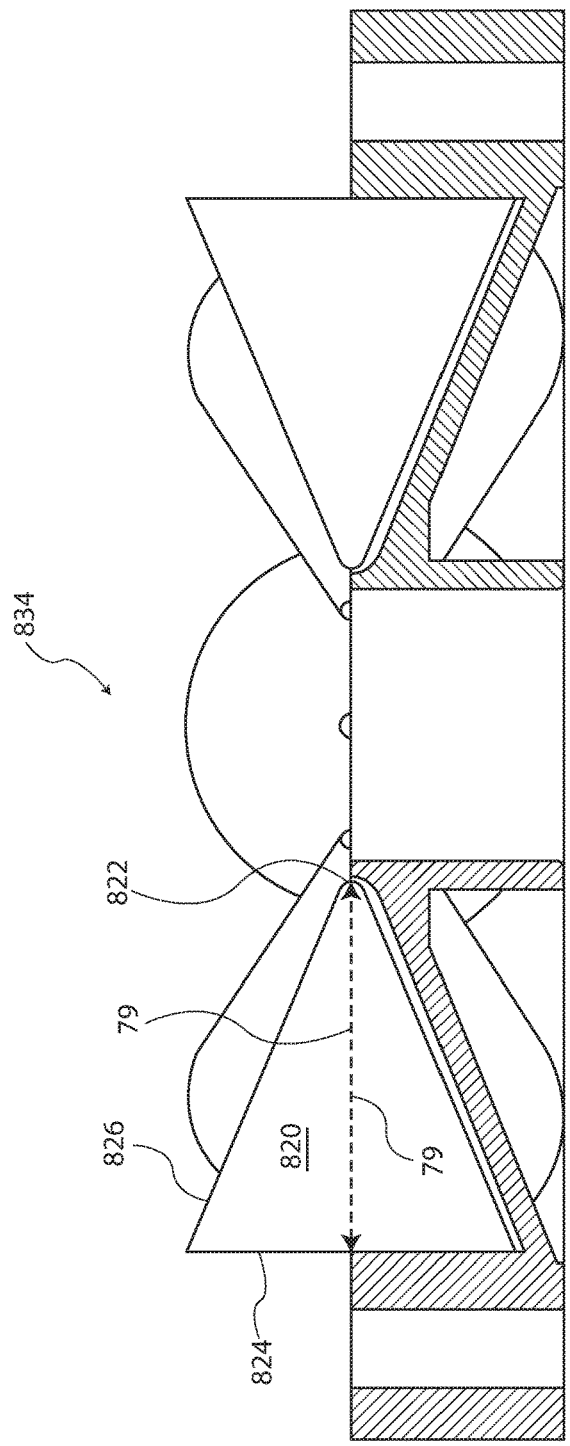

FIG. 56 is a section taken along section lines 56-56 of FIG. 55.

Figure 57:
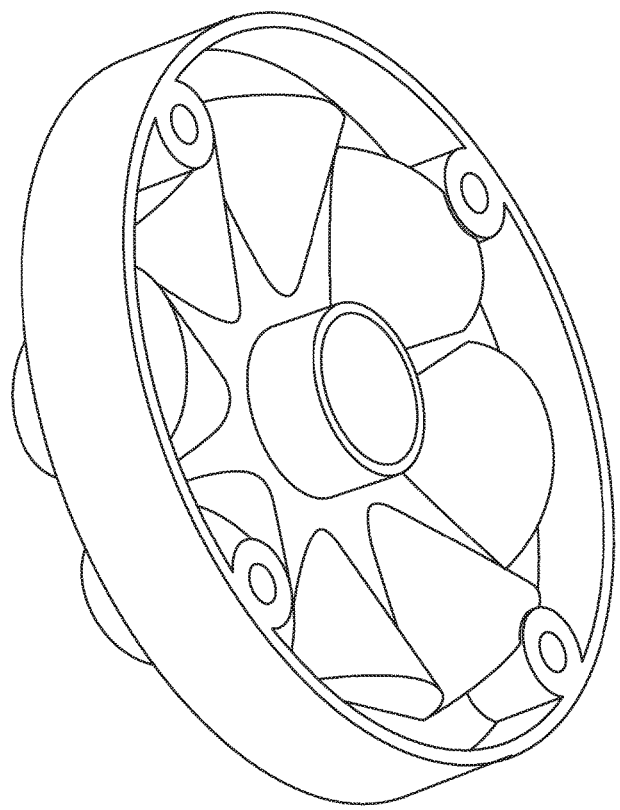

FIG. 57 is a perspective view of the upper or lower shelf support 836 (the upper and lower shelf supports optionally can be identical).

Figure 58:
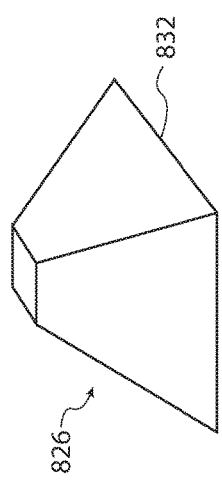

FIG. 58 shows an alternative frustopyramidal magnet shape usable according to the present invention.

Figure 59:
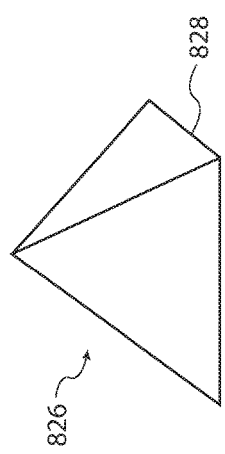

FIG. 59 shows an alternative pyramidal magnet shape usable according to the present invention.

Figure 60:
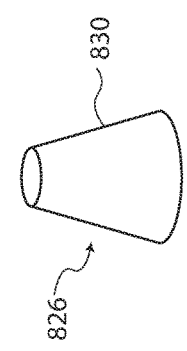

FIG. 60 shows an alternative frustoconical magnet shape usable according to the present invention.

Figure 61:
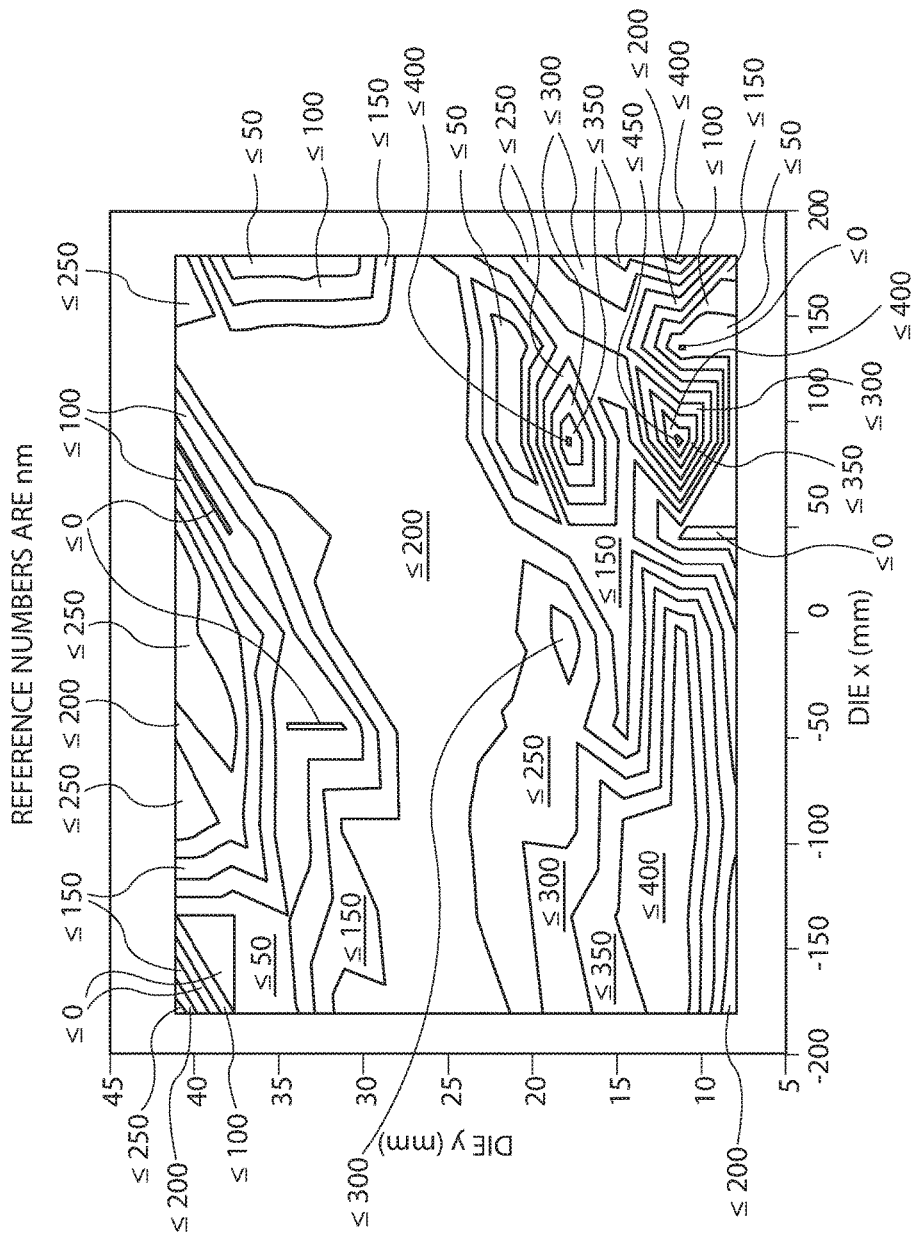

FIG. 61 is a map of the coating or layer thickness on the interior surface of a medical barrel.

Figure 62:
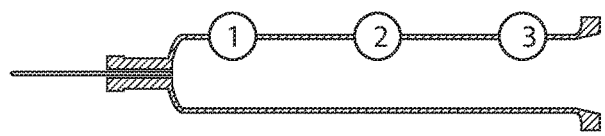

FIG. 62 is a diagrammatic representation of the medical barrel.

Figure 63:
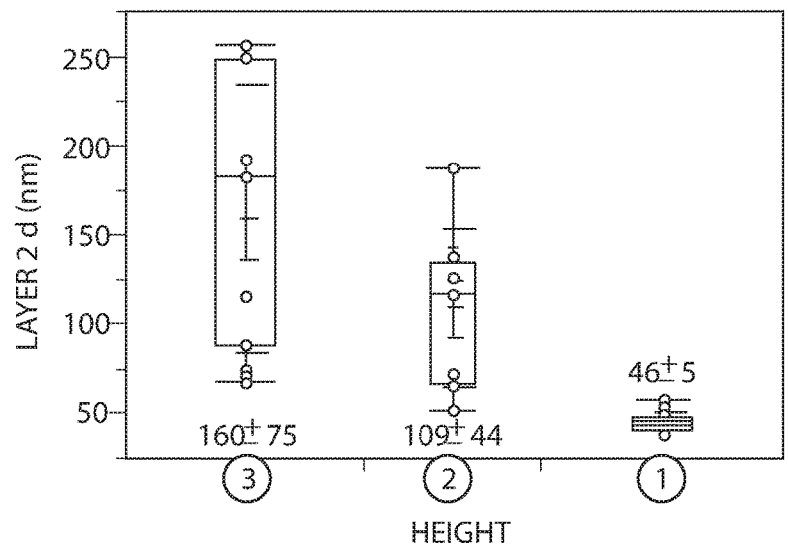

FIG. 63 is a further diagrammatic representation of the coating or layer thickness on the generally cylindrical interior surface of the medical barrel of FIG. 61.

Figure 64:
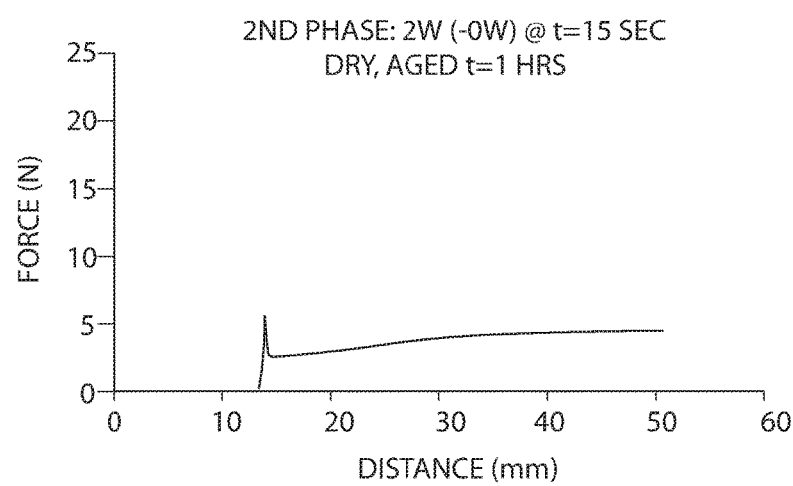

FIG. 64 is a plot of coating or layer thickness versus distance from the back of the medical barrel of FIGS. 61-63.

Figure 65:
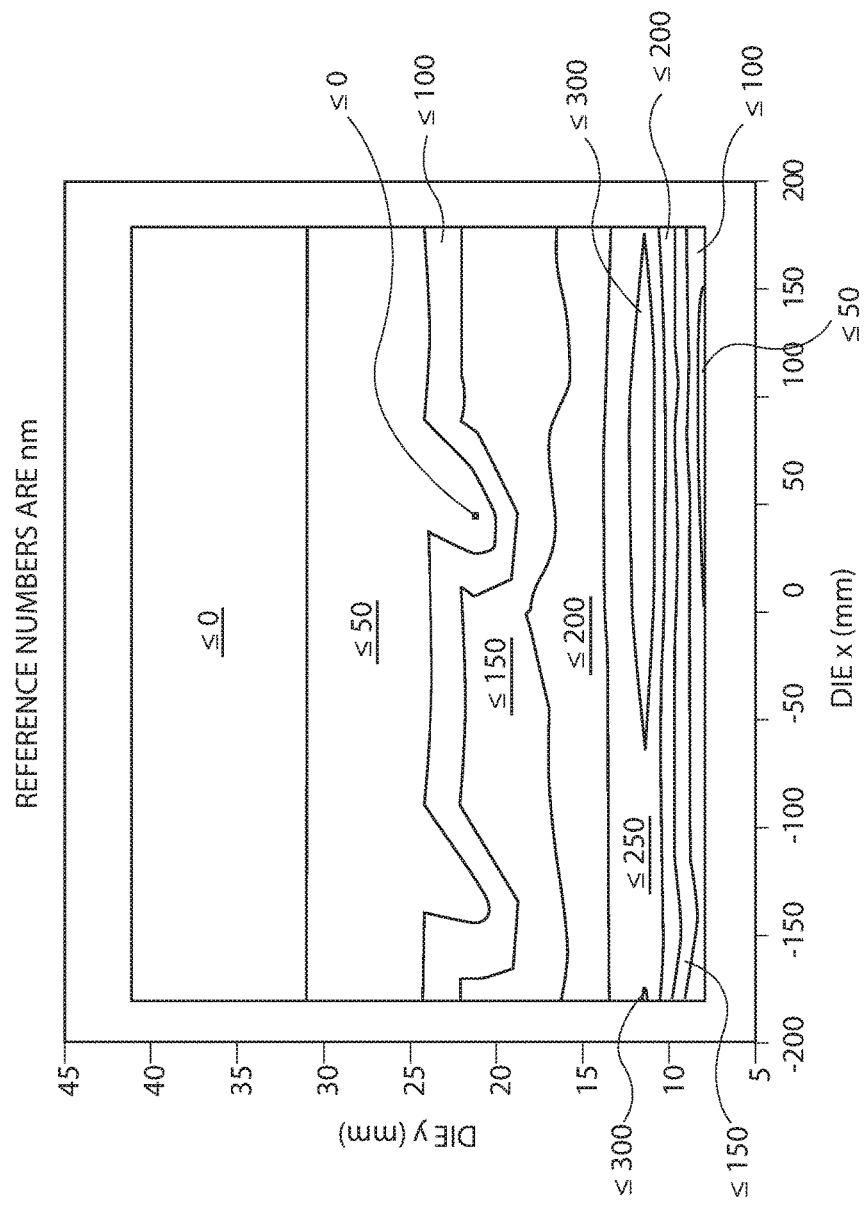

FIG. 65 is a map of coating or layer thickness.

Figure 66:
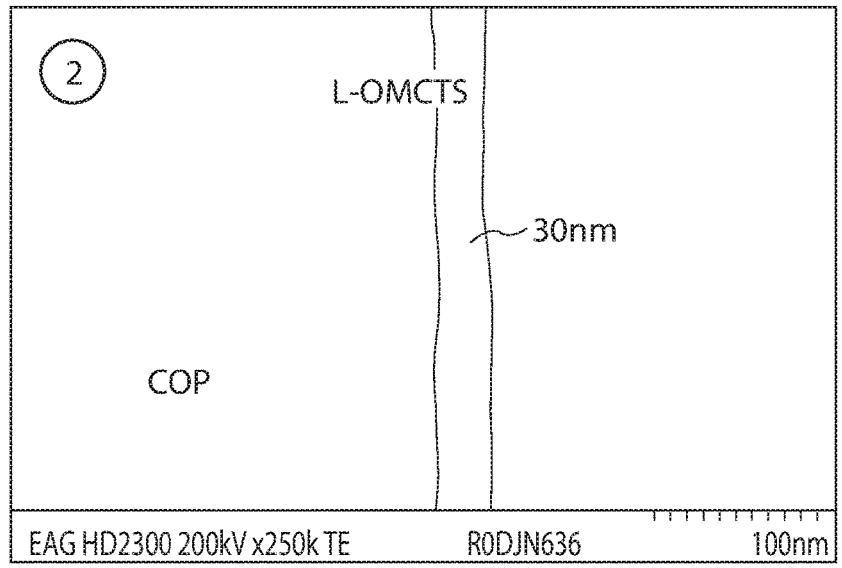

FIG. 66 is a photomicrograph of the coating or layer thickness on the generally cylindrical interior surface of the medical barrel of FIG. 65.

Figure 67:
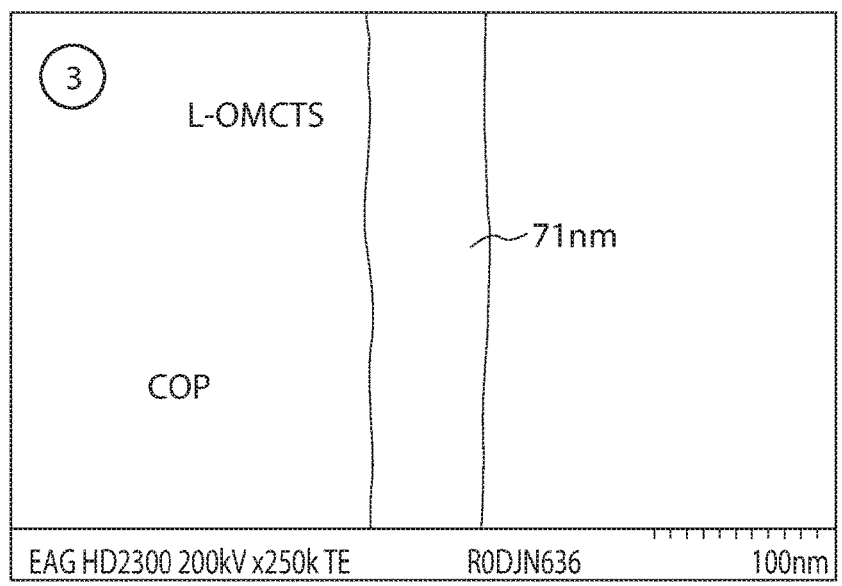

FIG. 67 is a second photomicrograph of the coating or layer thickness on the generally cylindrical interior surface of the medical barrel of FIG. 65.

Figure 68:
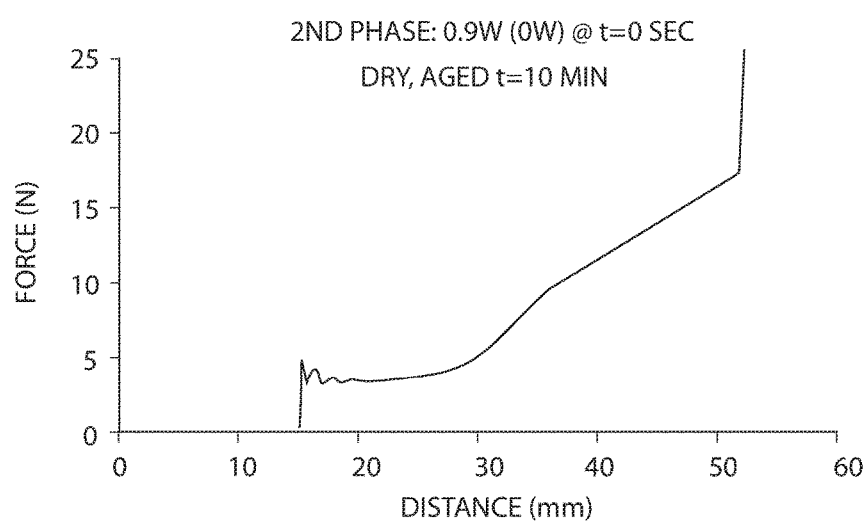

FIG. 68 is a plot of $F_m$ for Example 9, after inserting a plunger and aging the syringe for 10 minutes.

Figure 69:
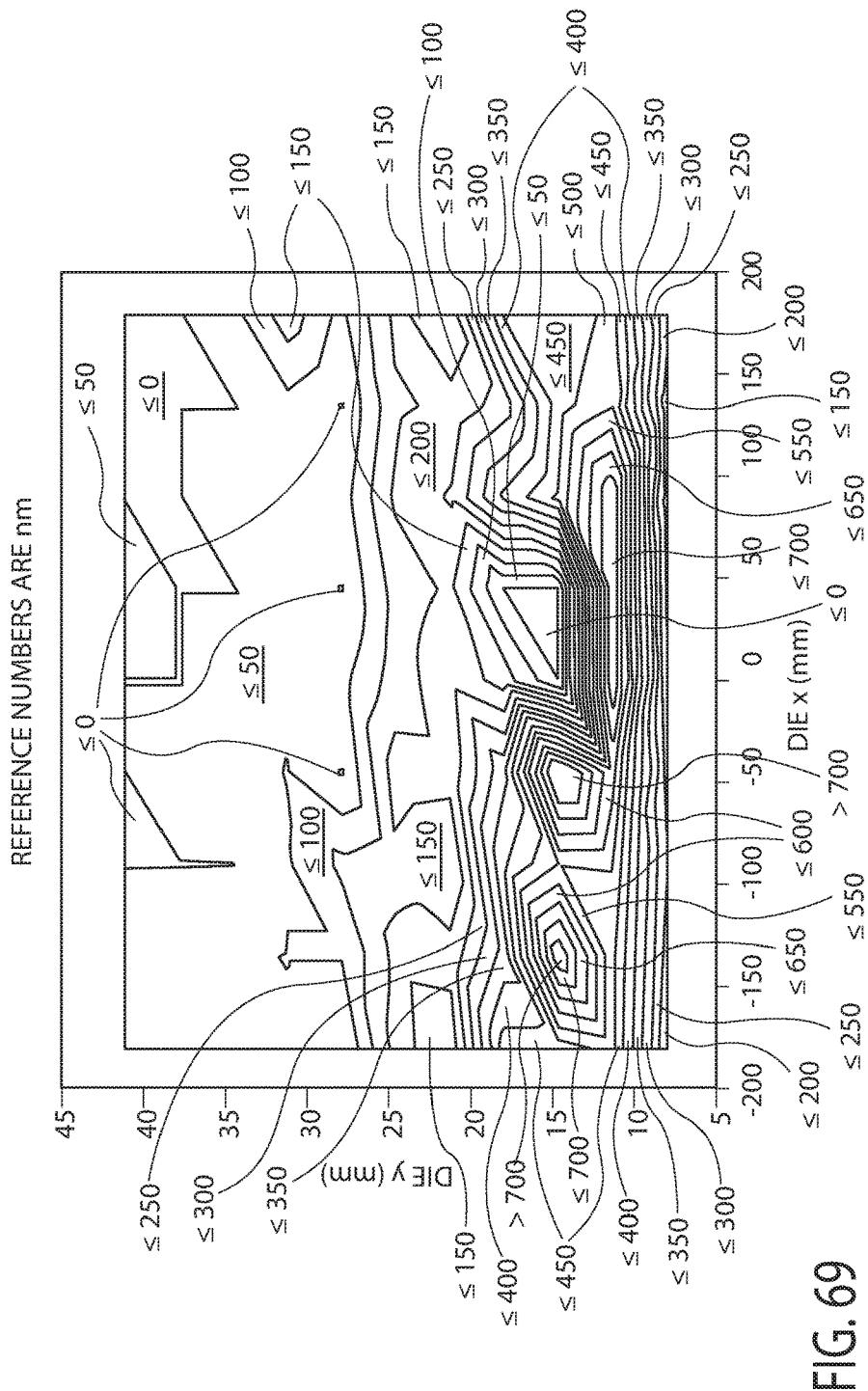

FIG. 69 is a map of the coating or layer thickness on the third lubricity coated medical barrel.

Figure 70:
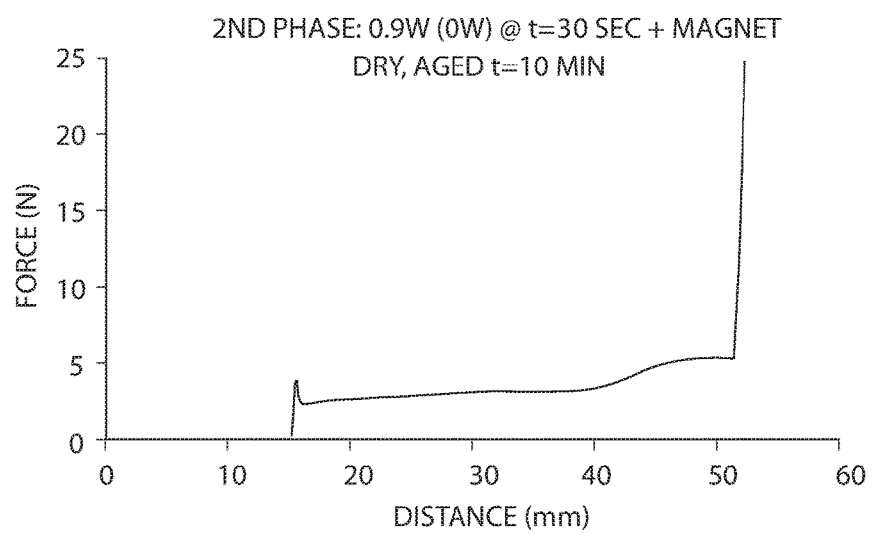

FIG. 70 is a plot of $F_m$ for Example 10.

Figure 71:
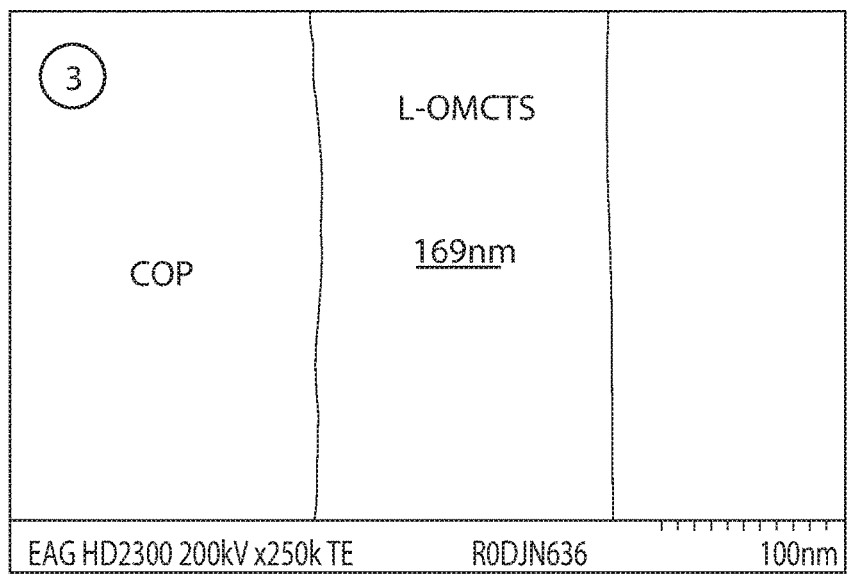

FIG. 71 shows a photomicrograph of the coating or layer thickness on the generally cylindrical interior surface of a medical barrel.

Figure 72:
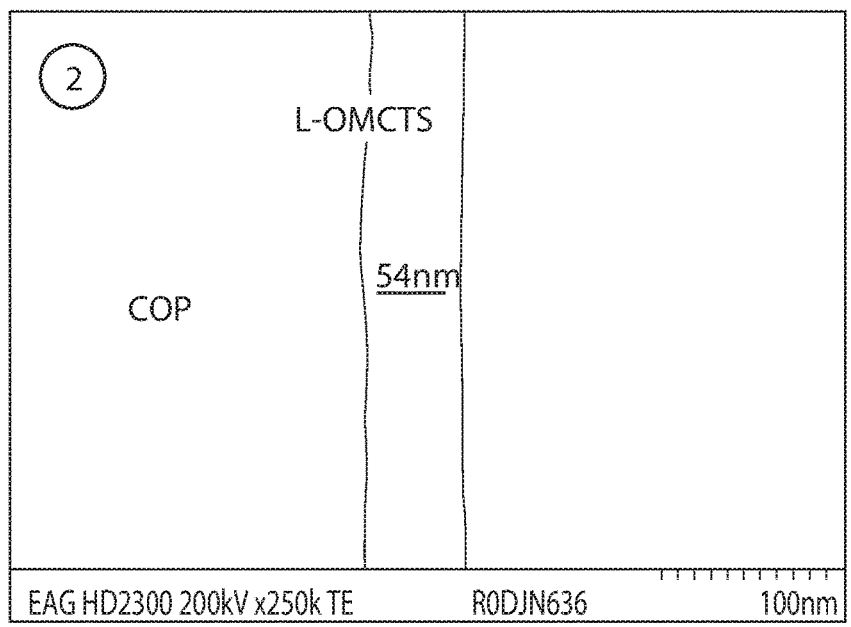

FIG. 72 shows a second photomicrograph of the coating or layer thickness on the generally cylindrical interior surface of a medical barrel.

Figure 73:
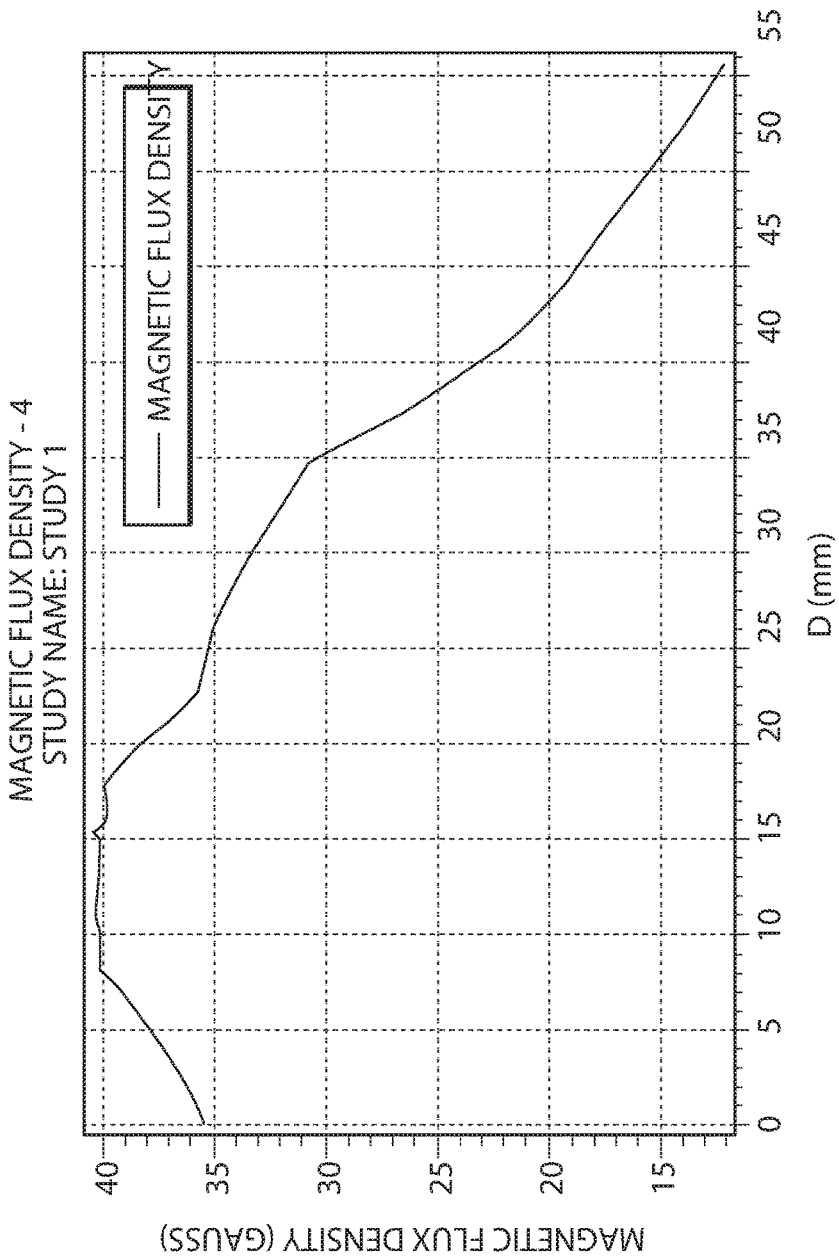

FIG. 73 shows the magnetic field strength profile for the NdFe magnet used to generate the data of FIGS. 69, 70, 71, and 72.

Figure 74:
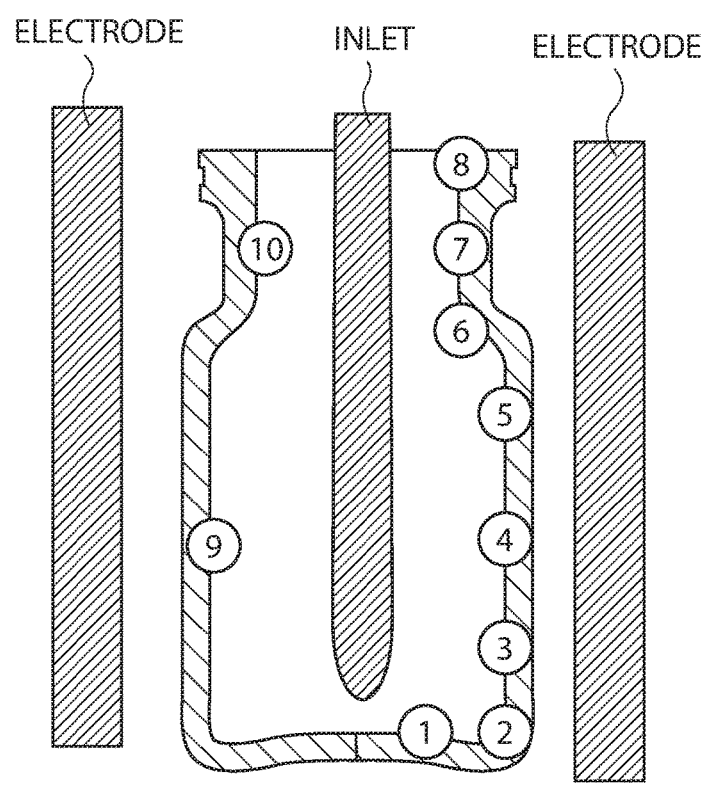

FIG. 74 shows the TEM (transmission electron microscope) test locations on the vial walls of the vials tested in Example 11.

The following reference characters are used in the drawing figures:

| | |
|---|---|
| 10 | Vial |
| 12 | Capped assembly or workpiece |
| 14 | medical barrel or similar device |
| 16 | generally cylindrical interior surface 16 |
| 18 | medical barrel lumen |
| 20 | Dispensing portion |
| 22 | Dispensing end |
| 24 | Distal opening |
| 26 | Dispensing portion lumen |
| 27 | Shield |
| 30 | Barrier coating or layer |
| 32 | Back end |
| 34 | pH protective coating or layer |
| 36 | Plunger or piston |
| 38 | Push rod |
| 40 | Fluid composition |
| 42 | Rib |
| 44 | generally cylindrical interior surface 16 |
| 46 | Barb |
| 48 | Catch |
| 50 | Vessel support |
| 52 | Plot |
| 54 | Plot |
| 60 | coating station |
| 61 | Quadro couple magnet |
| 62 | Quadro couple magnet |
| 63 | Quadro couple magnet |
| 64 | Quadro couple magnet |
| 65 | Axial magnet |
| 66 | Axial magnet |
| 67 | Axial magnet |
| 68 | Axial magnet |
| 69 | Axial magnet |
| 70 | Axial magnet |
| 71 | Axial magnet |
| 72 | Axial magnet |
| 73 | Segmented ring magnet |
| 74 | Segmented ring magnet |
| 75 | Axial ring magnet |
| 76 | Axial ring magnet |
| 77 | Axial ring magnet |
| 78 | Axial ring magnet |
| 79 | Polar axis of magnet |
| 80 | Axis of workpiece |
| 81 | Recess between magnets or within coil |
| 82 | Opening |
| 83 | Magnetic line |
| 84 | Closed end |
| 85 | First end (of 86) |
| 86 | Solenoid |
| 87 | Second end (of 86) |
| 88 | Toroid coil |
| 89 | First winding (of 86) |
| 90 | Toroid coil |
| 91 | Section (of 90) |
| 92 | Vessel port |
| 93 | Toroid alternate section (of 90) |
| 94 | Vacuum duct |
| 95 | Cross section (of 93) |
| 96 | Vacuum port |
| 97 | Second winding (of 86) (electron mirror) |
| 98 | Vacuum source |
| 99 | Third winding (of 86) (electron mirror) |
| 100 | O-ring (of 92) |
| 101 | Capacitor |
| 102 | O-ring (of 96) |
| 103 | Electron path |
| 104 | Gas inlet port |
| 106 | O-ring (of 100) |
| 107 | Shell electrode (−) |
| 108 | Probe (inner electrode) |
| 109 | Shell electrode (+) |
| 110 | Gas delivery port (of 108) |
| 114 | Housing (of 50) |
| 116 | Collar |
| 118 | Exterior surface (of 80) |
| 120 | End perforation |
| 122 | Side perforation |
| 124 | Side perforation |
| 126 | Bottom perforation |
| 128 | Top perforation |
| 130 | Side perforation |
| 132 | Side perforation |
| 134 | Top perforation |
| 135 | 270° perforation |
| 136 | 90° perforation |
| 137 | 315° perforation |
| 138 | 135° perforation |
| 139 | 0° perforation |
| 140 | 180° perforation |
| 141 | 45° perforation |
| 142 | 225° perforation |
| 144 | PECVD gas source |
| 152 | Pressure gauge |
| 160 | Outer Electrode |
| 162 | Power supply |
| 164 | Sidewall (of 160) |
| 166 | Sidewall (of 160) |
| 168 | Closed end (of 160) |
| 200 | Electrode |
| 210 | Prefilled syringe, auto-injector, or similar device |
| 268 | Sample collection tube, e.g. blood collection tube |
| 270 | Cap |
| 300 | Auto injector cartridge |
| 350 | Optical detector (350), for example a camera or an optical emissions spectrometer |
| 352 | Rogowski coil |
| 354 | Langmuir probe |
| 404 | Exhaust |
| 574 | Main vacuum valve |
| 576 | Vacuum line |
| 578 | Manual bypass valve |
| 580 | Bypass line |
| 582 | Vent valve |
| 584 | Main reactant gas valve |
| 586 | Main reactant feed line |
| 588 | Precursor gas |
| 590 | Organosilicon feed line (capillary) |
| 592 | Organosilicon shut-off valve |
| 594 | Oxidizing gas |
| 596 | Oxygen feed line |
| 598 | Mass flow controller |
| 600 | Oxygen shut-off valve |
| 602 | Diluent gas reservoir |
| 604 | Feed line |
| 606 | Shut-off valve |
| 614 | Headspace |
| 616 | Pressure source |
| 618 | Pressure line |
| 620 | Capillary connection |
| 700 | Beam of radiation |
| 702 | Radiation source |
| 704 | Radiation detector |
| 706 | Scattered radiation |
| 800 | First portion (of 16) |
| 802 | Second portion (of 16) |
| 804 | Third portion (of 16) |
| 806 | Back end (of 800) |
| 808 | Front end (of 800) |
| 810 | Back end (of 802) |

| | |
|---|---|
| 820 | Conical magnet |
| 822 | First pole |
| 824 | Second pole |
| 826 | Side (of 820 or 828-832) |
| 828 | Pyramidal magnet |
| 830 | Frustoconical magnet |
| 832 | Frustopyramidal magnet |
| 834 | Ring shaped array |
| 836 | Lower shell support |
| 838 | Tie coating or layer |

DEFINITION SECTION

In the context of the present invention, the following definitions and abbreviations are used:

"Plasma," unless otherwise indicated, refers to an energized state of matter similar to gas in which a certain portion of the particles of matter are ionized and free electrons are present. "Plasma" in another context in this specification can instead refer to the liquid component of blood, but only if the latter meaning is clear from the context of the disclosure.

RF is radio frequency electromagnetic energy.

The term "at least" in the context of the present invention means "equal or more" than the integer following the term. The word "comprising" does not exclude other elements or steps, and the indefinite article "a" or "an" does not exclude a plurality unless indicated otherwise. Whenever a parameter range is indicated, it is intended to disclose the parameter values given as limits of the range and all values of the parameter falling within said range.

For purposes of the present invention, an "organosilicon precursor" is a compound having at least one of the linkages:

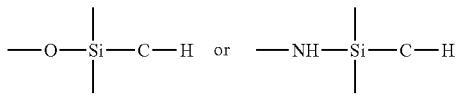

which is a tetravalent silicon atom connected to an oxygen or nitrogen atom and an organic carbon atom (an organic carbon atom being a carbon atom bonded to at least one hydrogen atom). A volatile organosilicon precursor, defined as such a precursor that can be supplied as a vapor in a PECVD apparatus, can be an optional organosilicon precursor. Optionally, the organosilicon precursor can be selected from the group consisting of a linear siloxane, a monocyclic siloxane, a polycyclic siloxane, a polysilsesquioxane, an alkyl trimethoxysilane, a linear silazane, a monocyclic silazane, a polycyclic silazane, a polysilsesquiazane, and a combination of any two or more of these precursors.

The feed amounts of PECVD precursors, gaseous reactant or process gases, and diluent gas are sometimes expressed in "standard volumes" in the specification and claims. The standard volume of a charge or other fixed amount of gas is the volume the fixed amount of the gas would occupy at a standard temperature and pressure (without regard to the actual temperature and pressure of delivery). Standard volumes can be measured using different units of volume, and still be within the scope of the present disclosure and claims. For example, the same fixed amount of gas could be expressed as the number of standard cubic centimeters, the number of standard cubic meters, or the number of standard cubic feet. Standard volumes can also be defined using different standard temperatures and pressures, and still be within the scope of the present disclosure and claims. For example, the standard temperature might be 0° C. and the standard pressure might be 760 Torr, or the standard temperature might be 20° C. and the standard pressure might be 1 Torr. But whatever standard is used in a given case, when comparing relative amounts of two or more different gases without specifying particular parameters, the same units of volume, standard temperature, and standard pressure are to be used relative to each gas, unless otherwise indicated.

The corresponding feed rates of PECVD precursors, gaseous reactant or process gases, and diluent gas are expressed in standard volumes per unit of time in the specification. For example, in the working examples the flow rates are expressed as standard cubic centimeters per minute, abbreviated as sccm. As with the other parameters, other units of time can be used, such as seconds or hours, but consistent parameters are to be used when comparing the flow rates of two or more gases, unless otherwise indicated.

A "vessel" in the context of the present invention can be any type of article with at least one opening and a wall defining an inner or generally cylindrical interior surface 16. The substrate can be the inside wall of a vessel having a lumen. Though the invention is not necessarily limited to pharmaceutical packages or other vessels of a particular volume, pharmaceutical packages or other vessels are contemplated in which the lumen can have a void volume from 0.5 to 50 mL, optionally from 1 to 10 mL, optionally from 0.5 to 5 mL, optionally from 1 to 3 mL. These dimensions are exemplary and do not represent limits. The substrate surface can be part or all of the inner or generally cylindrical interior surface 16 of a vessel having at least one opening and an inner or generally cylindrical interior surface 16.

A vessel in the context of the present invention can have one or more openings. One or two openings, like the openings of a common type of blister package well, vial or sample tube (one opening) or a common type of syringe or medical barrel (two openings) are preferred. If the vessel has two openings, they can be the same size or different sizes. If there is more than one opening, one opening can be used for the gas inlet for a PECVD coating method according to the present invention, while the other openings are either capped or open. A vessel according to the present invention can be a sample tube, for example for collecting or storing biological fluids like blood or urine, a syringe (or a part thereof, for example a medical barrel) for storing or delivering a biologically active compound or composition, for example a medicament or pharmaceutical composition, a vial for storing biological materials or biologically active compounds or compositions, a pipe, for example a catheter for transporting biological materials or biologically active compounds or compositions, or a cuvette for holding fluids, for example for holding biological materials or biologically active compounds or compositions.

The vessel can be provided with a reagent or preservative for sample collection (e.g. blood collection) or analysis. For example, a vessel for blood collection can have an inner or generally cylindrical interior surface defining a lumen and an exterior surface, the passivation layer or pH protective coating or layer can be on the inner or generally cylindrical interior surface 16, and the vessel can contain a compound or composition in its lumen, for example citrate or a citrate containing composition.

A vessel can be of any shape, a vessel having a generally cylindrical interior surface at or near at least one of its open ends being preferred. Generally, the interior surface of the vessel can be cylindrically shaped, like, for example in a sample tube or a medical barrel. Sample tubes and syringes or their parts (for example medical barrels) are contemplated.

A "hydrophobic coating or layer" in the context of the present invention means that the coating or layer lowers the wetting tension of a surface coated with the coating or layer, compared to the corresponding untreated surface. Hydrophobicity can be thus a function of both the untreated substrate and the coating or layer. The same applies with appropriate alterations for other contexts wherein the term "hydrophobic" is used. The term "hydrophilic" means the opposite, i.e. that the wetting tension is increased compared to reference sample. The present hydrophobic coatings or layers are primarily defined by their hydrophobicity and the process conditions providing hydrophobicity. Suitable hydrophobic coatings or layers and their application, properties, and use are described in U.S. Pat. No. 7,985,188. Dual functional passivation layers or pH protective coatings or layers that also have the properties of hydrophobic coatings or layers can be provided for any embodiment of the present invention.

The values of x and y stated together are applicable to the empirical composition $SiO_xC_y$ throughout this specification, except as a different usage is clearly indicated. The value of x stated alone is applicable to the empirical composition $SiO_x$ throughout this specification, except as a different usage is clearly indicated.) The values of x and y used throughout this specification should be understood as ratios of an empirical formula (for example for a coating or layer), rather than as a limit on the number or type of atoms in a molecule. For example, a molecular composition $Si_4O_4C_8$ can be described by the following empirical formula, arrived at by dividing each subscript in the molecular formula by 4, the largest common factor: $SiO_1C_2$. The values of x and y are also not limited to integers.

$Si_wO_xC_y$ or similar expressions having a "w" subscript, where w=1, are equivalent to $SiO_xC_y$ or similar expressions in this disclosure, as an alternative way of stating the same formulation.

"Average" and "mean" for a series of measurements or other values are both identically defined as equal to the statistical mean.

A "thickness range" for a coating or layer means a set of the maximum and minimum thickness measured for the coating or layer. For example, if three measurements of a coating at different points are 17 nm, 31 nm, and 34 nm, the thickness range of that coating is 17-34 nm.

The values of x and y stated together are applicable to the empirical composition $SiO_xC_y$ throughout this specification.

A "cylindrical" surface is defined here as a three-dimensional geometric surface extending between two congruent and parallel closed loops, which can be circles or any other shape (ovals, octagons, irregular loops, etc.). "Generally cylindrical" allows for minor deviations from truly cylindrical form, for example the taper of a syringe or medical barrel, surface roughness, sections of slightly different inside diameter, or other deviations that do not prevent a plunger from seating against and moving along the surface, in the case of a syringe. A single surface can include a generally cylindrical portion and another portion that is not generally cylindrical, such as the surfaces of a side wall and end wall of a syringe defining its lumen.

A "PECVD set" is all the coatings applied by PECVD to a particular surface, and can be one or more coatings.

"Rutherford backscattering spectrometry" is a method for measuring the hydrogen content of a PECVD coating or layer. This method can be used, for example, to supplement the characterization of a PECVD layer as $SiO_xC_y$ by X-ray photo-electron spectroscopy (XPS) (which does not detect hydrogen content), so the formulation can be presented as $SiO_xC_yH_z$.

"Wetting tension" is a specific measure for the hydrophobicity or hydrophilicity of a surface. An optional wetting tension measurement method in the context of the present invention is ASTM D 2578 or a modification of the method described in ASTM D 2578. This method uses standard wetting tension solutions (called dyne solutions) to determine the solution that comes nearest to wetting a plastic film surface for exactly two seconds. This is the film's wetting tension. The procedure utilized can be varied herein from ASTM D 2578 in that the substrates are not flat plastic films, but are tubes made according to the Protocol for Forming PET Tube and (except for controls) coated according to the Protocol for Coating Tube Interior with Hydrophobic coating or layer (see Example 9 of EP2251671 A2).

A "lubricity coating or layer" according to the present invention is a coating or layer which has a lower frictional resistance than the uncoated surface.

A "passivation layer or pH protective coating" according to the present invention passivates or protects an underlying surface or layer from a fluid composition contacting the layer (as more extensively defined elsewhere in this specification).

"Frictional resistance" can be static frictional resistance and/or kinetic frictional resistance.

One of the optional embodiments of the present invention can be a syringe part, for example a medical barrel or plunger tip, piston, stopper, or seal, coated with a lubricity and/or passivation layer or pH protective coating. In this contemplated embodiment, the relevant static frictional resistance in the context of the present invention is the breakout force as defined herein, and the relevant kinetic frictional resistance in the context of the present invention is the plunger sliding force as defined herein. For example, the plunger sliding force as defined and determined herein is suitable to determine the presence or absence and the lubricity and/or passivating or protective characteristics of a lubricity and/or passivation layer or pH protective coating or layer in the context of the present invention whenever the coating or layer is applied to any syringe or syringe part, for example to the inner wall of a medical barrel. The breakout force can be of particular relevance for evaluation of the coating or layer effect on a prefilled syringe, i.e. a syringe which can be filled after coating and can be stored for some time, for example several months or even years, before the plunger tip, piston, stopper, or seal is moved again (has to be "broken out").

The "plunger sliding force" (synonym to "glide force," "maintenance force", or Fm, also used in this description) in the context of the present invention is the force required to maintain movement of a plunger tip, piston, stopper, or seal in a medical barrel, for example during aspiration or dispense. It can advantageously be determined using the ISO 7886-1:1993 test described herein and known in the art. A synonym for "plunger sliding force" often used in the art is "plunger force" or "pushing force".

The "plunger breakout force" (synonym to "breakout force", "break loose force", "initiation force", Fi, also used in this description) in the context of the present invention is the initial force required to move the plunger tip, piston, stopper, or seal in a syringe, for example in a prefilled syringe.

Both "plunger sliding force" and "plunger breakout force" and methods for their measurement are described in more detail in subsequent parts of this description. These two forces can be expressed in N, lbs or kg and all three units are used herein. These units correlate as follows: 1N=0.102 kg=0.2248 lbs (pounds).

Sliding force and breakout force are sometimes used herein to describe the forces required to advance a stopper or other closure into a pharmaceutical package or other vessel, such as a medical sample tube or a vial, to seat the stopper in a vessel to close the vessel. Its use can be analogous to use in the context of a syringe and its plunger tip, piston, stopper, or seal, and the measurement of these forces for a vessel and its closure are contemplated to be analogous to the measurement of these forces for a syringe, except that at least in most cases no liquid is ejected from a vessel when advancing the closure to a seated position.

"Slidably" means that the plunger tip, piston, stopper, or seal or other removable part can be permitted to slide in a medical barrel or other vessel.

An "electron bottle" is a virtual container made up of magnetic and/or electrical fields that tend to confine within it the electrons having less energy than necessary to escape the bottle. The electron bottle should not be confused with a workpiece or chamber that has walls confining the contents. Positively and/or negatively charged ions in the plasma may also be confined by the electron bottle, and often can be more easily confined than electrons due to their lower energy, so an "electron bottle" is specially defined here to include a structure that tends to direct or confine ions.

The term "workpiece" as sometimes used in this disclosure refers to a medical barrel, auto-injector cartridge, or similar device having a lumen.

It will be appreciated by those skilled in the field that if the plasma is formed inside the walls of a container (whether the workpiece or a separate chamber), part of the confinement function can be performed by the container itself, and the electron bottle optionally can merely supplement that function. It will also be appreciated that the electron bottle and any physical container can coincide in space or not, and the magnetic container "walls" can be within the physical container, outside the physical container, intersect with a wall of the physical container, or different portions of it can be in any two or more of these positions at once.

Except to the extent the container in which the plasma is formed is made in part of ferromagnetic or ferrimagnetic material (for example a hypodermic needle of a syringe assembly), the container and the electron bottle may not substantially interact with each other. Moreover, an electron bottle need not necessarily provide 360-degree confinement of electrons or ions, as the goal is not necessarily to confine electrons or ions per se, but can be to improve the treatment of the workpiece. For example, when a vial, syringe barrel, or cartridge barrel is used with an electron bottle, the "bottle" optionally can be just a single axial electron mirror adjacent to one end of the vial, or adjacent to both ends of the vial, without substantial radial confinement. Alternatively, the "bottle" optionally can provide radial confinement, as by using the quadrupoles of FIG. 4-6, 21, 23, 25, 38-40 or 45 or uniformly wound coils, without adding substantial axial confinement.

The "standard deviation" is measured as follows, for example in the context of a PECVD coating or layer having a standard deviation less than the mean thickness. A Filmetrics test method is employed in some of the working examples in which the thickness of the coating is measured at multiple spaced points standard positions—eight points separated by 45-degree increments around the circumference of the surface at a first axial position, then at eight points separated by 45-degree increments around the circumference at a second axial position 6 mm away from the first axial position, and so forth over the portion of the coating being measured. This yields N measurements, $x_i$. Then the standard deviation of the thickness values at the respective points is calculated conventionally according to the formula:

$$s = \sqrt{\frac{\sum_{i=1}^{N}(x_i - \bar{x})^2}{N-1}}$$

In which s is the standard deviation, N is the number of thickness measurements, $x_i$ is each individual thickness measurement, and x with a line over it is the mean of all the thickness results.

The ratio of:
  the maximum amplitude of the Si—O—Si symmetrical stretch peak normally located between about 1000 and 1040 cm$^{-1}$ and
  the maximum amplitude of the Si—O—Si asymmetric stretch peak normally located between about 1060 and about 1100 cm$^{-1}$
is measured for the present purposes using FTIR—Fourier transform infrared spectroscopy. This is an analytical technique which is used to obtain an infrared spectrum of absorption of an $SiO_xC_y$ PECVD coating or layer. For the present purposes, an attenuated total reflection (ATR) sampler and FTIR machine are used to obtain an absorbance spectrum of a pH protective coating or layer 34 between wave numbers of about 1000 cm$^{-1}$ to 1100 cm$^{-1}$. The maximum amplitude of the Si—O—Si symmetrical stretch peak normally located between about 1000 and 1040 cm$^{-1}$ is determined, and the maximum amplitude of the Si—O—Si asymmetric stretch peak normally located between about 1060 and about 1100 cm$^{-1}$ is determined. Then the ratio of these maximum amplitudes is determined.

The oxygen barrier improvement factor (BIF) of the barrier coating or layer is determined by providing two groups of identical containers, adding a barrier coating or layer, PECVD set, or other treatment to the test group of containers (leaving the untreated containers as a control group). The oxygen transfer rate is measured on each test and control container. The ratio of the value of the oxygen transfer rate for the test vessels to the value for the control vessels is determined. The ratio is the "oxygen barrier improvement factor." For example, if the rate of outgassing through the barrier coating or layer is one-third the rate of outgassing without a barrier coating or layer, the barrier coating or layer has an oxygen BIF of 3.

The oxygen transmission rate is measured by testing the contents of the previously stored vessels for their oxygen content, and expressing the amount of oxygen permeating into the vessel in terms of cubic centimeters of oxygen gas per package per day. Ratios of the oxygen transmission rate (OTR) of the test vessels including a PECVD set and the control vessels with no PECVD set are then determined.

The barrier improvement factor can be determined in unused containers or after storage of a fluid composition in the containers, to determine the effect of the fluid storage on the barrier improvement factor. A Protocol For Measuring Barrier Improvement Factor (BIF) After Solution Storage is described below for measuring the barrier improvement factor after storage of a fluid in the container in contact with the PECVD set. The same oxygen transmission test described in the protocol can be used without the storage protocol to test as-made medical barrels for barrier improvement factor.

DETAILED DESCRIPTION

The present invention will now be described more fully, with reference to the accompanying drawings, in which several embodiments are shown. This invention can, however, be embodied in many different forms and should not be construed as limited to the embodiments set forth here. Rather, these embodiments are examples of the invention, which has the full scope indicated by the language of the claims. Like numbers refer to like or corresponding elements throughout. The following disclosure relates to all embodiments unless specifically limited to a certain embodiment.

Syringe

The vessel of FIGS. 1-7 is a syringe, which is a contemplated type of vessel having a medical barrel 14 including a generally cylindrical interior surface 16, also known as an "internal wall." The generally cylindrical interior surface 16 is provided with a PECVD set optionally including a barrier coating or layer, optionally a tie coating or layer, and optionally a passivation layer or pH protective coating. A PECVD set which is a "trilayer coating or layer" is one contemplated option in which the generally cylindrical internal surface 16 is successively built up with (1) a tie coating or layer, (2) a barrier coating or layer, and (3) a passivation layer or pH protection coating or layer.

Optionally, the medical barrel, before conducting PECVD, has an attached hypodermic needle, the barrel having a needle end, a back end, and a body portion between the ends. The needle end optionally can be capped during PECVD to reduce or eliminate flow through the attached hypodermic needle, as well as to protect the needle and those working near it during processing or use of the resulting syringe or cartridge.

The final syringe after processing can further comprise a plunger tip, piston, stopper, or seal 36. The plunger tip, piston, stopper, or seal 36 can be a relatively sliding part of the syringe, with respect to the medical barrel 250. The term "medical barrel" is broadly defined to include cartridges, injection "pens," and other types of medical barrels or reservoirs adapted to be assembled with one or more other components to provide a functional syringe. A "syringe" is also broadly defined to include related articles such as auto-injectors, which provide a mechanism for dispensing the contents.

As one non-limiting way to make the syringe, a capped assembly 12 can be provided comprising a medical barrel 14, a dispensing portion 20, and a shield 28. The capped assembly 12 can be a complete article or it can be a portion of a complete article adapted to dispense fluid, such as a syringe, a cartridge, a catheter, or other article.

The medical barrel 14 can have an generally cylindrical interior surface 16 defining a medical barrel lumen 18. Optionally in any embodiment, the medical barrel 14 can further include an opening 32 spaced from the dispensing portion 20 and communicating through the generally cylindrical interior surface 16. Such an opening can be conventional, for example, in a syringe or cartridge, where a typical example can be the back opening 32 of a prefilled medical barrel, through which the plunger tip, piston, stopper, or seal 36 can be inserted after the medical barrel lumen 18 is filled with a suitable pharmaceutical preparation or other fluid material 40 to be dispensed.

The medical barrel 14 can be formed, for example, by molding, although the manner of its formation is not critical and it can also be formed, for example, by machining a solid preform. Preferably, the medical barrel can be molded by injection molding thermoplastic material, although it can also be formed by blow molding or a combined method.

As one preferred example, the medical barrel 14 can be formed by placing a dispensing portion 20 as described below in an injection mold and injection molding thermoplastic material about the dispensing portion, thus forming the medical barrel and securing the dispensing portion to the medical barrel. Alternatively, the dispensing portion and the medical barrel can be molded or otherwise formed as a single piece, or can be formed separately and joined in other ways. The medical barrel of any embodiment can be made of any suitable material. Several medical barrel materials particularly contemplated are COC (cyclic olefin copolymer), COP (cyclic olefin polymer), PET (polyethylene terephthalate), and polypropylene.

The dispensing portion 20 of the capped assembly 12 can be provided to serve as an outlet for fluid dispensed from the medical barrel lumen 18 of a completed article made from the capped assembly 12. One example of a suitable dispensing portion illustrated in the Figures can be a hypodermic needle.

Alternatively, in any embodiment the dispensing portion 20 can instead be a needle-free dispenser. One example of a suitable needle-free dispenser can be a blunt or flexible dispensing portion intended to be received in a complementary coupling to transfer fluid material 40. Such blunt or flexible dispensing portions are well known for use in syringes, intravenous infusion systems, and other systems and equipment to dispense material while avoiding the hazard of working with a sharp needle that may accidentally stick a health professional or other person. Another example of a needle-free dispenser can be a fluid jet or spray injection system that injects a free jet or spray of fluid directly through a patient's skin, without the need for an intermediate needle. Any type of dispensing portion 20, whether a hypodermic needle or any form of needle-free dispenser, is contemplated for use according to any embodiment of the present invention.

The dispensing portion 20 is or can be secured to the medical barrel 14 and includes a proximal opening 22, a distal opening 24, and a dispensing portion lumen 26. The proximal opening 22 communicates with the medical barrel lumen 18. The distal opening 24 can be located outside the medical barrel 14. The dispensing portion lumen 26 communicates between the proximal and distal openings 22, 24 of the dispensing portion 20. In the illustrated embodiment, the distal opening 24 can be at the sharpened tip of a hypodermic needle 20.

The shield 28 can be secured to the medical barrel 14 and at least substantially isolates the distal opening 24 of the dispensing portion 20 from pressure conditions outside the shield 28. Optionally in any embodiment, the shield 28 sufficiently isolates portions of the capped assembly 12 to provide a sufficient bio-barrier to facilitate safe use of the capped assembly 12 for transdermal injections.

The shield 28 can isolate the distal opening 24 in various ways. Effective isolation can be provided at least partially due to contact between the shield 28 and the distal opening 24, as shown in present FIGS. 2, 3, 4, and 7. In the illustrated embodiment, the tip of the dispensing portion 20 can be buried in the material of the shield 28. Alternatively in any embodiment, effective isolation can be provided at least partially due to contact between the shield 28 and the medical barrel 14, as also shown in present FIGS. 2, 3, 4, and 7. In the illustrated embodiment, the primary line of contact between the shield 28 and the medical barrel 14 can be at a rib 42 (best seen in FIG. 3) encircling and seated against a generally cylindrical surface 44 at the nose of the medical barrel 14. Alternatively in any embodiment, effective isolation can be provided due to both of these types of contact as illustrated in FIGS. 2-3, or in other ways, without limitation.

The shield 28 of any embodiment optionally can have a latching mechanism, best shown in FIG. 3, including a barb 46 and a catch 48 which engage to hold the shield 28 in place. The catch 48 can be made of sufficiently resilient material to allow the shield 28 to be removed and replaced easily.

If the dispensing portion 20 is a hypodermic needle, the shield 28 can be a specially formed needle shield. The original use of a needle shield is to cover the hypodermic needle before use, preventing accidental needle sticks and preventing contamination of the needle before it is injected in a patient or an injection port. A comparable shield preferably is used, even if the dispensing portion 20 is a needle-free dispenser, to prevent contamination of the dispenser during handling.

The shield 28 can be formed in any suitable way. For example, the shield 28 can be formed by molding thermoplastic material. Optionally in any embodiment, the thermoplastic material can be elastomeric material or other material that can be suitable for forming a seal. One suitable category of elastomeric materials is known generically as thermoplastic elastomer (TPE). An example of a suitable thermoplastic elastomer for making a shield 28 is Stelmi® Formulation 4800 (flexible shield formulation). Any other material having suitable characteristics can instead be used in any embodiment.

As another optional feature in any embodiment the shield 28 can be sufficiently permeable to a sterilizing gas to sterilize the portions of the capped assembly 12 isolated by the shield. One example of a suitable sterilizing gas is ethylene oxide. Shields 28 are available that are sufficiently permeable to the sterilizing gas that parts isolated by the shield can nonetheless be sterilized. An example of a shield formulation sufficiently permeable to accommodate ethylene oxide gas sterilization can be Stelmi® Formulation 4800.

As an optional feature of any of the foregoing embodiments the polymeric material can be a silicone elastomer or a thermoplastic polyurethane, as two examples, or any material suitable for contact with blood, or with insulin. For example, the use of a coated substrate according to any described embodiment is contemplated for storing insulin.

Optionally, as for the embodiments of FIG. 7, the pharmaceutical package 210 comprises a medical barrel.

Optionally, the pharmaceutical package comprises a cartridge.

Figure 8:
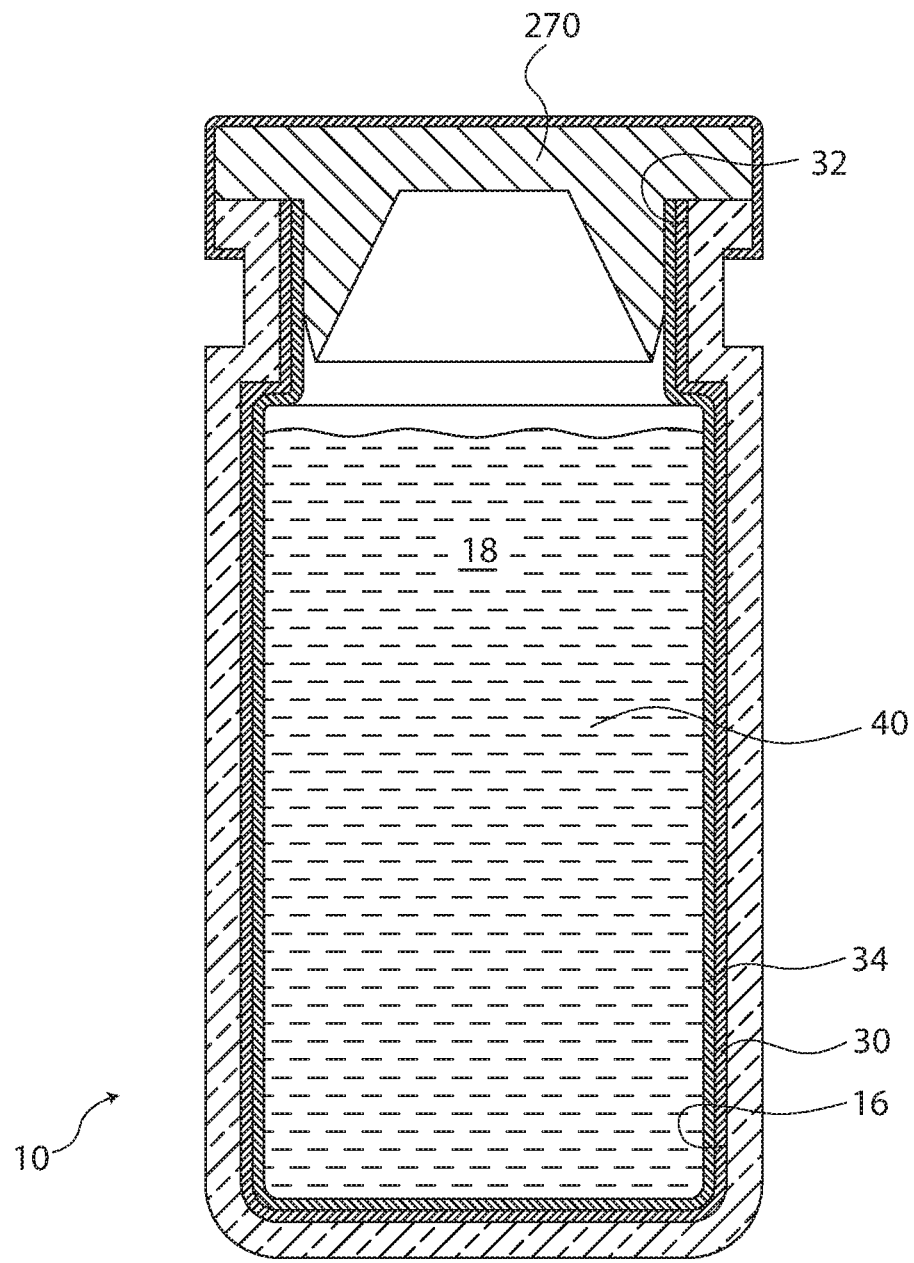
FIG. 8 is a longitudinal section of a vial fitted with a closure (septum and crimp) and having the same barrier coating or layer, passivation layer or pH protective coating, and other common features.

Optionally, as for the embodiments of FIG. 8, the pharmaceutical package 210 comprises a vial.

Optionally, the pharmaceutical package 210 comprises a blister package or ampoule.

Figure 29:
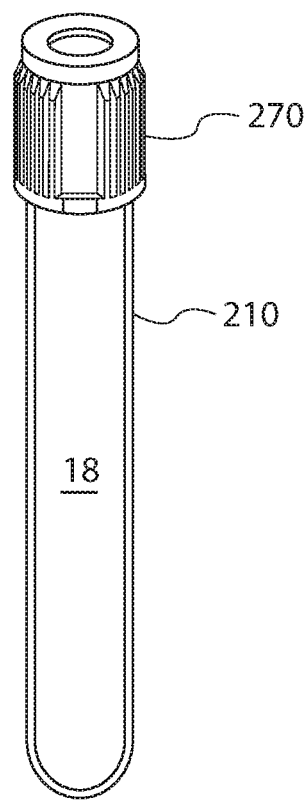
FIG. 29 is a perspective view of a medical sample tube, usable with the cap 270 removed on the PECVD apparatus of FIGS. 4-6 and 9-28 in any embodiment.

Optionally, the pharmaceutical package comprises a medical sample tube of FIG. 29.

Alternatively, the vessel can be a length of tubing from about 1 cm to about 200 cm, optionally from about 1 cm to about 150 cm, optionally from about 1 cm to about 120 cm, optionally from about 1 cm to about 100 cm, optionally from about 1 cm to about 80 cm, optionally from about 1 cm to about 60 cm, optionally from about 1 cm to about 40 cm, optionally from about 1 cm to about 30 cm long, and processing it with a probe electrode as described below. Particularly for the longer lengths in the above ranges, it is contemplated that relative motion between the PECVD or other chemical vapor deposition probe and the vessel can be useful during passivation layer or pH protective coating or layer formation. This can be done, for example, by moving the vessel with respect to the probe or moving the probe with respect to the vessel.

Optionally, a barrier coating or layer 30 of $SiO_x$ can be deposited by plasma enhanced chemical vapor deposition (PECVD) or other chemical vapor deposition processes on the vessel of a pharmaceutical package, in particular a thermoplastic package, to serve as a barrier coating or layer preventing oxygen, air, carbon dioxide, or other gases from entering the vessel and/or to prevent leaching of the pharmaceutical material into or through the package wall. The barrier coating or layer can be effective to reduce the ingress of atmospheric gas, for example oxygen, into the lumen compared to a vessel without a passivation layer or pH protective coating Optionally in any embodiment, the chemical vapor deposition-deposited coating or layer optionally can also, or alternatively, be a solute barrier coating or layer. A concern of converting from glass to plastic syringes centers around the potential for leachable materials from plastics. With plasma coating or layer technology, the coatings or layers derived from non-metal gaseous precursors, for example HMDSO, TMDSO, OMCTS, or other organosilicon compounds, will contain no trace metals and function as a barrier to inorganic, metals and organic solutes, preventing leaching of these species from the coated substrate into syringe fluids. In addition to leaching control of plastic syringes, the same plasma passivation layer or pH protective coating or layer technology offers potential to provide a solute barrier to the plunger tip, piston, stopper, or seal, typically made of elastomeric plastic compositions containing even higher levels of leachable organic oligomers and catalysts.

Moreover, certain syringes prefilled with synthetic and biological pharmaceutical formulations are very oxygen and moisture sensitive. A factor in the conversion from glass to plastic medical barrels will be the improvement of plastic oxygen and moisture barrier performance. The plasma passivation layer or pH protective coating or layer technology can be suitable to maintain the $SiO_x$ barrier coating or layer for protection against oxygen and moisture over an extended shelf life.

Examples of solutes in drugs usefully excluded by a barrier coating or layer in any embodiment include antibacterial preservatives, antioxidants, chelating agents, pH buffers, and combinations of any of these. In any embodiment the vapor-deposited coating or layer optionally can be a solvent barrier coating or layer for a solvent comprising a co-solvent used to increase drug solubilization.

In any embodiment the vapor-deposited coating or layer optionally can be a barrier coating or layer for water, glycerin, propylene glycol, methanol, ethanol, n-propanol, isopropanol, acetone, benzyl alcohol, polyethylene glycol, cotton seed oil, benzene, dioxane, or combinations of any two or more of these.

In any embodiment the vapor-deposited coating or layer optionally can be a metal ion barrier coating or layer.

In any embodiment the vapor-deposited coating or layer optionally can be a medical barrel wall material barrier coating or layer, to prevent or reduce the leaching of medical barrel material such as any of the base medical barrel resins mentioned previously and any other ingredients in their respective compositions.

The inventors have found, however, that such barrier coatings or layers of $SiO_x$ are eroded or dissolved by some fluid compositions, for example aqueous compositions having a pH above about 5. Since coatings or layers applied by chemical vapor deposition can be very thin—tens to hundreds of nanometers thick—even a relatively slow rate of erosion can remove or reduce the effectiveness of the barrier coating or layer in less time than the desired shelf life of a product package. This can be particularly a problem for fluid pharmaceutical compositions, since many of them have a pH of roughly 7, or more broadly in the range of 5 to 9, similar to the pH of blood and other human or animal fluids. The higher the pH of the pharmaceutical preparation, the more quickly it erodes or dissolves the $SiO_x$ coating.

The inventors have further found that without a protective coating or layer borosilicate glass surfaces are eroded or dissolved by some fluid compositions, for example aqueous compositions having a pH above about 5. This can be particularly a problem for fluid pharmaceutical compositions, since many of them have a pH of roughly 7, or more broadly in the range of 5 to 9, similar to the pH of blood and other human or animal fluids. The higher the pH of the pharmaceutical preparation, the more quickly it erodes or dissolves the glass. Delamination of the glass can also result from such erosion or dissolution, as small particles of glass are undercut by the aqueous compositions having a pH above about 5.

The inventors have further found that certain passivation layers or pH protective coatings or layers of $SiO_xC_y$ or $SiN_xC_y$ formed from cyclic polysiloxane precursors, which passivation layers or pH protective coatings or layers have a substantial organic component, do not erode quickly when exposed to fluid compositions, and in fact erode or dissolve more slowly when the fluid compositions have higher pHs within the range of 5 to 9. For example, at pH 8, the dissolution rate of a passivation layer or pH protective coating or layer made from organosilicon precursors, for example octamethylcyclotetrasiloxane (OMCTS) or tetramethyldisiloxane (TMDSO), can be quite slow. These passivation layers or pH protective coatings or layers of $SiO_xC_y$ or $SiN_xC_y$ can therefore be used to cover a barrier coating or layer of $SiO_x$, retaining the benefits of the barrier coating or layer by passivating or protecting it from the fluid composition in the pharmaceutical package. These passivation layers or pH protective coatings or layers of $SiO_xC_y$ or $SiN_xC_y$ also can be used to cover a glass surface, for example a borosilicate glass surface, preventing delamination, erosion and dissolution of the glass, by passivating or protecting it from the fluid composition in the pharmaceutical package.

Although the present invention does not depend upon the accuracy of the following theory, it is believed that the material properties of an effective $SiO_xC_y$ passivation layer or pH protective coating or layer and those of an effective lubricity coating or layer as described in U.S. Pat. No. 7,985,188 and in International Application PCT/US11/36097 are similar in some instances, such that a coating or layer having the characteristics of a lubricity coating or layer as described in certain working examples of this specification, U.S. Pat. No. 7,985,188, or International Application PCT/US11/36097 will also in certain cases serve as well as a passivation layer or pH protective coating or layer to passivate or protect the barrier coating or layer of the package and vice versa.

PECVD Treated Pharmaceutical Packages or other Vessels

A vessel with a barrier coating or layer and preferably a passivation layer or pH protective coating or layer as described herein and/or prepared according to a method described herein can be used for reception and/or storage and/or delivery of a compound or composition. The compound or composition can be sensitive, for example air-sensitive, oxygen-sensitive, sensitive to humidity and/or sensitive to mechanical influences. It can be a biologically active compound or composition, for example a pharmaceutical preparation or medicament like insulin or a composition comprising insulin. A prefilled syringe can be especially considered which contains injectable or other liquid drugs like insulin.

In another aspect, the compound or composition can be a biological fluid, optionally a bodily fluid, for example blood or a blood fraction. In certain aspects of the present invention, the compound or composition can be a product to be administrated to a subject in need thereof, for example a product to be injected, like blood (as in transfusion of blood from a donor to a recipient or reintroduction of blood from a patient back to the patient) or insulin.

A vessel with a passivation layer or pH protective coating or layer as described herein and/or prepared according to a method described herein can further be used for protecting a compound or composition contained in its interior space against mechanical and/or chemical effects of the surface of the vessel material. For example, it can be used for preventing or reducing precipitation and/or clotting or platelet activation of the compound or a component of the composition, for example insulin precipitation or blood clotting or platelet activation.

It can further be used for protecting a compound or composition contained in its interior against the environment outside of the pharmaceutical package or other vessel, for example by preventing or reducing the entry of one or more compounds from the environment surrounding the vessel into the interior space of the vessel. Such environmental compound can be a gas or liquid, for example an atmospheric gas or liquid containing oxygen, air, and/or water vapor.

Referring to the Figures, in particular FIG. 2, an aspect of the invention can be a method in which a tie coating or layer 838, barrier coating or layer 30, and passivation layer or pH protective coating or layer 34 are applied directly or indirectly applied to at least a portion of the interior generally cylindrical interior surface 16 of a vessel, such as any of the pharmaceutical packages 210 of FIGS. 7-8 and 29, a sample collection tube, for example a blood collection tube and/or a closed-ended sample collection tube; a conduit; a cuvette; or a vessel part, for example a plunger tip, piston, stopper, or seal for contact with and/or storage and/or delivery of a compound or composition.

Vessel Wall Construction

Optionally for any of the embodiments of FIG. 7-8 or 29, at least a portion of the generally cylindrical interior surface 16 of the pharmaceutical package 210 comprises or consists essentially of a polymer, for example a polyolefin (for example a cyclic olefin polymer, a cyclic olefin copolymer, or polypropylene), a polyester, for example polyethylene terephthalate or polyethylene naphthalate, a polycarbonate, polylactic acid, or any combination, composite or blend of any two or more of the above materials.

Optionally for any of the embodiments of FIGS. 7-8 and 29, at least a portion of the generally cylindrical interior surface 16 of the pharmaceutical package 210 comprises or consists essentially of glass, for example borosilicate glass.

As an optional feature of any of the foregoing embodiments the polymeric material can be a silicone elastomer or a thermoplastic polyurethane, as two examples, or any material suitable for contact with blood, or with insulin. For example, the use of a coated substrate according to any described embodiment is contemplated for storing insulin.

Optionally, as for the embodiments of FIG. 7, the pharmaceutical package 210 comprises a medical barrel.

Optionally, the pharmaceutical package comprises a cartridge.

Optionally, as for the embodiments of FIG. 8, the pharmaceutical package 210 comprises a vial.

Optionally, the pharmaceutical package 210 comprises a blister package or ampoule.

Optionally, the pharmaceutical package comprises a medical sample tube of FIG. 29.

Alternatively, the vessel can be a length of tubing from about 1 cm to about 200 cm, optionally from about 1 cm to about 150 cm, optionally from about 1 cm to about 120 cm, optionally from about 1 cm to about 100 cm, optionally from about 1 cm to about 80 cm, optionally from about 1 cm to about 60 cm, optionally from about 1 cm to about 40 cm, optionally from about 1 cm to about 30 cm long, and processing it with a probe electrode as described below. Particularly for the longer lengths in the above ranges, it is contemplated that relative motion between the PECVD or other chemical vapor deposition probe and the vessel can be useful during passivation layer or pH protective coating or layer formation. This can be done, for example, by moving the vessel with respect to the probe or moving the probe with respect to the vessel.

In these embodiments, it is contemplated that the barrier coating or layer discussed below can be thinner or less complete than would be preferred to provide the high gas barrier integrity needed in an evacuated blood collection tube, while still providing the long shelf life needed to store a liquid material in contact with the barrier coating or layer for an extended period.

As an optional feature of any of the foregoing embodiments the vessel can have a central axis. As an optional feature of any of the foregoing embodiments the vessel wall can be sufficiently flexible to be flexed at least once at 20° C., without substantially breaking the wall, over a range from at least substantially straight to a bending radius at the central axis of not more than 100 times as great as the outer diameter of the vessel.

As an optional feature of any of the foregoing embodiments the bending radius at the central axis can be, for example, not more than 90 times as great as, or not more than 80 times as great as, or not more than 70 times as great as, or not more than 60 times as great as, or not more than 50 times as great as, or not more than 40 times as great as, or not more than 30 times as great as, or not more than 20 times as great as, or not more than 10 times as great as, or not more than 9 times as great as, or not more than 8 times as great as, or not more than 7 times as great as, or not more than 6 times as great as, or not more than 5 times as great as, or not more than 4 times as great as, or not more than 3 times as great as, or not more than 2 times as great as, or not more than, the outer diameter of the vessel.

As an optional feature of any of the foregoing embodiments the vessel wall can be a fluid-contacting surface made of flexible material.

As an optional feature of any of the foregoing embodiments the vessel lumen can be the fluid flow passage of a pump.

As an optional feature of any of the foregoing embodiments the vessel can be a blood containing vessel. The passivation layer or pH protective coating or layer can be effective to reduce the clotting or platelet activation of blood exposed to the inner or generally cylindrical interior surface 16 44, compared to the same type of wall uncoated with a hydrophobic coating or layer.

It is contemplated that the incorporation of a hydrophobic coating or layer will reduce the adhesion or clot forming tendency of the blood, as compared to its properties in contact with an unmodified polymeric or $SiO_x$ surface. This property is contemplated to reduce or potentially eliminate the need for treating the blood with heparin, as by reducing the necessary blood concentration of heparin in a patient undergoing surgery of a type requiring blood to be removed from the patient and then returned to the patient, as when using a heart-lung machine during cardiac surgery. It is contemplated that this will reduce the complications of surgery involving the passage of blood through such a pharmaceutical package or other vessel, by reducing the bleeding complications resulting from the use of heparin.

Another embodiment can be a vessel including a wall and having an inner or generally cylindrical interior surface 16 44 defining a lumen. The inner or generally cylindrical interior surface 16 44 can have an at least partial passivation layer or pH protective coating or layer that presents a hydrophobic surface, the thickness of the passivation layer or pH protective coating or layer being from monomolecular thickness to about 1000 nm thick on the inner or generally cylindrical interior surface 16 44, the passivation layer or pH protective coating or layer being effective to reduce the clotting or platelet activation of blood exposed to the inner or generally cylindrical interior surface 16 44.

Several non-limiting examples of such a vessel are a blood transfusion bag, a blood sample collection tube (e.g. blood collection tube) or other vessel in which a sample has been collected, the tubing of a heart-lung machine, a flexible-walled blood collection bag, or tubing used to collect a patient's blood during surgery and reintroduce the blood into the patient's vasculature. If the vessel includes a pump for pumping blood, a particularly suitable pump can be a centrifugal pump or a peristaltic pump. The vessel can have a wall; the wall can have an inner or generally cylindrical interior surface 16 44 defining a lumen. The inner or generally cylindrical interior surface 16 44 of the wall can have an at least partial passivation layer or pH protective coating or layer of a protective coating or layer, which optionally also presents a hydrophobic surface. The passivation layer or pH protective coating or layer can be as thin as monomolecular thickness or as thick as about 1000 nm. Optionally, the vessel can contain blood viable for return to the vascular system of a patient disposed within the lumen in contact with the hydrophobic coating or layer.

An embodiment can be a blood containing vessel including a wall and having an inner or generally cylindrical interior surface 16 44 defining a lumen. The inner or generally cylindrical interior surface 16 44 can have an at least partial passivation layer or pH protective coating or layer that optionally also presents a hydrophobic surface. The passivation layer or pH protective coating or layer can also comprise or consist essentially of $SiO_xC_y$, where x and y are as defined in this specification. The vessel contains blood viable for return to the vascular system of a patient disposed within the lumen in contact with the hydrophobic coating or layer.

An embodiment can be carried out under conditions effective to form a hydrophobic passivation layer or pH protective coating or layer on the substrate. Optionally, the hydrophobic characteristics of the passivation layer or pH protective coating or layer can be set by setting the ratio of the oxidizing gas to the organosilicon precursor in the gaseous reactant, and/or by setting the electric power used for generating the plasma. Optionally, the passivation layer or pH protective coating or layer can have a lower wetting tension than the uncoated surface, optionally a wetting tension of from 20 to 72 dyne/cm, optionally from 30 to 60 dynes/cm, optionally from 30 to 40 dynes/cm, optionally 34 dyne/cm. Optionally, the passivation layer or pH protective coating or layer can be more hydrophobic than the uncoated surface.

As an optional feature of any of the foregoing embodiments, the vessel can have an inside diameter of at least 2 mm, optionally at least 4 mm, optionally at least 5 mm, optionally at least 6 mm. In an optional embodiment, the vessel can have an inside diameter of at most 15 mm, optionally at most 12 mm, optionally at most 10 mm, optionally at most 9 mm. Some non-limiting examples of double-ended ranges are from 4 to 15 mm, optionally from 5 to 10 mm, optionally from 6 to 10 mm.

As an optional feature of any of the foregoing embodiments the vessel can be a tube.

As an optional feature of any of the foregoing embodiments the lumen can have at least two open ends.

Syringe

The vessel of FIGS. 1-7 is a syringe, which is a contemplated type of vessel provided with a barrier coating or layer and a passivation layer or pH protective coating. The syringe can comprise a medical barrel 14 and a plunger tip, piston, stopper, or seal 36. The generally cylindrical interior surface 16 can define at least a portion of the medical barrel 250. The plunger tip, piston, stopper, or seal 36 can be a relatively sliding part of the syringe, with respect to the medical barrel 250. The term "syringe" is broadly defined to include cartridges, injection "pens," and other types of medical barrels or reservoirs adapted to be assembled with one or more other components to provide a functional syringe. A "syringe" is also broadly defined to include related articles such as auto-injectors, which provide a mechanism for dispensing the contents.

As one non-limiting way to make the syringe, a capped assembly 12 can be provided comprising a medical barrel 14, a dispensing portion 20, and a shield 28. The capped assembly 12 can be a complete article or it can be a portion of a complete article adapted to dispense fluid, such as a syringe, a cartridge, a catheter, or other article.

The medical barrel 14 can have a generally cylindrical interior surface 16 defining a medical barrel lumen 18. Optionally in any embodiment, the medical barrel 14 can further include an opening 32 spaced from the dispensing portion 20 and communicating through the generally cylindrical interior surface 16. Such an opening can be conventional, for example, in a syringe or cartridge, where a typical example can be the back opening 32 of a prefilled medical barrel, through which the plunger tip, piston, stopper, or seal 36 can be inserted after the medical barrel lumen 18 is filled with a suitable pharmaceutical preparation or other fluid material 40 to be dispensed.

The medical barrel 14 can be formed, for example, by molding, although the manner of its formation is not critical and it can also be formed, for example, by machining a solid preform. Preferably, the medical barrel can be molded by injection molding thermoplastic material, although it can also be formed by blow molding or a combined method.

As one preferred example, the medical barrel 14 can be formed by placing a dispensing portion 20 as described below in an injection mold and injection molding thermoplastic material about the dispensing portion, thus forming the medical barrel and securing the dispensing portion to the medical barrel. Alternatively, the dispensing portion and the medical barrel can be molded or otherwise formed as a single piece, or can be formed separately and joined in other ways. The medical barrel of any embodiment can be made of any suitable material. Several medical barrel materials particularly contemplated are COC (cyclic olefin copolymer), COP (cyclic olefin polymer), PET (polyethylene terephthalate), and polypropylene.

The dispensing portion 20 of the capped assembly 12 can be provided to serve as an outlet for fluid dispensed from the medical barrel lumen 18 of a completed article made from the capped assembly 12. One example of a suitable dispensing portion illustrated in the Figures can be a hypodermic needle.

Alternatively, in any embodiment the dispensing portion 20 can instead be a needle-free dispenser. One example of a suitable needle-free dispenser can be a blunt or flexible dispensing portion intended to be received in a complementary coupling to transfer fluid material 40. Such blunt or flexible dispensing portions are well known for use in syringes, intravenous infusion systems, and other systems and equipment to dispense material while avoiding the hazard of working with a sharp needle that may accidentally stick a health professional or other person. Another example of a needle-free dispenser can be a fluid jet or spray injection system that injects a free jet or spray of fluid directly through a patient's skin, without the need for an intermediate needle. Any type of dispensing portion 20, whether a hypodermic needle or any form of needle-free dispenser, is contemplated for use according to any embodiment of the present invention.

The dispensing portion 20 is or can be secured to the medical barrel 14 and includes a proximal opening 22, a distal opening 24, and a dispensing portion lumen 26. The proximal opening 22 communicates with the medical barrel lumen 18. The distal opening 24 can be located outside the medical barrel 14. The dispensing portion lumen 26 communicates between the proximal and distal openings 22, 24 of the dispensing portion 20. In the illustrated embodiment, the distal opening 24 can be at the sharpened tip of a hypodermic needle 20.

The shield 28 can be secured to the medical barrel 14 and at least substantially isolates the distal opening 24 of the dispensing portion 20 from pressure conditions outside the shield 28. Optionally in any embodiment, the shield 28 sufficiently isolates portions of the capped assembly 12 to provide a sufficient bio-barrier to facilitate safe use of the capped assembly 12 for transdermal injections.

The shield 28 can isolate the distal opening 24 in various ways. Effective isolation can be provided at least partially due to contact between the shield 28 and the distal opening 24, as shown in present FIGS. 2, 3, 4, and 7. In the illustrated embodiment, the tip of the dispensing portion 20 can be buried in the material of the shield 28. Alternatively in any embodiment, effective isolation can be provided at least partially due to contact between the shield 28 and the medical barrel 14, as also shown in present FIGS. 2, 3, 4, and 7. In the illustrated embodiment, the primary line of contact between the shield 28 and the medical barrel 14 can be at a rib 42 (best seen in FIG. 3) encircling and seated against a generally cylindrical surface 44 at the nose of the medical barrel 14. Alternatively in any embodiment, effective isolation can be provided due to both of these types of contact as illustrated in FIGS. 2-3, or in other ways, without limitation.

The shield 28 of any embodiment optionally can have a latching mechanism, best shown in FIG. 3, including a barb 46 and a catch 48 which engage to hold the shield 28 in place. The catch 48 can be made of sufficiently resilient material to allow the shield 28 to be removed and replaced easily.

If the dispensing portion 20 is a hypodermic needle, the shield 28 can be a specially formed needle shield. The original use of a needle shield is to cover the hypodermic needle before use, preventing accidental needle sticks and preventing contamination of the needle before it is injected in a patient or an injection port. A comparable shield preferably is used, even if the dispensing portion 20 is a needle-free dispenser, to prevent contamination of the dispenser during handling.

The shield 28 can be formed in any suitable way. For example, the shield 28 can be formed by molding thermoplastic material. Optionally in any embodiment, the thermoplastic material can be elastomeric material or other material that can be suitable for forming a seal. One suitable category of elastomeric materials is known generically as thermoplastic elastomer (TPE). An example of a suitable thermoplastic elastomer for making a shield 28 is Stelmi® Formulation 4800 (flexible shield formulation). Any other material having suitable characteristics can instead be used in any embodiment.

As another optional feature in any embodiment the shield 28 can be sufficiently permeable to a sterilizing gas to sterilize the portions of the capped assembly 12 isolated by the shield. One example of a suitable sterilizing gas is ethylene oxide. Shields 28 are available that are sufficiently permeable to the sterilizing gas that parts isolated by the shield can nonetheless be sterilized. An example of a shield formulation sufficiently permeable to accommodate ethylene oxide gas sterilization can be Stelmi® Formulation 4800.

Coatings or layers of $SiO_x$ are deposited by plasma enhanced chemical vapor deposition (PECVD) or other chemical vapor deposition processes on the vessel of a pharmaceutical package, in particular a thermoplastic package, to serve as a barrier coating or layer preventing oxygen, air, carbon dioxide, or other gases from entering the vessel and/or to prevent leaching of the pharmaceutical material into or through the package wall. The barrier coating or layer can be effective to reduce the ingress of atmospheric gas, for example oxygen, into the lumen compared to a vessel without a passivation layer or pH protective coating.

Moreover, certain syringes prefilled with synthetic and biological pharmaceutical formulations are very oxygen and moisture sensitive. A critical factor in the conversion from glass to plastic medical barrels will be the improvement of plastic oxygen and moisture barrier performance. The plasma passivation layer or pH protective coating or layer technology can be suitable to maintain the $SiO_x$ barrier coating or layer for protection against oxygen and moisture over an extended shelf life.

Examples of solutes in drugs usefully excluded by a barrier coating or layer in any embodiment include antibacterial preservatives, antioxidants, chelating agents, pH buffers, and combinations of any of these. In any embodiment the vapor-deposited coating or layer optionally can be a solvent barrier coating or layer for a solvent comprising a co-solvent used to increase drug solubilization.

In any embodiment the vapor-deposited coating or layer optionally can be a barrier coating or layer for water, glycerin, propylene glycol, methanol, ethanol, n-propanol, isopropanol, acetone, benzyl alcohol, polyethylene glycol, cotton seed oil, benzene, dioxane, or combinations of any two or more of these.

In any embodiment the vapor-deposited coating or layer optionally can be a metal ion barrier coating or layer.

In any embodiment the vapor-deposited coating or layer optionally can be a medical barrel wall material barrier coating or layer, to prevent or reduce the leaching of medical barrel material such as any of the base medical barrel resins mentioned previously and any other ingredients in their respective compositions.

The inventors have found, however, that such barrier coatings or layers of $SiO_x$ are eroded or dissolved by some fluid compositions, for example aqueous compositions having a pH above about 5. Since coatings or layers applied by chemical vapor deposition can be very thin—tens to hundreds of nanometers thick—even a relatively slow rate of erosion can remove or reduce the effectiveness of the barrier coating or layer in less time than the desired shelf life of a product package. This can be particularly a problem for fluid pharmaceutical compositions, since many of them have a pH of roughly 7, or more broadly in the range of 5 to 9, similar to the pH of blood and other human or animal fluids. The higher the pH of the pharmaceutical preparation, the more quickly it erodes or dissolves the $SiO_x$ coating or layer.

The inventors have further found that without a protective coating or layer borosilicate glass surfaces are eroded or dissolved by some fluid compositions, for example aqueous compositions having a pH above about 5. This can be particularly a problem for fluid pharmaceutical compositions, since many of them have a pH of roughly 7, or more broadly in the range of 5 to 9, similar to the pH of blood and other human or animal fluids. The higher the pH of the pharmaceutical preparation, the more quickly it erodes or dissolves the glass. Delamination of the glass can also result from such erosion or dissolution, as small particles of glass are undercut by the aqueous compositions having a pH above about 5.

Although the present invention does not depend upon the accuracy of the following theory, it is believed that the material properties of an effective $SiO_xC_y$ passivation layer or pH protective coating or layer and those of an effective lubricity coating or layer as described in U.S. Pat. No. 7,985,188 and in International Application PCT/US11/36097 are similar in some instances, such that a coating or layer having the characteristics of a lubricity coating or layer as described in certain working examples of this specification, U.S. Pat. No. 7,985,188, or International Application PCT/US11/36097 will also in certain cases serve as well as a passivation layer or pH protective coating or layer to passivate or protect the barrier coating or layer of the package and vice versa.

Three embodiments of the invention having many common features are those of FIGS. 7, 8 and 29. Some of their common features are the following, indicated in many cases by common reference characters or names. The nature of the features of each embodiment can be as described later in the specification.

The pharmaceutical packages of FIGS. 7-8 and 29 each include a vessel 210, a fluid composition 40, an $SiO_x$ barrier coating or layer 30, and a passivation layer or pH protective coating or layer 34. Each vessel 210 can have a lumen 18 defined at least in part by a wall interior portion 16 made of thermoplastic material.

The generally cylindrical interior surface 16 can have a generally cylindrical interior surface 16 44 254 facing the lumen 18 and an outer surface 216.

The fluid composition 40 can be contained in the lumen 18 and can have a pH between 4 and 10, alternatively between 5 and 9.

Barrier Coating or Layer

In the filled pharmaceutical package or other vessel 210 the barrier coating or layer 30 can be located between the inner or generally cylindrical interior surface 16 of the thermoplastic generally cylindrical interior surface 16 and the fluid material 40. The barrier coating or layer 286 of $SiO_x$ can be supported by the thermoplastic generally cylindrical interior surface 16. The barrier coating or layer 286 can have the characteristic of being subject to being measurably diminished in barrier improvement factor in less than six months as a result of attack by the fluid material 40. The barrier coating or layer 286 as described elsewhere in this specification, or in U.S. Pat. No. 7,985,188, can be used in any embodiment.

The barrier coating or layer 30 can be effective to reduce the ingress of atmospheric gas into the lumen 18, compared to an uncoated container otherwise the same as the pharmaceutical package or other vessel 210. The barrier coating or layer for any embodiment defined in this specification (unless otherwise specified in a particular instance) is optionally applied by PECVD as indicated in U.S. Pat. No. 7,985,188.

The barrier improvement factor (BIF) of the barrier coating or layer can be determined by providing two groups of identical containers, adding a barrier coating or layer, PECVD set, or other treatment to one group of containers, testing a barrier property (such as the rate of outgassing in micrograms per minute or another suitable measure) on containers having a barrier coating or layer, doing the same test on containers lacking a barrier coating or layer, and taking a ratio of the properties of the materials with versus without a barrier coating or layer. For example, if the rate of outgassing through the barrier coating or layer is one-third the rate of outgassing without a barrier coating or layer, the barrier coating or layer has a BIF of 3.

The barrier improvement factor can be determined in unused containers by the test outlined above, but it can also be used after storage of a fluid composition in the containers, to determine the effect of the fluid storage on the barrier improvement factor. A Protocol For Measuring Barrier Improvement Factor (BIF) After Solution Storage is described below for measuring the barrier improvement factor after storage of a fluid in the container in contact with the PECVD set.

The barrier coating or layer optionally can be characterized as an "$SiO_x$" coating or layer, and contains silicon, oxygen, and optionally other elements, in which x, the ratio of oxygen to silicon atoms, can be from about 1.5 to about 2.9, or 1.5 to about 2.6, or about 2. These alternative definitions of x apply to any use of the term $SiO_x$ in this specification. The barrier coating or layer can be applied, for example to the interior of a pharmaceutical package or other vessel, for example a sample collection tube (e.g. a blood collection tube), a medical barrel, a vial, or another type of vessel.

The barrier coating or layer 30 comprises or consists essentially of $SiO_x$, from 2 to 1000 nm thick (mean thickness), optionally in any embodiment a mean thickness from 10 to 500 nm with a standard deviation less than the mean thickness. Optionally in any embodiment, the barrier coating or layer 30 can have a thickness range from 10 to 500 nm.

The barrier coating or layer 30 of $SiO_x$ has a generally cylindrical interior surface 16 facing the lumen 18 and an outer surface facing the generally cylindrical interior surface 16. The barrier coating or layer 30 can be effective to reduce the ingress of atmospheric gas into the lumen 18 compared to an uncoated pharmaceutical package 210. One suitable barrier composition can be one where x is 2.3, for example.

For example, the barrier coating or layer such as 30 of any embodiment can be applied at a thickness of at least 2 nm, or at least 4 nm, or at least 7 nm, or at least 10 nm, or at least 20 nm, or at least 30 nm, or at least 40 nm, or at least 50 nm, or at least 100 nm, or at least 150 nm, or at least 200 nm, or at least 300 nm, or at least 400 nm, or at least 500 nm, or at least 600 nm, or at least 700 nm, or at least 800 nm, or at least 900 nm. The barrier coating or layer can be up to 1000 nm, or at most 900 nm, or at most 800 nm, or at most 700 nm, or at most 600 nm, or at most 500 nm, or at most 400 nm, or at most 300 nm, or at most 200 nm, or at most 100 nm, or at most 90 nm, or at most 80 nm, or at most 70 nm, or at most 60 nm, or at most 50 nm, or at most 40 nm, or at most 30 nm, or at most 20 nm, or at most 10 nm, or at most 5 nm thick. Specific thickness ranges composed of any one of the minimum thicknesses expressed above, plus any equal or greater one of the maximum thicknesses expressed above, are expressly contemplated. Another contemplated thickness range is 20-80 nm for the barrier coating or layer. The desired variation in thickness of the barrier coating or layer is +/−30% from the mean thickness, more preferably +/−15% from the mean thickness and most preferably, +/−5% from the mean thickness. The thickness of the $SiO_x$ or other barrier coating or layer can be measured, for example, by transmission electron microscopy (TEM), and its composition can be measured by X-ray photoelectron spectroscopy (XPS). The passivation layer or pH protective coating or layer described herein can be applied to a variety of pharmaceutical packages or other vessels made from plastic or glass, for example to plastic tubes, vials, and syringes.

Passivation Layer or pH Protective Coating or Layer

A passivation layer or pH protective coating or layer 34 of $SiO_xC_y$ can be applied, for example, by PECVD directly or indirectly to the barrier coating or layer 30 so it can be located between the barrier coating or layer 30 and the fluid material 40 in the finished article. The passivation layer or pH protective coating or layer 34 can have a generally cylindrical interior surface 16 facing the lumen 18 and an outer surface facing the generally cylindrical interior surface 16 of the barrier coating or layer 30. The passivation layer or pH protective coating or layer 34 can be supported by the thermoplastic generally cylindrical interior surface 16. The passivation layer or pH protective coating or layer 34 can be effective to keep the barrier coating or layer 30 at least substantially undissolved as a result of attack by the fluid material 40 for a period of at least six months, in one non-limiting embodiment.

Optionally, the passivation layer or pH protective coating or layer can be composed of $SiO_wC_yH_z$ or $SiN_wC_yH_z$, where w is 1, x is from about 0.5 to about 2.4, y is from about 0.6 to about 3, and z (if defined) is from about 2 to about 9.

The atomic ratio can be determined by XPS (X-ray photoelectron spectroscopy). XPS does not detect hydrogen atoms, so it is customary, when determining the atomic ratio by XPS, to omit hydrogen from the stated formulation. The formulation thus can be typically expressed as $SiO_xC_y$ or $SiO_xC_y$, where w is 1, x is from about 0.5 to about 2.4, and y is from about 0.6 to about 3, with no limitation on z.

The atomic ratios of Si, O, and C in the "lubricity and/or passivation layer or pH protective coating or layer" can be, as several options:

Si 100: O 50-150: C 90-200 (i.e. w=1, x=0.5 to 1.5, y=0.9 to 2);

Si 100: O 70-130: C 90-200 (i.e. w=1, x=0.7 to 1.3, y=0.9 to 2)

Si 100: O 80-120: C 90-150 (i.e. w=1, x=0.8 to 1.2, y=0.9 to 1.5)

Si 100: O 90-120: C 90-140 (i.e. w=1, x=0.9 to 1.2, y=0.9 to 1.4), or

Si 100: O 92-107: C 116-133 (i.e. w=1, x=0.92 to 1.07, y=1.16 to 1.33)

Typically, such a coating or layer would contain 36% to 41% carbon normalized to 100% carbon plus oxygen plus silicon. Alternatively, the passivation layer or pH protective coating or layer can have atomic concentrations normalized to 100% carbon, oxygen, and silicon, as determined by X-ray photoelectron spectroscopy (XPS) of less than 50% carbon and more than 25% silicon. Alternatively, the atomic concentrations can be from 25 to 45% carbon, 25 to 65% silicon, and 10 to 35% oxygen. Alternatively, the atomic concentrations can be from 30 to 40% carbon, 32 to 52% silicon, and 20 to 27% oxygen. Alternatively, the atomic concentrations can be from 33 to 37% carbon, 37 to 47% silicon, and 22 to 26% oxygen.

Optionally, the atomic concentration of carbon in the protective coating or layer, normalized to 100% of carbon, oxygen, and silicon, as determined by X-ray photoelectron spectroscopy (XPS), can be greater than the atomic concentration of carbon in the atomic formula for the organosilicon precursor. For example, embodiments are contemplated in which the atomic concentration of carbon increases by from 1 to 80 atomic percent, alternatively from 10 to 70 atomic percent, alternatively from 20 to 60 atomic percent, alternatively from 30 to 50 atomic percent, alternatively from 35 to 45 atomic percent, alternatively from 37 to 41 atomic percent.

Optionally, the atomic ratio of carbon to oxygen in the passivation layer or pH protective coating or layer can be increased in comparison to the organosilicon precursor, and/or the atomic ratio of oxygen to silicon can be decreased in comparison to the organosilicon precursor.

Optionally, the passivation layer or pH protective coating or layer can have an atomic concentration of silicon, normalized to 100% of carbon, oxygen, and silicon, as determined by X-ray photoelectron spectroscopy (XPS), less than the atomic concentration of silicon in the atomic formula for the feed gas. For example, embodiments are contemplated in which the atomic concentration of silicon decreases by from 1 to 80 atomic percent, alternatively by from 10 to 70 atomic percent, alternatively by from 20 to 60 atomic percent, alternatively by from 30 to 55 atomic percent, alternatively by from 40 to 50 atomic percent, alternatively by from 42 to 46 atomic percent.

As another option, a passivation layer or pH protective coating or layer is contemplated that can be characterized by a sum formula wherein the atomic ratio C:O can be increased and/or the atomic ratio Si:O can be decreased in comparison to the sum formula of the organosilicon precursor.

The passivation layer or pH protective coating or layer can have a density between 1.25 and 1.65 g/cm$^3$, alternatively between 1.35 and 1.55 g/cm$^3$, alternatively between 1.4 and 1.5 g/cm$^3$, alternatively between 1.4 and 1.5 g/cm$^3$, alternatively between 1.44 and 1.48 g/cm$^3$, as determined by X-ray reflectivity (XRR). Optionally, the organosilicon compound used as the precursor for the passivation layer or pH protective coating or layer can be octamethylcyclotetrasiloxane or tetramethyldisiloxane.

The passivation layer or pH protective coating or layer optionally can have an RMS surface roughness value (measured by AFM) of from about 2 to about 9, optionally from about 6 to about 8, optionally from about 6.4 to about 7.8. The $R_a$ surface roughness value of the passivation layer or pH protective coating or layer, measured by AFM, can be from about 4 to about 6, optionally from about 4.6 to about 5.8. The $R_{max}$ surface roughness value of the passivation layer or pH protective coating or layer, measured by AFM, can be from about 70 to about 160, optionally from about 84 to about 142, optionally from about 90 to about 130.

The rate of erosion, dissolution, or leaching (different names for related concepts) of the construction including a passivation layer or pH protective coating or layer 34, if directly contacted by the fluid material 40, can be less than the rate of erosion, dissolution, or leaching of the barrier coating or layer 30, if directly contacted by the fluid material 40.

The passivation layer or pH protective coating or layer 34 can be effective to isolate or protect the barrier coating or layer 30 from the fluid material 40 at least for sufficient time to allow the barrier coating or layer to act as a barrier during the shelf life of the pharmaceutical package or other vessel 210.

Optionally an FTIR absorbance spectrum of the passivation layer or pH protective coating or layer 34 of any embodiment of FIG. 7-8 or 29 can have a ratio greater than 0.75 between the maximum amplitude of the Si—O—Si symmetrical stretch peak normally located between about 1000 and 1040 cm$^{-1}$, and the maximum amplitude of the Si—O—Si asymmetric stretch peak normally located between about 1060 and about 1100 cm$^{-1}$. Alternatively in any embodiment, this ratio can be at least 0.8, or at least 0.9, or at least 1.0, or at least 1.1, or at least 1.2. Alternatively in any embodiment, this ratio can be at most 1.7, or at most 1.6, or at most 1.5, or at most 1.4, or at most 1.3. Any minimum ratio stated here can be combined with any maximum ratio stated here, as an alternative embodiment of the invention of FIGS. 7-8 and 29.

Optionally, in any embodiment the passivation layer or pH protective coating or layer, in the absence of the medicament, can have a non-oily appearance. This appearance has been observed in some instances to distinguish an effective passivation layer or pH protective coating or layer from a lubricity coating or layer, which in some instances has been observed to have an oily (i.e. shiny) appearance.

Optionally, in any embodiment the silicon dissolution rate by a 50 mm potassium phosphate buffer diluted in water for injection, adjusted to pH 8 with concentrated nitric acid, and containing 0.2 wt. % polysorbate-80 surfactant, (measured in the absence of the medicament, to avoid changing the dissolution reagent), at 40° C., can be less than 170 ppb/day. (Polysorbate-80 is a common ingredient of pharmaceutical preparations, available for example as Tween®-80 from Uniqema Americas LLC, Wilmington Del.) The silicon dissolution rate can be measured by determining the total silicon leached from the vessel into its contents, and does not distinguish between the silicon derived from the passivation layer or pH protective coating or layer 34, the lubricity coating or layer 287, the barrier coating or layer 30, or other materials present.

Optionally, in any embodiment the silicon dissolution rate can be less than 160 ppb/day, or less than 140 ppb/day, or less than 120 ppb/day, or less than 100 ppb/day, or less than 90 ppb/day, or less than 80 ppb/day. Optionally, in any embodiment the silicon dissolution rate can be more than 10 ppb/day, or more than 20 ppb/day, or more than 30 ppb/day, or more than 40 ppb/day, or more than 50 ppb/day, or more than 60 ppb/day. Any minimum rate stated here can be combined with any maximum rate stated here, as an alternative embodiment of the invention of FIGS. 7-8 and 29.

Optionally, in any embodiment the total silicon content of the passivation layer or pH protective coating or layer and barrier coating or layer, upon dissolution into a test composition with a pH of 8 from the vessel, can be less than 66 ppm, or less than 60 ppm, or less than 50 ppm, or less than 40 ppm, or less than 30 ppm, or less than 20 ppm.

Optionally, in any embodiment the calculated shelf life of the package (total Si/Si dissolution rate) can be more than six months, or more than 1 year, or more than 18 months, or more than 2 years, or more than 2½ years, or more than 3 years, or more than 4 years, or more than 5 years, or more than 10 years, or more than 20 years. Optionally, in any embodiment of FIGS. 7-8 and 29 the calculated shelf life of the package (total Si/Si dissolution rate) can be less than 60 years.

Any minimum time stated here can be combined with any maximum time stated here, as an alternative embodiment.

O-Parameter or P-Parameter

The passivation layer or pH protective coating or layer 34 optionally can have an O-Parameter measured with attenuated total reflection (ATR) of less than 0.4, measured as:

$$\text{O-Parameter} = \frac{\text{Intensity at } 1253 \text{ cm}^{-1}}{\text{Maximum intensity in the range } 1000 \text{ to } 1100 \text{ cm}^{-1}}.$$

The O-Parameter is defined in U.S. Pat. No. 8,067,070, which claims an O-parameter value of most broadly from 0.4 to 0.9. It can be measured from physical analysis of an FTIR amplitude versus wave number plot to find the numerator and denominator of the above expression. The O-Parameter can also be measured from digital wave number versus absorbance data.

U.S. Pat. No. 8,067,070 asserts that its claimed O-parameter range provides a superior passivation layer or pH protective coating or layer, relying on experiments only with HMDSO and HMDSN, which are both non-cyclic siloxanes. Surprisingly, it has been found by the present inventors that O-parameters outside the ranges claimed in U.S. Pat. No. 8,067,070 can provide better results than are obtained in U.S. Pat. No. 8,067,070.

Alternatively, the O-parameter can have a value of from 0.1 to 0.39, or from 0.15 to 0.37, or from 0.17 to 0.35.

Even another aspect of the invention can be a composite material as just described, exemplified in FIGS. 7-8 and 29, wherein the passivation layer or pH protective coating or layer shows an N-Parameter measured with attenuated total reflection (ATR) of less than 0.7, measured as:

$$\text{N-Parameter} = \frac{\text{Intensity at } 840 \text{ cm}^{-1}}{\text{Intensity at } 799 \text{ cm}^{-1}}.$$

The N-Parameter is also described in U.S. Pat. No. 8,067,070, and can be measured analogously to the O-Parameter except that intensities at two specific wave numbers are used—neither of these wave numbers is a range. U.S. Pat. No. 8,067,070 claims a passivation layer or pH protective coating or layer with an N-Parameter of 0.7 to 1.6. Again, the present inventors have made better coatings or layers employing a passivation layer or pH protective coating or layer 34 having an N-Parameter lower than 0.7, as described above. Alternatively, the N-parameter can have a value of 0.3 to lower than 0.7, or from 0.4 to 0.6, or from at least 0.53 to lower than 0.7.

Theory of Operation

The inventors offer the following theory of operation of the passivation layer or pH protective coating or layer described here. The invention is not limited by the accuracy of this theory or to the embodiments predictable by use of this theory.

The dissolution rate of the $SiO_x$ barrier coating or layer, or of glass, is believed to be dependent on SiO bonding within the layer or glass. Oxygen bonding sites (silanols) are believed to increase the dissolution rate.

It is believed that the OMCTS or TMDSO based passivation layer or pH protective coating or layer bonds with the silanol sites on the $SiO_x$ barrier coating or layer, or glass, to "heal" or passivate the $SiO_x$ surface or glass and thus dramatically reduce the dissolution rate. In this hypothesis, the thickness of the passivation layer or pH protective coating or layer is not the primary means of protection—the primary means can be passivation of the $SiO_x$ or glass surface. It is contemplated that a passivation layer or pH protective coating or layer as described in this specification can be improved by increasing the crosslink density of the passivation layer or pH protective coating or layer.

Optional Graded Composite Coatings or Layers

The passivation layer or pH protective coating or layer 34 and lubricity coating or layer can be either separate coatings or layers with a sharp transition or a single, graduated coating or layer that transitions between the passivation layer or pH protective coating or layer 34 and the lubricity coating or layer, without a sharp interface between them. Another optional expedient contemplated here, for adjacent coatings or layers of $SiO_x$ and a passivation layer or pH protective coating or layer, can be a graded composite of $SiO_x$ and $SiO_xC_y$, or its equivalent $SiO_xC_y$, as defined in the Definition Section.

A graded composite can be separate coatings or layers of a lubricity and/or protective and/or barrier coating or layer with a transition or interface of intermediate composition between them, or separate coatings or layers of a lubricity and/or protective and/or hydrophobic coating or layer and $SiO_x$ with an intermediate distinct passivation layer or pH protective coating or layer of intermediate composition between them, or a single coating or layer that changes continuously or in steps from a composition of a lubricity and/or protective and/or hydrophobic coating or layer to a composition more like $SiO_x$, going through the passivation layer or pH protective coating or layer in a normal direction.

The grade in the graded composite can go in either direction. For example, the composition of $SiO_x$ can be applied directly to the substrate and graduate to a composition further from the surface of a passivation layer or pH protective coating or layer, and optionally can further graduate to another type of coating or layer, such as a hydrophobic coating or layer or a lubricity coating or layer. Additionally, in any embodiment an adhesion coating or layer, for example $SiO_xC_y$, or its equivalent $SiO_xC_y$, another name for which is a tie coating or layer, optionally can be applied directly to the substrate before applying the barrier coating or layer.

A graduated passivation layer or pH protective coating or layer is particularly contemplated if a coating or layer of one composition is better for adhering to the substrate than another, in which case the better-adhering composition can, for example, be applied directly to the substrate. It is contemplated that the more distant portions of the graded passivation layer or pH protective coating or layer can be less compatible with the substrate than the adjacent portions of the graded passivation layer or pH protective coating or layer, since at any point the passivation layer or pH protective coating or layer can be changing gradually in properties, so adjacent portions at nearly the same depth of the passivation layer or pH protective coating or layer have nearly identical composition, and more widely physically separated portions at substantially different depths can have more diverse properties. It is also contemplated that a passivation layer or pH protective coating or layer portion that forms a better barrier against transfer of material to or from the substrate can be directly against the substrate, to prevent the more remote passivation layer or pH protective coating or layer portion that forms a poorer barrier from being contaminated with the material intended to be barred or impeded by the barrier.

The applied coatings or layers, instead of being graded, optionally can have sharp transitions between one coating or layer and the next, without a substantial gradient of composition. Such passivation layer or pH protective coating or layer can be made, for example, by providing the gases to produce a coating or layer as a steady state flow in a non-plasma state, then energizing the system with a brief plasma discharge to form a coating or layer on the substrate. If a subsequent passivation layer or pH protective coating or layer is to be applied, the gases for the previous passivation layer or pH protective coating or layer are cleared out and the gases for the next passivation layer or pH protective coating or layer are applied in a steady-state fashion before energizing the plasma and again forming a distinct coating or layer on the surface of the substrate or its outermost previous passivation layer or pH protective coating or layer, with little if any gradual transition at the interface.

A preferred PECVD set, sometimes referred to here as a trilayer coating, can be applied to the medical barrel: a tie layer is applied based on TMDSO, a barrier layer is applied based on HDMSO, and a pH protective layer is applied based on TDMSO.

PECVD Apparatus

The present apparatus can be used for plasma modifying a workpiece such as a medical barrel 12 having a surface to be treated, for example a workpiece such as a medical barrel having a lumen 18 surrounded by a generally cylindrical interior surface 16 defining a surface to be treated. The present apparatus and method can also be used to treat other types of surfaces, such as the exterior surface of a plunger tip, stopper, piston, or stopper. The apparatus generally includes a plasma generator for providing plasma under conditions effective for plasma modification of the generally cylindrical interior surface 16 of the workpiece 12. The apparatus also includes one or more magnetic field generators, further explained in a later section, (for example, for example any of 61-78, 86-91, 93, 95, 97, or 99) for providing a magnetic field in at least a portion of the lumen 18, or more broadly in or near the plasma. The magnetic field has a position, orientation, and field strength effective to improve the uniformity of plasma modification of the surface.

The apparatus also includes a support for supporting a workpiece 12 in the apparatus in an operative position.

The low-pressure PECVD process described in U.S. Pat. No. 7,985,188, modified by any arrangement of magnets described or claimed in this specification, can be used to provide the barrier coating or layer, lubricity coating or layer, and/or passivation layer or pH protective coating or layer described in this specification. A brief synopsis of that process follows, with reference to present FIGS. 4-6.

A PECVD apparatus or coating station 60 suitable for the present purpose includes a vessel support 50, an inner electrode defined by the probe 108, an outer electrode 160, which optionally is generally cylindrical, and a power supply 162. The inner electrode 108 is located at least partially within the lumen of the medical barrel during PECVD processing, and the outer electrode 160 is located outside the lumen of the medical barrel during PECVD processing. The pre-capped assembly 12 seated on the vessel support 50 has a medical barrel that defines a plasma reaction chamber, which optionally can be a vacuum chamber. Optionally, a source of vacuum 98, a reactant gas source 144, a gas feed (probe 108) or a combination of two or more of these can be supplied.

In any embodiment of the invention, the PECVD apparatus is contemplated for applying a PECVD set of one or more coatings on a medical barrel, particularly on its wall having a generally cylindrical inner surface defining a lumen, the generally cylindrical inner surface having a diameter in the range from 4 to 15 mm.

The PECVD apparatus can be used for atmospheric-pressure PECVD, in which case the plasma reaction chamber defined by the pre-capped assembly 12 does not need to function as a vacuum chamber.

Figure 4:
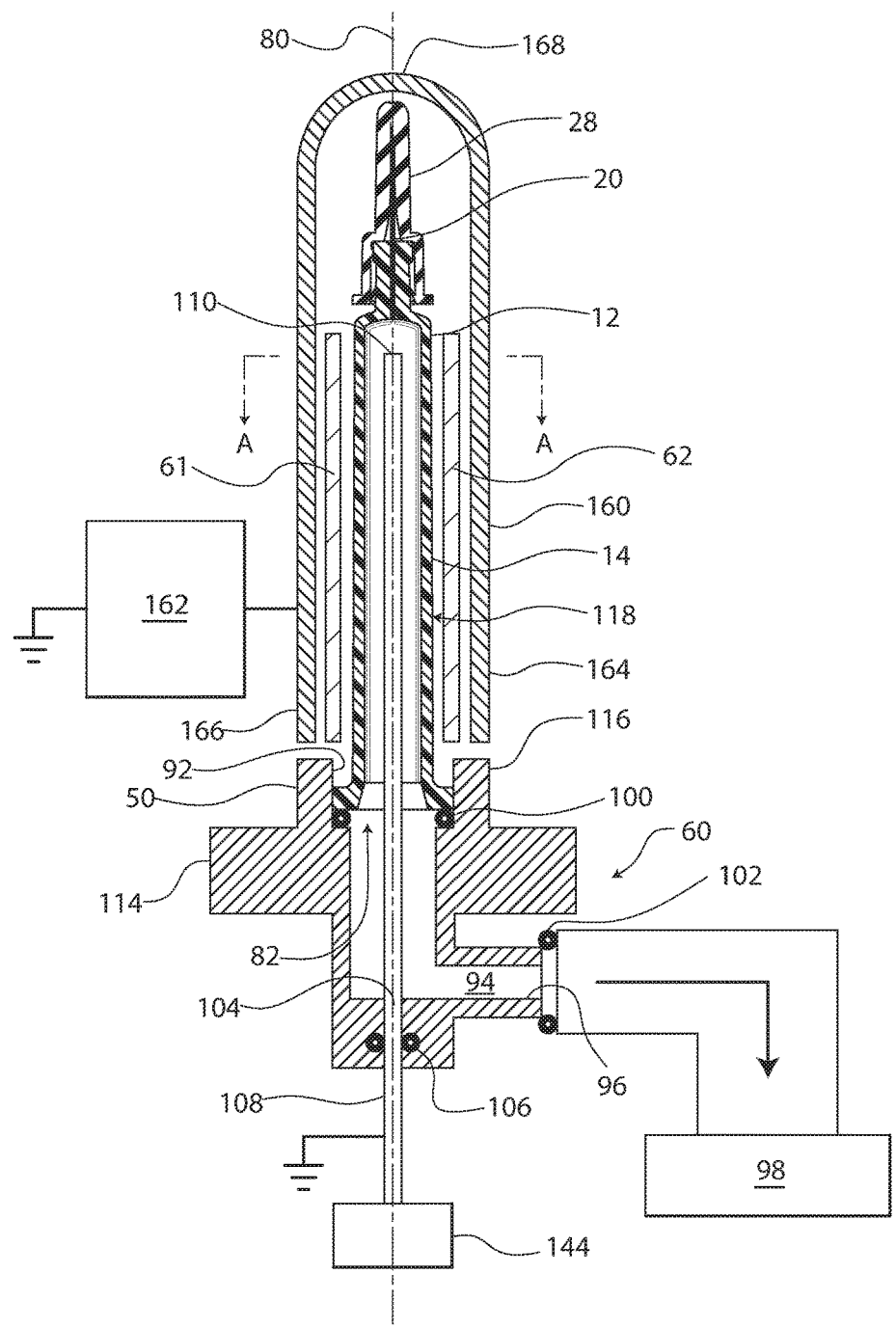
FIG. 4 is a schematic longitudinal section of the capped assembly of FIGS. 1 and 2 seated on a chemical vapor deposition coating station.

Referring to FIGS. 4-6, the vessel support 50 comprises a gas inlet port 104 for conveying a gas into the pre-capped assembly 12 seated on the opening 82. The gas inlet port 104 can have a sliding seal provided for example by at least one O-ring 106, or two O-rings in series, or three O-rings in series, which can seat against a cylindrical probe 108 when the probe 108 is inserted through the gas inlet port 104. The probe 108 can be a gas inlet conduit that extends to a gas delivery port at its distal end 110. The distal end 110 of the illustrated embodiment can be inserted at an appropriate depth in the pre-capped assembly 12 for providing one or more PECVD reactants and other precursor feed or process gases. The inner electrode defined by the probe 108 has an outer surface including an end or distal portion 110 extending into the lumen and coaxial with and (optionally) radially spaced from 1.2 to 6.9 mm. from the generally cylindrical inner surface. The inner electrode 108 has an internal passage 110 for supplying feed materials, having at least one outlet for introducing a gaseous PECVD precursor into the lumen, here any of the perforations 120-142 or the port 110, for example.

Electromagnetic energy can be applied to the outer electrode 160 under conditions effective to form a plasma enhanced chemical vapor deposition (PECVD) gas barrier coating having a mean thickness on the generally cylindrical inner surface FIG. 6 shows additional optional details of the coating station 60 that are usable, for example, with all the illustrated embodiments. The coating station 60 can also have a main vacuum valve 574 in its vacuum line 576 leading to the pressure sensor 152. A manual bypass valve 578 can be provided in the bypass line 580. A vent valve 582 controls flow at the vent 404.

Flow out of the PECVD gas or precursor source 144 can be controlled by a main reactant gas valve 584 regulating flow through the main reactant feed line 586. One component of the gas source 144 can be the organosilicon liquid reservoir 588, containing the precursor. The contents of the reservoir 588 can be drawn through the organosilicon capillary line 590, which optionally can be provided at a suitable length to provide the desired flow rate. Flow of organosilicon vapor can be controlled by the organosilicon shut-off valve 592. Pressure can be applied to the headspace 614 of the liquid reservoir 588, for example a pressure in the range of 0-15 psi (0 to 78 cm. Hg), from a pressure source 616 such as pressurized air connected to the headspace 614 by a pressure line 618 to establish repeatable organosilicon liquid delivery that is not dependent on atmospheric pressure (and the fluctuations therein). The reservoir 588 can be sealed and the capillary connection 620 can be at the bottom of the reservoir 588 to ensure that only neat organosilicon liquid (not the pressurized gas from the headspace 614) flows through the capillary tube 590. The organosilicon liquid optionally can be heated above ambient temperature, if necessary or desirable to cause the organosilicon liquid to evaporate, forming an organosilicon vapor. To accomplish this heating, the apparatus can advantageously include heated delivery lines from the exit of the precursor reservoir to as close as possible to the gas inlet into the syringe. Preheating can be useful, for example, when feeding OMCTS.

Oxidant gas can be provided from the oxidant gas tank 594 via an oxidant gas feed line 596 controlled by a mass flow controller 598 and provided with an oxidant shut-off valve 600.

Optionally in any embodiment, other precursor, oxidant, and/or diluent gas reservoirs such as 602 can be provided to supply additional materials if needed for a particular deposition process. Each such reservoir such as 602 can have an appropriate feed line 604 and shut-off valve 606.

Referring especially to FIG. 4, the processing station 60 can include an outer electrode 160 fed by a radio frequency power supply 162 for providing an electric field for generating plasma within the pre-capped assembly 12 during processing. In this embodiment, the probe 108 can be electrically conductive and can be grounded, thus providing a counter-electrode within the pre-capped assembly 12. Alternatively, in any embodiment the outer electrode 160 can be grounded and the probe 108 can be directly connected to the power supply 162.

In the embodiment of FIGS. 4-6, the outer electrode 160 can either be generally cylindrical as illustrated in FIGS. 4 and 5 or a generally U-shaped elongated channel. Each illustrated embodiment can have one or more sidewalls, such as 164 and 166, and optionally a top end 168, disposed about the pre-capped assembly 12 in close proximity.

Optionally in any embodiment, the outer electrode (160) can be made of foraminous material, for example a metal wire mesh material. Alternatively, the outer electrode (160) can be made of continuous material (meaning not perforated, woven, knitted or felted, for example), such as a metal cylinder.

Optionally in any embodiment, the inner electrode (108) extends axially into the lumen (18).

Optionally in any embodiment, the plasma modification of the surface (16) of the workpiece (12) comprises chemical vapor deposition, optionally plasma enhanced chemical vapor deposition (PECVD).

As was previously indicated, the inner electrode (108) optionally can do double duty as a material supply tube (104) for providing gaseous material to the lumen (18). The material supply tube (104) optionally, in any embodiment, has a wall disposed within the lumen (18). Optionally in any embodiment, the wall has perforations (any of 122-142) to pass gaseous material to the lumen (18). See in particular FIGS. 4-5 and 26-28.

Figure 26:
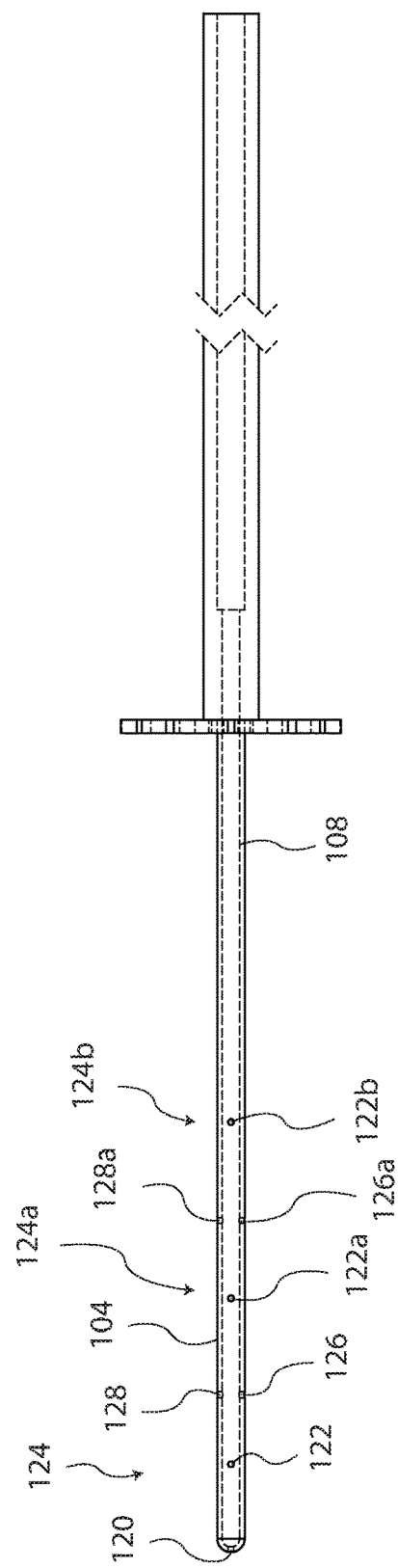
FIG. 26 is a side elevation of a first alternative gas inlet and inner electrode with a 90-degree perforation pattern, usable analogous to the corresponding structure 108 of FIG. 5 in any embodiment of the invention.
Figure 27:
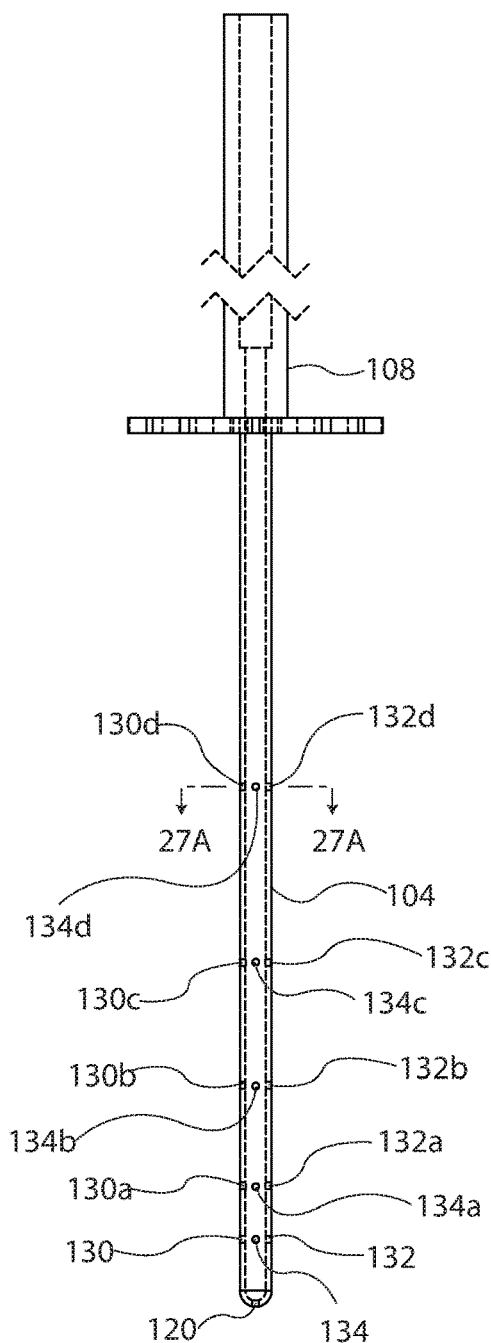
FIG. 27 is a side elevation of a second alternative gas inlet and inner electrode with a triangular or 120-degree perforation pattern, usable analogous to the corresponding structure 108 of FIG. 5 in any embodiment of the invention.
Figure 27A:
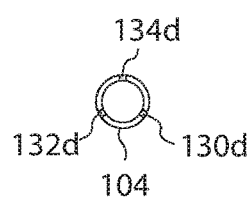
Figure 28:
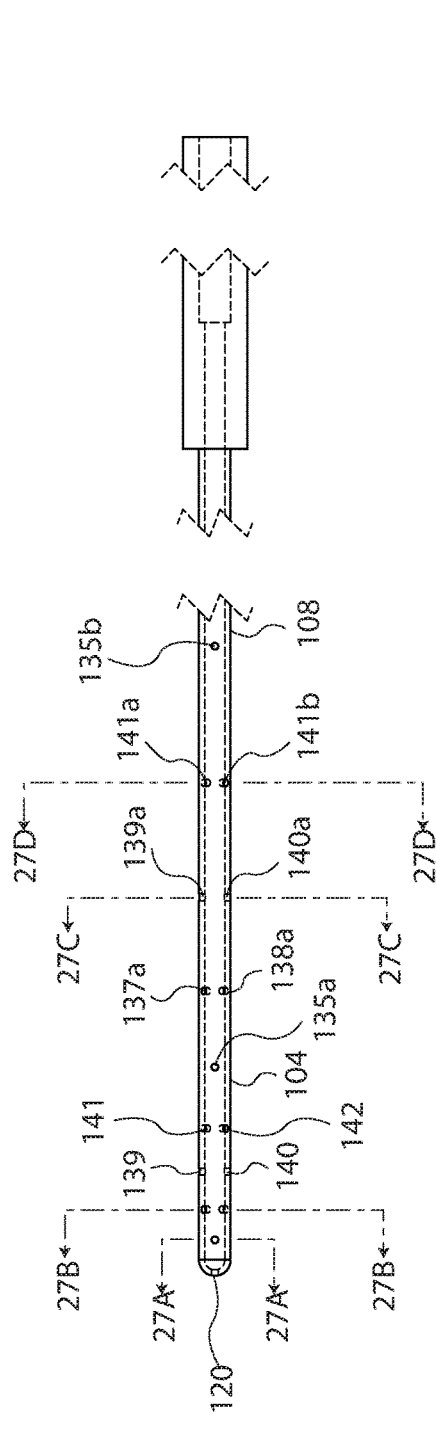
FIG. 28 is a side elevation of a third alternative gas inlet and inner electrode with a spiral or 45-degree perforation array, usable analogous to the corresponding structure 108 of FIG. 5 in any embodiment of the invention.
Figure 28A:
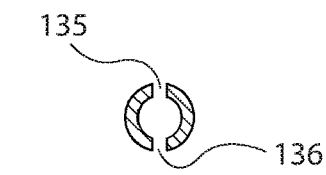
Figure 28B:
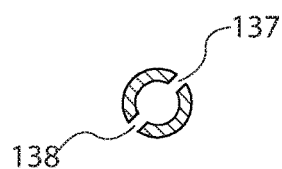
Figure 28C:
Figure 28D:
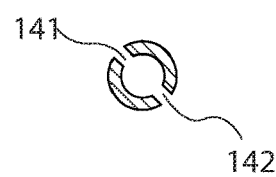

Optionally in any embodiment, the perforations (e.g. 122, 122a, 122b; 134, 134a, 134b, 134c, 134d; or 135, 135a, 135b) can be distributed axially along the generally cylindrical interior surface 16, as shown in FIGS. 26-28. The perforations (e.g. 122, 124; 130, 132, 134; or 139, 140) optionally can be distributed circumferentially along the generally cylindrical interior surface 16, as shown in FIGS. 26-28.

The perforations (any of 122-142) can be distributed as circumferentially spaced series of two or more perforations, the respective series spaced axially along the generally cylindrical interior surface 16, as shown in FIGS. 26-28. The perforations (any of 122-128 or 135-142) can be distributed as plural circumferentially spaced series of two diametrically opposed perforations per series, the respective series spaced axially along the generally cylindrical interior surface 16, as shown in FIGS. 26 and 28. The diametrically opposed perforations of a first series (e.g. 122 and 124) can be displaced circumferentially about 90 degrees on the generally cylindrical interior surface 16 with respect to the diametrically opposed perforations of an adjacent second series (e.g. 126 and 128), as shown in FIG. 26. The diametrically opposed perforations of a first series (e.g. 135 and 136) can be displaced circumferentially about 45 degrees on the generally cylindrical interior surface 16 with respect to the diametrically opposed perforations of the adjacent second series (e.g. 137 and 138), as shown in FIG. 28. The perforations can be distributed as plural circumferentially spaced series of at least three 120-degree-spaced perforations per series (e.g. 130, 132, and 134), the respective series (e.g. 130, 132, and 134, vs. 130a, 132a, and 134a) spaced axially along the generally cylindrical interior surface 16, as shown in FIG. 27.

As another option, combinations of these different patterns of perforations, or other patterns known or obvious to those skilled in the art, can be used in a single material supply tube 104.

Application of Barrier Coating or Layer

When carrying out the present method, a barrier coating or layer 30 can be applied directly or indirectly to at least a portion of the generally cylindrical interior surface 16 of the medical barrel 14. In the illustrated embodiment, the barrier coating or layer 30 can be applied while the pre-capped assembly 12 is capped, though this is not a requirement. The barrier coating or layer 30 can be an $SiO_x$, barrier coating or layer applied by plasma enhanced chemical vapor deposition (PECVD), under conditions substantially as described in U.S. Pat. No. 7,985,188. The barrier coating or layer 30 can be applied under conditions effective to maintain communication between the medical barrel lumen 18 and the dispensing portion lumen 26 via the proximal opening 22 at the end of the applying step.

In any embodiment the barrier coating or layer 30 optionally can be applied through the opening 32.

In any embodiment the barrier coating or layer 30 optionally can be applied by introducing a vapor-phase precursor material through the opening and employing chemical vapor deposition to deposit a reaction product of the precursor material on the generally cylindrical interior surface 16 of the medical barrel.

In any embodiment the precursor material for forming the barrier coating or layer optionally can be any of the precursors described in U.S. Pat. No. 7,985,188 or in this specification for formation of the passivation layer or pH protective coating or layer.

In any embodiment the reactant vapor material optionally can be a precursor material mixture with one or more oxidant gases and a diluent gas in a partial vacuum through the opening and employing chemical vapor deposition to deposit a reaction product of the precursor material mixture on the generally cylindrical interior surface 16 of the medical barrel.

In any embodiment the reactant vapor material optionally can be passed through the opening at sub-atmospheric pressure.

In any embodiment plasma optionally can be generated in the medical barrel lumen 18 by placing an inner electrode into the medical barrel lumen 18 through the opening 32, placing an outer electrode outside the medical barrel 14 and using the electrodes to apply plasma-inducing electromagnetic energy which optionally can be radio frequency energy, in the medical barrel lumen 18. If a different arrangement is used, the plasma-inducing electromagnetic energy can be microwave energy or other forms of electromagnetic energy.

In any embodiment the electromagnetic energy optionally can be direct current.

In any embodiment the electromagnetic energy optionally can be alternating current. The alternating current optionally can be modulated at frequencies including audio, or microwave, or radio, or a combination of two or more of audio, microwave, or radio.

In any embodiment the electromagnetic energy optionally can be applied across the medical barrel lumen (18).

Application of Passivation Layer or pH Protective Coating or Layer

In any embodiment, in addition to applying a first coating or layer as described above, the method optionally can include applying second or further coating or layer of the same material or a different material. As one example useful in any embodiment, particularly contemplated if the first coating or layer is an $SiO_x$ barrier coating or layer, a further coating or layer can be placed directly or indirectly over the barrier coating or layer. One example of such a further coating or layer useful in any embodiment is a passivation layer or pH protective coating or layer 34.

Precursors

The precursor for any of the processes for forming the barrier coating or layer, the passivation layer or pH protective coating or layer, or a lubricity coating or layer can include any of the following precursors.

The precursor can be an organosilicon or related compound. The organosilicon precursor is broadly defined as an organometallic precursor. An organometallic precursor is defined in this specification as comprehending compounds of metal elements from Group III and/or Group IV of the Periodic Table having organic residues, for example hydrocarbon, aminocarbon or oxycarbon residues. Organometallic compounds as presently defined include any precursor having organic moieties bonded to silicon or other Group III/IV metal atoms directly, or optionally bonded through oxygen or nitrogen atoms. The relevant elements of Group III of the Periodic Table are Boron, Aluminum, Gallium, Indium, Thallium, Scandium, Yttrium, and Lanthanum, Aluminum and Boron being preferred. The relevant elements of Group IV of the Periodic Table are Silicon, Germanium, Tin, Lead, Titanium, Zirconium, Hafnium, and Thorium, with Silicon and Tin being preferred. Other volatile organic compounds can also be contemplated. However, organosilicon compounds are preferred for performing present invention.

An organosilicon precursor is contemplated, where an "organosilicon precursor" is defined throughout this specification most broadly as a compound having compound having at least one of the linkages:

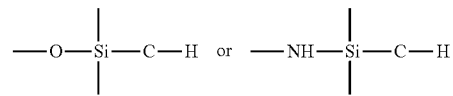

which is a tetravalent silicon atom connected to an oxygen atom and an organic carbon atom (an organic carbon atom being a carbon atom bonded to at least one hydrogen atom). Another contemplated structure is a tetravalent silicon atom connected to an —NH— linkage and an organic carbon atom (an organic carbon atom being a carbon atom bonded to at least one hydrogen atom). A further description and many examples of organosilicon precursors can be found in U.S. Pat. No. 7,985,188.

The organosilicon precursor can be delivered at a rate of equal to or less than 10 sccm, optionally equal to or less than 6 sccm, optionally equal to or less than 2.5 sccm, optionally equal to or less than 1.5 sccm, optionally equal to or less than 1.25 sccm. Larger pharmaceutical packages or other vessels or other changes in conditions or scale may require more or less of the precursor.

Another example of a suitable type of precursor is a fluorinated precursor for a fluorinated polymer coating or layer. The fluorinated polymer can be deposited directly or with intervening coatings or layers on the sliding surface of a plunger tip, piston, stopper, or seal 36, the generally cylindrical interior surface 16, or both. The fluorinated polymer optionally is applied by chemically modifying a precursor, while on or in the vicinity of the fluid receiving generally cylindrical interior surface 16.

Optionally, the precursor comprises:
dimeric tetrafluoroparaxylylene,
difluorocarbene,
monomeric tetrafluoroethylene,
oligomeric tetrafluoroethylene having the formula $F_2C=CF(CF_2)_xF$ in which x is from 1 to 100, optionally 2 to 50, optionally 2-20, optionally 2-10,
sodium chlorodifluoroacetate,
chlorodifluoromethane,
bromodifluoromethane,
hexafluoropropylene oxide,
1H,1H,2H,2H-perfluorodecyl acrylate (FDA),
a bromofluoroalkane in which the alkane moiety has from 1 to 6 carbon atoms,
an iodofluoroalkane in which the alkane moiety has from 1 to 6 carbon atoms, or
a combination of any two or more of these.

Ratios of Components for Passivation Layer or pH Protective Coating or Layer

Generally, for a passivation layer or pH protective coating or layer, $O_2$ can be present in an amount (which can, for example be expressed by the flow rate in sccm) which can be less than one order of magnitude greater than the organosilicon amount. In contrast, in order to achieve a barrier coating or layer, the amount of $O_2$ typically can be at least one order of magnitude higher than the amount of organosilicon precursor.

As some specific examples of suitable proportions of the respective constituents, the volume ratio (in sccm) of organosilicon precursor to $O_2$ for a passivation layer or pH protective coating or layer can be in the range from 0.1:1 to 10:1, optionally in the range from 0.3:1 to 8:1, optionally in the range from 0.5:1 to 5:1, optionally from 1:1 to 3:1. Some non-exhaustive alternative selections and suitable proportions of the precursor gas, oxygen, and a diluent gas are provided below.

The process gas can contain this ratio of gases for preparing a lubricity and/or passivation layer or pH protective coating or layer:

from 0.5 to 10 standard volumes of the precursor;
from 1 to 100 standard volumes of a diluent gas,
from 0.1 to 10 standard volumes of an oxidizing agent.

Exemplary reaction conditions for preparing a passivation layer or pH protective coating or layer in a 3 ml sample size syringe with a ⅛" diameter tube (open at the end) are as follows:

Flow Rate Ranges:
OMCTS: 0.5-10 sccm
Oxygen: 0.1-10 sccm
Argon: 1.0-200 sccm
Power: 0.1-500 watts The presence of the precursor and $O_2$ in the volume ratios as given in the working examples can be specifically suitable to achieve a passivation layer or pH protective coating or layer.

In one aspect of the invention, a carrier or diluent gas (two different names for an inert gas feed in PECVD) can be absent in the reaction mixture; in another aspect of the invention, it can be present. Suitable diluent gases include any noble gas, for example Argon, Helium, Neon, Xenon or combinations of two or more of these. When the diluent gas is present in the reaction mixture, it is typically present in a volume (in sccm) exceeding the volume of the organosilicon precursor. For example, the ratio of the organosilicon precursor to diluent gas can be from 1:1 to 1:50, optionally from 1:5 to 1:40, optionally from 1:10 to 1:30. One function of the diluent gas can be to dilute the reactants in the plasma, encouraging the formation of a coating or layer on the substrate instead of powdered reaction products that do not adhere to the substrate and are largely removed with the exhaust gases.

The addition of Argon gas has been found to improve the performance of the passivation layer or pH protective coating or layer 34. It is believed that additional ionization of the molecule in the presence of Argon contributes to this performance. The Si—O—Si bonds of the molecule have a high bond energy followed by the Si—C, with the C—H bonds being the weakest. Passivation or pH protection appear to be achieved when a portion of the C—H bonds are broken. This allows the connecting (cross-linking) of the structure as it grows. Addition of oxygen (with the Argon) is understood to enhance this process. A small amount of oxygen can also provide C—O bonding to which other molecules can bond. The combination of breaking C—H bonds and adding oxygen all at low pressure and power leads to a chemical structure that can be solid while providing passivation or pH protection.

In any of the disclosed embodiments, one preferred combination of process gases includes octamethylcyclotetrasiloxane (OMCTS), TMDSO, HMDSO or another organosilicon compound as the precursor; $O_2$, nitrous oxide ($N_2O$), ozone ($O_3$), water vapor (which can decompose in the plasma to yield oxygen) or another oxidizing gas, which means any other gas that oxidizes the precursor during PECVD at the conditions employed, preferably $O_2$; and a diluent gas, for example a noble gas, for example helium, argon, krypton, xenon, neon, or a combination of two or more of these. Helium and argon are particularly contemplated.

The gaseous reactant or process gas optionally can be at least substantially free of nitrogen. This combination is contemplated to improve the resulting passivation layer or pH protective coating or layer.

Application Method

A passivation layer or pH protective coating or layer 34 optionally can be applied directly or indirectly over the barrier coating or layer 30, and optionally can be applied to a pre-assembly such as 12 while the pre-assembly is capped, under conditions effective to maintain communication between the medical barrel lumen 18 and the dispensing portion lumen 26 via the proximal opening 22 at the end of applying the passivation layer or pH protective coating or layer 34.

Vessel Made of Glass

Optionally in any embodiment, the passivation layer or pH protective coating or layer 34 can be applied as the first or sole PECVD-deposited coating or layer 30, instead of or in addition to its application as a further coating or layer. This expedient may be useful, for example, where the medical barrel is made of glass. The presently disclosed passivation layer or pH protective coating or layer also can reduce the dissolution of glass by contents having the pH values indicated as attacking $SiO_x$ coatings or layers.

A pharmaceutical package 210 is contemplated as shown in any embodiment, for example FIGS. 7-8 and 29, comprising a vessel or vessel part made of glass; optionally a barrier coating or layer such as 30 on the vessel or vessel part; a passivation layer or pH protective coating or layer such as 34 on the vessel, vessel part, or barrier coating or layer; and a pharmaceutical composition or preparation contained within the vessel.

In this glass embodiment the barrier coating or layer can be optional because a glass vessel wall in itself is an extremely good barrier coating or layer. It is contemplated to optionally provide a barrier coating or layer primarily to provide isolation: in other words, to prevent contact and interchange of material of any kind, such as ions of the glass or constituents of the pharmaceutical composition or preparation between the vessel wall and the contents of the vessel. The protective coating or layer as defined in this specification can be contemplated to perform the isolation function independently, at least to a degree. This passivation layer or pH protection coating or layer can be contemplated to provide a useful function on glass in contact with the pharmaceutical composition or preparation, as borosilicate glass, commonly used today for pharmaceutical packaging, can be dissolved by a fluid composition having a pH exceeding 5. Particularly in applications where such dissolution can be disadvantageous or perceived to be disadvantageous, the present passivation layers or protective coatings or layers will find utility.

The vessel can be made, for example of glass of any type used in medical or laboratory applications, such as soda-lime glass, borosilicate glass, or other glass formulations. One function of a passivation layer or pH protective coating or layer on a glass vessel can be to reduce the ingress of ions in the glass, either intentionally or as impurities, for example sodium, calcium, or others, from the glass to the contents of the pharmaceutical package or other vessel, such as a reagent or blood in an evacuated blood collection tube. Alternatively, a dual functional protective/lubricity coating or layer can be used on a glass vessel in whole or in part, such as selectively at surfaces contacted in sliding relation to other parts, to provide lubricity, for example to ease the insertion or removal of a stopper or passage of a sliding element such as a piston in a syringe, as well as to provide the isolation of a passivation layer or pH protective coating or layer. Still another reason to coat a glass vessel, for example with a dual functional hydrophobic and passivation layer or pH protective coating or layer, can be to prevent a reagent or intended sample for the pharmaceutical package or other vessel, such as blood, from sticking to the wall of the vessel or an increase in the rate of coagulation of the blood in contact with the wall of the vessel, as well as to provide the isolation of a passivation layer or pH protective coating or layer.

A related embodiment can be a vessel as described in the previous paragraphs, in which the barrier coating or layer can be made of soda lime glass, borosilicate glass, or another type of glass coating or layer on a substrate.

Plasma Conditions for Passivation Layer or pH Protective Coating or Layer

The precursor can be contacted with a plasma made by energizing the vicinity of the precursor with electrodes powered at radio frequency, optionally a frequency of 10 kHz to 2.45 GHz, optionally from 10 kHz to less than 300 MHz, optionally from 1 to 50 MHz, optionally from 10 to 15 MHz, alternatively from about 13 to about 14 MHz, optionally at or about 13.56 MHz. Typically, the plasma in the PECVD process can be generated at RF frequency, although microwave or other electromagnetic energy can also be used. For providing a protective coating or layer on the interior of a vessel by a plasma reaction carried out within the vessel, the plasma of any embodiment can be generated with an electric power of from 0.1 to 500 W, optionally from 0.1 to 400 W, optionally from 0.1 to 300 W, optionally from 1 to 250 W, optionally from 1 to 200 W, even optionally from 10 to 150 W, optionally from 20 to 150 W, for example of 40 W, optionally from 40 to 150 W, even optionally from 60 to 150 W.

For any PECVD process in any embodiment herein, PECVD can be initiated by applying an initial higher power level within the stated range, followed by a subsequent lower power level within the stated range. The initial higher power level can be applied, for example, for from 1 to 3 seconds. The subsequent lower power level can be applied, for example, for the remainder of PECVD.

For forming a coating or layer intended to provide lubricity in addition to passivation or pH protection, the precursor can be contacted with a plasma made by energizing the vicinity of the precursor with electrodes supplied with electric power at from 0.1 to 25 W, optionally from 1 to 22 W, optionally from 1 to 10 W, even optionally from 1 to 5 W, optionally from 2 to 4 W, for example of 3 W, optionally from 3 to 17 W, even optionally from 5 to 14 W, for example 6 or 7.5 W, optionally from 7 to 11 W, for example of 8 W.

The ratio of the electrode power to the plasma volume can be less than 100 W/ml, optionally can be from 0.1 to 100 W/mL, optionally can be from 5 W/ml to 75 W/ml, optionally can be from 6 W/ml to 60 W/ml, optionally can be from 10 W/ml to 50 W/ml, optionally from 20 W/ml to 40 W/ml. These power levels are suitable for applying passivation layers or protective coatings or layers to syringes and sample tubes and pharmaceutical packages or other vessels of similar geometry having a void volume of 5 mL in which PECVD plasma can be generated. It is contemplated that for larger or smaller objects the power applied, in Watts, should be increased or reduced accordingly to scale the process to the size of the substrate.

For forming a coating or layer intended to provide lubricity in addition to passivation or pH protection, the precursor can be contacted with a plasma made by energizing the vicinity of the precursor with electrodes supplied with electric power density at less than 10 W/ml of plasma volume, alternatively from 6 W/ml to 0.1 W/ml of plasma volume, alternatively from 5 W/ml to 0.1 W/ml of plasma volume, alternatively from 4 W/ml to 0.1 W/ml of plasma volume, alternatively from 2 W/ml to 0.2 W/ml of plasma volume, alternatively from 10 W/ml to 50 W/ml, optionally from 20 W/ml to 40 W/ml.

Optionally, in any embodiment of FIGS. 7-8 and 29 the passivation layer or pH protective coating or layer can be applied by PECVD at a power level per of more than 22,000 kJ/kg of mass of precursor, or more than 30,000 kJ/kg of mass of precursor, or more than 40,000 kJ/kg of mass of precursor, or more than 50,000 kJ/kg of mass of precursor, or more than 60,000 kJ/kg of mass of precursor, or more than 62,000 kJ/kg of mass of precursor, or more than 70,000 kJ/kg of mass of precursor, or more than 80,000 kJ/kg of mass of precursor, or more than 100,000 kJ/kg of mass of precursor, or more than 200,000 kJ/kg of mass of precursor, or more than 300,000 kJ/kg of mass of precursor, or more than 400,000 kJ/kg of mass of precursor, or more than 500,000 kJ/kg of mass of precursor.

Optionally, in any embodiment of FIGS. 7-8 and 29 the passivation layer or pH protective coating or layer 34 can be applied by PECVD at a power level per of less than 2,000,000 kJ/kg of mass of precursor, or less than 1,000,000 kJ/kg of mass of precursor, or less than 700,000 kJ/kg of mass of precursor, or less than 500,000 kJ/kg of mass of precursor, or less than 100,000 kJ/kg of mass of precursor, or less than 90,000 kJ/kg of mass of precursor, or less than 81,000 kJ/kg of mass of precursor.

For a PECVD process the deposition time can be from 1 to 30 sec, alternatively from 2 to 10 sec, alternatively from 3 to 9 sec. The purposes for optionally limiting deposition time can be to avoid overheating the substrate, to increase the rate of production, and to reduce the use of process gas and its constituents. The purposes for optionally extending deposition time can be to provide a thicker passivation layer or pH protective coating or layer for particular deposition conditions.

Other methods can be used to apply the passivation layer or pH protective coating or layer. For example, hexamethylene disilazane (HMDZ) can be used as the precursor. HMDZ has the advantage of containing no oxygen in its molecular structure. This passivation layer or pH protective coating or layer treatment is contemplated to be a surface treatment of the $SiO_x$ barrier coating or layer with HMDZ. It is contemplated that HMDZ will react with the —OH sites that are present in the silicon dioxide coating or layer, resulting in the evolution of NH3 and bonding of S—$(CH_3)_3$ to the silicon (it is contemplated that hydrogen atoms will be evolved and bond with nitrogen from the HMDZ to produce NH3).

It is contemplated that this HMDZ passivation layer or pH protective coating or layer can be accomplished through several possible paths.

One contemplated path can be dehydration/vaporization of the HMDZ at ambient temperature. First, an $SiO_x$ surface can be deposited, for example using hexamethylene disiloxane (HMDSO). The as-coated silicon dioxide surface then can be reacted with HMDZ vapor. In any embodiment, as soon as the $SiO_x$ surface is deposited onto the article of interest, the vacuum can be maintained. The HMDSO and oxygen are pumped away and a base vacuum is achieved. Once base vacuum is achieved, HMDZ vapor can be flowed over the surface of the silicon dioxide (as coated on the part of interest) at pressures from the mTorr range to many Torr. The HMDZ then can be pumped away (with the resulting $NH_3$ that is a by-product of the reaction). The amount of $NH_3$ in the gas stream can be monitored (with a residual gas analyzer—RGA—as an example) and when there is no more $NH_3$ detected, the reaction is complete. The part then can be vented to atmosphere (with a clean dry gas or nitrogen). The resulting surface then can be found to have been passivated or protected. It is contemplated that this method optionally can be accomplished without forming a plasma.

Alternatively, after formation of the $SiO_x$ barrier coating or layer, the vacuum can be broken before dehydration/vaporization of the HMDZ. Dehydration/vaporization of the HMDZ can then be carried out in either the same apparatus used for formation of the $SiO_x$ barrier coating or layer or different apparatus.

Dehydration/vaporization of HMDZ at an elevated temperature is also contemplated. The above process can alternatively be carried out at an elevated temperature exceeding room temperature up to about 150° C. The maximum temperature can be determined by the material from which the coated part is constructed. An upper temperature should be selected that will not distort or otherwise damage the part being coated.

Dehydration/vaporization of HMDZ with a plasma assist is also contemplated. After carrying out any of the above embodiments of dehydration/vaporization, once the HMDZ vapor is admitted into the part, plasma can be generated. The plasma power can range from a few watts to 100+ watts (similar powers as used to deposit the $SiO_x$). The above is not limited to HMDZ and could be applicable to any molecule that will react with hydrogen, for example any of the nitrogen-containing precursors described in this specification.

Surprisingly, it has been found that the above stated coatings or layers can be applied to the capped assembly 12 with substantially no deposition of the vapor-deposited coating or layer 30 in the dispensing portion lumen 26.

In certain embodiments, the generation of uniform plasma throughout the portion of the vessel to be coated is contemplated, as it has been found in certain instances to generate a better passivation layer or pH protective coating or layer. Uniform plasma means regular plasma that does not include a substantial amount of hollow cathode plasma (which has higher emission intensity than regular plasma and can be manifested as a localized area of higher intensity interrupting the more uniform intensity of the regular plasma).

It is further contemplated that any embodiment of the passivation layer or pH protective coating or layer processes described in this specification can also be carried out without using the article to be coated to contain the plasma. For example, external surfaces of medical devices, for example catheters, surgical instruments, closures, and others can be passivated or protected.

Non-Organosilicon Passivation Layer or pH Protective Coating or Layer

Another way of applying the passivation layer or pH protective coating or layer can be to apply as the passivation layer or pH protective coating or layer an amorphous carbon or fluorinated polymer coating or layer, or a combination of the two.

Amorphous carbon coatings or layers can be formed by PECVD using a saturated hydrocarbon, (e.g. methane, ethane, ethylene or propane), or an unsaturated hydrocarbon (e.g. ethylene, acetylene), or a combination of two or more of these as a precursor for plasma polymerization.

It is contemplated that that amorphous carbon and/or fluorinated polymer coatings or layers will provide better passivation or protection of an $SiO_x$ barrier coating or layer than a siloxane coating or layer since an amorphous carbon and/or fluorinated polymer coating or layer will not contain silanol bonds.

It is further contemplated that fluorosilicon precursors can be used to provide a passivation layer or pH protective coating or layer over an $SiO_x$ barrier coating or layer. This can be carried out by using as a precursor a fluorinated silane precursor such as hexafluorosilane and a PECVD process. The resulting coating or layer would also be expected to be a non-wetting coating or layer.

Magnetic Treatment During PECVD

The apparatus described and illustrated in this specification, as in FIGS. 4-6, 9-28, 37 to 49, and 55-60, can be used in any embodiment in this specification to carry out a method of plasma modifying a workpiece 12 having a surface 14 or 16 to be treated. The method can be carried out by providing plasma and, at least part of the time while providing plasma, providing a magnetic field in or near the plasma.

Plasma can be provided in or near the generally cylindrical interior surface 16 of the workpiece 12, specific examples of which are a syringe or medical barrel 14 or a vial 10, under conditions effective for plasma modification of the generally cylindrical interior surface 16. Various types of modifications can be contemplated, individually or carried out successively or together, including but not limited to those described previously. For example, the modification can be an etching or ablating process in which the substrate can be eroded, a coating or layer process in which a coating or layer of material can be applied to the substrate, a chemical modification in which the generally cylindrical interior surface 16 can be changed in composition, which optionally can be done without either adding or etching away bulk material. Optionally in any embodiment, the plasma modification of the generally cylindrical interior surface 16 of the workpiece 12 can be chemical vapor deposition. Optionally in any embodiment, the plasma modification of the generally cylindrical interior surface 16 of the workpiece 12 can be plasma enhanced chemical vapor deposition (PECVD).

At least part of the time while providing plasma, a magnetic field can be provided in or near the plasma. The magnetic field can have a position, orientation, and field strength effective to improve the uniformity, density, or both of plasma modification of the generally cylindrical interior surface 16 of the workpiece 12.

Optionally in any embodiment, the generally cylindrical interior surface 16 can be on a generally cylindrical interior surface defining at least a portion of a lumen 18. For example, the generally cylindrical interior surface 16 optionally can be disposed on a vial 10, a medical barrel or medical barrel 14, a sample collection tube, e.g. blood collection tube 268, a rigid or flexible tube, or a flexible sample bag, to provide several examples. The present invention can be also useful for non-cylindrical surfaces. For example, the local magnetic field strength, the material supply, the plasma-forming energy or any combination of these can be varied in different parts of a non-cylindrical container to provide the coating or layer profile, whether uniform or varied, useful in a particular embodiment.

Where a uniform coating or layer profile is desired, as for the barrier coating or layer or the pH protective coating or layer, the desired thickness uniformity range, is +/−30% from the mean thickness, more preferably +/−15% from the mean thickness and most preferably, +/−5% from the mean thickness of the particular coating or layer. A less uniform coating or layer dictates the use of measures, such as magnetic confinement, to increase the coating or layer uniformity.

Optionally in any embodiment, providing the magnetic field improves the uniformity, density, or both of plasma distribution in at least a portion of the lumen. As one non-limiting example, providing the magnetic field can improve the axial uniformity, density, or both of plasma distribution along at least a portion of the generally cylindrical interior surface 16.

Optionally in any embodiment, the plasma can be plasma electrons and the magnetic field can be effective to improve confinement of the plasma electrons in the lumen, as by employing an electronic bottle as described in this specification. The inventors theorize, without intending to be bound by the accuracy or limits of this theory, that this confinement of electrons can be at least partially responsible for more uniformly distributing the plasma and for providing more intense yet uniform ionization of the precursor and other material in the plasma, and thus avoiding hot spots (where many or more energetic electrons collide with the vessel wall) and cool spots (where fewer or less energetic electrons collide) representing areas of differential treatment. Hot spots, for example, can cause areas of the substrate to become distorted or over-treated in the process of providing adequate treatment of the cool spots.

Optionally in any embodiment, the magnetic field can be provided by providing a magnetic field generator (for example any of 61-78, 86-91, 93, 95, 97, 99, 820, or 828-832 for example), alternatively at least two magnetic field generators, optionally at least three magnetic field generators, optionally at least four magnetic field generators, optionally at least five magnetic field generators, optionally at least six magnetic field generators, optionally at least seven magnetic field generators, optionally at least eight magnetic field generators, and optionally any desired number of magnetic field generators near the generally cylindrical interior surface 16, each magnetic field generator having a north pole and a south pole defining a polar axis. Optionally in any embodiment, some or all of the magnetic field generators can be placed outside the lumen (18). The principle types of magnetic field generators in common use can be permanent magnets and coils, although the invention is not limited to these types of magnetic field generators. Optionally in any embodiment, at least one magnetic field generator can be a permanent magnet (for example any of 61-78 or 86-91, 93, 95, 97, 99, 820, or 828-832) or a coil (for example any of 86-91, 93, 95, 97, or 99) or a combination of at least one permanent magnet and at least one coil. Either coils or permanent magnets can be used analogously to generate similar magnetic fields in various orientations.

Optionally, the magnetic field generators can be positioned near and extending axially along the length of the generally cylindrical surface.

Optionally in any embodiment, at least one permanent magnet (for example any of 61-72), alternatively at least two permanent magnets, alternatively at least three permanent magnets, alternatively at least four permanent magnets, alternatively at least five permanent magnets, alternatively at least six permanent magnets, alternatively at least seven permanent magnets, alternatively at least eight permanent magnets, alternatively all of the permanent magnets are bar magnets. These embodiments are illustrated by FIGS. 15, 16, 18-21, and 24-25. It will be noted that the polar axis of a bar magnet can be, but is not necessarily, parallel to the longest dimension of the bar magnet.

Optionally in any embodiment, at least one permanent magnet (73-78), alternatively at least two permanent magnets, alternatively at least three permanent magnets, alternatively at least four permanent magnets, alternatively at least five permanent magnets, alternatively at least six permanent magnets, alternatively at least seven permanent magnets, alternatively at least eight permanent magnets, alternatively all of the permanent magnets are ring magnets. Ring magnets are shown, for example, in FIGS. 14, 17, 22, 23, 38, 40, 41, 46, and 52. Optionally in any embodiment, as shown in FIGS. 14, 23, 38, 40, 41, 46, and 52, the north and south poles of at least one of the ring magnets (75-78) are its opposed annular faces.

Figure 17:
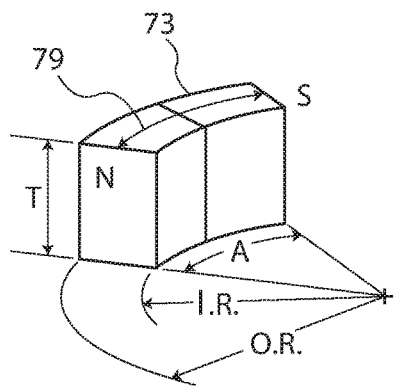
FIG. 17 shows the polar axis orientation of a multi-pole ring magnet (cutaway from a closed ring) having circumferential pole axes usable with any embodiment of the invention.
Figure 18:
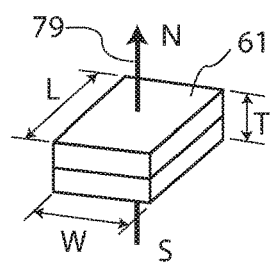
FIG. 18 shows the polar axis orientation of a bar magnet having a polar axis parallel to its shortest (thickness) dimension and perpendicular to its longest (length) dimension.
Figure 22:
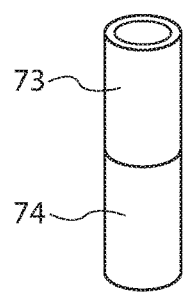
FIG. 22 is a perspective view of stacked multipole segmented ring magnet array, usable analogous to the magnet array of FIG. 19 in any embodiment of the invention.
Figure 23:
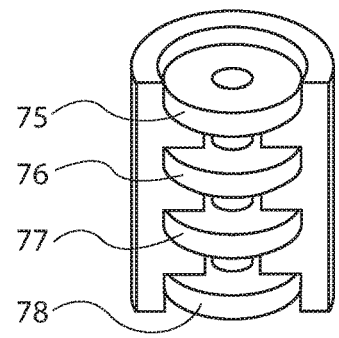
FIG. 23 is a perspective view of a stacked axial-pole ring magnet array, usable analogous to the magnet array of FIG. 19 in any embodiment of the invention.
Figure 24:
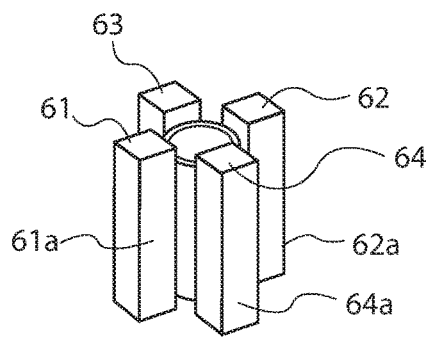
FIG. 24 is a perspective view of a stacked quadrupole magnet array, usable analogous to the magnet array of FIG. 19 in any embodiment of the invention.
Figure 25:
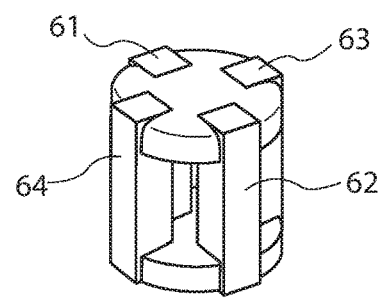
FIG. 25 is a perspective view of a quadrupole magnet array, usable analogous to the magnet array of FIG. 19 in any embodiment of the invention.

Optionally in any embodiment, the polar axis (79) of at least one of the ring magnets (e.g. 73 or 74) can be circumferential about the ring as shown in FIGS. 17 and 22, as is also the case with the toroidal coils discussed below. Optionally in any embodiment, the circumference of at least one of the ring magnets (73 or 74) can be divided into plural north-south pole domains.

Optionally in any embodiment, at least part of the time while providing the magnetic field, the magnetic field generator can be provided by positioning at least one coil (any of 86-91, 93, 95, 97, or 99) near the generally cylindrical surface and conducting an electrical current through the coil.

Optionally in any embodiment, at least one coil can be a solenoid 86. The solenoid optionally can be oriented with its axis 79 at least generally parallel to the axis 80 of the generally cylindrical surface, alternatively with its axis 79 at least generally collinear with the axis 80 of the generally cylindrical surface. Optionally in any embodiment, the generally cylindrical surface can be located entirely within the solenoid coil (86).

Optionally in any embodiment, at least one coil can be, or include, a generally toroidal coil 88 or 90 having a central opening and a geometric axis 80 passing through its central opening, as illustrated in FIGS. 10-13. Optionally in any embodiment, at least part of the time while providing the magnetic field, the generally toroidal coil 88 or 90 can be oriented with its geometric axis 80 at least generally parallel, optionally at least generally collinear with the axis 80 of the generally cylindrical interior surface 16. In this orientation of a toroidal coil the magnetic field in at least a portion of the lumen 18 is oriented with its polar axis extending around the axis 80 of the generally cylindrical interior surface 16 to be treated. Optionally in any embodiment, at least part of the time while providing the magnetic field, the generally cylindrical interior surface 16 can be located substantially entirely within the central opening, alternatively substantially entirely within the central openings of a stack of two or more of the generally toroidal coils 88 or 90.

Figure 12:
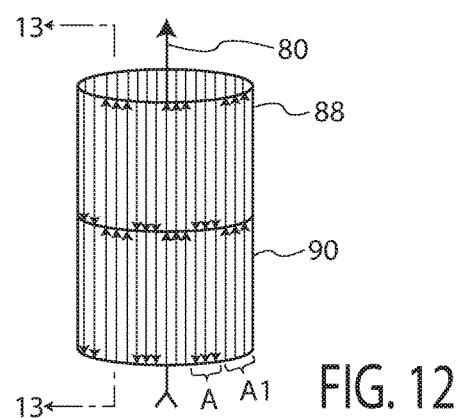
FIG. 12 is a view similar to FIG. 9a of a rectangular-section toroidal coil as an alternative magnet structure usable with any embodiment of the invention.
Figure 13:
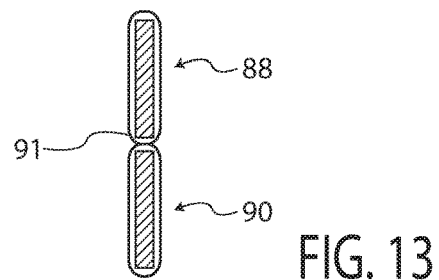
FIG. 13 is a section taken along section line 13-13 of FIG. 12.
Figure 14:
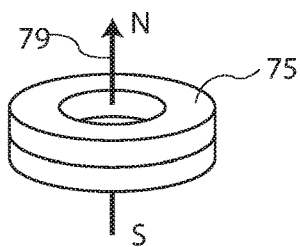
FIG. 14 shows the polar axis orientation of a ring magnet having a polar axis coinciding with its cylindrical axis usable with any embodiment of the invention.
Figure 15:
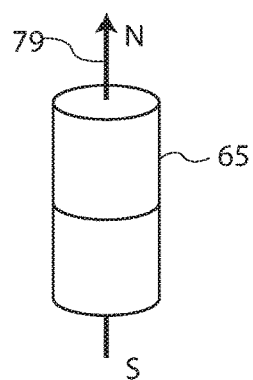
FIG. 15 shows the polar axis orientation of a round cylindrical bar magnet having a polar axis parallel to its longest dimension usable with any embodiment of the invention.
Figure 16:
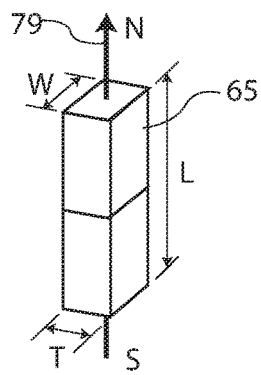
FIG. 16 shows the polar axis orientation of a square-section cylindrical bar magnet having a polar axis parallel to its longest dimension usable with any embodiment of the invention.

Optionally in any embodiment, illustrated in FIG. 12 for example, the generally toroidal coils 88 or 90 can have at least two arc segments A and A1, optionally at least four arc segments A and A1, optionally at least 6 arc segments A and A1, optionally at least eight arc segments A and A1, optionally at least eight 45° arc segments A and A1. Optionally in any embodiment, alternating segments can be wound in opposite directions. Optionally in any embodiment, the generally toroidal coils 88 or 90 can have cross-sections that can be substantially circular 95 or substantially rectangular 91 or another regular or irregular shape.

A coil can have a full length core, a partial length core, a solid core, a hollow core, or no core, and the core can be a permanent magnet that generates a magnetic field in itself, a temporarily magnetizable material that generates a magnetic field when energized by the coil, or a magnetically inactive form for winding the coil. A conventional magnetizable core material is an iron or ferrite body.

Optionally in any embodiment, the coil can be energized with DC or AC energy. It is contemplated that a coil energized with AC energy, for example 60 Hz alternating current, will periodically reverse poles, which is contemplated to improve the uniformity of deposition or other surface treatment, much like the moving quadrupole array described below functions.

Optionally in any embodiment, two or more magnetic field generators can be spaced to define a recess 81 between them, within which at least a portion of the generally cylindrical interior surface 16 of the workpiece can be positioned.

Various orientations of the magnetic fields have been found to be useful in improving the uniformity or other results of PECVD treatment. As one example, at least part of the time while providing the magnetic field, a magnetic field generator (for example any of 61-78 or 86-91, 93, 95, 97, or 99), alternatively at least two of the magnetic field generators, alternatively at least three of the magnetic field generators, alternatively at least four of the magnetic field generators, alternatively at least five of the magnetic field generators, alternatively at least six of the magnetic field generators, alternatively at least seven of the magnetic field generators, alternatively at least eight of the magnetic field generators, alternatively all of the magnetic field generators, can have their polar axes 79 generally parallel to the axis 80 of the generally cylindrical interior surface 16. Examples of this orientation are found in FIGS. 9, 9a, 14-16, 20, 23, 24, 37, magnets 75 of FIGS. 38 and 40, and FIGS. 41-44 and 46, for example, optionally can have polar axes (78) generally parallel to the axis (80) of the surface (16). Where the surface (16) is generally cylindrical, its axis is the center of the cylinder. For a non-cylindrical surface the axis can be any particular line passing through the surface.

As another example, at least part of the time while providing the magnetic field, at least two of the magnetic field generators (for example any of 61-78 or 86-91, 93, 95, 97, or 99), alternatively at least three of the magnetic field generators, alternatively at least four of the magnetic field generators, alternatively at least five of the magnetic field generators, alternatively at least six of the magnetic field generators, alternatively at least seven of the magnetic field generators, alternatively at least eight of the magnetic field generators, alternatively all of the magnetic field generators, can be circumferentially distributed around the generally cylindrical interior surface 16 when the workpiece and magnetic field generators are in the operative position for plasma treatment, as illustrated in FIGS. 4, 5, 9-9a, 10-14, 19-25, and 37-46, for example. The circumferential distribution can be even or uneven, although even distribution is specifically contemplated as one alternative.

Optionally in any embodiment, an even number of at least four magnetic field generators (for example, the magnets 61-64 or 61a-64a of FIGS. 19, 21, 25, 38-40, 45, 49, and 55-60) are arranged about a center, with their polar axes alternately oriented radially toward the center and away from the center to provide a quadrupole or analogous structure. Quadrupoles and their 8-magnet analogs are discussed further below in connection with electron bottles and in the working examples.

Optionally in any embodiment, at least part of the time while providing the magnetic field, at least two of the magnetic field generators, alternatively at least three of the magnetic field generators, alternatively at least four of the magnetic field generators, alternatively at least five of the magnetic field generators, alternatively at least six of the magnetic field generators, alternatively at least seven of the magnetic field generators, alternatively at least eight of the magnetic field generators, alternatively all of the magnetic field generators, can be substantially circumferentially equidistant from the adjacent magnetic field generators when the workpiece and magnetic field generators are in the operative position. This is illustrated in FIGS. 4, 5, 19-21, 24-25, and 38-40, 49, and 55-56 for example.

Optionally in any embodiment, at least part of the time while providing the magnetic field, at least two of the magnetic field generators (for example any of 61-78 or 86-91, 93, 95, 97, or 99), alternatively at least three of the magnetic field generators, alternatively at least four of the magnetic field generators, alternatively at least five of the magnetic field generators, alternatively at least six of the magnetic field generators, alternatively at least seven of the magnetic field generators, alternatively at least eight of the magnetic field generators, alternatively all of the magnetic field generators, can be axially stacked with respect to the generally cylindrical surface, as illustrated for example in FIGS. 10-13, 22-24, 37-41, and 46, and usable to form any illustrated magnetic field generator. Additionally, the axially oriented solenoid coils of FIGS. 9, 9a, 37 referring to either coil 86a or 86b), and 42-43 are conceptually similar, as the successive turns are "stacked" axially as well, and each is a magnetic field generator from a more granular perspective.

Optionally in any embodiment, at least part of the time while providing the magnetic field, at least two of the axially stacked magnetic field generators (for example any of 61-78 or 86-91, 93, 95, 97, or 99), alternatively at least three of the axially stacked magnetic field generators, alternatively at least four of the axially stacked magnetic field generators, alternatively at least five of the axially stacked magnetic field generators, alternatively at least six of the axially stacked magnetic field generators, alternatively at least seven of the axially stacked magnetic field generators, alternatively at least eight of the axially stacked magnetic field generators, alternatively all of the axially stacked magnetic field generators, can be axially spaced from each other. This orientation is illustrated, for example, in FIGS. 23, 37, 38, and 52.

Optionally in any embodiment, at least part of the time while providing the magnetic field, at least two of the axially stacked magnetic field generators (for example any of 61-78 or 86-91, 93, 95, 97, or 99), alternatively at least three of the axially stacked magnetic field generators, alternatively at least four of the axially stacked magnetic field generators, alternatively at least five of the axially stacked magnetic field generators, alternatively at least six of the axially stacked magnetic field generators, alternatively at least seven of the axially stacked magnetic field generators, alternatively at least eight of the axially stacked magnetic field generators, alternatively all of the axially stacked magnetic field generators, axially abut each other.

Optionally in any embodiment, at least part of the time while providing the magnetic field, at least one magnetic field generator can be oriented with its polar axis 79 at least generally parallel to the axis 80 of the surface. Alternatively or in addition, at least part of the time while providing the magnetic field, at least one magnetic field generator can be oriented with its polar axis 79 at least generally collinear with the axis 80 of the surface. These orientations are illustrated by FIGS. 9, 9a, 20, 24, 37, 38 and 40 (magnets 75), 41-44, 46, and 52, for example.

Optionally in any embodiment, at least part of the time while providing the magnetic field, the magnetic field generator can have a passage extending along its polar axis and the surface can be located entirely within the passage. These orientations are illustrated by FIGS. 9, 9a, 20, 24, 37, 38 and 40 (magnets 75), 41-44, 46, and 52, for example.

Figure 37:
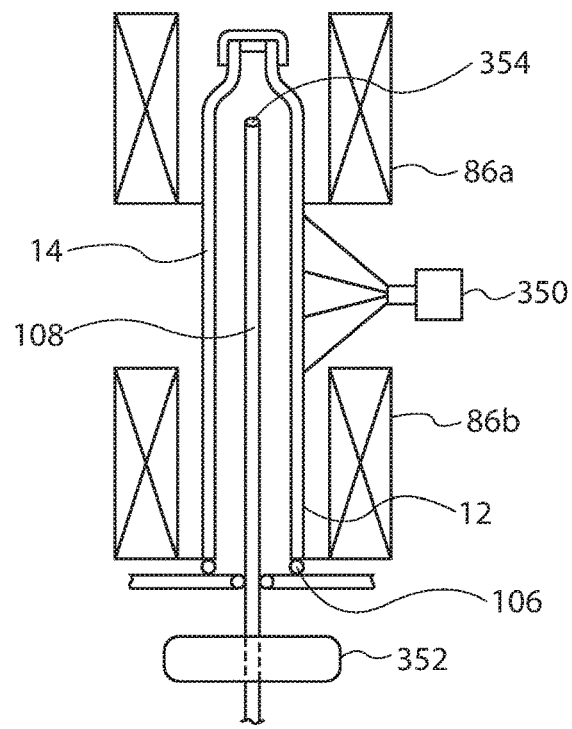
FIG. 37 is a view similar to FIG. 4 showing certain optional features usable separately or in combination in any embodiment, including a Helmholtz coil (86a, 86b), an optical detector (350), a Rogowski coil (352), and a Langmuir probe (354).

Optionally in any embodiment, the magnetic field generator can be a Helmholtz coil, which, as illustrated in FIG. 37, can be a pair of solenoids 86a and 86b with space between them. In a Helmholtz coil, the space between the solenoids 86a and 86b, if not too great, provides a substantially uniform magnetic field in the space between the solenoids. Optionally in any embodiment, the space between the first and second spaced solenoids 86a and 86b optionally provides a viewing window allowing the plasma to be viewed while the method is in progress (to the extent it can be seen through other apparatus). For example, the outer electrode 160 (FIG. 4) optionally can be U-shaped (in an alternative from FIGS. 5 and 9) and the vessel wall 14 can be transparent, thus allowing the plasma to be viewed easily.

Optionally in any embodiment, at least part of the time while providing the magnetic field, the magnetic field generator can provide a field strength that varies along the workpiece generally cylindrical interior surface 16. This varying field strength can be provided in various ways. Optionally in any embodiment, at least part of the time while providing the magnetic field, the distance between at least one magnetic field generator and the generally cylindrical inner surface can vary along the workpiece generally cylindrical interior surface 16, as illustrated in FIG. 52. As another example, at least part of the time while providing the magnetic field, the field strength can vary along the generally cylindrical inner surface to define a profile of varying field strength, shown for example in FIGS. 9a, 23, 37 (the Helmholtz coils minimize the non-uniformity, but some may persist in certain embodiments), 38, 41-44, 46, and 52-53.

Optionally in any embodiment, at least part of the time while providing the plasma and not providing the magnetic field, the plasma modification of the generally cylindrical interior surface 16 of the workpiece 12 varies along the generally cylindrical inner surface to define a profile of varying plasma modification. In other words, without applying the magnetic field, the degree or kind of plasma modification at various points on the generally cylindrical inner surface might not be uniform for given apparatus operated under given conditions. This variation might be desirable or undesirable. If undesirable in a particular embodiment, at least part of the time while providing the magnetic field, the magnetic field generators can be configured and operated under conditions such that variations in the profile of magnetic field strength tend to counteract variations of plasma modification. By counteracting variations in the plasma process with magnetic variations, the uniformity, density, or both of plasma modification of the generally cylindrical interior surface 16 of the workpiece 12 can be made more uniform.

Optionally in any embodiment, at least part of the time while providing the magnetic field, at least a portion of the plasma can be at least partially confined to the vicinity of the workpiece in an "electron bottle." Electron bottles can be created in various ways.

Figure 39:
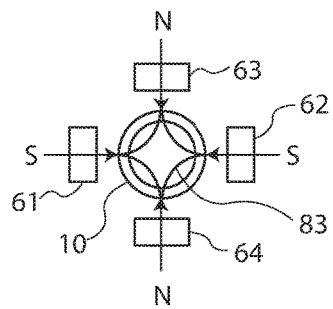
FIG. 39 is a section of FIG. 38 taken along section lines 39-39.

One example of an electron bottle is shown in FIGS. 38-40. The side of the electron bottle can be a quadrupole formed by the magnets 61, 62, 63, and 64 arranged with their north poles alternatively extending radially toward and radially away from the medical barrel 10. As FIG. 39 shows, this quadrupole orientation produces magnetic lines 83 arcing from radially inward at one magnet to radially outward at the adjacent magnet, providing a pattern resembling four-sided closed loops in any radial plane. Electrons travel helically around and along the magnetic lines 83, thus in a circuit around and within the medical barrel 10. This confines the electrons radially to the space 81 enclosed by the magnets.

The ends of the electron bottle are optional, and if used can be defined in FIGS. 38 and 40 by ring magnets 75 that have a smaller inside diameter, and a greater field strength, than the magnets 61-64 around the perimeter. The ring magnets 75 can be oriented with their polar axes aligned with the geometric axes of the quadrupole 61-64 and medical barrel 10. FIG. 38 shows that the magnetic field lines bow out and can be further apart at an axial distance away from the ring magnets 75 (since these generally axial lines can be primarily generated by the ring magnets 75), indicating a lower magnetic flux near the axial center of the quadrupole than within the magnets 75. The ring magnets 75 thus act as opposed electron mirrors, tending to reverse the direction of travel of electrons approaching them back toward the medical barrel 10.

FIG. 41 shows a different type of electron bottle, and in this case the workpiece can be a medical barrel and needle capped assembly 12, the assembly having a needle end, a back end opposite the needle end, and a body portion between the needle end and back end. The electron bottle of FIG. 41 can be defined by a stack of ring magnets 75, all oriented with their north poles toward the top of the sheet and their south poles toward the bottom of the sheet. The ends of the electron bottle can be bar magnets 65, sometimes referred to as cap magnets, which have no central aperture and have the same magnetic orientation as the ring magnets 65, with their north poles toward the top of the sheet. Since the cap magnets 65 can be made of magnetically permeable material, the flux can be stronger within the body of each cap magnet than outside it on either side, so the cap magnets act as electron mirrors. The magnetic lines of FIG. 41, if shown, would look much like the magnetic lines 83 of FIG. 42.

Figure 9:
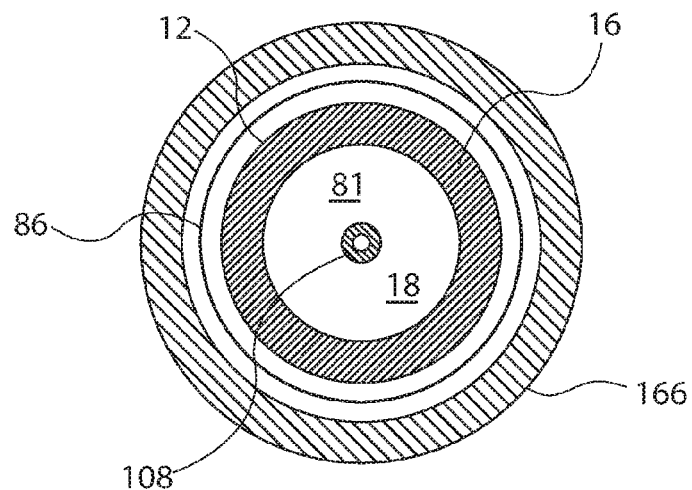
FIG. 9 is a view similar to FIG. 5 of a solenoid coil as an alternative magnet structure usable with any embodiment of the invention, and part 9a is an isolated perspective view of the solenoid coil.
Figure 9A:
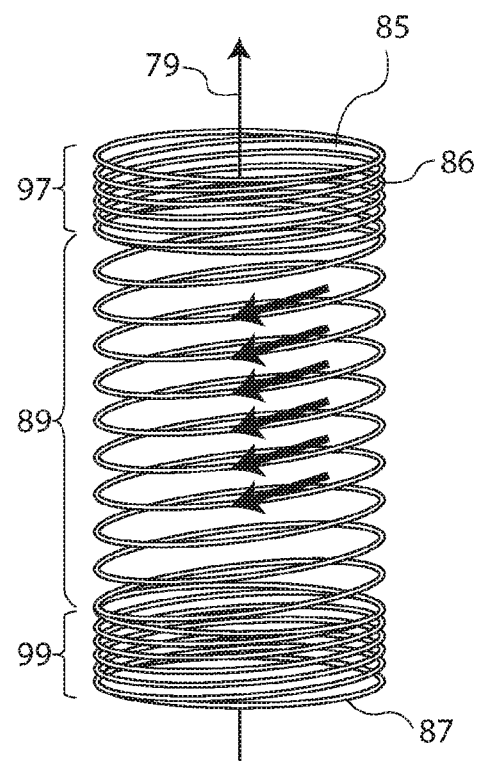
Figure 10:
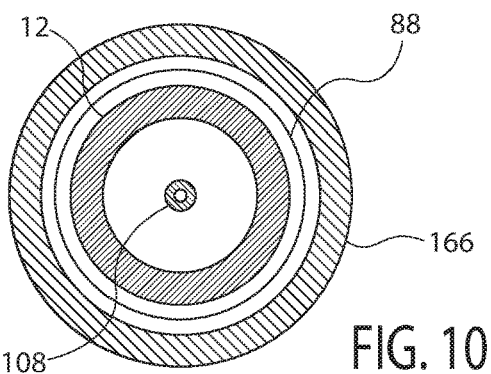
FIG. 10 is a view similar to FIG. 5 of a round-section toroidal coil as an alternative magnet structure usable with any embodiment of the invention.
Figure 11:
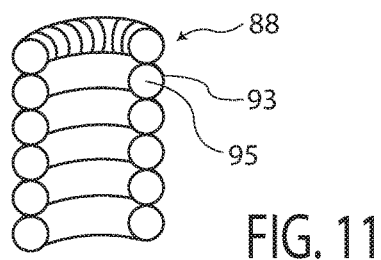
FIG. 11 is an isolated cutaway perspective view of the toroidal coil in FIG. 10.

FIGS. 9a and 42 show electron bottles formed by a coil having a central portion 89 providing a generally axially extending magnetic field adjacent to a central portion of the vial 10 and end portions 97 and 99 providing a similarly oriented magnetic field having a stronger flux than the central portion 89. The end portions 97 and 99 provide a stronger flux because the windings of the end portions can be closer together than those of the central portion 89. The end portions 97 and 99 also provide a stronger flux because the voltage drop across the central portion can be 30 Volts (as an illustration, not limiting the scope of the invention), while the voltage drop across each of the end portions can be 60 Volts (as an illustration, not limiting the scope of the invention), and the resistance of each end portion 97, 99 can be the same as the resistance of the central portion 89 (as an illustration, not limiting the scope of the invention), so the amperage flowing through the end portions 97, 99 can be higher than that flowing through the central portion 89. This difference in flux is reflected by the magnetic lines 83, as indicated before. Thus, the end portions 97 and 99 again define opposed electron mirrors. Either expedient for increasing the flux at the ends of the electron bottle can be used independently, as other alternatives.

Optionally, the electron bottle is defined by structure providing a stronger magnetic field at or near one end of the generally cylindrical surface than between the ends of the generally cylindrical surface. As another option, the electron bottle is defined by structure providing a stronger magnetic field at or near one end of the generally cylindrical surface than at or near at the other end of the generally cylindrical surface.

FIG. 43 shows another type of electron bottle formed by a solenoid having a uniform winding 89, forming a magnetic field represented by generally parallel magnetic lines 83. The magnetic field constrains electrons to travel along a corkscrew or helical axial path 103. As another option, the electron bottle can comprise a negatively charged object or portion of an object positioned adjacent to at least one end of the generally cylindrical portion. For example, a charged capacitor 101 can be placed at one or both ends of the solenoid, with the respective negatively charged plates facing toward the solenoid and the positively charged plates facing away from the solenoid. The negatively charged plates act as electron mirrors to repel approaching electrons, returning them to the interior of the solenoid. FIG. 43 differs from the electron bottles of FIGS. 9a and 38-42 in that the mirrors reflecting electrons back into the bottle can be electrostatic rather than magnetic. For the present purposes, it is still considered an "electron bottle," as it functions in an analogous manner to confine electrons.

FIG. 44 shows another type of electron bottle in which ring magnets 75 (alternatively other types of magnetic field generators such as solenoids) at each end define electron mirrors and the electrons can be also laterally confined by an inner, negatively charged shell electrode 107 disposed within an outer, positively charged shell electrode 109. Again, the electrons can be reflected or repelled inward toward the axis of the apparatus. This apparatus also can have the advantage that positively charged ions formed within the vial 10 can be attracted toward the wall of the vial as it is treated by the plasma, while electrons can be repelled inward, which tends to keep the walls cooler during operation. The walls of the vial 10 confine the ions so they cannot escape.

An alternative to FIG. 44 would be to use the outer electrode 160 as the negatively charged shell 107 and the inner electrode 108 as the positively charged counter electrode. This can be done by adding a DC bias voltage to the electrodes 108 and 160, as well as the RF alternating current. This construction would have the similar result of attracting electrons in the vial 10 away from its walls and the positively charged ions in the vial 10 toward its walls.

Moreover, the individual features of any of the embodiments of FIGS. 1-29 and 36 to 44 can be substituted in any of those embodiments, without limitation. For example, any of the axial electron mirrors defined by the ring magnets 75 of FIG. 38 or 44, the cap magnets 65 of FIG. 41, the solenoid windings 97 and 99 of FIGS. 9a and 42, and the electrostatic plates 101 of FIG. 43 can be used individually in any of the embodiments of FIGS. 1-29 and 36 to 44, and can be used in any combination in any of those embodiments. The same can be true of the expedients for radial confinement, such as the quadrupole magnets 61-64 of FIG. 38, the ring magnets 75 of FIG. 41, the solenoid winding 89 of FIG. 42 or 43, the electrostatic shells 107 and 109, or a bias between the inner and outer electrodes 108 and 160. Any of these electronic bottle features can be used in any embodiment, individually or in any combination, and can be used with any type of workpiece such as vials 10, capped pre-assemblies 12, syringe or medical barrels 14, sample tubes 210, or others of FIGS. 1-3, 7-8, 29, and 36, and with any plasma generation and material feed and exhaust apparatus or combination or substitution of apparatus, such as that of FIG. 4-6, 9-28, or 37-44.

Thus, optionally in any syringe embodiment of the invention, for example one in which the workpiece is a syringe or medical barrel 14 or medical barrel and needle capped assembly 12, any of which have a needle end (whether or not the needle is present at the time), a back end opposite the needle end, and a body portion between the needle end and back end, the electron bottle can be defined by structure providing a stronger magnetic field at or near the needle end than at or near at least part of the body portion.

Optionally in any syringe embodiment of the invention, the electron bottle can be defined by structure providing a stronger magnetic field at or near the back end than at or near at least part of the body portion, illustrated in FIGS. 9 and 9a, 37-42, or 44, for example. The electron bottle can be defined by structure providing stronger magnetic fields at or near the needle end and the back end than at or near at least part of the body portion, illustrated in the same Figures. The electron bottle can be defined by structure providing an electron mirror at or near the needle end, as shown in FIGS. 9, 9a, 23, 37, 41, and in FIGS. 38-40, 42-44, and 52 if a syringe is substituted for the illustrated vial 10. The electron bottle can be further defined by structure providing an electron mirror at or near the back end, as in the same FIGS. 9, 9a, 23, 37, 41, and in FIGS. 38-40, 42-44, and 52 if a syringe is substituted for the illustrated vial 10.

For embodiments in which the workpiece is a vial 10 having an open end, a closed end, and a body portion between the ends, the electron bottle can be defined by structure providing a stronger magnetic field at or near the closed end of the vial than at or near at least part of the body portion of the vial as in the Figures mentioned in connection with syringe treatment or vial treatment above. The electron bottle can be defined by structure providing a stronger magnetic field at or near the open end of the vial than at or near at least part of the body portion of the vial. The electron bottle can be defined by structure providing stronger magnetic fields at or near the closed end and the open end of the vial than at or near at least part of the body portion of the vial. The electron bottle can be defined by structure providing an electron mirror at or near the closed end of the vial. The electron bottle can be further defined by structure providing an electron mirror at or near the open end of the vial.

Optionally in any embodiment, the structure providing an electron mirror can be at least a portion of a magnetic field generator, as in FIGS. 9, 9a, 23, 37-42, 44, and 52-53 (in FIG. 53, the lower portions of the magnets 61 and 62 provide a stronger magnetic field than the upper portions of the same magnets, thus a magnetic mirror). Optionally in any embodiment, the structure providing an electron mirror can comprise a ferromagnetic material, as in any of the permanent magnet embodiments of FIGS. 23, 38-41, and 52-53. Optionally in any embodiment, the structure providing an electron mirror can comprise a ferromagnetic material, such as the cores on which the windings of coils are supported in FIG. 9-13, 37, 42, or 43. Optionally in any embodiment, the structure providing an electron mirror can be a negatively charged object or portion of an object, shown for example in FIGS. 43 (axial mirrors) and 44 (radial mirror In the embodiment of FIG. 54, the magnets 65-72 are axial, meaning that their polar axes extend along their length, and they are arrayed to provide a strong axially extending magnetic field through the apertures that receive the syringe or other vessel being processed. They do not define a quadrupole. The magnets 65-72 can be, for example, NdFeB magnets providing a very strong magnetic field. The inventors contemplate that these magnets can improve the uniformity of deposition of PECVD coatings or layers without rotating the magnet array, although they can be rotated to, for example, compensate for any deviations from concentricity or equal magnetic strength of the assembly in use.

Now refer in particular to FIG. 51, showing a prefilled syringe 210 illustrating an aspect of the invention optionally used to apply a localized lubricity coating or layer to the generally cylindrical interior surface 16 of the medical barrel 14. The syringe 210 includes a medical barrel 14, which alternatively can be an auto-injector cartridge 300 (FIG. 36) or similar device. The medical barrel 14 has a dispensing end 22, a back end 32, and a generally cylindrical interior surface 16. The generally cylindrical interior surface 16 has a generally cylindrical interior surface 16 44 defining a lumen 18. The generally cylindrical interior surface 16 44 of the generally cylindrical interior surface 16 extends at least part of the distance, and here at least almost the entire distance, between the dispensing end 22 and the back end 32 of the medical barrel 14, auto-injector cartridge, or similar device. The generally cylindrical interior surface 16 44 of the generally cylindrical interior surface 16 is configured to receive a slidable plunger or piston 36.

The generally cylindrical interior surface 16 44 of the generally cylindrical interior surface 16 has a first portion 800 extending back from a front end 808 at or near the dispensing end 22 of the medical barrel 14, auto-injector cartridge, or similar device to a back end 806.

The generally cylindrical interior surface 16 44 of the generally cylindrical interior surface 16 has a second portion 802 extending back from the first portion 800 of the generally cylindrical interior surface 16 44. The second portion 802 can either extend all the way back from the first portion 800 of the generally cylindrical interior surface 16 44 to the back end 32 of the generally cylindrical interior surface 16, or the second portion 802 can have a back end 810 spaced forward from the back end 32 of the generally cylindrical interior surface 16. In other words, there can either be, or not be, a third portion 804 behind the second portion 802.

Optionally, if the second portion 802 of the generally cylindrical interior surface 16 44 has a back end 810 spaced forward from the back end 36 of the generally cylindrical interior surface 16, the generally cylindrical interior surface 16 44 can have a third portion 804 extending back from the second portion 802 of the generally cylindrical interior surface 16 44 to the back end of the generally cylindrical interior surface 16.

While in the illustrated embodiment the first portion 800 is forward of the plunger or piston 36, the second portion 802 is adjacent to the plunger or piston 36, and there is a third portion 804 behind the plunger or piston 36, these relationships are optional features. Also, since syringes 210 commonly are supplied in standard sizes, each accommodating a range of doses, the rest position of the plunger or piston 36 in a given instance will vary according to the volume of the dose of fluid in the lumen 18.

The second portion 802 of the generally cylindrical interior surface 16 44 of the generally cylindrical interior surface 16 has a lubricity coating or layer 34 applied by PECVD.

One option is that the first portion 800 of the generally cylindrical interior surface 16 44 of the generally cylindrical interior surface 16 has no lubricity coating or layer 34 applied by PECVD. The other option, illustrated here, is that the first portion 800 of the generally cylindrical interior surface 16 44 of the generally cylindrical interior surface 16 has a lubricity coating or layer 34 applied by PECVD that is, on mean, thinner than the lubricity coating or layer 34 on the second portion 802 of the generally cylindrical interior surface 16 44 of the generally cylindrical interior surface 16.

The syringe 210, auto-injector, or similar device has a medical barrel 14 or cartridge as described above, combined with a plunger or piston 36. The plunger or piston 36 is disposed in the lumen 18 of the medical barrel 14 or cartridge. The plunger or piston 36 is slidable between a resting position contacting the second portion 802 of the generally cylindrical interior surface 16 44, as shown in FIG. 7, and an advanced position contacting the first portion 800 of the generally cylindrical interior surface 16 44.

The syringe 210, auto-injector, or similar device as described above, as illustrated in FIG. 7, is prefilled with a fluid composition. The fluid composition is disposed in the lumen 18 between the plunger or piston 36 and the dispensing end 22 of the medical barrel 14 or cartridge.

Optionally in any embodiment, the lubricity coating or layer 34 can have a transition of thickness between the first 800) and second (802) portions of the generally cylindrical interior surface 16 (16.

Optionally in any embodiment, the minimum mean thickness of the lubricity coating or layer (34) in the first portion (800) is 0 nm and the maximum mean thickness of the lubricity coating or layer (34) is 0.8 times, optionally 0.7 times, optionally 0.6 times, optionally 0.5 times, optionally 0.4 times, optionally 0.3 times, optionally 0.2 times, optionally 0.1 times, optionally 0.09 times, optionally 0.08 times, optionally 0.07 times, optionally 0.06 times, optionally 0.05 times, optionally 0.04 times, optionally 0.03 times, optionally 0.02 times, optionally 0.01 times the mean thickness of the lubricity coating or layer (34) in the second portion (802. Optionally in any embodiment, the second portion (802) of the generally cylindrical interior surface 16 can have a smaller inside diameter than the rear end of the first portion (800) of the generally cylindrical interior surface 16.

Optionally in any embodiment, at least one magnetic field generator (for example any of 61-78, 86, 88, 90, or 820), alternatively at least two magnetic field generators, alternatively at least three magnetic field generators, alternatively at least four magnetic field generators, alternatively at least five magnetic field generators, alternatively at least six magnetic field generators, alternatively at least seven magnetic field generators, alternatively at least eight magnetic field generators, alternatively all of the magnetic field generators are permanent magnets (for example any of 61-78 or 820, for example) having opposed first and second poles (822, 824) defining a polar axis (80) and first and second ends respectively corresponding to the first and second poles, the permanent magnets having one or more sides (820) extending from the first pole (822) to the second pole (824), in which at least one side (826) is tapered inward between the first pole (822) and the second pole (824).

Optionally in any embodiment, the second end (824) of at least one magnetic field generator (for example for example any of 61-78, 86, 88, 90, or 820), alternatively at least two magnetic field generators, alternatively at least three magnetic field generators, alternatively at least four magnetic field generators, alternatively at least five magnetic field generators, alternatively at least six magnetic field generators, alternatively at least seven magnetic field generators, alternatively at least eight magnetic field generators, alternatively all of the magnetic field generators is larger than the first end (822).

Optionally in any embodiment, at least one magnetic field generator (for example for example any of 61-78, 86, 88, 90, or 820), alternatively at least two magnetic field generators, alternatively at least three magnetic field generators, alternatively at least four magnetic field generators, alternatively at least five magnetic field generators, alternatively at least six magnetic field generators, alternatively at least seven magnetic field generators, alternatively at least eight magnetic field generators, alternatively all of the magnetic field generators are generally conical like the permanent magnets 820 of FIGS. 55 and 56, or frustoconical like the permanent magnets 830 of FIG. 60, pyramidal like the permanent magnets 828 of FIG. 59, or frustopyramidal like the permanent magnets 832 of FIG. 58.

Optionally in any embodiment, at least one magnetic field generator (for example for example any of 61-78, 86, 88, 90, or 820), alternatively at least two magnetic field generators, alternatively at least three magnetic field generators, alternatively at least four magnetic field generators, alternatively at least five magnetic field generators, alternatively at least six magnetic field generators, alternatively at least seven magnetic field generators, alternatively at least eight magnetic field generators, alternatively all of the magnetic field generators are generally conical with a rounded smaller end (822) as shown in FIG. 56.

Optionally in any embodiment, at least one magnetic field generator (820), alternatively at least two magnetic field generators, alternatively at least three magnetic field generators, alternatively at least four magnetic field generators, alternatively at least five magnetic field generators, alternatively at least six magnetic field generators, alternatively at least seven magnetic field generators, alternatively at least eight magnetic field generators, alternatively all of the magnetic field generators are oriented in a ring-shaped array (834, FIGS. 55 and 56) with their smaller ends (822) disposed radially inward and their larger ends (824) disposed radially outward.

Optionally in any embodiment, at least one magnetic field generator (for example for example any of 61-78, 86, 88, 90, or 820), alternatively at least two magnetic field generators, alternatively at least three magnetic field generators, alternatively at least four magnetic field generators, alternatively at least five magnetic field generators, alternatively at least six magnetic field generators, alternatively at least seven magnetic field generators, alternatively at least eight magnetic field generators, alternatively all of the magnetic field generators are oriented with the pole of the same sign (North or South) disposed radially inward and their first ends disposed radially outward.

Optionally in any embodiment, at least one magnetic field generator (for example for example any of 61-78, 86, 88, 90, or 820), alternatively at least two magnetic field generators, alternatively at least three magnetic field generators, alternatively at least four magnetic field generators, alternatively at least five magnetic field generators, alternatively at least six magnetic field generators, alternatively at least seven magnetic field generators, alternatively at least eight magnetic field generators, alternatively all of the magnetic field generators are oriented with their North poles disposed radially inward.

Optionally in any embodiment, at least one magnetic field generator (for example for example any of 61-78, 86, 88, 90, or 820), alternatively at least two magnetic field generators, alternatively at least three magnetic field generators, alternatively at least four magnetic field generators, alternatively at least five magnetic field generators, alternatively at least six magnetic field generators, alternatively at least seven magnetic field generators, alternatively at least eight magnetic field generators, alternatively all of the magnetic field generators are oriented with their south poles disposed radially inward.

Optionally in any embodiment, at least one magnetic field generator 73-78, alternatively at least two magnetic field generators, alternatively at least three magnetic field generators, alternatively at least four magnetic field generators, alternatively at least five magnetic field generators, alternatively at least six magnetic field generators, alternatively at least seven magnetic field generators, alternatively at least eight magnetic field generators, alternatively all of the magnetic field generators can be ring magnets having central apertures sized to receive the medical barrel generally cylindrical interior surface 16, as shown in for example any of FIG. 14, 22, 23, 38, 40, 41, 46, or 52. Optionally at least one magnetic field generator, optionally a ring magnet, has a passage extending along its polar axis. As one option, the generally cylindrical surface can be located entirely within the passage. As another option, one or more ring magnets can be spaced axially, which may be useful if it is desired to view or receive light from the plasma during production.

Optionally in any embodiment, the north and south poles of at least one of the ring magnets 75-78 can be its opposed annular faces as shown in for example any of FIG. 14, 22, 23, 38, 40, 41, 46, or 52. Optionally in any embodiment, the magnetic field can be provided at least in part by a stack of:

at least one interior ring magnet having the medical barrel generally cylindrical interior surface 16 within its central recess when in its operative position, and at least one cap magnet axially aligned with but outside the stack of interior ring magnets, the cap magnet comprising either a ring magnet or a bar magnet, in which the interior ring magnets provide a first magnetic field strength radially adjacent to the medical barrel generally cylindrical interior surface 16 that is less than the magnetic field strength provided by the cap magnet axially adjacent to the medical barrel generally cylindrical interior surface 16. This construction is illustrated, for example, in FIG. 41, and other FIGS. show multiple ring magnets that can be adapted to provide the same construction.

Optionally in any embodiment, one or more additional magnets can be positioned between a cap magnet and the stack of interior ring magnets illustrated, for example, in FIG. 41. Optionally in any embodiment, the polar axis 79 of at least one of the ring magnets 73 or 74 can be circumferential about the ring as shown in FIGS. 17 and 22. Optionally in any embodiment, the circumference of at least one of the ring magnets 73 or 74 can include plural north-south pole domains as shown in FIGS. 17 and 22.

Optionally in any embodiment, at least part of the time while providing the magnetic field, an even number of at least four magnetic field generators 61-64 or 61a-64a can be arranged about an axis to provide a quadrupole or analogous structure, as shown in FIG. 4-6, 21, 25, 38-40, 45, or 53. Optionally in any embodiment, the magnetic field generators can be relatively movable between an effective position providing the quadrupole or analogous structure and a non-functional position in which the magnetic field generators do not provide a quadrupole or analogous structure. Optionally in any embodiment, at least part of the time while providing the magnetic field, the quadrupole and medical barrel can be relatively positioned with the axis passing through the generally cylindrical inner surface 14.

Optionally in any embodiment, at least part of the time while providing the magnetic field, the quadrupole can be effective to at least partially confine the plasma at or near at least a portion of the workpiece surface. Optionally in any embodiment, at least part of the time while providing the magnetic field, a magnetic field generator having an axial polar axis can be positioned at or near at least one of the axially spaced ends. Optionally in any embodiment, at least part of the time while providing the magnetic field, magnetic field generators having axial polar axes can be positioned at or near both of the axially spaced ends.

Optionally in any embodiment, at least one of the magnetic field generators having axial polar axes can be a ring magnet. Optionally in any embodiment, at least one of the magnetic field generators having axial polar axes can be a cap magnet. Optionally in any embodiment, at least one of the magnetic field generators having axial polar axes can be a bar magnet.

Optionally in any embodiment, at least part of the time while providing the magnetic field, a magnetic field generator (for example for example any of 61-78 or 86-91, 93, 95, 97, or 99), alternatively at least two of the magnetic field generators, alternatively at least three of the magnetic field generators, alternatively at least four of the magnetic field generators, alternatively at least five of the magnetic field generators, alternatively at least six of the magnetic field generators, alternatively at least seven of the magnetic field generators, alternatively at least eight of the magnetic field generators, alternatively all of the magnetic field generators, can be rotated about the generally cylindrical interior surface 16, or the surface can rotate with respect to one, more than one, or all of the magnetic field generators, or both, during at least a portion of the plasma treatment. This is illustrated in or usable with the embodiments of FIGS. 4-6, 19-28, and 37-46, for example.

Figure 19:
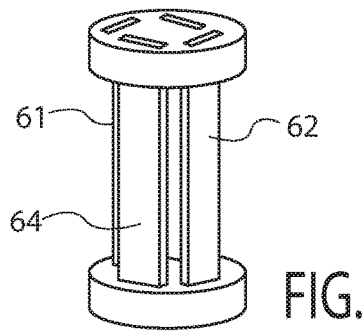
FIG. 19 is a perspective view of the quadrupole magnet array of FIG. 5, usable in any embodiment of the invention.
Figure 20:
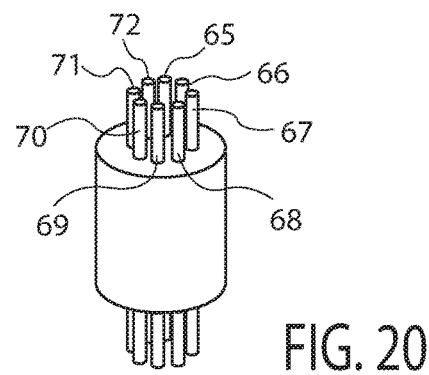
FIG. 20 is a perspective view of an axial magnet array, usable analogous to the magnet array of FIG. 19 in any embodiment of the invention.
Figure 21:
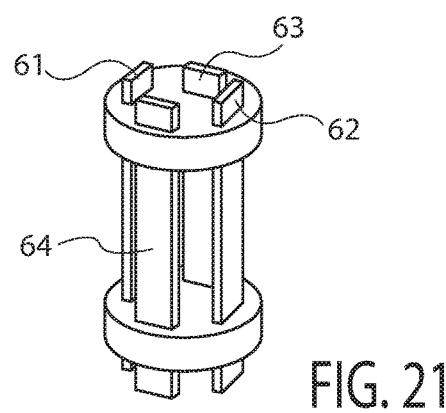
FIG. 21 is a perspective view of a quadrupole magnet array, usable analogous to the magnet array of FIG. 19 in any embodiment of the invention.

Referring in particular to FIG. 19, the illustrated quadrupole array can be rotated, for example at 10-1000 rpm, alternatively 40 to 200 RPM, to improve the uniformity of the deposition of PECVD coatings or layers within the perimeter of the magnets. For example, a rotation rate of 47 RPM has been used successfully, although faster rotation than that is contemplated to improve uniformity.

Optionally in any embodiment, at least one magnetic field generator, the generally cylindrical inner surface, or both, can be rotated at a rate effective to improve the uniformity, density, or both of the mean magnetic field strength, or to improve the uniformity, reduce the intensity, or both of workpiece heating about a circumference of the generally cylindrical inner surface, as illustrated in the working examples. Optionally in any embodiment, the rotation can be concentric or eccentric. Concentric rotation or closely circumferentially spaced magnetic field generators or uniform magnetic field strength generated by the various generators, or any combination of two or more of these, can be contemplated to provide more uniform treatment of the whole surface at the same time, while eccentric rotation or more widely circumferentially spaced magnetic field generators or variations in the magnetic strength of the magnetic field generators, or any combination of two or more of these, can be contemplated to periodically increase and decrease the magnetic field strength and heating at any particular point around the circumference of the treated surface, allowing a particular point around the circumference some cooling time between more intense applications of magnetic energy.

Instead or in addition to rotation of the magnetic field generators, the generally cylindrical inner surface can rotate with respect to one, more than one, or all of the magnetic field generators, or both, during at least a portion of the plasma treatment. This is illustrated in or usable with the embodiments of FIGS. 4-6, 19-28, and 37-46, for example.

Optionally in any embodiment, at least part of the time while providing the magnetic field, at least one of the magnetic field generators can be translated (moved in a straight line), for example axially, along the generally cylindrical inner surface, or the generally cylindrical inner surface can be translated with respect to the magnetic field generator, or both, at a rate effective to improve the uniformity of workpiece heating along the axis of the generally cylindrical inner surface. The embodiments of FIGS. 4-6, 9, 9a-13, 19-28, and 37-46, for example, can be operated while translating the magnetic field generator, and thus the magnetic field.

Optionally in any embodiment, an array of coils employed as magnetic field generators can be energized in a way causing the magnetic field about the workpiece to move, without physical motion of the coils or workpiece. For example, a series of eight solenoids arranged to form a quadrupole about a center, with their axes oriented radially, can be energized with alternating current with the phase of each coil 45 degrees ahead of the coil to its left and 45 degrees behind the coil to its right. As the phases change, the effect is similar to that provided by rotating the same quadrupole about its center, with its adjacent magnets energized with constant DC currents of opposite direction.

Optionally in any embodiment the PECVD parameters are controlled such that the distance between the inlet tube and the wall of the medical barrel or other part undergoing PECVD is:

greater than the Debye Length,
optionally at least 2 times as great as the Debye Length,
optionally at least 3 times as great as the Debye Length,
optionally at least 4 times as great as the Debye Length,
optionally at least 5 times as great as the Debye Length,
optionally at least 6 times as great as the Debye Length,
optionally at least 7 times as great as the Debye Length,
optionally at least 8 times as great as the Debye Length,
optionally at least 9 times as great as the Debye Length,
optionally at least 10 times as great as the Debye Length,
optionally at least 20 times as great as the Debye Length,
optionally at least 30 times as great as the Debye Length,
optionally at least 40 times as great as the Debye Length,
optionally at least 50 times as great as the Debye Length,
optionally at least 60 times as great as the Debye Length,
optionally at least 70 times as great as the Debye Length,
optionally at least 80 times as great as the Debye Length,
optionally at least 90 times as great as the Debye Length,
optionally at least 100 times as great as the Debye Length.
The Debye Length is defined by the following equation:

$$\lambda_D = \sqrt{\frac{\varepsilon_0 k_B / q_e^2}{n_e / T_e + \sum_{ij} j^2 n_{ij} / T_i}}$$

in which $\lambda_D$ is the Debye length,
$\varepsilon_0$ is the permittivity of free space,
$k_B$ is the Boltzmann constant,
$q_e$ is the charge of an electron,
$T_e$ and $T_i$ are the temperatures of the electrons and ions, respectively,
$n_e$ is the density of electrons,
$n_{ij}$ is the density of atomic species i, with positive ionic charge $jq_e$ Optionally in any embodiment, the uniformity of plasma modification can be expressed as a ratio of one standard deviation of coating or layer thickness, as the numerator, and the mean coating or layer thickness, as the denominator, and the ratio can be less than 0.69, alternatively from 0.69 to 0.01, alternatively from 0.69 to 0.05, alternatively from 0.66 to 0.1, alternatively from 0.66 to 0.2, alternatively from 0.66 to 0.21, alternatively less than 0.6, alternatively from 0.6 to 0.01, alternatively from 0.6 to 0.05, alternatively from 0.6 to 0.1, alternatively from 0.6 to 0.2, alternatively from 0.6 to 0.21, alternatively less than 0.5, alternatively from 0.5 to 0.01, alternatively from 0.5 to 0.05, alternatively from 0.5 to 0.1, alternatively from 0.5 to 0.2, alternatively from 0.5 to 0.21, alternatively less than 0.4, alternatively from 0.4 to 0.01, alternatively from 0.4 to 0.05, alternatively from 0.4 to 0.1, alternatively from 0.4 to 0.2, alternatively from 0.4 to 0.21, alternatively less than 0.3, alternatively from 0.3 to 0.01, alternatively from 0.3 to 0.05, alternatively from 0.3 to 0.1, alternatively from 0.3 to 0.2, alternatively from 0.3 to 0.21

Optionally in any embodiment, the plasma modification can be application of a coating or layer having a mean thickness between 1 and 1000 nm and a standard deviation of less than 190 nm, alternatively from 190 to 10 nm, alternatively from 190 to 20 nm, alternatively from 190 to 30 nm, alternatively from 190 to 40 nm, alternatively from 190 to 50 nm, alternatively from 190 to 60 nm, alternatively from 190 to 70 nm, alternatively from 190 to 80 nm, alternatively less than 161 nm, alternatively from 160 to 10 nm, alternatively from 160 to 20 nm, alternatively from 160 to 30 nm, alternatively from 160 to 40 nm, alternatively from 160 to 50 nm, alternatively from 160 to 60 nm, alternatively from 160 to 70 nm, alternatively from 160 to 80 nm, alternatively less than 140 nm, alternatively from 140 to 10 nm, alternatively from 140 to 20 nm, alternatively from 140 to 30 nm, alternatively from 140 to 40 nm, alternatively from 140 to 50 nm, alternatively from 140 to 60 nm, alternatively from 140 to 70 nm, alternatively from 140 to 80 nm, alternatively less than 122 nm, alternatively from 120 to 10 nm, alternatively from 120 to 20 nm, alternatively from 120 to 30 nm, alternatively from 120 to 40 nm, alternatively from 120 to 50 nm, alternatively from 120 to 60 nm, alternatively from 120 to 70 nm, alternatively from 120 to 80 nm, alternatively less than 100 nm, alternatively from 100 to 10 nm, alternatively from 100 to 20 nm, alternatively from 100 to 30 nm, alternatively from 100 to 40 nm, alternatively from 100 to 50 nm, alternatively from 100 to 60 nm, alternatively from 100 to 70 nm, alternatively from 100 to 80 nm, alternatively less than 80 nm, alternatively from 80 to 10 nm, alternatively from 80 to 20 nm, alternatively from 80 to 30 nm, alternatively from 80 to 40 nm, alternatively from 80 to 50 nm, alternatively from 80 to 60 nm, alternatively from 80 to 70 nm.

Magnetic Treatment Apparatus

Additional details of apparatus usable in any embodiment for plasma modifying a workpiece 12 supported on a workpiece support 114 in the presence of a magnetic field are illustrated for example in FIGS. 4-6, 9-11, 19-28, 37-39, 55-61, and 63-70. The apparatus includes the workpiece support 114 for holding a workpiece 12 in the apparatus, a plasma generator, and a magnetic field generator. The plasma generator here includes an inner electrode such as 108 (optionally further including any of the features 120 to 142, for example), an outer electrode such as 160, power supply 162, material supplies through the gas delivery port 110. The magnetic field generator in FIGS. 4-5 optionally can be for example any of the magnets 61, 62, 63, and 64 (alternatively in the respective embodiments including for example any of the magnets 61-78, coils 86-99, or electrodes 107 or 109, for example).

The workpiece 12 used in any embodiment optionally has a lumen 18 surrounded by a generally cylindrical interior surface 16. At least part of the generally cylindrical interior surface 16, here, substantially the entire generally cylindrical interior surface 16, can define a surface to be treated.

The plasma generator can be used for providing plasma within the lumen 18 of a workpiece 12 supported on the workpiece support 114 under conditions effective for plasma modification of the generally cylindrical interior surface 16 of the workpiece 12.

The magnetic field generator can be used for providing a magnetic field in at least a portion of the lumen 18 of a workpiece 12 supported on the workpiece support 114. The resulting magnetic field can have an orientation and field strength effective to improve the uniformity, density, or both of plasma modification of the generally cylindrical interior surface 16 of the generally cylindrical interior surface 16.

Optionally in any embodiment, the interior portion 81 of the solenoid 86 can be an interior winding 89. At least one of the end portions 86 or 87 providing a stronger magnetic field when energized can be a separate exterior winding 97 or 99. For example, the interior winding 89 can be provided with lower amperage than the separate exterior winding 97 or 99 when the windings can be energized, or the interior winding 89 can have fewer total turns per cm of the axis than the exterior winding 97 or 99.

As a more specific, non-limiting example, the solenoid can have a single winding extending along the interior portion 81 and the first and second opposed end portions 86 and 87, the winding having more turns per cm along the axis at or near the first and second opposed end portions 86 and 87 than along the interior portion 81.

Optionally in any embodiment, magnetic field generators can be arranged to provide the following capabilities, individually or in combination: The material supply tube 104 can rotate with respect to the magnetic field provided by the magnetic field generators (for example for example any of 61-78 or 86-91, 93, 95, 97, 99, or 820-832) and the workpiece support 114. The magnetic field provided by the magnetic field generators can rotate with respect to the material supply tube and the workpiece support. The workpiece support can rotate with respect to the material supply tube and the magnetic field provided by the magnetic field generators. The material supply tube and the magnetic field provided by the magnetic field generators can rotate at the same or different rotation rates and directions with respect to the workpiece support. The magnetic field provided by the magnetic field generators and the workpiece support can rotate at the same or different rotation rates and directions with respect to the material supply tube. The material supply tube and the workpiece support can rotate at the same or different rotation rates and directions with respect to the magnetic field provided by the magnetic field generators.

Optionally in any embodiment, apparatus can be provided for measuring plasma characteristics. As one example, an optical detector 350, for example a camera, can be provided and configured to show whether the plasma in a container includes streamers of non-uniform plasma versus a complete fill of the exposed portions of the container with uniform plasma. As another example, an optical emissions spectrometer can be provided to determine the uniformity of the plasma spectrum. As still another example, a Rogowski Coil 352 can be disposed about the inner electrode or its power supply conductor to determine the uniformity of the current supplied to the plasma. As even another example, a Langmuir probe 354 can be provided to measure the electron temperature of the plasma. The probe 354 can either be mounted on the internal electrode 108 or provided as a separate part or system.

Fluid Material

Optionally for any of the embodiments of FIGS. 7-8, 29, 36, and 48-51, the fluid material 40 contained in a pharmaceutical or other fluid package can have a pH between 5 and 6, optionally between 6 and 7, optionally between 7 and 8, optionally between 8 and 9, optionally between 6.5 and 7.5, optionally between 7.5 and 8.5, optionally between 8.5 and 9.

Optionally for any of the embodiments of FIGS. 7-8 and 29, the fluid material 40 can be a liquid at 20° C. and ambient pressure at sea level, which is defined as a pressure of 760 mm Hg.

Optionally for any of the embodiments of FIGS. 7-8 and 29, the fluid material 40 can be an aqueous liquid.

Optionally for any of the embodiments of FIGS. 7-8 and 29, the fluid material 40 comprises a member or a combination of two or more of the drugs listed later in this specification.

As several examples, the fluid material 40 can be an inhalation anesthetic, a drug, or a diagnostic test material. Any of these fluid materials 40 can be an injectable material, a volatile material capable of being inhaled, or otherwise capable of being introduced into a subject.

Other Uses of the Passivation Layer or pH Protective Coating or Layer

A vessel with a passivation layer or pH protective coating or layer as described herein can also be evacuated and stored in an evacuated state. For example, the passivation layer or pH protective coating or layer allows better maintenance of the vacuum in comparison to a corresponding vessel without a passivation layer or pH protective coating or layer. In one aspect of this embodiment, the vessel with a passivation layer or pH protective coating or layer can be a blood collection tube. The tube can also contain an agent for preventing blood clotting or platelet activation, for example EDTA or heparin.

Even another embodiment can be a medical or diagnostic kit including a vessel having a passivation layer or pH protective coating or layer as defined in any embodiment herein on a substrate as defined in any embodiment herein. Optionally, the kit additionally includes a medicament or diagnostic agent as defined in any embodiment herein which is contained in the vessel with a passivation layer or pH protective coating or layer in contact with the coating or layer; and/or a hypodermic needle, double-ended needle, or other delivery conduit; and/or an instruction sheet.

Use of the passivation layer or pH protective coating or layer according to any described embodiment is contemplated for preventing or reducing precipitation and/or clotting or platelet activation of a compound or a component of the composition in contact with the coating or layer.

The use of a coated substrate according to any described embodiment is contemplated for storing insulin. As one option, precipitation of the insulin can be prevented or reduced by providing vessel to contain the insulin having a contact surface including a passivation layer or pH protective coating or layer.

As another option, the compound or a component of the composition can be blood or a blood fraction, and blood clotting or platelet activation can be prevented or reduced by storing the blood in the blood collection tube in contact with a passivation layer or pH protective coating or layer. Optionally, the blood collection tube can contain an agent for preventing blood clotting or platelet activation, for example ethylenediamineteetraacetic acid (EDTA), a sodium salt thereof, or heparin. The blood collection tube can include a passivation layer or pH protective coating or layer for preventing the agent from attacking an $SiO_x$ barrier coating or layer in the vessel. The use of a coated substrate according to any described embodiment is contemplated for storing blood. Optionally, the stored blood can be viable for return to the vascular system of a patient.

Use of a coating or layer according to any described embodiment can be contemplated as (i) a lubricity coating or layer having a lower frictional resistance than the uncoated surface; and/or (ii) a passivation layer or pH protective coating or layer preventing dissolution of the barrier coating or layer in contact with a fluid, and/or (iii) a hydrophobic coating or layer that can be more hydrophobic than the uncoated surface.

Optional Embodiments

Optionally in any embodiment, the lubricity coating or layer (34) has a transition of thickness between the first (800) and second (802) portions of the generally cylindrical interior surface 16.

Optionally in any embodiment, the minimum mean thickness of the lubricity coating or layer (34) in the first portion (800) is 0 nm and the maximum mean thickness of the lubricity coating or layer (34) is 0.8 times, optionally 0.7 times, optionally 0.6 times, optionally 0.5 times, optionally 0.4 times, optionally 0.3 times, optionally 0.2 times, optionally 0.1 times, optionally 0.09 times, optionally 0.08 times, optionally 0.07 times, optionally 0.06 times, optionally 0.05 times, optionally 0.04 times, optionally 0.03 times, optionally 0.02 times, optionally 0.01 times the mean thickness of the lubricity coating or layer (34) in the second portion (802).

Optionally in any embodiment, a third portion of the generally cylindrical interior surface 16 is provided between the second portion (802) of the generally cylindrical interior surface 16 and the back end (32) of the medical barrel or cartridge (14).

Optionally in any embodiment, the second portion (802) of the generally cylindrical interior surface 16 has a smaller inside diameter than the rear end of the first portion (800) of the generally cylindrical interior surface 16.

Optionally in any embodiment, the break loose force (Fi) of the plunger or piston (36) from its rest position is less than 12 N, alternatively less than 10 N, alternatively less than 8 N, alternatively less than 6 N, alternatively less than 4 N, after two weeks' storage with the plunger or piston (36) in the rest position.

Optionally in any embodiment, the break loose force (Fi) of the plunger or piston (36) from its rest position is at least 3 N, after two weeks' storage with the plunger or piston (36) in the rest position Optionally in any embodiment, the maintenance force (Fm) of the plunger or piston (36) is between 2 and 8 N.

Optionally in any embodiment, the dissolved Si extraction from the lubricity coating or layer (34) is less than 10, alternatively less than 5, alternatively less than 4, alternatively less than three micrograms.

Optionally in any embodiment, the dissolved Si extraction from the lubricity coating or layer (34) is more than 2 micrograms.

Optionally in any embodiment, the linear and cyclic siloxanes extracted using aqueous media from the lubricity coating or layer (34) by gas chromatography and mass spectroscopy is less than 10, alternatively less than 1, alternatively less than 0.7, alternatively less than 0.08 microgram per gram, optionally less than the detection limit for aqueous extraction of coated plastic components.

Optionally in any embodiment, the first portion (800) of the generally cylindrical interior surface 16 is essentially free of lubricity coating or layer material.

Optionally in any embodiment, the first portion (800) of the generally cylindrical interior surface 16 is free of detectable lubricity coating or layer material.

Optionally in any embodiment, the first portion (800) of the generally cylindrical interior surface 16 has a draft angle from 0° to less than 1°, optionally from 0 to 0.5°, optionally from 0° to 0.25°, optionally from 0° to 0.16°, optionally from 0° to 0.03°, optionally from 0° to 0.014°, optionally from 0° to 0.01°.

Optionally in any embodiment, the generally cylindrical interior surface 16 has a third portion between the second portion (802) and the back end (32), the third portion having a front end adjacent to the rear end of the second portion (802) and a rear end.

Optionally in any embodiment, the third portion of the generally cylindrical interior surface 16 comprises a lubricity coating or layer (34) applied by PECVD.

Optionally in any embodiment, the generally cylindrical interior surface 16 comprises a polycarbonate, an olefin polymer (for example polypropylene (PP) or polyethylene (PE)), a cyclic olefin copolymer (COC), a cyclic olefin polymer (COP), polymethylpentene, a polyester (for example polyethylene terephthalate, polyethylene naphthalate, or polybutylene terephthalate (PBT)), PVdC (polyvinylidene chloride), polyvinyl chloride (PVC), polycarbonate, polylactic acid, polystyrene, hydrogenated polystyrene, poly(cyclohexylethylene) (PCHE), epoxy resin, nylon, polyurethane polyacrylonitrile (PAN), polyacrylonitrile (PAN), an ionomeric resin (for example Surlyn®), glass (for example borosilicate glass), or a combination of any two or more of these; preferably comprises a cyclic olefin polymer, a polyethylene terephthalate or a polypropylene; and more preferably comprises COP.

Optionally in any embodiment, the lubricity coating or layer (34) has an atomic ratio $SiO_xC_y$ or $SiN_xC_y$ as measured by XPS, in which x is from about 0.5 to about 2.4, y is from about 0.6 to about 3.

Optionally in any embodiment, the lubricity coating or layer (34) comprises a graded composite of $SiO_xC_y$ to $SiO_x$ or vice versa.

Optionally in any embodiment, the lubricity coating or layer (34) has a mean thickness of from 1 to 5000 nm, preferably of from 30 to 1000 nm, more preferably of from 100 to 500 nm.

Optionally in any embodiment, the mean thickness of a coating or layer is determined by spectral reflectance.

Optionally in any embodiment, the lubricity coating or layer (34):

(i) has a lower wetting tension than the uncoated surface, preferably a wetting tension of from 20 to 72 dyne/cm, more preferably a wetting tension of from 30 to 60 dynes/cm, more preferably a wetting tension of from 30 to 40 dynes/cm, preferably 34 dyne/cm; and/or (ii) is more hydrophobic than the uncoated surface.

Optionally in any embodiment, the pharmaceutical composition comprises a biologically active compound or composition or a biological fluid, preferably (i) citrate or a citrate containing composition, (ii) a medicament, in particular insulin or an insulin containing composition, or (iii) blood or blood cells.

Optionally in any embodiment, the plunger initiation force, Fi, is from 2.5 to 15 N and the plunger maintenance force Fm is from 2.5 to 25 N after 1 week.

Optionally in any embodiment, a barrier coating or layer is provided on at least the first portion (800) of the generally cylindrical interior surface 16.

Optionally in any embodiment, the barrier coating or layer comprises $SiO_x$, in which x is from 1.5 to 2.9 as measured by XPS.

Optionally in any embodiment, the barrier coating or layer is from 2 to 1000 nm thick, optionally from 20 to 300 nm thick.

Optionally in any embodiment, the organosilicon precursor for the barrier coating or layer is a linear siloxane, preferably HMDSO or TMDSO.

Optionally in any embodiment, a tie coating or layer is provided on at least the first portion (800) of the generally cylindrical interior surface 16.

Optionally in any embodiment, an adhesion coating or layer or tie coating or layer (two different terms for the same layer) comprises $SiO_xC_y$ or $SiN_xC_y$, in which x is from about 0.5 to about 2.4 and y is from about 0.6 to about 3 as measured by XPS.

Optionally in any embodiment, the tie coating or layer is from 2 to 1000 nm thick.

Optionally in any embodiment, the organosilicon precursor for the tie coating or layer is a siloxane, preferably OMCTS or TMDSO.

Optionally in any embodiment, a pH protective coating or layer is provided on at least the first portion of the generally cylindrical interior surface 16.

Optionally in any embodiment, the pH protective coating or layer comprises $SiO_xC_y$ or $SiN_xC_y$, in which x is from about 0.5 to about 2.4 and y is from about 0.6 to about 3 as measured by XPS.

Optionally in any embodiment, the pH protective coating or layer is from 2 to 1000 nm thick.

Optionally in any embodiment, a hydrophobic coating or layer is provided on at least the first portion (800) of the generally cylindrical interior surface 16.

Optionally in any embodiment, the hydrophobic coating or layer comprises $SiO_xC_y$ or $SiN_xC_y$, in which x is from about 0.5 to about 2.4 and y is from about 0.6 to about 3 as measured by XPS.

Optionally in any embodiment, the hydrophobic coating or layer is from 2 to 1000 nm thick.

Optionally in any embodiment, the organosilicon precursor for the hydrophobic coating or layer is a linear siloxane, preferably OMCTS or TMDSO.

Optionally in any embodiment, a tie coating or layer, a barrier coating or layer, and a pH protective coating or layer are provided on at least the first portion of the generally cylindrical interior surface 16.

Optionally in any embodiment, the lubricity coating or layer (34) overlies the tie coating or layer, the barrier coating or layer, and the pH protective coating or layer.

Optionally in any embodiment, the conditions effective to deposit a lubricity coating or layer (34) on the second portion (802) of the generally cylindrical interior surface 16 having a greater mean thickness include applying the electromagnetic energy at a sufficiently low power level to reduce the thickness of the lubricity coating or layer (34) applied to the first portion (800) of the generally cylindrical interior surface 16, relative to the thickness of the lubricity coating or layer (34) applied to the second portion (802) of the generally cylindrical interior surface 16.

Optionally in any embodiment, a portion of the precursor gas (588) undergoes a chemical reaction in the plasma, forming a reaction product, and the conditions effective to deposit a lubricity coating or layer (34) on the second portion (802) of the generally cylindrical interior surface 16 having a greater mean thickness include exhausting the reaction product through the back end (32) of the medical barrel, auto-injector cartridge, or similar device (14).

Optionally in any embodiment, the precursor gas (588) comprises a linear siloxane, a monocyclic siloxane, a polycyclic siloxane, a polysilsesquioxane, a linear silazane, a monocyclic silazane, a polycyclic silazane, a polysilsesquiazane, a silatrane, a silquasilatrane, a silproatrane, an azasilatrane, an azasilquasiatrane, an azasilproatrane, or a combination of any two or more of these precursors; optionally a monocyclic siloxane, optionally octamethylcyclotetrasiloxane; optionally a linear siloxane, optionally tetramethyldisiloxane.

Optionally in any embodiment, the nominal capacity of the medical barrel, auto-injector cartridge, or similar device (14) is from 0.1 to 5 mL, optionally from 0.5 to 3 mL, optionally from 0.7 to 2 mL, optionally 1 mL.

Optionally in any embodiment, the electromagnetic energy is applied at a minimum power level of 0.5 Watts to a maximum power level of 15 Watts.

Optionally in any embodiment, the electromagnetic energy is applied at a minimum power level of 0.6 Watts, optionally 0.7 Watts, optionally 0.8 Watts, optionally 0.9 Watts, optionally 1 Watt, optionally 2 Watts.

Optionally in any embodiment, the electromagnetic energy is applied at a maximum power of 3 Watts, optionally 4 Watts, optionally 5 Watts, optionally 6 Watts, optionally 7 Watts, optionally 8 Watts, optionally 9 Watts, optionally 10 Watts.

Optionally in any embodiment, while applying a lubricity coating or layer (34) to the generally cylindrical interior surface 16 by PECVD, a magnetic field is applied at the second portion (802) of the generally cylindrical interior surface 16, such that the net mean magnetic field strength present at the second portion (802) of the generally cylindrical interior surface 16 when depositing the lubricity coating or layer (34) is greater, optionally at least 2 times as great, optionally at least 5 times as great, optionally at least 10 times as great, optionally at least 20 times as great, optionally at least 30 times as great, optionally at least 40 times as great, optionally 50 times as great, optionally 100 times as great, optionally 200 times as great, optionally 500 times as great, as the mean magnetic field strength at the first portion (800) of the generally cylindrical interior surface 16.

Optionally in any embodiment, while applying a lubricity coating or layer (34) to the generally cylindrical interior surface 16 by PECVD, the minimum mean magnetic field strength when depositing the lubricity coating or layer (34), in Gauss, at the second portion (802) of the generally cylindrical interior surface 16 is greater than 1 Gauss (100 µT, microTesla), optionally at least 2 Gauss, optionally at least 5 Gauss, optionally at least 10 Gauss, optionally at least 15 Gauss, optionally at least 20 Gauss, optionally at least 25 Gauss, optionally at least 30 Gauss, optionally at least 35 Gauss, optionally at least 40 Gauss.

Optionally in any embodiment, while applying a lubricity coating or layer (34) to the generally cylindrical interior surface 16 by PECVD, the maximum mean magnetic field strength when depositing the lubricity coating or layer (34), in Gauss, at the second portion (802) of the generally cylindrical interior surface 16 is 100 Gauss (10,000 µT, microTesla), optionally 80 Gauss, optionally 60 Gauss, optionally 50 Gauss, optionally 45 Gauss.

Optionally in any embodiment, the magnetic field has a position, orientation, and field strength effective to improve the uniformity, density, or both of plasma modification of the surface of the medical barrel, auto-injector cartridge, or similar device.

Optionally in any embodiment, the magnetic field improves the axial uniformity, density, or both of plasma distribution along at least a portion of the surface.

Optionally in any embodiment, providing the magnetic field improves the radial uniformity, density, or both of plasma distribution along at least a portion of the surface.

Optionally in any embodiment, the plasma comprises plasma electrons and the magnetic field is effective to improve confinement of the plasma electrons in the lumen (18).

Optionally in any embodiment, the magnetic field is provided by providing a magnetic field generator (for example for example any of 61-78, 86, 88, 90, or 820), alternatively at least two magnetic field generators, optionally at least three magnetic field generators, optionally at least four magnetic field generators, optionally at least five magnetic field generators, optionally at least six magnetic field generators, optionally at least seven magnetic field generators, optionally at least eight magnetic field generators near the surface, each magnetic field generator having a first pole and a second pole defining a polar axis (80).

Optionally in any embodiment, at least part of the time while providing the magnetic field, a magnetic field generator (for example for example any of 61-78, 86, 88, 90, or 820), alternatively at least two of the magnetic field generators, alternatively at least three of the magnetic field generators, alternatively at least four of the magnetic field generators, alternatively at least five of the magnetic field generators, alternatively at least six of the magnetic field generators, alternatively at least seven of the magnetic field generators, alternatively at least eight of the magnetic field generators, alternatively all of the magnetic field generators, have their polar axes generally parallel to the axis of the surface.

Optionally in any embodiment, at least part of the time while providing the magnetic field, at least two of the magnetic field generators, alternatively at least three of the magnetic field generators, alternatively at least four of the magnetic field generators, alternatively at least five of the magnetic field generators, alternatively at least six of the magnetic field generators, alternatively at least seven of the magnetic field generators, alternatively at least eight of the magnetic field generators, alternatively all of the magnetic field generators, are circumferentially distributed around the surface in the operative position.

Optionally in any embodiment, the magnetic field generators (for example for example any of 61-78, 86, 88, 90, or 820) have their polar axes extending axially with respect to the surface.

Optionally in any embodiment, the magnetic field generators (for example for example any of 61-78, 86, 88, 90, or 820) are kept stationary during PECVD.

Optionally in any embodiment, at least part of the time while providing the magnetic field, at least two of the magnetic field generators (for example for example any of 61-78, 86, 88, 90, or 820), alternatively at least three of the magnetic field generators, alternatively at least four of the magnetic field generators, alternatively at least five of the magnetic field generators, alternatively at least six of the magnetic field generators, alternatively at least seven of the magnetic field generators, alternatively at least eight of the magnetic field generators, alternatively all of the magnetic field generators, are substantially circumferentially equidistant from the adjacent magnetic field generators.

Optionally in any embodiment, at least part of the time while providing the magnetic field, a magnetic field generator (for example for example any of 61-78, 86, 88, 90, or 820), alternatively at least two of the magnetic field generators (for example for example any of 61-78, 86, 88, 90, or 820), alternatively at least three of the magnetic field generators, alternatively at least four of the magnetic field generators, alternatively at least five of the magnetic field generators, alternatively at least six of the magnetic field generators, alternatively at least seven of the magnetic field generators, alternatively at least eight of the magnetic field generators, alternatively all of the magnetic field generators, are rotated about the surface, or the surface rotates with respect to the magnetic field generators, or both, during at least a portion of the plasma treatment.

Optionally in any embodiment, at least one magnetic field generator (for example for example any of 61-78, 86, 88, 90, or 820) is a permanent magnet or a coil or a combination of at least one permanent magnet and at least one coil.

Optionally in any embodiment, two or more magnetic field generators (for example any of 61-78, 86, 88, 90, or 820) are spaced to define a recess between them, within which at least a portion of the surface of the medical barrel, auto-injector cartridge, or similar device is positioned.

Optionally in any embodiment, at least part of the time while providing the magnetic field, at least one magnetic field generator (for example any of 61-78, 86, 88, 90, or 820), the medical barrel, auto-injector cartridge, or similar device surface, or both, is rotated at a rate effective to improve the uniformity, density, or both of the mean magnetic field strength about a circumference of the medical barrel, auto-injector cartridge, or similar device surface. More broadly, at least one of the magnetic field generators or the generally cylindrical surface is rotated relative to the other.

Optionally in any embodiment, at least part of the time while providing the magnetic field, at least one magnetic field generator (for example any of 61-78, 86, 88, 90, or 820), the medical barrel, auto-injector cartridge, or similar device surface, or both, is rotated at a rate effective to improve the uniformity, reduce the intensity, or both of medical barrel, auto-injector cartridge, or similar device heating about a circumference of the medical barrel, auto-injector cartridge, or similar device surface.

Optionally in any embodiment, at least part of the time while providing the magnetic field at least one of the magnetic field generators (for example any of 61-78, 86, 88, 90, or 820) is translated axially along the medical barrel, auto-injector cartridge, or similar device surface, or translating the medical barrel, auto-injector cartridge, or similar device surface with respect to the magnetic field generator (for example any of 61-78, 86, 88, 90, or 820), or both, at a rate effective to improve the uniformity of medical barrel, auto-injector cartridge, or similar device heating along the axis of the medical barrel, auto-injector cartridge, or similar device surface.

Optionally in any embodiment, at least part of the time while providing the magnetic field, at least two of the magnetic field generators (for example any of 61-78, 86, 88, 90, or 820), alternatively at least three of the magnetic field generators, alternatively at least four of the magnetic field generators, alternatively at least five of the magnetic field generators, alternatively at least six of the magnetic field generators, alternatively at least seven of the magnetic field generators, alternatively at least eight of the magnetic field generators, alternatively all of the magnetic field generators, are axially stacked with respect to the generally cylindrical surface.

Optionally in any embodiment, at least part of the time while providing the magnetic field, at least two of the axially stacked magnetic field generators (for example any of 61-78, 86, 88, 90, or 820), alternatively at least three of the axially stacked magnetic field generators, alternatively at least four of the axially stacked magnetic field generators, alternatively at least five of the axially stacked magnetic field generators, alternatively at least six of the axially stacked magnetic field generators, alternatively at least seven of the axially stacked magnetic field generators, alternatively at least eight of the axially stacked magnetic field generators, alternatively all of the axially stacked magnetic field generators, are axially spaced from each other.

Optionally in any embodiment, at least part of the time while providing the magnetic field, at least two of the axially stacked magnetic field generators (for example any of 61-78, 86, 88, 90, or 820), alternatively at least three of the axially stacked magnetic field generators, alternatively at least four of the axially stacked magnetic field generators, alternatively at least five of the axially stacked magnetic field generators, alternatively at least six of the axially stacked magnetic field generators, alternatively at least seven of the axially stacked magnetic field generators, alternatively at least eight of the axially stacked magnetic field generators, alternatively all of the axially stacked magnetic field generators, axially abut each other.

Optionally in any embodiment, at least part of the time while providing the magnetic field, the magnetic field generator (for example any of 61-78, 86, 88, 90, or 820) is provided by positioning at least one coil near the surface and conducting an electrical current through the coil. Optionally in any embodiment, the at least one coil comprises a solenoid coil.

Optionally in any embodiment, the at least one coil comprises a generally toroidal coil 8 or 9 having a central opening and a geometric axis passing through its central opening.

Optionally in any embodiment, at least part of the time while providing the magnetic field, the generally toroidal coil 8 or 9 is oriented with its geometric axis at least generally parallel, optionally at least generally collinear with the axis of the surface.

Optionally in any embodiment, the generally toroidal coils 8 or 9 have at least two arc segments, optionally at least four arc segments, optionally at least 6 arc segments, optionally at least eight arc segments, optionally at least eight 45° arc segments, and alternating segments are wound in opposite directions.

Optionally in any embodiment, the generally toroidal coils have cross-sections that are substantially circular or substantially rectangular.

Optionally in any embodiment, at least part of the time while providing the magnetic field, at least one magnetic field generator (for example any of 61-78, 86, 88, 90, or 820) is oriented with its polar axis (80) at least generally parallel to the axis of the surface.

Optionally in any embodiment, at least part of the time while providing the magnetic field, at least one magnetic field generator (for example any of 61-78, 86, 88, 90, or 820) is oriented with its polar axis (80) at least generally collinear with the axis of the surface.

Optionally in any embodiment, at least part of the time while providing the magnetic field, the magnetic field generator (for example any of 61-78, 86, 88, 90, or 820) has a passage extending along its polar axis (80) and the surface is located entirely within the passage.

Optionally in any embodiment, the magnetic field generator (for example any of 61-78, 86, 88, 90, or 820) is a Helmholtz coil.

Optionally in any embodiment, the Helmholtz coil comprises first and second spaced solenoid coils with a space between them providing a viewing window allowing the plasma to be viewed while the method is in progress.

Optionally in any embodiment, at least part of the time while providing the magnetic field, the magnetic field generator (for example any of 61-78, 86, 88, 90, or 820) provides a field strength that varies along the medical barrel, auto-injector cartridge, or similar device surface.

Optionally in any embodiment, at least a portion of the medical barrel, auto-injector cartridge, or similar device surface is generally cylindrical.

Optionally in any embodiment, at least part of the time while providing the magnetic field, the distance between at least one magnetic field generator (for example any of 61-78, 86, 88, 90, or 820) and the medical barrel, auto-injector cartridge, or similar device surface varies along the medical barrel, auto-injector cartridge, or similar device surface.

Optionally in any embodiment, at least part of the time while providing the magnetic field, the field strength varies along the medical barrel, auto-injector cartridge, or similar device surface to define a profile of varying field strength.

Optionally in any embodiment, at least part of the time while providing the plasma and not providing the magnetic field, the plasma modification of the surface of the medical barrel, auto-injector cartridge, or similar device varies along the medical barrel, auto-injector cartridge, or similar device surface to define a profile of varying plasma modification.

Optionally in any embodiment, at least part of the time while providing the magnetic field, the magnetic field generators (for example any of 61-78, 86, 88, 90, or 820) are configured such that variations in the profile of field strength tend to counteract variations of plasma modification, improving the uniformity, density, or both of plasma modification of the surface of the medical barrel, auto-injector cartridge, or similar device.

Optionally in any embodiment, providing an electron mirror is provided at or near the back end (32) of the medical barrel, auto-injector cartridge, or similar device (14).

Optionally in any embodiment, the structure providing an electron mirror comprises at least a portion of a magnetic field generator.

Optionally in any embodiment, the structure providing an electron mirror comprises a ferromagnetic or ferromagnetic material.

Optionally in any embodiment, the structure providing an electron mirror comprises a magnetic field generator.

Optionally in any embodiment, the structure providing an electron mirror comprises a negatively charged object or portion of an object.

Optionally in any embodiment, at least part of the time while providing the magnetic field, at least a portion of the magnetic field in at least a portion of the lumen (18) is oriented with its polar axis (80) generally parallel to the axis of the surface to be treated.

Optionally in any embodiment, at least part of the time while providing the magnetic field, at least a portion of the magnetic field in at least a portion of the lumen (18) is oriented with its polar axis (80) extending around the axis of the surface to be treated.

Optionally in any embodiment, at least part of the time while providing the magnetic field, at least a portion of the magnetic field in at least a portion of the lumen (18) is oriented with its polar axis (80) extending generally in radial planes with respect to the surface to be treated.

Optionally in any embodiment, at least one magnetic field generator (for example any of 61-78, 86, 88, 90, or 820), alternatively at least two magnetic field generators, alternatively at least three magnetic field generators, alternatively at least four magnetic field generators, alternatively at least five magnetic field generators, alternatively at least six magnetic field generators, alternatively at least seven magnetic field generators, alternatively at least eight magnetic field generators, alternatively all of the magnetic field generators are permanent magnets (for example any of 61-78 or 820) having opposed first and second poles (822, 824) defining a polar axis (80) and first and second ends respectively corresponding to the first and second poles, the permanent magnets having one or more sides (820) extending from the first pole (822) to the second pole (824), in which at least one side (826) is tapered inward between the first pole (822) and the second pole (824).

Optionally in any embodiment, the second end (824) of at least one magnetic field generator (for example any of 61-78, 86, 88, 90, or 820), alternatively at least two magnetic field generators, alternatively at least three magnetic field generators, alternatively at least four magnetic field generators, alternatively at least five magnetic field generators, alternatively at least six magnetic field generators, alternatively at least seven magnetic field generators, alternatively at least eight magnetic field generators, alternatively all of the magnetic field generators is larger than the first end (822).

Optionally in any embodiment, at least one magnetic field generator (for example any of 61-78, 86, 88, 90, or 820), alternatively at least two magnetic field generators, alternatively at least three magnetic field generators, alternatively at least four magnetic field generators, alternatively at least five magnetic field generators, alternatively at least six magnetic field generators, alternatively at least seven magnetic field generators, alternatively at least eight magnetic field generators, alternatively all of the magnetic field generators are generally conical, frustoconical, pyramidal, or frustopyramidal.

Optionally in any embodiment, at least one magnetic field generator (for example any of 61-78, 86, 88, 90, or 820), alternatively at least two magnetic field generators, alternatively at least three magnetic field generators, alternatively at least four magnetic field generators, alternatively at least five magnetic field generators, alternatively at least six magnetic field generators, alternatively at least seven magnetic field generators, alternatively at least eight magnetic field generators, alternatively all of the magnetic field generators are generally conical with a rounded smaller end (822).

Optionally in any embodiment, at least one magnetic field generator (820), alternatively at least two magnetic field generators, alternatively at least three magnetic field generators, alternatively at least four magnetic field generators, alternatively at least five magnetic field generators, alternatively at least six magnetic field generators, alternatively at least seven magnetic field generators, alternatively at least eight magnetic field generators, alternatively all of the magnetic field generators are oriented in a ring-shaped array (834) with their smaller ends (822) disposed radially inward and their larger ends (824) disposed radially outward. This is an example of the optional practice of orienting at least a portion of the magnetic field in at least a portion of the lumen is oriented with its polar axis extending generally in radial planes with respect to the generally cylindrical surface to be treated.

Optionally in any embodiment, at least one magnetic field generator (for example any of 61-78, 86, 88, 90, or 820), alternatively at least two magnetic field generators, alternatively at least three magnetic field generators, alternatively at least four magnetic field generators, alternatively at least five magnetic field generators, alternatively at least six magnetic field generators, alternatively at least seven magnetic field generators, alternatively at least eight magnetic field generators, alternatively all of the magnetic field generators are oriented with the pole of the same sign (North or South) disposed radially inward and their first ends disposed radially outward.

Optionally in any embodiment, at least one magnetic field generator (for example any of 61-78, 86, 88, 90, or 820), alternatively at least two magnetic field generators, alternatively at least three magnetic field generators, alternatively at least four magnetic field generators, alternatively at least five magnetic field generators, alternatively at least six magnetic field generators, alternatively at least seven magnetic field generators, alternatively at least eight magnetic field generators, alternatively all of the magnetic field generators are oriented with their North poles disposed radially inward.

Optionally in any embodiment, at least one magnetic field generator (for example any of 61-78, 86, 88, 90, or 820), alternatively at least two magnetic field generators, alternatively at least three magnetic field generators, alternatively at least four magnetic field generators, alternatively at least five magnetic field generators, alternatively at least six magnetic field generators, alternatively at least seven magnetic field generators, alternatively at least eight magnetic field generators, alternatively all of the magnetic field generators are oriented with their South poles disposed radially inward.

Optionally in any embodiment, at least one magnetic field generator (for example any of 61-78, 86, 88, 90, or 820), alternatively at least two magnetic field generators, alternatively at least three magnetic field generators, alternatively at least four magnetic field generators, alternatively at least five magnetic field generators, alternatively at least six magnetic field generators, alternatively at least seven magnetic field generators, alternatively at least eight magnetic field generators, alternatively all of the magnetic field generators are bar magnets.

Optionally in any embodiment, at least one magnetic field generator (any of 73-78), alternatively at least two magnetic field generators, alternatively at least three magnetic field generators, alternatively at least four magnetic field generators, alternatively at least five magnetic field generators, alternatively at least six magnetic field generators, alternatively at least seven magnetic field generators, alternatively at least eight magnetic field generators, alternatively all of the magnetic field generators are ring magnets having central apertures sized to receive the medical barrel, auto-injector cartridge, or similar device surface.

Optionally in any embodiment, the north and second poles of at least one of the ring magnets (any of 73-78) are its opposed annular faces.

Optionally in any embodiment, the magnetic field is provided at least in part by a stack of:

- at least one interior ring magnet (any of 73-78) having the medical barrel, auto-injector cartridge, or similar device surface within its central recess when in its operative position,
- at least one cap magnet (any of 65-78 or 820) axially aligned with but outside the stack of interior ring magnets,
- in which the interior ring magnets provide a first magnetic field strength radially adjacent to the medical barrel, auto-injector cartridge, or similar device surface that is less than the magnetic field strength provided by the cap magnet axially adjacent to the medical barrel, auto-injector cartridge, or similar device surface, and
- optionally one or more additional magnets, positioned between a cap magnet and the stack of interior ring magnets.

Optionally in any embodiment, the polar axis (80) of at least one of the ring magnets (73-78) is circumferential about the ring.

Optionally in any embodiment, the circumference of at least one of the ring magnets (73-78) comprises plural north-second pole domains.

Optionally in any embodiment, at least part of the time while providing the magnetic field, an even number of at least four magnetic field generators (61, 62) are arranged about an axis to provide a quadrupole or analogous structure between axially spaced ends. This is an example of the optional practice of orienting at least a portion of the magnetic field in at least a portion of the lumen with its polar axis extending generally in radial planes with respect to the generally cylindrical surface to be treated. Optionally, at least two of the magnetic field generators are distributed circumferentially about the axis of the generally cylindrical surface with alternating magnetic field generators oriented with their polar axes reversed.

Optionally in any embodiment, the magnetic field generators are relatively movable between an effective position (834) and a non-functional position (834a).

Optionally in any embodiment, at least part of the time while providing the magnetic field, the quadrupole and medical barrel, auto-injector cartridge, or similar device are relatively positioned with the axis passing through the medical barrel, auto-injector cartridge, or similar device surface.

Optionally in any embodiment, at least part of the time while providing the magnetic field, the quadrupole is effective to at least partially confine the plasma at or near at least a portion of the medical barrel, auto-injector cartridge, or similar device surface.

Optionally in any embodiment, at least part of the time while providing the magnetic field, a magnetic field generator (for example any of 61-78, 86, 88, 90, or 820) having an axial polar axis (80) is positioned at or near at least one of the axially spaced ends.

Optionally in any embodiment, at least part of the time while providing the magnetic field, magnetic field generators having axial polar axes are positioned at or near both of the axially spaced ends.

Optionally in any embodiment, at least one of the magnetic field generators having axial polar axes comprises a ring magnet.

Optionally in any embodiment, at least one of the magnetic field generators having axial polar axes comprises a cap magnet.

Optionally in any embodiment, at least one of the magnetic field generators having axial polar axes comprises a bar magnet.

Optionally in any embodiment, optimizing the Fi value of a medical barrel, auto-injector cartridge, or similar device (14) is optimized by choosing the inside diameter of its generally cylindrical interior surface 16.

Optionally in any embodiment, the Fm value of a medical barrel, auto-injector cartridge, or similar device (14) is optimized by choosing the inside diameter of its generally cylindrical interior surface 16.

Optionally in any embodiment, the fluid composition (40) is a pharmaceutical composition suitable for parenteral administration to a human, such as any of those listed in the present specification.

Optionally in any embodiment, the fluid composition (40) is a diagnostic composition, such as any of those listed in the present specification.

Optionally in any embodiment, the fluid composition (40) is an anaesthetic composition suitable for administration to a human, such as any of those listed in the present specification.

Measurement of Coating or Layer Thickness

The thickness of a PECVD coating or layer such as the passivation layer or pH protective coating or layer, the barrier coating or layer, the lubricity coating or layer, and/or a composite of any two or more of these coatings or layers can be measured, for example, by transmission electron microscopy (TEM) or using a spectral reflectance instrument.

The TEM can be carried out, for example, as follows. Samples can be prepared for Focused Ion Beam (FIB) cross-sectioning in two ways. Either the samples can be first coated with a thin layer of carbon (50-100 nm thick) and then coated with a sputtered coating or layer of platinum (50-100 nm thick) using a K575X Emitech system, or the samples can be coated directly with the sputtered Pt layer. The coated samples can be placed in an FEI FIB200 FIB system. An additional coating or layer of platinum can be FIB-deposited by injection of an organometallic gas while rastering the 30 kV gallium ion beam over the area of interest. The area of interest for each sample can be chosen to be a location half way down the length of the medical barrel. Thin cross sections measuring approximately 15 μm ("micrometers") long, 2 μm wide and 15 μm deep can be extracted from the die surface using an in-situ FIB lift-out technique. The cross sections can be attached to a 200 mesh copper TEM grid using FIB-deposited platinum. One or two windows in each section, measuring about 8 μm wide, can be thinned to electron transparency using the gallium ion beam of the FEI FIB.

Cross-sectional image analysis of the prepared samples can be performed utilizing either a Transmission Electron Microscope (TEM), or a Scanning Transmission Electron Microscope (STEM), or both. All imaging data can be recorded digitally. For STEM imaging, the grid with the thinned foils can be transferred to a Hitachi HD2300 dedicated STEM. Scanning transmitted electron images can be acquired at appropriate magnifications in atomic number contrast mode (ZC) and transmitted electron mode (TE). The following instrument settings can be used.

| Instrument | Scanning Transmission Electron Microscope |
|---|---|
| Manufacturer/Model | Hitachi HD2300 |
| Accelerating Voltage | 200 kV |
| Objective Aperture | #2 |
| Condenser Lens 1 Setting | 1.672 |
| Condenser Lens 2 Setting | 1.747 |
| Approximate Objective Lens | 5.86 |

| Instrument | Scanning Transmission Electron Microscope |
|---|---|
| Setting | |
| ZC Mode Projector Lens | 1.149 |
| TE Mode Projector Lens | 0.7 |
| Image Acquisition | |
| Pixel Resolution | 1280 × 960 |
| Acquisition Time | 20 sec. (×4) |

For TEM analysis the sample grids can be transferred to a Hitachi HF2000 transmission electron microscope. Transmitted electron images can be acquired at appropriate magnifications. The relevant instrument settings used during image acquisition can be those given below.

| Instrument | Transmission Electron Microscope |
|---|---|
| Manufacturer/Model | Hitachi HF2000 |
| Accelerating Voltage | 200 kV |
| Condenser Lens 1 | 0.78 |
| Condenser Lens 2 | 0 |
| Objective Lens | 6.34 |
| Condenser Lens Aperture | #1 |
| Objective Lens Aperture for imaging | #3 |
| Selective Area Aperture for SAD | N/A |

Basic Protocols for Forming and Coating Medical Barrels

The pharmaceutical packages or other vessels tested in the subsequent working examples were formed and coated according to the following exemplary protocols, except as otherwise indicated in individual examples. Particular parameter values given in the following basic protocols, for example the electric power and gaseous reactant or process gas flow, are typical values. When parameter values were changed in comparison to these typical values, this will be indicated in the subsequent working examples. The same applies to the type and composition of the gaseous reactant or process gas.

In some instances, the reference characters and Figures mentioned in the following protocols and additional details can be found in U.S. Pat. No. 7,985,188.

Protocol for Coating Medical Barrel Interior with $SiO_x$

The apparatus and protocol generally as found in U.S. Pat. No. 7,985,188 were used for coating or layer medical barrel interiors with an $SiO_x$ barrier coating or layer, in some cases with minor variations or with the addition of magnetic field generators. A similar apparatus and protocol were used for coating or layer vials with an $SiO_x$ barrier coating or layer, in some cases with minor variations.

Protocol for Coating Medical Barrel Interior with Passivation Layer or pH Protective Coating or Layer Medical barrels already interior coated with a barrier coating or layer of $SiO_x$, as previously identified, are further interior coated with a passivation layer or pH protective coating or layer as previously identified, generally following the protocols of U.S. Pat. No. 7,985,188 for applying the lubricity coating or layer, except with modified conditions in certain instances as noted in the working examples. The conditions given here are for a COC medical barrel, and can be modified as appropriate for medical barrels made of other materials. The apparatus as generally shown in FIG. 4 can be used to hold a medical barrel with butt sealing at the base of the medical barrel.

The medical barrel is carefully moved into the sealing position over the extended probe or counter electrode 108 and pushed against a plasma screen. The plasma screen is fit snugly around the probe or counter electrode 108 insuring good electrical contact. The probe or counter electrode 108 is grounded to the casing of the RF matching network.

The gas delivery port 110 is connected to a manual ball valve or similar apparatus for venting, a thermocouple pressure gauge and a bypass valve connected to the vacuum pumping line. In addition, the gas system is connected to the gas delivery port 110 allowing the gaseous reactant or process gas to be flowed through the gas delivery port 110 (under process pressures) into the interior of the medical barrel.

If OMCTS or another low-boiling gaseous reactant or process gas is used, the gas system can include a commercially available heated mass flow vaporization system that heats the OMCTS to about 100° C. The heated mass flow vaporization system is connected to liquid octamethylcyclotetrasiloxane (Alfa Aesar® Part Number A12540, 98%). The precursor flow rate is set to the specific organosilicon precursor flow reported for a particular example.

Once the medical barrel is installed, the vacuum pump valve is opened to the vessel support 50 and the interior of the COC medical barrel. A vacuum pump and blower comprise the vacuum pump system. The pumping system allows the interior of the COC medical barrel to be reduced to pressure(s) of less than 100 mTorr while the gaseous reactant or process gases is flowing at the indicated rates.

Once the base vacuum level is achieved, the vessel support 50 assembly is moved into the outer electrode 160 assembly. The gas stream (OMCTS, HMDSO, or TMDSO vapor, for example) is flowed into the gas delivery port 110 (by adjusting the 3-way valve from the pumping line to the gas delivery port 110. The plasma for PECVD, if used, can be generated at reduced pressure and the reduced pressure can be less than 300 mTorr, optionally less than 200 mTorr, even optionally less than 100 mTorr. Pressure inside the COC medical barrel can be, as one example, approximately 140 mTorr as measured by a capacitance manometer (MKS) installed on the pumping line near the valve that controls the vacuum. In addition to the COC medical barrel pressure, the pressure inside the gas delivery port 110 and gas system is also measured with the thermocouple vacuum gauge that is connected to the gas system. This pressure is typically less than 6 Torr.

Once the gas is flowing to the interior of the COC medical barrel, the RF power supply is turned on to its fixed power level or as otherwise indicated in a specific example or description. The physical and chemical properties of the passivation layer or pH protective coating or layer can be set by setting the ratio of oxidizing gas to the organosilicon precursor in the gaseous reactant, and/or by setting the electric power used for generating the plasma. A 600 Watt RF power supply is used (at 13.56 MHz) at a fixed power level or as otherwise indicated in a specific example or description. The RF power supply is connected to an auto match which matches the complex impedance of the plasma (to be created in the vessel) to the output impedance of the RF power supply. The forward power is as stated and the reflected power is 0 Watts so that the stated power is delivered to the interior of the vessel. The RF power supply is controlled by a laboratory timer and the power on time set to 10 seconds (or a different time stated in a given example).

Upon initiation of the RF power, uniform plasma is established inside the interior of the vessel. The plasma is maintained for the entire passivation layer or pH protective coating or layer time, until the RF power is terminated by the timer. The plasma produces a passivation layer or pH protective coating or layer on the interior of the vessel.

After applying the passivation layer or pH protective coating or layer, the gas flow is diverted back to the vacuum line and the vacuum valve is closed. The vent valve is then opened, returning the interior of the COC medical barrel to atmospheric pressure (approximately 760 Torr). The treated vessel is then carefully removed from the vessel support 50 assembly (after moving the vessel support 50 assembly out of the outer electrode 160 assembly).

A similar protocol is used, with changes to the PECVD conditions, for applying a passivation layer, pH protective coating or layer, or lubricity coating or layer to syringes or other vessels.

Spectral Reflectance Protocol for Thickness Mapping

A Filmetrics Thin-Film Analyzer Model 205-0436 F40 spectral reflectance instrument was used. The syringe was placed in a holder with the back end facing up and index marks on the back end dividing the circumference into 8 equal 45-degree segments. The instrument camera was focused on the coating or layer and a thickness measurement was acquired at 0 degrees on the circumference and 6 mm from the back end of the mapped area of the medical barrel. Then the syringe was shifted 45 degrees, remaining at 6 mm axially, and another measurement was acquired. The process was repeated at 45 degree intervals around the syringe at 6 mm. The syringe was then advanced axially to 11 mm from the back end of the mapped area, and eight measurements were taken around the circumference. The syringe was successively advanced by 5 mm increments axially and 45 degree increments circumferentially to complete the map. The data was mapped using Filmetrics software.

Protocol for Total Silicon Measurement

This protocol is used to determine the total amount of silicon coatings or layers present on the entire vessel wall. A supply of 0.1 N potassium hydroxide (KOH) aqueous solution is prepared, taking care to avoid contact between the solution or ingredients and glass. The water used is purified water, 18 M'Ω quality. A Perkin Elmer Optima Model 7300DV ICP-OES instrument is used for the measurement except as otherwise indicated.

Each device (vial, syringe, tube, or the like) to be tested and its cap and crimp (in the case of a vial) or other closure are weighed empty to 0.001 g, then filled completely with the KOH solution (with no headspace), capped, crimped, and reweighed to 0.001 g. In a digestion step, each vial is placed in a sonicating water bath at 40° C. for a minimum of 8-10 hours. The digestion step is carried out to quantitatively remove the silicon coatings or layers from the vessel wall into the KOH solution. After this digestion step, the vials are removed from the sonicating water bath and allowed to cool to room temperature. The contents of the vials are transferred into 15 ml ICP tubes. The total Si concentration is run on each solution by ICP/OES following the operating procedure for the ICP/OES.

The total Si concentration is reported as parts per billion of Si in the KOH solution. This concentration represents the total amount of silicon coatings or layers that were on the vessel wall before the digestion step was used to remove it.

The total Si concentration can also be determined for fewer than all the silicon coatings or layers on the vessel, as when an $SiO_x$ barrier coating or layer is applied, an $SiO_xC_y$ second coating or layer (for example, a lubricity coating or layer or a passivation layer or pH protective coating or layer) is then applied, and it is desired to know the total silicon concentration of just the $SiO_xC_y$ coating or layer. This determination is made by preparing two sets of vessels, one set to which only the $SiO_x$ coating or layer is applied and the other set to which the same $SiO_x$ coating or layer is applied, followed by the $SiO_xC_y$ coating or layer or other coatings or layers of interest. The total Si concentration for each set of vessels is determined in the same manner as described above. The difference between the two Si concentrations is the total Si concentration of the $SiO_xC_y$ second coating or layer.

Protocol for Measuring Dissolved Silicon in a Vessel

The amount of silicon dissolved from the wall of the vessel by a test solution can be determined, in parts per billion (ppb), for example to evaluate the dissolution rate of the test solution. This determination of dissolved silicon is made by storing the test solution in a vessel provided with an $SiO_x$ and/or $SiO_xC_y$ coating or layer under test conditions, then removing a sample of the solution from the vessel and testing the Si concentration of the sample. The test is done in the same manner as the Protocol for Total Silicon Measurement, except that the digestion step of that protocol is replaced by storage of the test solution in the vessel as described in this protocol. The total Si concentration is reported as parts per billion of Si in the test solution Protocol for Determining Mean Dissolution Rate Mean dissolution rates can be determined as follows. A series of test vessels having a known total silicon measurement are filled with the desired test solution analogous to the manner of filling the vials with the KOH solution in the Protocol for Total Silicon Measurement. (The test solution can be a physiologically inactive test solution as employed in the present working examples or a physiologically active pharmaceutical preparation intended to be stored in the vessels to form a pharmaceutical package). The test solution is stored in respective vessels for several different amounts of time, then analyzed for the Si concentration in parts per billion in the test solution for each storage time. The respective storage times and Si concentrations are then plotted. The plots are studied to find a series of substantially linear points having the steepest slope.

The plot of dissolution amount (ppb Si) versus days decreases in slope with time. It is believed that the dissolution rate is not flattening out because the Si coating or layer has been fully digested by the test solution.

For tPC194 test data, linear plots of dissolution versus time data are prepared by using a least squares linear regression program to find a linear plot corresponding to the first five data points of each of the experimental plots. The slope of each linear plot is then determined and reported as representing the mean dissolution rate applicable to the test, measured in parts per billion of Si dissolved in the test solution per unit of time.

Protocol for Determining Calculated Shelf Life

The calculated shelf life values reported in the working examples below are determined by extrapolation of the total silicon measurements and mean dissolution rates, respectively determined as described in the Protocol for Total Silicon Measurement and the Protocol for Determining Mean Dissolution Rate. The assumption is made that under the indicated storage conditions the $SiO_xC_y$ passivation layer or pH protective coating or layer will be removed at the mean dissolution rate until the coating or layer is entirely removed. Thus, the total silicon measurement for the vessel, divided by the dissolution rate, gives the period of time required for the test solution to totally dissolve the $SiO_xC_y$ coating or layer. This period of time is reported as the calculated shelf life. Unlike commercial shelf life calculations, no safety factor is calculated. Instead, the calculated shelf life is the calculated time to failure.

It should be understood that because the plot of ppb Si versus hours decreases in slope with time, an extrapolation from relatively short measurement times to relatively long calculated shelf lives is believed to be a "worst case" test that tends to underestimate the calculated shelf life actually obtainable.

Protocol for Measuring Barrier Improvement Factor (BIF) after Solution Storage

This protocol can be used in any embodiment for measuring the barrier improvement factor (BIF) of a PECVD coating or layer or PECVD set after fluid storage.

Multiple identically formed blow molded cyclic olefin polymer (COP) vials, commonly referred to in the art as "5 mL vials" (although the total volume within the vial is greater), are provided. The vials used in this case have a generally cylindrical lumen surrounded by a generally cylindrical interior surface 16, which is reduced in inside diameter to form a short neck at the top of the vial. The top of the wall has a flange for receiving a crimp. The vial dimensions are an overall height of 40 mm, an inside diameter of the generally cylindrical interior surface of 21 mm, and an outside diameter of the wall forming the generally cylindrical interior surface of 22 mm. The inside diameter at the flange is 12.6 mm.

The vials are divided into multiple test vessels and control vessels. The test vessels are provided with the PECVD set to be tested for BIF. The control vessels do not have the PECVD set to be tested.

One or more test fluids having a specified composition are used. Several test fluids having different pH values are used with this protocol in the present working examples.

The pH 8 phosphate/Tween test fluid is 50 mmol potassium phosphate buffer diluted in U.S. Pharmacopeia (USP) Water for Injection, adjusted to pH 8 with concentrated nitric acid, and containing 0.2 wt. % polysorbate-80 surfactant and 20 mM phosphate. (Polysorbate-80 is a common ingredient of pharmaceutical preparations, available for example as Tween®-80 from Uniqema Americas LLC, Wilmington Del., and has been found to accelerate silicon dissolution.)

The pH 7.4 double phosphate test fluid is double strength phosphate buffered saline, provided at pH 7.4 and approx. 600 mOsm/kg.

The pH 7 WFI test fluid is USP Water for Injection, having a pH of 7.0. Water for injection is within USP specifications at a pH from 5 to 7, but for this test fluid is more particularly specified to have a pH of 7.0.

The pH 3.5 Citrate test fluid is WFI buffered with 20 mM citrate.

The test fluid being used is placed in the test and control vials. The vials are filled completely with the test fluid (with no headspace), capped, crimped, and stored for a predetermined time at a predetermined temperature. The storage time for this protocol is three months and the predetermined storage temperature is 25° C.

After the storage time has elapsed, the vials are uncapped and the test fluid is poured out of the test and control vials. The vials are prepared for oxygen transmission rate testing by filling them with nitrogen at ambient pressure. This is done by placing the open vials in a glove box filled with nitrogen gas, allowing time for the oxygen to escape and be displaced by nitrogen, then capping them. The nitrogen filled vials are then stored at 20° C. in ambient air at the ambient external barometric pressure The barrier improvement factor (BIF) is measured by analyzing the contents of the previously stored vessels for their oxygen content, and expressing the amount of oxygen found in the vessels in terms of cubic centimeters of oxygen gas per package per day. Ratios of the OTRs of the test vessels including a PECVD set and the control vessels with no PECVD set are then determined. For example, if the OTR into a package without a PECVD set is three times as great as the OTR into a package having a PECVD set, the PECVD set has a BIF of 3.

SEM Procedure

SEM Sample Preparation: Each syringe sample was cut in half along its length (to expose the inner or generally cylindrical interior surface 16). The top of the syringe (Luer end) was cut off to make the sample smaller.

The sample was mounted onto the sample support with conductive graphite adhesive, then put into a Denton Desk IV SEM Sample Preparation System, and a thin (approximately 50 Å) gold layer was sputtered onto the inner or generally cylindrical interior surface 16 of the syringe. The gold layer is required to eliminate charging of the surface during measurement.

The sample was removed from the sputter system and mounted onto the sample stage of a Jeol JSM 6390 SEM (Scanning Electron Microscope). The sample was pumped down to at least $1\times10^{-6}$ Torr in the sample compartment. Once the sample reached the required vacuum level, the slit valve was opened and the sample was moved into the analysis station.

The sample was imaged at a coarse resolution first, then higher magnification images were accumulated.

AFM (Atomic Force Microscopy) Procedure.

AFM images were collected using a NanoScope III Dimension 3000 machine (Digital Instruments, Santa Barbara, Calif., USA). The instrument was calibrated against a NIST traceable standard. Etched silicon scanning probe microscopy (SPM) tips were used. Image processing procedures involving auto-flattening, plane fitting or convolution were employed. One 10 μm×10 μm area was imaged. Roughness analyses were performed and were expressed in: (1) Root-Mean-Square Roughness, RMS; 2 Mean Roughness, Ra; and (3) Maximum Height (Peak-to-Valley), Rmax, all measured in nm (see Table 5). For the roughness analyses, each sample was imaged over the 10 μm×10 μm area, followed by three cross sections selected by the analyst to cut through features in the 10 μm×10 μm images. The vertical depth of the features was measured using the cross section tool. For each cross section, a Root-Mean-Square Roughness (RMS) in nanometers was reported.

Additional analysis of the 10 μm×10 μm images can be carried out. For this analysis three cross sections are extracted from each image. The locations of the cross sections were selected by the analyst to cut through features in the images. The vertical depth of the features was measured using the cross section tool.

The Digital Instruments Nanoscope III AFM/STM acquires and stores 3-dimensional representations of surfaces in a digital format. These surfaces can be analyzed in a variety of ways.

The Nanoscope III software can perform a roughness analysis of any AFM or STM image. The product of this analysis is a single page reproducing the selected image in top view. To the upper right of the image is the "Image Statistics" box, which lists the calculated characteristics of the whole image minus any areas excluded by a stopband (a box with an X through it). Similar additional statistics can be calculated for a selected portion of the image and these are listed in the "Box Statistics" in the lower right portion of the page. What follows is a description and explanation of these statistics.

Image Statistics:

Z Range (Rp): The difference between the highest and lowest points in the image. The value is not corrected for tilt in the plane of the image; therefore, plane fitting or flattening the data will change the value.

Mean: The mean of all of the Z values in the imaged area. This value is not corrected for the tilt in the plane of the image; therefore, plane fitting or flattening the data will change this value.

RMS (Rq): This is the standard deviation of the Z values (or RMS roughness) in the image. It is calculated according to the formula:

$$Rq=\{\Sigma(Z1-Zavg)2/N\}$$

where Zavg is the mean Z value within the image; Z1 is the current value of Z; and N is the number of points in the image. This value is not corrected for tilt in the plane of the image; therefore, plane fitting or flattening the data will change this value.

Mean roughness (Ra): This is the mean value of the surface relative to the Center Plane and is calculated using the formula:

$$Ra=[1/(LxLy)]\int oLy\int oLx\{f(x,y)\}dxdy$$

where f(x,y) is the surface relative to the Center plane, and Lx and Ly are the dimensions of the surface.

Max height (Rmax): This is the difference in height between the highest and lowest points of the surface relative to the Mean Plane.

Surface area: (Optical calculation): This is the area of the 3-dimensional surface of the imaged area. It is calculated by taking the sum of the areas of the triangles formed by 3 adjacent data points throughout the image.

Surface area diff: (Optional calculation) This is the amount that the Surface area is in excess of the imaged area. It is expressed as a percentage and is calculated according to the formula:

$$\text{Surface area diff}=100[(\text{Surface area}/S12-1]$$

where S1 is the length (and width) of the scanned area minus any areas excluded by stopbands.

Center Plane: A flat plane that is parallel to the Mean Plane. The volumes enclosed by the image surface above and below the center plane are equal.

Mean Plane: The image data has a minimum variance about this flat plane. It results from a first order least squares fit on the Z data.

WORKING EXAMPLES

Comparative Example 1

Thickness Profile for pH-protective Coating or Layer

A pH protective coating or layer (e.g. 34) was applied to the surface (16) of the wall of a 1 mL long syringe having an inside diameter of 6.3 mm, an interior length of 54 mm, an aspect ratio between the medical barrel length and inside diameter of 8.6, and a staked needle. These 1 mL long syringes with staked needles are used in the respective examples below unless otherwise indicated. The gas inlet and inner electrode used was provided with the 90-degree perforation pattern shown in FIG. 26. The outer electrode was a solid metallic tube. The protocol provided above was generally followed, using 30 Watts of RF energy, OMCTS as a precursor at a flow rate of 2 sccm, argon as a diluent at a flow rate of 20 sccm, oxygen gas as an oxidizing gas at a flow rate of 0.5 sccm, and a continuous plasma energization time of 10 sec. No magnets were used in this example.

Figure 30:
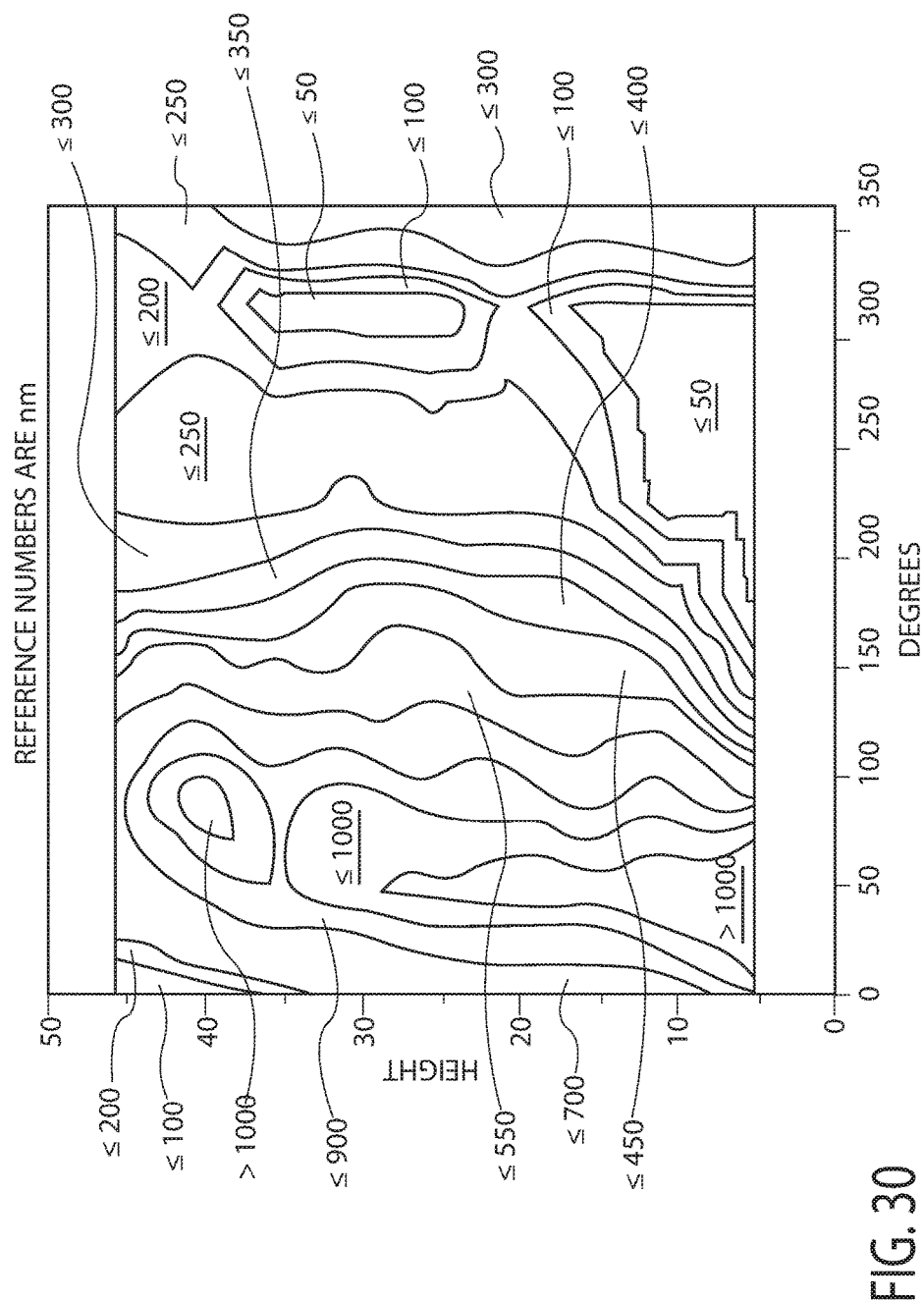
FIG. 30 is a plot of coating or layer thickness versus position on the generally cylindrical interior surface 16 of a medical barrel, in the experiment of Example 1.

A plot of the coating or layer thickness as a function of the position on a cylindrical portion of the medical barrel is provided as FIG. 30. The plot shows a region of very thick deposition at about 50 degrees around the circumference of the syringe, regions of very little deposition thickness as measured at about 220 to 300 degrees, and gradations of deposition up the full height of the syringe surface between 270 and 800 degrees. The statistical data captured during this test is as follows:

| Quantiles | | |
|---|---|---|
| 100.00% | maximum | 1279 |
| 99.5% |  | 1279 |
| 97.5% |  | 1187.3 |
| 90.0% |  | 849.44 |
| 75.0% | Quartile | 547.35 |
| 50.0% | Median | 329.3 |
| 25.0% | Quartile | 158.95 |
| 10.0% |  | 25.088 |
| 2.5% |  | 0.5 |
| .5% |  | 0.5 |
| 0.0% | Minimum | 0.5 |

| Moments | |
|---|---|
| Mean | 384.7021 |
| Std Dev. | 306.1763 |
| Std Err Mean | 34.019589 |
| Upper 95% Mean | 452.40324 |
| Lower 95% Mean | 317.00096 |
| N | 81 |

The above tables show that the standard deviation of thickness was 306 nm, the mean thickness was 385 nm, and the ratio of (one) standard deviation to the mean thickness was 0.79. This high standard deviation and high ratio is indicative of a non-uniform coating or layer, relative to the examples below. The thickness range shown in FIG. 30 is from ≤50 nm to >1000 nm.

Example 2

Thickness Profile for pH-protective Coating or Layer

A pH protective coating or layer (e.g. 34) was applied to the surface (16) of the wall of a 1 mL long syringe. The gas inlet and inner electrode used was provided with the 120-degree or triangular perforation pattern shown in FIG. 27. The protocol provided above was generally followed, using 20 Watts of RF energy, OMCTS as a precursor at a flow rate of 2 sccm, argon as a diluent at a flow rate of 20 sccm, oxygen gas as an oxidizing gas at a flow rate of 0.5 sccm, and a continuous plasma energization time of 5 sec. A stationary quadrupole magnet array using ceramic magnets, generally as shown in FIGS. 4-5, was used, as was a wire mesh outer electrode.

The coating or layer did not dissolve in standard 0.1 M KOH. A plot of the coating or layer thickness as a function of the position on a cylindrical portion of the medical barrel is provided as FIG. 31. The plot shows more uniform deposition of the coating or layer and a coating or layer desirably more resistant to dissolution, with isolated regions of thicker deposition at about 80, 200, and 320 degrees around the circumference of the syringe and 15, 25, and 40 mm along the height of the syringe surface. These discontinuities are believed to result from the perforation pattern in the gas inlet. The statistical data captured during this test is as follows:

| Quantiles | | |
|---|---|---|
| 100.00% | maximum | 1070 |
| 99.5% |  | 1070 |
| 97.5% |  | 855.63 |
| 90.0% |  | 533.02 |
| 75.0% | Quartile | 437.35 |
| 50.0% | Median | 359.4 |
| 25.0% | Quartile | 276.25 |
| 10.0% |  | 195.8 |
| 2.5% |  | 90.7975 |
| .5% |  | 45.47 |
| 0.0% | Minimum | 45.47 |

| Moments | |
|---|---|
| Mean | 369.0484 |
| Std Dev. | 161.4856 |
| Std Err Mean | 17.942845 |
| Upper 95% Mean | 404.75579 |
| Lower 95% Mean | 333.341 |
| N | 81 |

Figure 31:
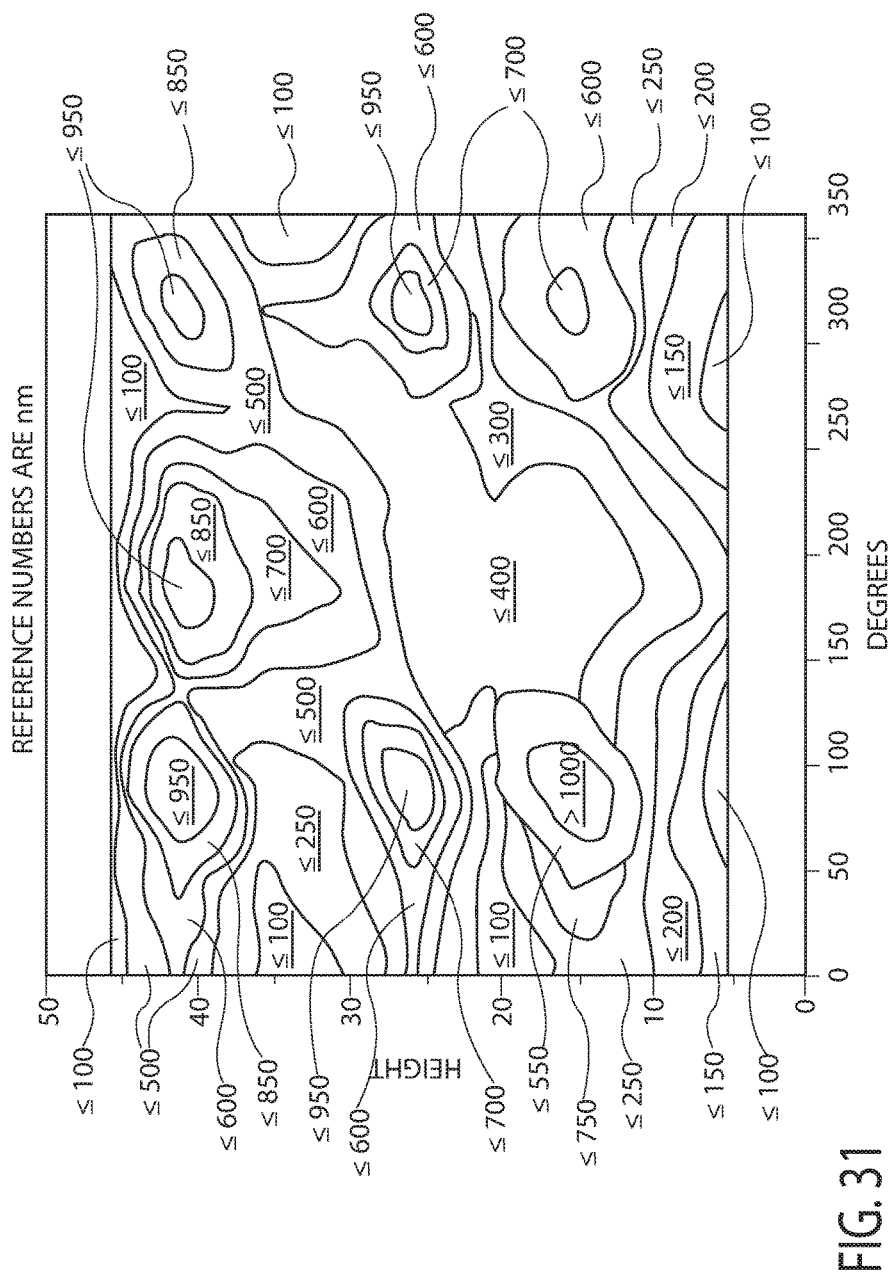
FIG. 31 is a plot of coating or layer thickness versus position on the generally cylindrical interior surface 16 of a medical barrel, in the experiment of Example 2.

The above tables show that the standard deviation of thickness was 161 nm, the mean thickness was 369 nm (similar to Example 1), and the ratio of (one) standard deviation to the mean thickness was 0.44. This much lower standard deviation and ratio is indicative of a much more uniform coating or layer relative to Example 1 which is attributed to the use of the quadrupole magnets. The thickness range shown in FIG. 31 is from ≤100 nm to >1000 nm.

Example 3

Thickness Profile for pH-protective Coating or Layer

A pH protective coating or layer (e.g. 34) was applied to the generally cylindrical interior surface 16 of the wall of a 1 mL long syringe. The gas inlet and inner electrode used was provided with the 45-degree or spiral perforation pattern shown in FIG. 28. The protocol provided above was generally followed, using 20 Watts of RF energy, OMCTS as a precursor at a flow rate of 2 sccm, argon as a diluent at a flow rate of 20 sccm, oxygen gas as an oxidizing gas at a flow rate of 0.5 sccm, and a continuous plasma energization time of 10 sec. A stationary quadrupole magnet array using neodymium-iron-boron (NdFeB or neodymium) magnets, generally as shown in FIGS. 4-5, was used, as was a wire mesh outer electrode.

Figure 32:
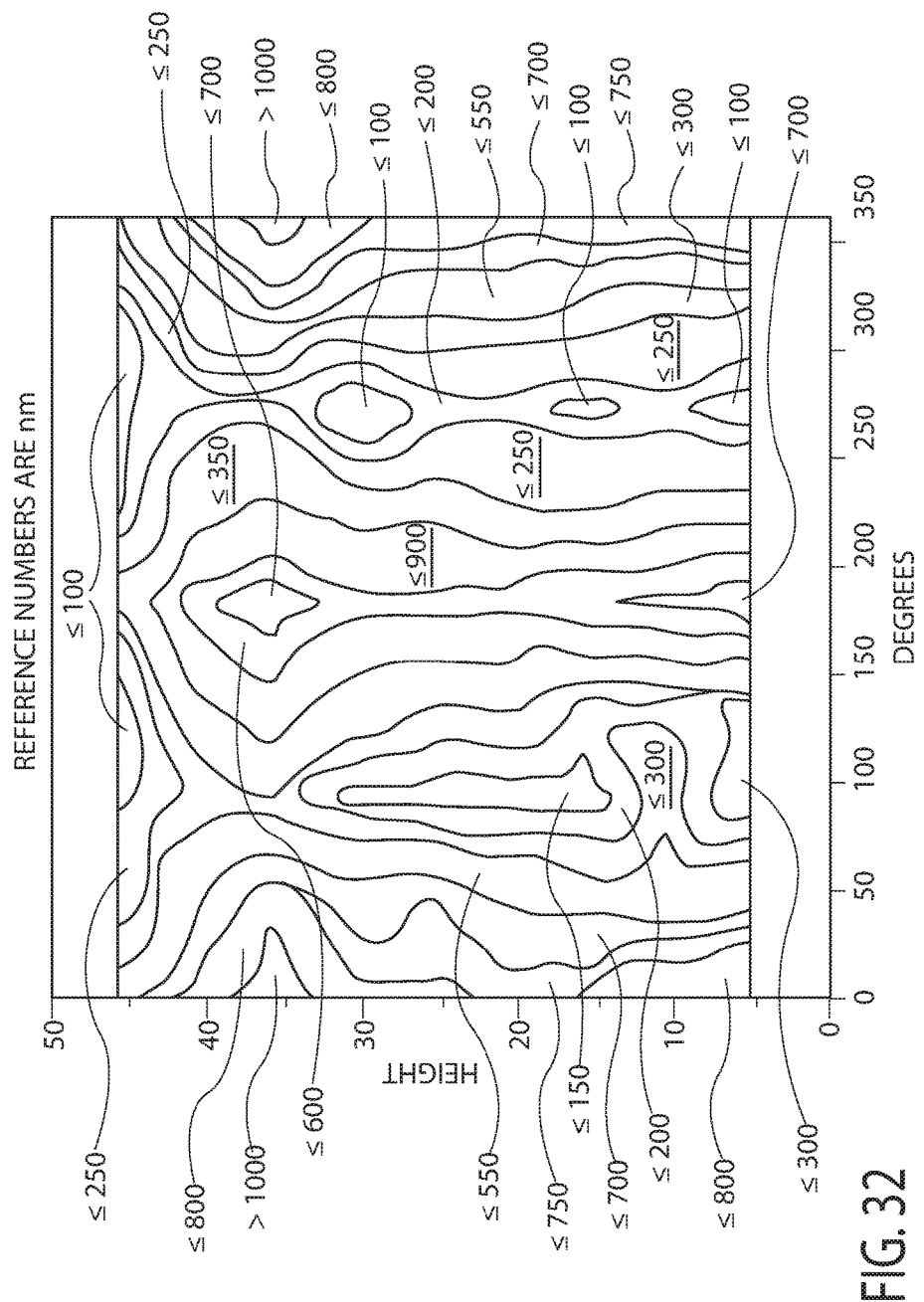
FIG. 32 is a plot of coating or layer thickness versus position on the generally cylindrical interior surface 16 of a medical barrel, in the experiment of Example 3.

A plot of the coating or layer thickness as a function of the position on a cylindrical portion of the medical barrel is provided as FIG. 32. The plot shows more uniform deposition of the coating or layer, with isolated regions of thicker deposition across the height at about 0 and 180 degrees around the circumference of the syringe. While the reason for this variation in thickness is not known, comparison with Example 4 suggests that this variation may be the result of different deposition thickness in a region confronting a north pole versus a south pole of the quadrupole array. The statistical data captured during this test is as follows:

| Quantiles | | |
|---|---|---|
| 100.00% | maximum | 1077 |
| 99.5% | | 1077 |
| 97.5% | | 1018.51 |
| 90.0% | | 839.7 |
| 75.0% | Quartile | 748.4 |
| 50.0% | Median | 555.7 |
| 25.0% | Quartile | 380.95 |
| 10.0% | | 211.8 |
| 2.5% | | 177.64 |
| .5% | | 109.3 |
| 0.0% | Minimum | 109.3 |

| Moments | |
|---|---|
| Mean | 588.68025 |
| Std Dev. | 233.19587 |
| Std Err Mean | 25.910652 |
| Upper 95% Mean | 610.24409 |
| Lower 95% Mean | 507.11641 |
| N | 81 |

The above tables show that the standard deviation of thickness was 233 nm, the mean thickness was much thicker than previous examples, at 559 nm, and the ratio of (one) standard deviation to the mean thickness was 0.42. This standard deviation ratio was similar to Example 2. The thickness range shown in FIG. 32 is from ≤100 nm to >1000 nm.

Example 4

Thickness Profile for pH-protective Coating or Layer

A pH protective coating or layer (e.g. 34) was applied to the surface (16) of the wall of a 1 mL long syringe. The gas inlet and inner electrode used was provided with the 45-degree or spiral perforation pattern shown in FIG. 28. The protocol provided above was generally followed, using 20 Watts of RF energy, OMCTS as a precursor at a flow rate of 2 sccm, argon as a diluent at a flow rate of 20 sccm, oxygen gas as an oxidizing gas at a flow rate of 0.5 sccm, and a continuous plasma energization time of 10 sec. The same quadrupole magnet array and wire mesh outer electrode of Example 3 was used, except that the quadrupole magnet array was rotated about its axis during deposition.

Figure 33:
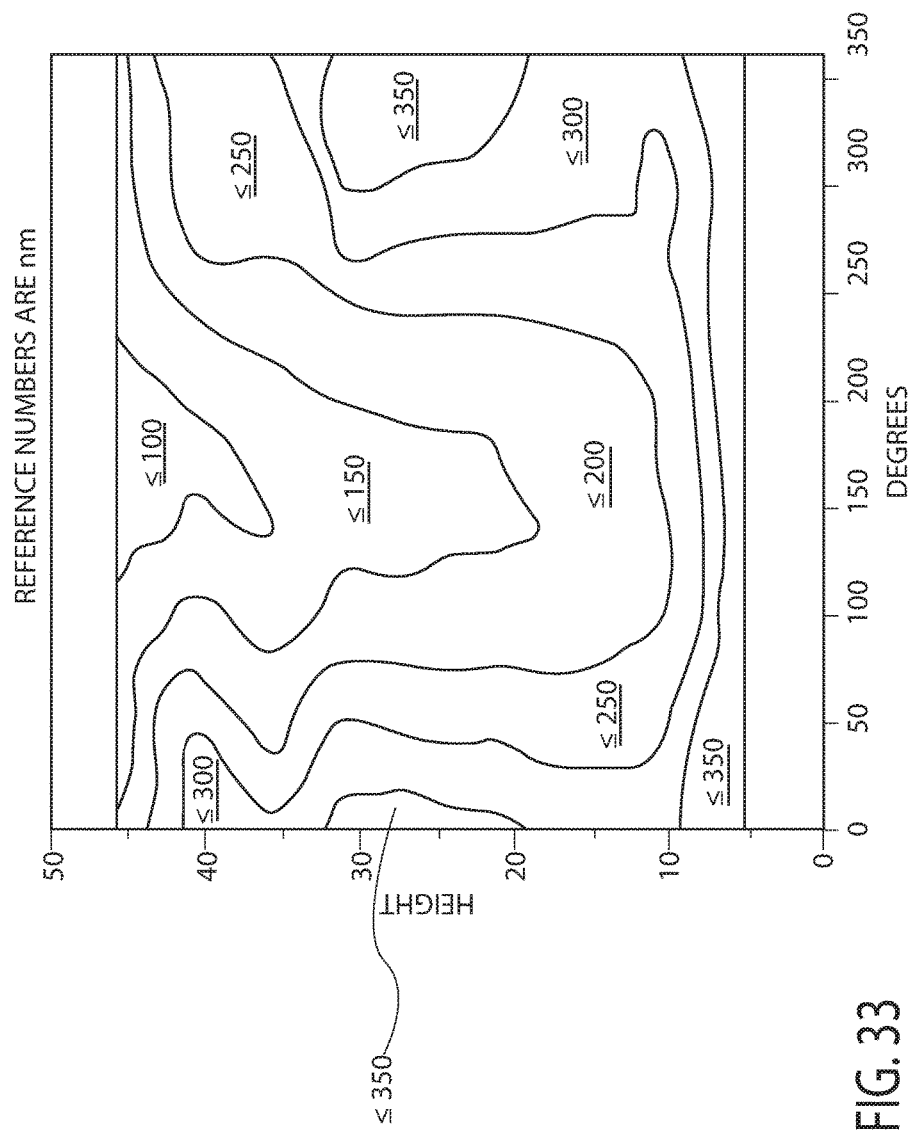
FIG. 33 is a plot of coating or layer thickness versus position on the generally cylindrical interior surface 16 of a medical barrel, in the experiment of Example 4.

A plot of the coating or layer thickness as a function of the position on a cylindrical portion of the medical barrel is provided as FIG. 33. The plot shows still more uniform deposition of the coating or layer than previous examples, with less variation of deposition thickness around the circumference and relatively little difference in deposition thickness across the height. The statistical data captured during this test is as follows:

| Quantiles | | |
|---|---|---|
| 100.00% | maximum | 510 |
| 99.5% | | 510 |
| 97.5% | | 507.13 |
| 90.0% | | 477.18 |
| 75.0% | Quartile | 429.75 |
| 50.0% | Median | 365.8 |
| 25.0% | Quartile | 299.2 |
| 10.0% | | 259.76 |
| 2.5% | | 233.045 |
| .5% | | 229.8 |
| 0.0% | Minimum | 229.8 |

| Moments | |
|---|---|
| Mean | 367.92963 |
| Std Dev. | 78.695841 |
| Std Err Mean | 8.7439823 |
| Upper 95% Mean | 385.33071 |
| Lower 95% Mean | 350.52855 |
| N | 81 |

The above tables show that the standard deviation of thickness was 79 nm, the mean thickness was 367 nm, and the ratio of (one) standard deviation to the mean thickness was 0.22. This standard deviation ratio was much smaller, showing a much more uniform coating, than Examples 1-3. The thickness range shown in FIG. 33 is from ≤100 nm to ≤350 nm.

Example 5

Thickness Profile for pH-protective Coating or Layer

A pH protective coating or layer (e.g. 34) was applied to the surface (16) of the wall of a 1 mL long syringe. The gas inlet and inner electrode used was provided with the 45-degree or spiral perforation pattern shown in FIG. 28. The protocol provided above was generally followed, using 20 Watts of RF energy, OMCTS as a precursor at a flow rate of 2 sccm, argon as a diluent at a flow rate of 20 sccm, oxygen gas as an oxidizing gas at a flow rate of 0.5 sccm, and a continuous plasma energization time of 10 sec. A stack of two multi-pole NdFeB ring magnets was used as the magnet array and a solid tubular electrode was used. The magnet array was stationary during deposition.

Figure 34:
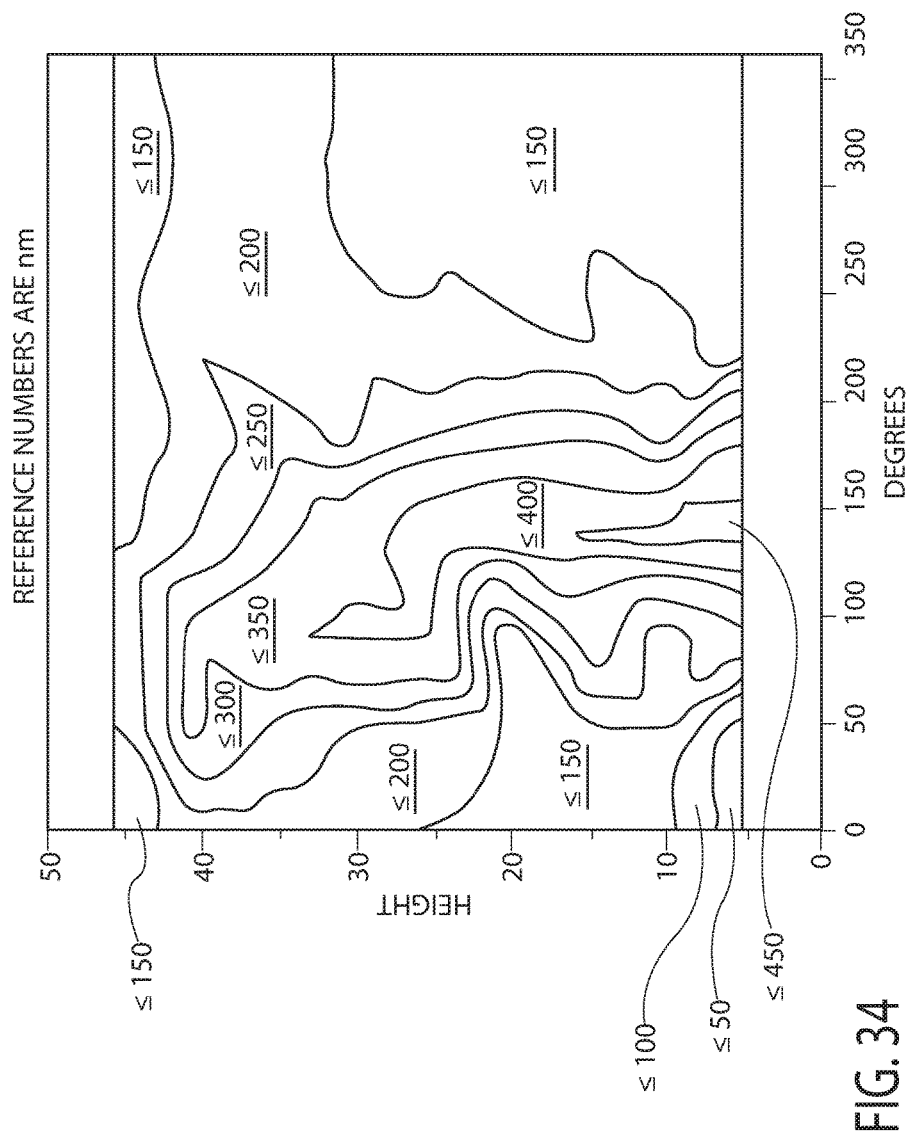
FIG. 34 is a plot of coating or layer thickness versus position on the generally cylindrical interior surface 16 of a medical barrel, in the experiment of Example 5.

A plot of the coating or layer thickness as a function of the position on a cylindrical portion of the medical barrel is provided as FIG. 34. The plot shows more uniform deposition of the coating or layer than previous Example 1. The statistical data captured during this test is as follows:

| Quantiles | | |
|---|---|---|
| 100.00% | maximum | 573.3 |
| 99.5% | | 573.3 |
| 97.5% | | 571.42 |
| 90.0% | | 409.1 |
| 75.0% | Quartile | 231.35 |
| 50.0% | Median | 152.3 |
| 25.0% | Quartile | 133.8 |
| 10.0% | | 113.22 |
| 2.5% | | 20.2345 |
| .5% | | 7.37 |
| 0.0% | Minimum | 7.37 |

| Moments | |
|---|---|
| Mean | 200.46383 |
| Std Dev. | 121.7286 |
| Std Err Mean | 13.5254 |
| Upper 95% Mean | 227.38023 |
| Lower 95% Mean | 173.54742 |
| N | 81 |

The above tables show that the standard deviation of thickness was 122 nm, the mean thickness was 200 nm, and the ratio of (one) standard deviation to the mean thickness was 0.61. The results appear to be skewed by a spot of zero measured deposition at minimal height and an angle of 0 to 50 degrees. The thickness range shown in FIG. 34 is from ≤100 nm to ≤550 nm.

Example 6

Thickness Profile for Barrier Coating or Layer

A $SiO_x$ barrier coating or layer (e.g. 30) was applied to the surface (16) of the wall of a 1 mL long syringe. The gas inlet and inner electrode used was provided with the 45-degree or spiral perforation pattern shown in FIG. 28. The barrier coating or layer protocol provided above was generally followed, using 35 Watts of RF energy, HMDSO as a precursor at a flow rate of 10 sccm, no diluents, oxygen gas as an oxidizing gas at a flow rate of 25 sccm, and a continuous plasma energization time of 10 sec, applied three times (total energization time 30 sec). The NdFeB quadrupole of previous examples was used as the magnet array and a mesh electrode was used. The magnet array was stationary during deposition.

Figure 35:
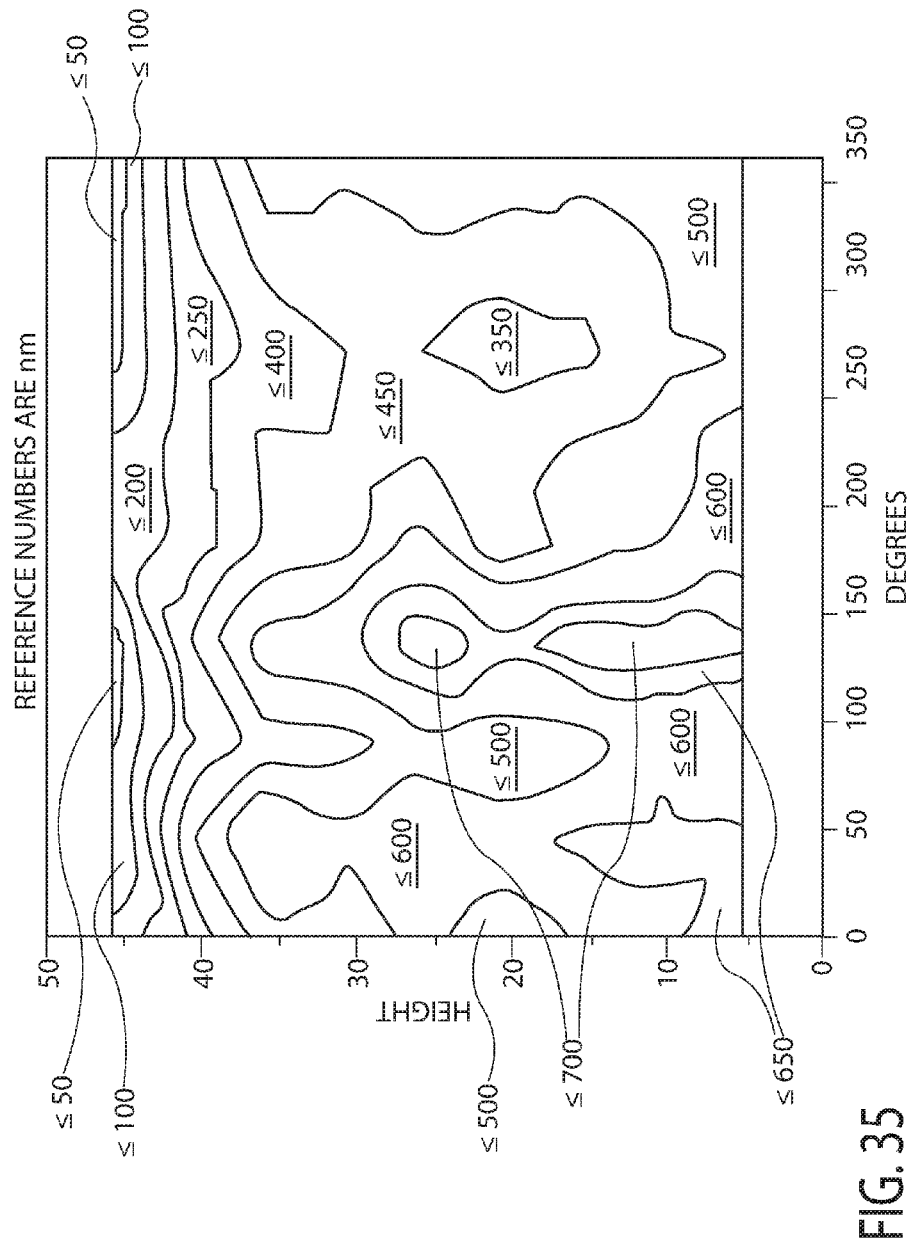
FIG. 35 is a plot of coating or layer thickness versus position on the generally cylindrical interior surface 16 of a medical barrel, in the experiment of Example 6.
Figure 36:
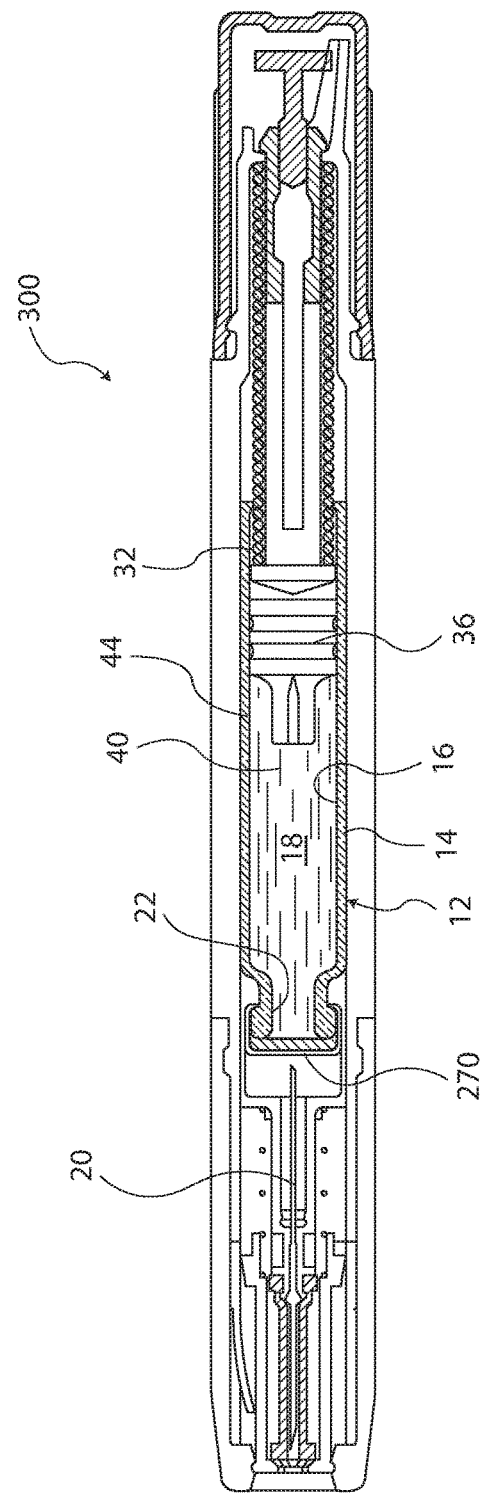
FIG. 36 is a longitudinal section of an auto injector assembly including a cartridge, which is a type of medical barrel.

A plot of the coating or layer thickness as a function of the position on a cylindrical portion of the medical barrel is provided as FIG. 35. The plot shows still more uniform deposition of the coating or layer than previous example 1. The statistical data captured during this test is as follows:

| Quantiles | | |
|---|---|---|
| 100.00% | maximum | 631.1 |
| 99.5% | | 631.1 |
| 97.5% | | 546.955 |
| 90.0% | | 417.6 |
| 75.0% | Quartile | 375.2 |
| 50.0% | Median | 301.6 |
| 25.0% | Quartile | 246.5 |
| 10.0% | | 111.44 |
| 2.5% | | 23.7965 |
| .5% | | 14.92 |
| 0.0% | Minimum | 14.92 |

| Moments | |
|---|---|
| Mean | 296.8616 |
| Std Dev. | 122.54112 |
| Std Err Mean | 13.61568 |
| Upper 95% Mean | 323.95767 |
| Lower 95% Mean | 236.76554 |
| N | 81 |

The above tables show that the standard deviation of thickness was 123 nm, the mean thickness was 297 nm, and the ratio of (one) standard deviation to the mean thickness was 0.41. The barrier improvement factor of the coating or layer was found to be 4.5, indicating value of the coating or layer as a barrier coating or layer. The thickness range shown in FIG. 35 is from ≤200 nm to ≤700 nm.

Examples 7 to 10

Thickness Profile for Lubricity Coating or Layer

These examples were carried out to test different methods for providing lubricity coatings or layers on 1 mL long syringes having a normal fill volume range of 0.4 to 1 mL. The lubricity coatings or layers had a greater mean thickness near the back of the medical barrel than at the front of the medical barrel (near the hypodermic needle).

Lubricity coatings or layers were applied to multiple 1 mL medical barrels with hypodermic needles and caps in place, using the PECVD apparatus generally as illustrated in FIGS. 2 and 6, except that in Examples 7-9 no magnet array 834 or magnets 820 were used and in Example 10 a ring magnet was substituted. The inner electrode 108 used in each instance was a ⅛ inch (3 mm) brass tube with the gas delivery port 110 positioned at the back end 32 of the medical barrel (at 0 mm on the y axes of the coating or layer maps of FIGS. 61, 65, and 69, and on the x axes of the plots of FIGS. 64, 68, and 70). The outer electrode 160 used in each instance was a cylindrical electrode with slits. OMCTS was used as the precursor, using a vaporizer and heating tape to vaporize the OMCTS. Other deposition conditions are presented in Table 11

TABLE 11

| Example | Magnet | Plasma Delay (Sec) | OMCTS (sccm) | Oxygen (sccm) | Argon (sccm) | Power (W) | Time (sec) |
|---|---|---|---|---|---|---|---|
| 7 | None | 15 | 4 | 4 | 7.5 | 50 | 1 |
|   | None | 3 | 4 | 4 | 7.5 | 2 | 15 |
| 8 | None | 15 | 4 | 4 | 7.5 | 50 | 1 |
|   | None | 3 | 4 | 4 | 7.5 | 2 | 30 |
| 9 | None | 15 | 4 | 4 | 7.5 | 50 | 1 |
|   | None | 3 | 4 | 4 | 7.5 | 0.9 | 30 |
| 10 | Ring | 15 | 4 | 4 | 7.5 | 50 | 1 |
|   | Ring | 3 | 4 | 4 | 7.5 | 0.9 | 30 |

As shown in Table 11, the plasma was ignited twice for each syringe. The first ignition of the plasma was delayed 15 sec. after flow of the reactants began, to ensure a uniform composition, then the plasma was ignited at a relatively high power level (50 W in each case) for one second to promote adhesion of the lubricity coating or layer. The second ignition of the plasma was then delayed for 3 seconds to allow time for the reaction products from the first ignition to be removed, and the plasma was ignited for 15 or 30 seconds at the indicated lower power level. The test results are shown in FIGS. 61 to 72 and discussed below.

The results of Example 7 are shown in FIGS. 61-64. FIG. 61 is a map of coating or layer thickness versus the axial position (y-axis) and circumferential position (x-axis) within the medical barrel, generated by Filmetrics analysis as described in the Filmetrics Protocol for coating or layer Thickness Mapping. FIG. 62-63 shows the mean thickness of the coating or layer at three positions along the medical barrel (approximating but not necessarily corresponding exactly to the first, second, and third portions of the medical barrel as defined in the present application). As illustrated, the mean lubricity coating or layer thickness at position 1 of FIG. 62 was 46±5 nm, the mean thickness at position 2 of FIG. 62 was 109±44 nm, and the mean thickness at position 3 of FIG. 62, nearest the bottom of the syringe, was 160±75 nm.

FIG. 64 shows a plot of Fm, the force to keep the plunger moving, versus position in the medical barrel for Example 7. This plot was generated as follows. A plunger was loaded into each syringe, which was dry (no fluid added). The syringe was aged for one hour, and testing was carried out using multiple samples on an Instron machine using a 50 N transducer. The result is a relatively uniform, low (not more than about 5 nm) Fm at different places along the length of the medical barrel.

A silicon dissolution test was performed using substantially the Protocol for Determining Mean Dissolution Rate explained above. The needles and needle shields of the tested coated syringes were removed, then each syringe was placed in a 15 mL polypropylene centrifuge tube and completely immersed with 7.5 mL of pH 8.0 potassium hydroxide (KOH) solution containing 0.2% Tween 80 surfactant. The containers immersed in the solution were then incubated at 40° C. for three days. The solution containing dissolved silicon was then analyzed using an ICP/OES Perkin Elmer Optima 7300 DV analyzer with a Perkin Elmer S10 autosampler. The results are reported as a dissolution time and the resulting micrograms of dissolved Si, In this case the dissolution time was 3 days and the dissolved Si was 10.2 micrograms.

In Example 8 a rectangular piece of Kapton® film was inserted near the front end of the syringe, masking the front half of the medical barrel to prevent the coating or layer from depositing near the front of the medical barrel. This was observed to block the coating or layer of the Kapton covered area. This test shows that an obstruction in the syringe can be used to tailor the thickness profile of the lubricity coating or layer.

In Example 9 the power level in the second stage of lubricity coating or layer was reduced to 0.9 watts, and no obstruction was used. The results of Example 9 are shown in FIGS. 65 and 68. The map of FIG. 65 shows essentially no coating or layer in section 1 near the dispensing end of the syringe, from about 24 mm to the front of the medical barrel, and radially even coverage. FIGS. 66-67 provides an SEM image of the coating or layer at position 2 on the syringe (30 nm, lubricity coating or layer) and position 3 at the back of the syringe (71 nm lubricity coating or layer). The coating or layer thickness at position 1 was about 0 nm. FIG. 68 is a plot of Fm for Example 9, after inserting a plunger and aging the syringe for 10 minutes. The plot shows that Fm increased substantially from a position on the map of about 28 nm or more, in the masked zone. A dissolved Si analysis on a similar sample shows 3.5 micrograms of dissolved silica after a day dissolution time.

In Example 10, a stationary ring magnet having an axial polar axis (i.e. the poles are the annular faces) was placed around the medical barrel adjacent to the back end of the syringe and within the outer electrode. The magnetic field strength at various points along the syringe is shown in FIG. 73. The conditions described in Table 11 were used to apply a lubricity coating or layer, which was mapped as shown in FIG. 69, SEM imaged for film thickness as shown in FIGS. 71 and 72, and tested for Fm as shown in FIG. 70. FIG. 69 shows that Position 1 of the syringe had a lubricity coating or layer thickness of about 0 nm, indicating no or essentially no coating or layer at that position. Position 2 had a lubricity coating or layer thickness of about 54 nm, and position 3 adjacent to the magnet during coating had a lubricity coating or layer thickness of about 169 nm. FIG. 70, the plot of Fm versus axial position of the plunger, shows a relatively uniform and low Fm, with only some increase in the essentially unlubricated area near the dispensing end of the syringe (much less than in Example 9). This Fm increase in the essentially unlubricated area can be addressed, for example, by increasing the medical barrel inside diameter and by reducing the power used to deposit the PECVD coatings or layers. The silicon dissolution test result was 2.1 micrograms Si after a dissolution time of four days, which also is an improvement over the dissolution results without a magnet. Similar results can also be obtained if the magnet is flipped to reverse its polarity.

Example 10 shows that in the presence of a magnet, most of the coating or layer can be steered to the vicinity of the magnet, allowing the coating or layer thickness to be tailored along the axial length of a syringe or other workpiece using a magnet. Improved Fm uniformity and dissolution results were also obtained.

Example 11

Stationary Axial Magnets

A PECVD process was used to deposit uniform barrier coatings or layers on 1 mL long syringes. The PECVD apparatus used was comparable to the schematic illustration of FIGS. 4-5, except using a magnet assembly similar to that of FIG. 49. Each magnet was oriented with its north pole up to create an axial field along the axis of the assembly.

More specifically, the magnet assembly design consisted of 8 columns, each of three N40 grade neodymium (NdFeB) bar magnets in an octagonal arrangement surrounding the syringe. The bar magnets were 1 inch×⅛ inch×¼ inch (25 mm×3 mm×6 mm) in each row (total length 3 inches, 76 mm). The separation of the inner faces (i.e. the inside diameter of the cylindrical space between the magnets) was ⅞ inch (22 mm). Each magnet's surface field strength was 4211 Gauss, and each magnet had a pull strength of 2.5 lbs. (1.1 kg).

Experiments were constructed to determine more optimal PECVD process conditions for reducing oxygen transmission rate or increasing the barrier improvement factor (BIF) of the syringes. The process was used to deposit a single silicon oxide ($SiO_x$) coating or layer on each syringe at varying process parameters. The process parameters explored were HMDSO as the precursor from 0.5 to 5 sccm; oxygen from 10 to 200 sccm; RF power from 5 to 100 Watts; and time from 1 to 30 seconds.

The best results of the experiments are shown in Table 12. Results are expressed as barrier improvement factor (BIF) (measured on the syringes as coated, without fluid storage).

TABLE 12

| Result | HMDSO (sccm) | Oxygen (sccm) | Power (Watts) | Time (seconds) | BIF |
|---|---|---|---|---|---|
| A | 1.2 | 40 | 45 | 10 | 7.5 |
| B | 1.2 | 40 | 35 | 10 | 5.7 |
| C | 0.8 | 40 | 45 | 10 | 5 |

The results show that a substantial barrier improvement factor can be provided in a very small inside diameter medical barrel using stationary magnets to improve the PECVD process. The improvement is believed to result from greater uniformity in application of the $SiO_x$ barrier coating or layer in the presence of an axially extending magnetic field.

Example 12

5 mL Vial Barrier Improvement Factor (BIF)

The previously stated Protocol For Measuring Barrier Improvement Factor (BIF) After Solution Storage was followed, using 5 mL vials. The PECVD set applied to the test vials was a trilayer coating or layer comprising:

an $SiO_xC_y$ tie coating or layer, which is the same coating or layer referred to as an adhesion coating or layer, for which x and y were each 1, formed on the inside of the COP vial wall, followed by:
an $SiO_x$ barrier coating or layer, for which x was 2.2, formed adjacent to the tie coating or layer, followed by:
a $SiO_xC_y$ pH protection coating or layer, for which x was 1.1 and y was 1, formed adjacent to the barrier coating or layer and directly facing the lumen of the vial.

The conditions for application of the PECVD set to the vials using HMDSO and TMDSO are summarized in Table 13, in which W is watts and sccm is standard cubic centimeters per minute. No magnets were used in this PECVD process.

The thickness and uniformity of the three PECVD coatings or layers deposited on the test vials is shown by reference to FIG. 74 and Table14 identifying the locations on the vial where the coating or layer thickness was tested, the thickness of each coating or layer in nm at the respective locations, and the standard deviation ("SD") and mean coating or layer thickness of the respective measurements in the table for that coating or layer. Transmission electron microscopy (TEM) was used to make the three measurements at each vial location. The ratio of one standard deviation to the mean coating or layer thickness for each set of thickness data was also calculated. The respective SD/mean ratios for the respective coatings or layers varied from 0.29 for the pH protective coating or layer, to 0.34 for the tie or adhesion coating or layer, to 0.44 for the barrier coating or layer.

The 3-month barrier improvement factors using the respective test fluids specified in the Protocol For Measuring Barrier Improvement Factor (BIF) After Solution Storage are given in Table 15.

These tests show that in the context of 10-mL vials having an aspect ratio of about 2:1 (40 mm overall length vs. 21 mm inside diameter) and a scale of 21 mm inside diameter, SD/mean ratios from 0.29 to 0.44 and barrier improvement factors of from 10 to 31 were obtained after 3 months of storage, depending on the test fluid used and the storage temperature. These results are commercially useful barrier improvement factors.

TABLE 13

PECVD Process-Parameters

| Parameter | Units | Tie | Barrier | pH Protection |
|---|---|---|---|---|
| Power | W | 70 | 115 | 70 |
| TMDSO Flow | sccm | 4 | 0 | 4 |
| HMDSO Flow | sccm | 0 | 1.56 | 0 |
| $O_2$ Flow | sccm | 2 | 30 | 2 |
| Argon Flow | sccm | 40 | 0 | 40 |
| Deposition Time | seconds | 2.5 | 15 | 10 |
| Tube Pressure | Torr | 1 | 0.59 | 1 |

TABLE 14

TEM Cross-Sections

| Vial Location | Tie (nm) | Barrier (nm) | Protection (nm) |
|---|---|---|---|
| 1 | 14 | 16 | 79 |
| 2 | 14 | 14 | 55 |
| 3 | 22 | 24 | 110 |
| 4 | 30 | 40 | 159 |
| 5 | 31 | 43 | 160 |
| 6 | 27 | 37 | 141 |
| 7 | 29 | 20 | 153 |
| 8 | 46 | 11 | 163 |
| 9 | 34 | 37 | 161 |
| 10 | 28 | 24 | 160 |
| SD | 9.4 | 11.7 | 39.2 |
| Mean | 27.5 | 26.6 | 134.1 |
| SD/Mean | 0.34 | 0.44 | 0.29 |

TABLE 15

3-Month Stability data
Barrier Improvement Factors (BIF) vs. uncoated COP

| TEST FLUID | 4° C. | 25° C. | 40° C. |
|---|---|---|---|
| Trilayer pH 3.5 | 12 | 19 | 11 |
| Trilayer pH 7.4 | 18 | 24 | 15 |
| Trilayer pH 8.0 | 19 | 10 | 7 |
| Trilayer WFI | 12 | 31 | 23 |

Hypothetical Example 13

Extrapolation of BIF Results to 1 mL Long Syringes

The 1 mL long syringe data of Examples 1-6 and 11 and the 10 mL vial data of Example 12 are summarized in Table 16.

TABLE 16

| Example | Magnet Array | SD/Mean | BIF |
|---|---|---|---|
| 1 mL long Syringe Data: 6.3 mm ID, 8.57 Aspect Ratio |||| 
| 1 | None | .79 | — |
| 2 | Stationary Quadrupole | .44 | — |
| 3 | Stationary Quadrupole | .42 | — |
| 4 | Rotating Quadrupole | .22 | — |
| 5 | Rings | .61 | — |
| 6 | Stationary Quadrupole | .41 | — |
| 11 | Stationary Axial | — | 7.5 |
| 10 mL Vial Data: 21 mm ID, 2 Aspect Ratio ||||
| 12 | None | 0.29 to 0.44 | 10-31 |

Table 16 shows that the use of magnets substantially improved the uniformity of an $SiO_xC_y$ or $SiO_x$ coating or layer in a very small inside diameter (6.3 mm), long aspect ratio (8.57) 1 mL long syringe, using an inner electrode and material supply tube. The improvement in uniformity, expressed as the reduction of the standard deviation/mean thickness ratio, is from 0.79 in Example 1 (no magnets) to 0.22, representing a substantial improvement, in Example 4 (rotating quadrupole array).

The 10 mL vial data shows a similar high uniformity (compared to magnet-assisted PECVD of 1 mL long syringes in other examples), with a SD/thickness ratio of from 0.29 to 0.44 (measured on fewer data points, thus tending to increase the standard deviation, and in a different manner), without using magnets, and 3-month barrier improvements of, for example 10-31. This comparison of the syringe and vial data shows two things.

First, this comparison of the syringe and vial data shows that magnetic confinement is particularly useful for PECVD on the interior of small inside diameter, large aspect ratio parts. Larger inside diameter, smaller aspect ratio parts can provide comparable performance without magnets.

Second, this comparison of the syringe and vial data suggests that a more uniform coating or layer provides a higher barrier improvement factor (BIF).

Based on this data, it is expected that small inside diameter, high aspect ratio medical barrels processed with a relatively uniform PECVD coating or layer thickness, as by using magnets, will also exhibit a higher barrier improvement factor, both as made and after storage with a fluid composition.

Working Ranges of Parameters (Combinations)

The accompanying tables show ranges of parameters useful together.

To use combination 1 of parameters, Step 1 is performed according to the "Combination 1 or 2 Step 1" table, then the Delay Time indicated in the "Combination 1 step 2" table is implemented, then Step 2 is performed according to the "Combination 1 step 2" table.

To use combination 2 of parameters, Step 1 is performed according to the "Combination 1 or 2 Step 1" table, then the Delay Time indicated in the "Combination 2 step 2" table is implemented, then Step 2 is performed according to the "Combination 2 step 2" table.

| Combination 1 or 2 Step 1 | | | | |
|---|---|---|---|---|
| Parameter | Units | Most Preferred | More Preferred | Preferred |
| Power | W | 35-70 | 20-100 | 10-150 |
| OMCTS Flow | sccm | 3-5 | 2-7 | 1-15 |
| $O_2$ Flow | sccm | 2.5-3.7 | 1.6-4.6 | 0.5-15 |
| Argon Flow | sccm | 5-10 | 2.5-15 | 0-20 |
| Deposition Time | seconds | 0.75-1.5 | 0.5-2 | 0.2-5 |
| Tube Pressure | Torr | .035-0.15 | .01-0.2 | .001-0.5 |
| Delay Time | Seconds | >=15 | >=10 | >=5 |

| Combination 1 Step 2 | | | | |
|---|---|---|---|---|
| Parameter | Units | Most Preferred | More Preferred | Preferred |
| Power | W | 1.7-3 | 1-5 | .7-10 |
| OMCTS Flow | sccm | 3-5 | 2-7 | 1-15 |
| $O_2$ Flow | sccm | 2.5-3.7 | 1.6-4.6 | 0.5-15 |
| Argon Flow | sccm | 5-10 | 2.5-15 | 0-20 |
| Deposition Time | seconds | 10-20 | 5-30 | 2-60 |
| Tube Pressure | Torr | .035-0.15 | .01-0.2 | .001-0.5 |
| Delay Time | seconds | >=3 | >=1 | >=0 |

| Combination 2 Step 2 | | | | |
|---|---|---|---|---|
| Parameter | Units | Most Preferred | More Preferred | Preferred |
| Power | W | 0.8-1.5 | 0.6-3 | 0.3-6 |
| OMCTS Flow | sccm | 3-5 | 2-7 | 1-15 |
| $O_2$ Flow | sccm | 2.5-3.7 | 1.6-4.6 | 0.5-15 |
| Argon Flow | sccm | 5-10 | 2.5-15 | 0-20 |
| Deposition Time | seconds | 20-40 | 10-60 | 5-120 |
| Tube Pressure | Torr | .035-0.15 | .01-0.2 | .001-0.5 |
| Delay Time | seconds | >=3 | >=1 | >=0 |

Pseudo Claims

The following pseudo claims are part of the summary of the invention, and represent alternative statements of invention.

aaa. A method of plasma modifying a medical barrel or medical barrel having a surface to be treated, the method comprising:

providing plasma in or near the surface under conditions effective for plasma modification of the surface of the medical barrel or medical barrel; and at least part of the time while providing plasma, providing a magnetic field in or near the plasma, the magnetic field having a position, orientation, and field strength effective to improve the uniformity, density, or both of plasma modification of the surface of the medical barrel.

aaa1. The invention of pseudo claim aaa, in which the aspect ratio between the length and inside diameter of the generally cylindrical interior surface subjected to PECVD is from 2 to 10.

aaa2. The invention of pseudo claim aaa, in which the plasma modification comprises application of a PECVD set comprising a barrier coating or layer and the oxygen barrier improvement factor of the wall and PECVD set, compared to the wall without the PECVD set, is from 15 to 12.

aaa3. The invention of pseudo claim aaa or aaa2, in which the PECVD set is effective to maintain an oxygen barrier improvement factor, versus a barrel without the PECVD set, of at least 5 after the PECVD set is stored in contact with U.S. Pharmacopeia Water for Injection having a pH of 7.0 for a period of three months at a temperature of 25° C.

aaa4. The medical barrel of pseudo claim aaa, aaa2 or aaa3, in which the PECVD set is effective to maintain an oxygen barrier improvement factor, versus a barrel without the PECVD set, of at most 31 after the PECVD set is stored in contact with U.S. Pharmacopeia Water for Injection having a pH of 7.0 for a period of three months at a temperature of 25° C.

aab. The invention of any previous pseudo claim, in which the surface is on a generally cylindrical interior surface defining at least a portion of a lumen, the surface optionally having in inside diameter of 4 to 15 mm, optionally at least 2 mm, optionally at least 4 mm, optionally at least 5 mm, optionally at least 6 mm, optionally at most 15 mm, optionally at most 12 mm, optionally at most 10 mm, optionally at most 9 mm, optionally from 4 to 15 mm, optionally from 5 to 10 mm, optionally from 6 to 10 mm.

aac. The invention of pseudo claim aab, in which providing the magnetic field improves the uniformity, density, or both of plasma distribution in at least a portion of the lumen.

aac1. The invention of any previous pseudo claim, in which the inward oxygen transmission rate through the wall and the PECVD set is from 0.0012 to 0.00048 cubic cm per package per day, at 20° C., at atmospheric pressure outside the wall.

aad. The invention of any previous pseudo claim, in which providing the magnetic field improves the axial uniformity, density, or both of plasma distribution along at least a portion of the surface.

aae. The invention of any previous pseudo claim, in which the plasma comprises plasma electrons and the magnetic field is effective to improve confinement of the plasma electrons in the lumen.

Method—Magnetism Limitations aaf. The invention of any previous pseudo claims aaa to aae, in which the magnetic field is provided by providing a magnetic field generator, alternatively at least two magnetic field generators, optionally at least three magnetic field generators, optionally at least four magnetic field generators, optionally at least five magnetic field generators, optionally at least six magnetic field generators, optionally at least seven magnetic field generators, optionally at least eight magnetic field generators near the surface, each magnetic field generator having a north pole and a south pole defining a polar axis.

aag. The invention of pseudo claim aaf, in which at least part of the time while providing the magnetic field, a magnetic field generator, alternatively at least two of the magnetic field generators, alternatively at least three of the magnetic field generators, alternatively at least four of the magnetic field generators, alternatively at least five of the magnetic field generators, alternatively at least six of the magnetic field generators, alternatively at least seven of the magnetic field generators, alternatively at least eight of the magnetic field generators, alternatively all of the magnetic field generators, have their polar axes generally parallel to the axis of the surface.

aah. The invention of pseudo claim aaf or aag, in which at least part of the time while providing the magnetic field, at least two of the magnetic field generators, alternatively at least three of the magnetic field generators, alternatively at least four of the magnetic field generators, alternatively at least five of the magnetic field generators, alternatively at least six of the magnetic field generators, alternatively at least seven of the magnetic field generators, alternatively at least eight of the magnetic field generators, alternatively all of the magnetic field generators, are circumferentially distributed around the surface in the operative position.

aai. The invention of pseudo claim aah, in which the magnetic field generators have their polar axes extending axially with respect to the surface.

aaj. The invention of pseudo claim aai, in which the magnetic field generators are kept stationary during PECVD.

aak. The invention of any previous pseudo claims aaf to aah, in which at least part of the time while providing the magnetic field, at least two of the magnetic field generators, alternatively at least three of the magnetic field generators, alternatively at least four of the magnetic field generators, alternatively at least five of the magnetic field generators, alternatively at least six of the magnetic field generators, alternatively at least seven of the magnetic field generators, alternatively at least eight of the magnetic field generators, alternatively all of the magnetic field generators, are substantially circumferentially equidistant from the adjacent magnetic field generators.

aal. The invention of any previous pseudo claims aaf to aak, in which at least part of the time while providing the magnetic field, a magnetic field generator, alternatively at least two of the magnetic field generators, alternatively at least three of the magnetic field generators, alternatively at least four of the magnetic field generators, alternatively at least five of the magnetic field generators, alternatively at least six of the magnetic field generators, alternatively at least seven of the magnetic field generators, alternatively at least eight of the magnetic field generators, alternatively all of the magnetic field generators, are rotated about the surface, or the surface rotates with respect to the magnetic field generators, or both, during at least a portion of the plasma treatment.

aam. The invention of any previous pseudo claim aaf to aal, in which at least one magnetic field generator is a permanent magnet or a coil 6-9 or a combination of at least one permanent magnet and at least one coil.

aan. The invention of any previous pseudo claim aaf to aam, in which two or more magnetic field generators are spaced to define a recess between them, within which at least a portion of the surface of the medical barrel is positioned.

aao. The invention of any previous pseudo claims aaf to aan, in which at least part of the time while providing the magnetic field, at least one magnetic field generator, the medical barrel surface, or both, is rotated at a rate effective to improve the uniformity, density, or both of the mean magnetic field strength about a circumference of the medical barrel surface.

aap. The invention of any previous pseudo claims aaf to aao, in which at least part of the time while providing the magnetic field, at least one magnetic field generator, the medical barrel surface, or both, is rotated at a rate effective to improve the uniformity, reduce the intensity, or both of medical barrel heating about a circumference of the medical barrel surface.

aaq. The invention of any previous pseudo claims aaf to aap, further comprising at least part of the time while providing the magnetic field, translating at least one of the magnetic field generators axially along the medical barrel surface, or translating the medical barrel surface with respect to the magnetic field generator, or both, at a rate effective to improve the uniformity of medical barrel heating along the axis of the medical barrel surface.

aar. The invention of any previous pseudo claims aaf to aaq, in which at least part of the time while providing the magnetic field, at least two of the magnetic field generators, alternatively at least three of the magnetic field generators, alternatively at least four of the magnetic field generators, alternatively at least five of the magnetic field generators, alternatively at least six of the magnetic field generators, alternatively at least seven of the magnetic field generators, alternatively at least eight of the magnetic field generators, alternatively all of the magnetic field generators, are axially stacked with respect to the generally cylindrical surface.

aas. The invention of any previous pseudo claims aaf to aar, in which at least part of the time while providing the magnetic field, at least two of the axially stacked magnetic field generators, alternatively at least three of the axially stacked magnetic field generators, alternatively at least four of the axially stacked magnetic field generators, alternatively at least five of the axially stacked magnetic field generators, alternatively at least six of the axially stacked magnetic field generators, alternatively at least seven of the axially stacked magnetic field generators, alternatively at least eight of the axially stacked magnetic field generators, alternatively all of the axially stacked magnetic field generators, are axially spaced from each other.

aat. The invention of any previous pseudo claims aaf to aas, in which at least part of the time while providing the magnetic field, at least two of the axially stacked magnetic field generators, alternatively at least three of the axially stacked magnetic field generators, alternatively at least four of the axially stacked magnetic field generators, alternatively at least five of the axially stacked magnetic field generators, alternatively at least six of the axially stacked magnetic field generators, alternatively at least seven of the axially stacked magnetic field generators, alternatively at least eight of the axially stacked magnetic field generators, alternatively all of the axially stacked magnetic field generators, axially abut each other.

aau. The invention of any previous pseudo claim aaf to aat, in which at least part of the time while providing the magnetic field, the magnetic field generator is provided by positioning at least one coil near the surface and conducting an electrical current through the coil.

aav. The invention of pseudo claim aau, in which the at least one coil comprises a solenoid coil.

aaw. The invention of pseudo claim aau, in which the at least one coil comprises a generally toroidal coil 8 or 9 having a central opening and a geometric axis passing through its central opening.

aax. The invention of pseudo claim aaw, in which at least part of the time while providing the magnetic field, the generally toroidal coil 8 or 9 is oriented with its geometric axis at least generally parallel, optionally at least generally collinear with the axis of the surface.

aay. The invention of pseudo claim aaw or aax, in which at least part of the time while providing the magnetic field, the surface is located substantially entirely within the central opening, alternatively substantially entirely within the central openings of a stack of two or more of the generally toroidal coils 8 or 9.

aaz. The invention of any previous pseudo claims aaw to aay, in which the generally toroidal coils 8 or 9 have at least two arc segments, optionally at least four arc segments, optionally at least 6 arc segments, optionally at least eight arc segments, optionally at least eight 45° arc segments, and alternating segments are wound in opposite directions.

aba. The invention of any previous pseudo claims aaw to aaz, in which the generally toroidal coils have cross-sections that are substantially circular or substantially rectangular.

abb. The invention of any previous pseudo claim aaf to aba, in which at least part of the time while providing the magnetic field, at least one magnetic field generator is oriented with its polar axis at least generally parallel to the axis of the surface.

abc. The invention of any previous pseudo claim aaf to abc, in which at least part of the time while providing the magnetic field, at least one magnetic field generator is oriented with its polar axis at least generally collinear with the axis of the surface.

abd. The invention of any previous pseudo claim aaf to abd, in which at least part of the time while providing the magnetic field, the magnetic field generator has a passage extending along its polar axis and the surface is located entirely within the passage.

abe. The invention of any previous pseudo claim aaf to abd, in which the magnetic field generator is a Helmholtz coil.

abf. The invention of pseudo claim abe, in which the Helmholtz coil comprises first and second spaced solenoid coils with a space between them providing a viewing window allowing the plasma to be viewed while the method is in progress.

abg. The invention of any previous pseudo claim aaf to abf, in which at least part of the time while providing the magnetic field, the magnetic field generator provides a field strength that varies along the medical barrel surface.

abh. The invention of pseudo claim abg, in which at least a portion of the medical barrel surface is generally cylindrical.

abi. The invention of pseudo claim abg or abh, in which at least part of the time while providing the magnetic field, the distance between at least one magnetic field generator and the medical barrel surface varies along the medical barrel surface.

abj. The invention of any previous pseudo claims abg, abh, or abi, in which at least part of the time while providing the magnetic field, the field strength varies along the medical barrel surface to define a profile of varying field strength.

abk. The invention of pseudo claim abj, in which at least part of the time while providing the plasma and not providing the magnetic field, the plasma modification of the surface of the medical barrel varies along the medical barrel surface to define a profile of varying plasma modification.

abl. The invention of pseudo claim abk, in which at least part of the time while providing the magnetic field, the magnetic field generators are configured such that variations in the profile of field strength tend to counteract variations of plasma modification, improving the uniformity, density, or both of plasma modification of the surface of the medical barrel.

abm. The invention of any previous pseudo claim, in which at least part of the time while providing the magnetic field, at least a portion of the plasma is at least partially confined to the vicinity of the medical barrel in an electron bottle.

abn. The invention of pseudo claim abm, in which the medical barrel is a medical barrel and needle assembly, the assembly having a needle end, a back end, and a body portion between the ends.

abo. The invention of pseudo claim abn, in which the electron bottle is defined by structure providing a stronger magnetic field at or near the needle end of the assembly than at or near at least part of the body portion of the assembly.

abp. The invention of pseudo claim abn or abo, in which the electron bottle is defined by structure providing a stronger magnetic field at or near the back end of the assembly than at or near at least part of the body portion of the assembly.

abq. The invention of pseudo claim abn, abo or abp, in which the electron bottle is defined by structure providing stronger magnetic fields at or near the needle end and the back end of the assembly than at or near at least part of the body portion of the assembly.

abr. The invention of any previous pseudo claims abm to abq, in which the electron bottle is defined by structure providing an electron mirror at or near the needle end of the assembly.

abs. The invention of pseudo claim abr, in which the electron bottle is further defined by structure providing an electron mirror at or near the back end of the assembly.

abt. The invention of pseudo claim abm, in which the medical barrel is a vial having an open end, a closed end, and a body portion between the ends.

abu. The invention of pseudo claim abt, in which the electron bottle is defined by structure providing a stronger magnetic field at or near the closed end of the vial than at or near at least part of the body portion of the vial.

abv. The invention of pseudo claim abt or abu, in which the electron bottle is defined by structure providing a stronger magnetic field at or near the open end of the vial than at or near at least part of the body portion of the vial.

abw. The invention of any previous pseudo claims abt to abv, in which the electron bottle is defined by structure providing stronger magnetic fields at or near the closed end and the open end of the vial than at or near at least part of the body portion of the vial.

abx. The invention of any previous pseudo claims abt to abw, in which the electron bottle is defined by structure providing an electron mirror at or near the closed end of the vial.

aby. The invention of any previous pseudo claims abt to abx, in which the electron bottle is further defined by structure providing an electron mirror at or near the open end of the vial.

abz. The invention of any previous pseudo claim abt to aby, in which the structure providing an electron mirror comprises at least a portion of a magnetic field generator.

aca. The invention of any previous pseudo claim abt to abz, in which the structure providing an electron mirror comprises a ferromagnetic or ferromagnetic material.

acb. The invention of any previous pseudo claim abt to aca, in which the structure providing an electron mirror comprises a magnetic field generator.

acc. The invention of any previous pseudo claim abt to acb, in which the structure providing an electron mirror comprises a negatively charged object or portion of an object.

acd. The invention of any previous pseudo claim, in which at least part of the time while providing the magnetic field, at least a portion of the magnetic field in at least a portion of the lumen is oriented with its polar axis generally parallel to the axis of the surface to be treated.

ace. The invention of any previous pseudo claim, in which at least part of the time while providing the magnetic field, at least a portion of the magnetic field in at least a portion of the lumen is oriented with its polar axis extending around the axis of the surface to be treated.

acf. The invention of any previous pseudo claim, in which at least part of the time while providing the magnetic field, at least a portion of the magnetic field in at least a portion of the lumen is oriented with its polar axis extending generally in radial planes with respect to the surface to be treated.

acg. The invention of any previous pseudo claim aaf to acf, in which at least one magnetic field generator, alternatively at least two magnetic field generators, alternatively at least three magnetic field generators, alternatively at least four magnetic field generators, alternatively at least five magnetic field generators, alternatively at least six magnetic field generators, alternatively at least seven magnetic field generators, alternatively at least eight magnetic field generators, alternatively all of the magnetic field generators are bar magnets.

ach. The invention of any previous pseudo claim aaf to acg, in which at least one magnetic field generator, alternatively at least two magnetic field generators, alternatively at least three magnetic field generators, alternatively at least four magnetic field generators, alternatively at least five magnetic field generators, alternatively at least six magnetic field generators, alternatively at least seven magnetic field generators, alternatively at least eight magnetic field generators, alternatively all of the magnetic field generators are ring magnets having central apertures sized to receive the medical barrel surface.

aci. The invention of pseudo claim ach, in which the north and south poles of at least one of the ring magnets are its opposed annular faces.

acj. The invention of pseudo claim aci, in which the magnetic field is provided at least in part by a stack of:
at least one interior ring magnet having the medical barrel surface within its central recess when in its operative position,
at least one cap magnet axially aligned with but outside the stack of interior ring magnets, the cap magnet comprising either a ring magnet or a bar magnet,
in which the interior ring magnets provide a first magnetic field strength radially adjacent to the medical barrel surface that is less than the magnetic field strength provided by the cap magnet axially adjacent to the medical barrel surface, and
optionally one or more additional magnets, positioned between a cap magnet and the stack of interior ring magnets.

ack. The invention of any previous pseudo claims ach to acj, in which the polar axis of at least one of the ring magnets is circumferential about the ring.

acl. The invention of pseudo claim ack, in which the circumference of at least one of the ring magnets comprises plural north-south pole domains.

acm. The invention of any previous pseudo claim aaf to acl, in which at least part of the time while providing the magnetic field, an even number of at least four magnetic field generators are arranged about an axis to provide a quadrupole or analogous structure between axially spaced ends.

acn. The invention of pseudo claim acm, in which the magnetic field generators are relatively movable between an effective position providing the quadrupole or analogous structure and a non-functional position in which the magnetic field generators do not provide a quadrupole or analogous structure.

aco. The invention of pseudo claim acm or acn, in which at least part of the time while providing the magnetic field, the quadrupole and medical barrel are relatively positioned with the axis passing through the medical barrel surface.

acp. The invention of pseudo claim acm to aco, in which at least part of the time while providing the magnetic field, the quadrupole is effective to at least partially confine the plasma at or near at least a portion of the medical barrel surface.

acq. The invention of any previous pseudo claims acm to acp, in which at least part of the time while providing the magnetic field, a magnetic field generator having an axial polar axis is positioned at or near at least one of the axially spaced ends.

acr. The invention of any previous pseudo claims acg to acq, in which at least part of the time while providing the magnetic field, magnetic field generators having axial polar axes are positioned at or near both of the axially spaced ends.

acs. The invention of any previous pseudo claims acm to acr, in which at least one of the magnetic field generators having axial polar axes comprises a ring magnet.

act. The invention of any previous pseudo claims acm to acs, in which at least one of the magnetic field generators having axial polar axes comprises a cap magnet.

acu. The invention of any previous pseudo claims acm to act, in which at least one of the magnetic field generators having axial polar axes comprises a bar magnet.

Method—PECVD Energy/Electrode Limitations acv. The invention of any previous pseudo claim, further comprising generating the plasma using radio-frequency energy.

acw. The invention of pseudo claim acv, in which radio frequency energy is generated by providing an outer electrode outside the medical barrel wall and an inner electrode at least partially inside the lumen of the medical barrel and energizing the electrodes.

acx. The invention of pseudo claim acw, in which the outer electrode is generally cylindrical and the surface is disposed within the outer electrode.

acy. The invention of pseudo claim acw or acx, in which the outer electrode is made of foraminous material.

acz. The invention of pseudo claim acw to acy, in which the outer electrode is made of mesh material.

ada. The invention of pseudo claim acw or acx, in which the outer electrode is made of continuous material.

adb. The invention of any previous pseudo claims acw to ada, in which the inner electrode extends axially into the lumen.

adc. The invention of any previous pseudo claim, in which the plasma modification of the surface of the medical barrel comprises chemical vapor deposition.

add. The invention of any previous pseudo claim, in which the plasma modification of the surface of the medical barrel comprises plasma enhanced chemical vapor deposition (PECVD).

ade. The invention of pseudo claim adc or add, in which the inner electrode comprises a material supply tube for providing gaseous material to the lumen.

adf. The invention of pseudo claim ade, in which the material supply tube has a generally cylindrical interior surface 16 disposed within the lumen.

adg. The invention of pseudo claim adf, in which the material supply tube generally cylindrical interior surface 16 has perforations to pass gaseous material to the lumen.

adh. The invention of pseudo claim adg, in which the perforations are distributed axially along the generally cylindrical interior surface 16.

adi. The invention of pseudo claim adg or adh, in which the perforations are distributed circumferentially along the generally cylindrical interior surface 16.

adj. The invention of pseudo claim adg to adi, in which the perforations are distributed as circumferentially spaced series of two or more perforations, the respective series spaced axially along the generally cylindrical interior surface 16.

adk. The invention of pseudo claim adj, in which the perforations are distributed as plural circumferentially spaced series of two diametrically opposed perforations per series, the respective series spaced axially along the generally cylindrical interior surface 16.

adl. The invention of pseudo claim adk, in which the diametrically opposed perforations of a first series are displaced circumferentially about 90 degrees on the generally cylindrical interior surface 16 with respect to the diametrically opposed perforations of an adjacent second series.

adm. The invention of pseudo claim adk, in which the diametrically opposed perforations of a first series are displaced circumferentially about 45 degrees on the generally cylindrical interior surface 16 with respect to the diametrically opposed perforations of the adjacent second series.

adn. The invention of pseudo claim adl, in which the perforations are distributed as plural circumferentially spaced series of at least three 120-degree-spaced perforations per series spaced axially along the generally cylindrical interior surface 16.

Method—Use of Medical Barrel as its Own Vacuum Chamber ado. The invention of any previous pseudo claim, in which the plasma modification is carried out at least in part at a subatmospheric pressure.

adp. The invention of pseudo claim ado, in which the subatmospheric pressure is generated by at least partially evacuating a lumen at or near the surface during at least a portion of the plasma modification.

adq. The invention of pseudo claim ado or adp, in which the exterior of the medical barrel is exposed to atmospheric pressure during at least a portion of the plasma modification.

Method—Material Limitations adr. The invention of any previous pseudo claim, in which the material supplied to the lumen during at least a portion of the plasma modification comprises:
  a precursor;
  optionally an oxidizing gas; and
  optionally a diluent gas.

ads. The invention of pseudo claim adr, in which the precursor comprises an organosiloxane, a fluorocarbon, a parylene, or a combination of two or more of these.

adt. The invention of pseudo claim adr or ads, in which the precursor comprises an organosiloxane.

adv. The invention of any previous pseudo claims adr to adt, in which the precursor comprises Parylene N or poly(paraxylylene); Parylene C or poly(2-chloroparaxylylene); Parylene D or poly(2,5-dichloropara-xylylene); Parylene HT® or poly(tetrafluoropara-xylylene), or their dimers, or a combination of two or more of these.

adw. The invention of any previous pseudo claims adr to adt, in which the precursor comprises
  dimeric tetrafluoroparaxylylene,
  difluorocarbene,
  monomeric tetrafluoroethylene,
  oligomeric tetrafluoroethylene having the formula $F_2C=CF(CF_2)_xF$ in which x is from 1 to 100, optionally 2 to 50, optionally 2-20, optionally 2-10,
  sodium chlorodifluoroacetate,
  chlorodifluoromethane,
  bromodifluoromethane,
  hexafluoropropylene oxide,
  1H,1H,2H,2H-perfluorodecyl acrylate (FDA),
  a bromofluoroalkane in which the alkane moiety has from 1 to 6 carbon atoms,
  an iodofluoroalkane in which the alkane moiety has from 1 to 6 carbon atoms, or
  a combination of any two or more of these.

adx. The invention of any previous pseudo claims adr to adw, in which the oxidizing gas comprises oxygen, nitrous oxide, water vapor, or a combination of two or more of these.

ady. The invention of any previous pseudo claims adr to ady, in which the diluent gas comprises helium, argon, krypton, xenon, neon, or a combination of two or more of these.

Method—Coating or Layer Limitations adz. The invention of any previous pseudo claim, in which the plasma modification comprises application of a coating or layer to the surface of the medical barrel.

aea. The invention of any previous pseudo claim, in which the plasma modification comprises application of a barrier coating or layer to the surface of the medical barrel.

aeb. The invention of pseudo claim aea, in which the barrier coating or layer consists essentially of $SiO_x$, in which x is from 1.5 to 2.9 as determined by X-ray photoelectron spectroscopy.

aec. The invention of pseudo claim aea or aeb, in which the plasma modification comprises application of a pH protective coating or layer to the surface of the medical barrel layer between the barrier coating or layer and the lumen.

aed. The invention of pseudo claim aec, in which the pH protective coating or layer consists essentially of $SiO_xC_y$ or $SiN_xC_y$, in which x is from about 0.5 to about 2.4, optionally from about 0.5 to 1, and y is from about 0.6 to about 3, optionally from about 2 to about 3 as determined by X-ray photoelectron spectroscopy.

aed1. The invention of any previous pseudo claim aec or aed, in which the pH protective coating or layer consists essentially of the following atomic ratios of silicon, oxygen, and carbon as determined by X-ray photoelectron spectroscopy, and atomic ratio of hydrogen as determined by Rutherford backscattering spectrometry:

| ATOMIC RATIOS | | | |
| --- | --- | --- | --- |
| Si | O | C | H |
| 1 | 0.5 to 2.4 | 0.6 to 3 | 2 to 9 | aed2. The invention of any previous pseudo claim aec, aed, or aed1, in which the pH protective coating or layer consists essentially of the following atomic ratios of silicon, oxygen, and carbon as determined by X-ray photoelectron spectroscopy, and atomic ratio of hydrogen as determined by Rutherford backscattering spectrometry:

| ATOMIC RATIOS | | | |
| --- | --- | --- | --- |
| Si | O | C | H |
| 1 | 0.5 to 1 | 2 to 3 | 6 to 9 | aed3. The invention of pseudo claim aec or aed, in which the pH protective coating or layer between the barrier coating or layer and the lumen consists essentially of the following atomic ratios of silicon, nitrogen, and carbon as determined by X-ray photoelectron spectroscopy, and atomic ratio of hydrogen as determined by Rutherford backscattering spectrometry:

| ATOMIC RATIOS | | | |
| --- | --- | --- | --- |
| Si | N | C | H |
| 1 | 0.5 to 2.4 | 0.6 to 3 | 2 to 9 | aed4. The invention of pseudo claim aed3, in which the pH protective coating or layer between the barrier coating or layer and the lumen consists essentially of the following atomic ratios of silicon, nitrogen, and carbon as determined by X-ray photoelectron spectroscopy, and atomic ratio of hydrogen as determined by Rutherford backscattering spectrometry:

| ATOMIC RATIOS | | | |
| --- | --- | --- | --- |
| Si | N | C | H |
| 1 | 0.5 to 1 | 2 to 3 | 6 to 9 | aed5. The invention of any previous pseudo claim aec to aed4, in which the pH protective coating or layer has a mean thickness from 50 to 500 nm.

aed6. The invention of any previous pseudo claim aec to aed5, in which an FTIR absorbance spectrum of the pH protective coating or layer has a ratio greater than 0.75 between:
the maximum amplitude of the Si—O—Si symmetrical stretch peak between about 1000 and 1040 $cm^{-1}$, and
the maximum amplitude of the Si—O—Si asymmetric stretch peak between about 1060 and about 1100 $cm^{-1}$.

aee. The invention of any pseudo claim aea to aed, in which the plasma modification comprises application of a lubricity coating or layer to the surface of the medical barrel.

aef. The invention of pseudo claim aee, in which the lubricity coating or layer consists essentially of $SiO_xC_y$, in which x is from about 0.5 to about 2.4, optionally from about 0.5 to 1, and y is from about 0.6 to about 3, optionally from about 2 to about 3, each as measured by X-ray photoelectron spectroscopy.

aef1. The invention of pseudo claim aee or aef, in which the lubricity coating or layer consists essentially of the following atomic ratios of silicon, oxygen, and carbon as determined by X-ray photoelectron spectroscopy, and atomic ratio of hydrogen as determined by Rutherford backscattering spectrometry:

| ATOMIC RATIOS | | | |
| --- | --- | --- | --- |
| Si | O | C | H |
| 1 | 0.5 to 2.4 | 0.6 to 3 | 2 to 9 | aef2. The invention of any previous pseudo claim aee or aef, in which the lubricity coating or layer consists essentially of the following atomic ratios of silicon, oxygen, and carbon as determined by X-ray photoelectron spectroscopy, and atomic ratio of hydrogen as determined by Rutherford backscattering spectrometry:

| ATOMIC RATIOS | | | |
| --- | --- | --- | --- |
| Si | O | C | H |
| 1 | 0.5 to 1 | 2 to 3 | 6 to 9 | aef3. The invention of pseudo claim aee or aef, in which the lubricity coating or layer between the barrier coating or layer and the lumen consists essentially of the following atomic ratios of silicon, nitrogen, and carbon as determined by X-ray photoelectron spectroscopy, and atomic ratio of hydrogen as determined by Rutherford backscattering spectrometry:

| ATOMIC RATIOS | | | |
| --- | --- | --- | --- |
| Si | N | C | H |
| 1 | 0.5 to 2.4 | 0.6 to 3 | 2 to 9 | aef4. The invention of pseudo claim aee or aef, in which the lubricity coating or layer between the barrier coating or layer and the lumen consists essentially of the following atomic ratios of silicon, nitrogen, and carbon as determined by X-ray photoelectron spectroscopy, and atomic ratio of hydrogen as determined by Rutherford backscattering spectrometry:

| ATOMIC RATIOS | | | |
|---|---|---|---|
| Si | N | C | H |
| 1 | 0.5 to 1 | 2 to 3 | 6 to 9 |

Method—Coating or Layer Uniformity Limitations aeg. The invention of any previous pseudo claim, in which the uniformity of plasma modification is expressed as a ratio of:

one standard deviation of coating or layer thickness/
mean coating or layer thickness and the ratio is less than 0.69, alternatively from 0.69 to 0.01, alternatively from 0.69 to 0.05, alternatively from 0.66 to 0.1, alternatively from 0.66 to 0.2, alternatively from 0.66 to 0.21, alternatively less than 0.6, alternatively from 0.6 to 0.01, alternatively from 0.6 to 0.05, alternatively from 0.6 to 0.1, alternatively from 0.6 to 0.2, alternatively from 0.6 to 0.21, alternatively less than 0.5, alternatively from 0.5 to 0.01, alternatively from 0.5 to 0.05, alternatively from 0.5 to 0.1, alternatively from 0.5 to 0.2, alternatively from 0.5 to 0.21, alternatively less than 0.4, alternatively from 0.4 to 0.01, alternatively from 0.4 to 0.05, alternatively from 0.4 to 0.1, alternatively from 0.4 to 0.2, alternatively from 0.4 to 0.21, alternatively less than 0.3, alternatively from 0.3 to 0.01, alternatively from 0.3 to 0.05, alternatively from 0.3 to 0.1, alternatively from 0.3 to 0.2, alternatively from 0.3 to 0.21.

aeh. The invention of any previous pseudo claim, in which the plasma modification is application of a coating or layer having a mean thickness between 1 and 1000 nm and a standard deviation of less than 190 nm, alternatively from 190 to 10 nm, alternatively from 190 to 20 nm, alternatively from 190 to 30 nm, alternatively from 190 to 40 nm, alternatively from 190 to 50 nm, alternatively from 190 to 60 nm, alternatively from 190 to 70 nm, alternatively from 190 to 80 nm, alternatively less than 161 nm, alternatively from 160 to 10 nm, alternatively from 160 to 20 nm, alternatively from 160 to 30 nm, alternatively from 160 to 40 nm, alternatively from 160 to 50 nm, alternatively from 160 to 60 nm, alternatively from 160 to 70 nm, alternatively from 160 to 80 nm, alternatively less than 140 nm, alternatively from 140 to 10 nm, alternatively from 140 to 20 nm, alternatively from 140 to 30 nm, alternatively from 140 to 40 nm, alternatively from 140 to 50 nm, alternatively from 140 to 60 nm, alternatively from 140 to 70 nm, alternatively from 140 to 80 nm, alternatively less than 122 nm, alternatively from 120 to 10 nm, alternatively from 120 to 20 nm, alternatively from 120 to 30 nm, alternatively from 120 to 40 nm, alternatively from 120 to 50 nm, alternatively from 120 to 60 nm, alternatively from 120 to 70 nm, alternatively from 120 to 80 nm, alternatively less than 100 nm, alternatively from 100 to 10 nm, alternatively from 100 to 20 nm, alternatively from 100 to 30 nm, alternatively from 100 to 40 nm, alternatively from 100 to 50 nm, alternatively from 100 to 60 nm, alternatively from 100 to 70 nm, alternatively from 100 to 80 nm, alternatively less than 80 nm, alternatively from 80 to 10 nm, alternatively from 80 to 20 nm, alternatively from 80 to 30 nm, alternatively from 80 to 40 nm, alternatively from 80 to 50 nm, alternatively from 80 to 60 nm, alternatively from 80 to 70 nm.

aei. The method of pseudo claim aec, in which the interior PECVD coating or layer comprises a barrier coating or layer.

aej. The method of pseudo claim aei, in which the interior PECVD coating or layer comprises a passivation layer or pH protective coating.

aek. The method of any previous pseudo claims aei to aej, in which the interior PECVD coating or layer comprises a lubricity coating or layer.

Apparatus ael. Apparatus for plasma modifying a medical barrel supported on a medical barrel support, the medical barrel having a lumen surrounded by a wall, at least part of the wall defining a surface to be treated, the apparatus comprising:
 a medical barrel support for holding a medical barrel in the apparatus;
 a plasma generator for providing plasma within the lumen of a medical barrel supported on the medical barrel support 1 under conditions effective for plasma modification of the surface of the medical barrel;
 a magnetic field generator for providing a magnetic field in at least a portion of the lumen of a medical barrel supported on the medical barrel support 1, the magnetic field having an orientation and a field strength effective to improve the uniformity, density, or both of plasma modification of the generally cylindrical interior surface 16 of the generally cylindrical interior surface 16.

Apparatus—Magnetism Limitations aem. The invention of pseudo claim ael, comprising at least one magnetic field generator, alternatively at least two magnetic field generators, optionally at least three magnetic field generators, optionally at least four magnetic field generators, optionally at least five magnetic field generators, optionally at least six magnetic field generators, optionally at least seven magnetic field generators, optionally at least eight magnetic field generators outside a medical barrel in the operative position.

aen. The invention of pseudo claim ael or aem, in which at least one of the magnetic field generators, alternatively at least two of the magnetic field generators, alternatively at least three of the magnetic field generators, alternatively at least four of the magnetic field generators, alternatively at least five of the magnetic field generators, alternatively at least six of the magnetic field generators, alternatively at least seven of the magnetic field generators, alternatively at least eight of the magnetic field generators, alternatively all of the magnetic field generators, have polar axes generally parallel to the axis of the surface of a medical barrel in the operative position.

aeo. The invention of any previous pseudo claims ael to aen, in which at least two of the magnetic field generators, alternatively at least three of the magnetic field generators, alternatively at least four of the magnetic field generators, alternatively at least five of the magnetic field generators, alternatively at least six of the magnetic field generators, alternatively at least seven of the magnetic field generators, alternatively at least eight of the magnetic field generators, alternatively all of the magnetic field generators, are circumferentially distributed around the surface in the operative position.

aep. The invention of any previous pseudo claims ael to aeo, in which at least two of the magnetic field generators, alternatively at least three of the magnetic field generators, alternatively at least four of the magnetic field generators, alternatively at least five of the magnetic field generators, alternatively at least six of the magnetic field generators, alternatively at least seven of the magnetic field generators, alternatively at least eight of the magnetic field generators, alternatively all of the magnetic field generators, are substantially circumferentially equidistant from each other.

aeq. The invention of any previous pseudo claims ael to aep, in which at least one of the magnetic field generators, alternatively at least two of the magnetic field generators, alternatively at least three of the magnetic field generators, alternatively at least four of the magnetic field generators, alternatively at least five of the magnetic field generators, alternatively at least six of the magnetic field generators, alternatively at least seven of the magnetic field generators, alternatively at least eight of the magnetic field generators, alternatively all of the magnetic field generators, are rotated about the axis of the surface, or the surface is rotated around its axis, or both, in the operative position during at least a portion of the plasma treatment.

aer. The invention of any previous pseudo claims ael to aeq, in which at least two of the magnetic field generators, alternatively at least three of the magnetic field generators, alternatively at least four of the magnetic field generators, alternatively at least five of the magnetic field generators, alternatively at least six of the magnetic field generators, alternatively at least seven of the magnetic field generators, alternatively at least eight of the magnetic field generators, alternatively all of the magnetic field generators, are axially stacked with respect to the surface in the operative position.

aes. The invention of any previous pseudo claims ael to aer, in which at least two of the magnetic field generators, alternatively at least three of the magnetic field generators, alternatively at least four of the magnetic field generators, alternatively at least five of the magnetic field generators, alternatively at least six of the magnetic field generators, alternatively at least seven of the magnetic field generators, alternatively at least eight of the magnetic field generators, alternatively all of the magnetic field generators, are axially spaced from each other.

aet. The invention of pseudo claim ael to aes, in which at least two of the magnetic field generators, alternatively at least three of the magnetic field generators, alternatively at least four of the magnetic field generators, alternatively at least five of the magnetic field generators, alternatively at least six of the magnetic field generators, alternatively at least seven of the magnetic field generators, alternatively at least eight of the magnetic field generators, alternatively all of the magnetic field generators, are axially abutting each other.

aeu. The invention of any previous pseudo claims ael to aet, in which at least one magnetic field generator is at least one coil 6 or 8 conducting an electrical current.

aev. The invention of pseudo claim aeu, in which the at least one coil comprises a solenoid coil.

aew. The invention of pseudo claim aev, in which the solenoid coil is oriented with its axis at least generally parallel to the axis of the surface in the operative position.

aex. The invention of pseudo claim aev or aew, in which the solenoid coil has an interior portion adapted to receive the medical barrel surface in the operative position and first and second opposed end portions 5 and 8.

aey. The invention of any previous pseudo claims aev to aex, in which the first end portion, the second end portion, or both provide a stronger magnetic field, when energized, than the interior portion.

aez. The invention of pseudo claim aex to aey, in which the interior portion comprises an interior winding and at least one of the end portions 6 or 8 providing a stronger magnetic field when energized comprises a separate exterior winding 7 or 9.

afa. The invention of pseudo claim aez, in which the interior winding is provided with lower amperage than the separate exterior winding 7 or 9 when the windings are energized.

afb. The invention of pseudo claim aez or afa, in which the interior winding has fewer total turns per cm of the axis than the exterior winding 7 or 9.

afc. The invention of any previous pseudo claims aev to afb, in which the solenoid coil has a single winding extending along the interior portion and the first and second opposed end portions 6 and 8, the winding having more turns per cm along the axis at or near the first and second opposed end portions 6 and 8 than along the interior portion.

afd. The invention of any previous pseudo claims aev to afc, in which the solenoid coil is oriented with its axis at least generally collinear with the axis of the surface in the operative position.

afe. The invention of any previous pseudo claims aev to afd, in which the surface in the operative position is located entirely within the solenoid coil.

aff. The invention of pseudo claim aeu, in which the at least one coil comprises a generally toroidal coil 8 or 9.

afg. The invention of pseudo claim aff, in which the generally toroidal coil 8 or 9 is oriented with its axis at least generally parallel to the axis of the surface in the operative position.

afh. The invention of pseudo claim afg, in which the generally toroidal coil 8 or 9 is oriented with its axis at least generally collinear with the axis of the surface in the operative position.

afi. The invention of any previous pseudo claims aff to afh, in which the surface in the operative position is located substantially entirely within the generally toroidal coil 8 or 9, alternatively substantially entirely within a stack of two or more of the generally toroidal coils 8 or 9.

afj. The invention of any previous pseudo claims aff to afi, in which the generally toroidal coils 8 or 9 have plural arc segments, optionally at least four arc segments, optionally at least 6 arc segments, optionally at least eight arc segments, optionally at least eight 45° arc segments, and alternating segments are wound in opposite directions.

afk. The invention of any previous pseudo claims aff to afj, comprising more than one of the generally toroidal coils 8 or 9 having cross-sections that are substantially circular or substantially rectangular.

afl. The invention of any previous pseudo claim pseudo-claim ael to afk, in which at least a portion of the magnetic field in at least a portion of a medical barrel in the operative position is oriented with its polar axis generally parallel to the axis of the surface to be treated.

afm. The invention of any previous pseudo claim pseudo-claim ael to afl, in which at least a portion of the magnetic field in at least a portion of a medical barrel in the operative position is oriented with its polar axis extending around the axis of the surface to be treated.

afn. The invention of any previous pseudo claim ael to afm, in which at least a portion of the magnetic field in at least a portion of a medical barrel in the operative position is oriented with its polar axis extending generally in radial planes with respect to the surface to be treated.

afo. The invention of any previous pseudo claim aem to afn, in which at least one of the magnetic field generators, alternatively at least two of the magnetic field generators, alternatively at least three of the magnetic field generators, alternatively at least four of the magnetic field generators, alternatively at least five of the magnetic field generators, alternatively at least six of the magnetic field generators, alternatively at least seven of the magnetic field generators, alternatively at least eight of the magnetic field generators, alternatively all of the magnetic field generators, are bar magnets.

afp. The invention of pseudo claim afo, in which an even number of at least four magnetic field generators are arranged to provide a quadrupole or analogous structure.

afq. The invention of any previous pseudo claim ael to afp, in which at least one of the magnetic field generators, alternatively at least two of the magnetic field generators, alternatively at least three of the magnetic field generators, alternatively at least four of the magnetic field generators, alternatively at least five of the magnetic field generators, alternatively at least six of the magnetic field generators, alternatively at least seven of the magnetic field generators, alternatively at least eight of the magnetic field generators, alternatively all of the magnetic field generators, are ring magnets.

afr. The invention of pseudo claim afq, in which the north and south pole of at least one of the ring magnets is its opposed annular faces.

afs. The invention of pseudo claim afq or afr, in which the polar axis of at least one of the ring magnets is circumferential about the ring.

aft. The invention of pseudo claim afq, in which the circumference of at least one of the ring magnets is divided into plural north-south pole domains.

Apparatus—PECVD Energy/Electrode Limitations afu. The invention of any previous pseudo claim ael to aft, further comprising generating the plasma using radio-frequency energy.

afv. The invention of pseudo claim afu, in which radio frequency energy is generated by providing an outer electrode outside the medical barrel wall and an inner electrode at least partially inside the lumen of the medical barrel and energizing the electrodes.

afw. The invention of pseudo claim afv in which the outer electrode is generally cylindrical and the surface in the operative position is disposed within the outer electrode.

afx. The invention of pseudo claim afv or afw, in which the outer electrode is made of foraminous material.

afy. The invention of any previous pseudo claims afv to afx, in which the outer electrode is made of mesh material.

afz. The invention of pseudo claim afv or afw, in which the outer electrode is made of continuous material.

aga. The invention of any previous pseudo claims aeb to afz, in which the inner electrode 0 extends axially into a medical barrel in the operative position.

agb. The invention of any previous pseudo claims aaa to aga, in which the plasma modification of the surface of the medical barrel comprises chemical vapor deposition.

agc. The invention of any previous pseudo claims aaa to agb, in which the plasma modification of the surface of the medical barrel comprises plasma enhanced chemical vapor deposition (PECVD).

agd. The invention of pseudo claim agb or agc, in which the inner electrode 0 comprises a material supply tube for providing gaseous material to a medical barrel in the operative position.

age. The invention of pseudo claim agd, in which the material supply tube has a generally cylindrical interior surface 16 disposed within a medical barrel in the operative position.

agf. The invention of pseudo claim age, in which the material supply tube generally cylindrical interior surface 16 has perforations to pass gaseous material to a medical barrel in the operative position.

agg. The invention of pseudo claim agf, in which the perforations are distributed axially along the generally cylindrical interior surface 16.

agh. The invention of pseudo claim agf or agg, in which the perforations are distributed circumferentially along the generally cylindrical interior surface 16.

agi. The invention of any previous pseudo claims agf to agh, in which the perforations are distributed as circumferentially spaced series of two or more perforations, the respective series spaced axially along the generally cylindrical interior surface 16.

agj. The invention of pseudo claim agi, in which the perforations are distributed as plural circumferentially spaced series of two diametrically opposed perforations per series, the respective series spaced axially along the generally cylindrical interior surface 16.

agk. The invention of pseudo claim agj, in which the diametrically opposed perforations of a first series are displaced circumferentially about 90 degrees on the generally cylindrical interior surface 16 with respect to the diametrically opposed perforations of an adjacent second series.

agl. The invention of pseudo claim agj, in which the diametrically opposed perforations of a first series are displaced circumferentially about 45 degrees on the generally cylindrical interior surface 16 with respect to the diametrically opposed perforations of each adjacent second series.

agm. The invention of pseudo claim agi, in which the perforations are distributed as plural circumferentially spaced series of at least three 120-degree-spaced perforations per series, the respective series spaced axially along the generally cylindrical interior surface 16.

agn. The invention of any previous pseudo claims agd to agm, in which:
the material supply tube rotates with respect to the magnetic field provided by the magnetic field generators and the medical barrel support;
the magnetic field provided by the magnetic field generators rotates with respect to the material supply tube and the medical barrel support;
the medical barrel support rotates with respect to the material supply tube and the magnetic field provided by the magnetic field generators;
the material supply tube and the magnetic field provided by the magnetic field generators rotate at the same or different rotation rates and directions with respect to the medical barrel support;
the magnetic field provided by the magnetic field generators and the medical barrel support rotate at the same or different rotation rates and directions with respect to the material supply tube; or
the material supply tube and the medical barrel support rotate at the same or different rotation rates and directions with respect to the magnetic field provided by the magnetic field generators.

ago. The invention of any previous pseudo claims ael to agn, further comprising apparatus for measuring plasma characteristics, comprising at least one of:
an optical detector, for example a camera configured to show whether the plasma comprises streamers of non-uniform plasma versus complete fill with uniform plasma, or an optical emissions spectrometer to determine the uniformity of the plasma spectrum;

a Rogowski Coil disposed about the inner electrode or its power supply conductor to determine the uniformity of the current supplied to the plasma; or a Langmuir probe 5 to measure the electron temperature of the plasma.

Apparatus—Use of Medical Barrel as its Own Vacuum Chamber agp. The invention of any previous pseudo claims ael to ago, further comprising a vacuum pump for at least partially evacuating a medical barrel in the operative position during at least a portion of the plasma modification.

agq. The invention of any previous pseudo claim, comprising apparatus exposing the exterior of the medical barrel to atmospheric pressure during at least a portion of the plasma modification.

Apparatus—Material Limitations agr. The invention of any previous pseudo claim ael to agq, further comprising a source of each material supplied to a medical barrel in the operative position during at least a portion of the plasma modification, in which the materials comprise:
 a precursor;
 optionally an oxidizing gas; and
 optionally a diluent gas.

ags. The invention of pseudo claim agr, in which the precursor comprises an organosiloxane, a fluorocarbon, a parylene, or a combination of two or more of these.

agt. The invention of pseudo claim agr or ags, in which the precursor comprises an organosiloxane.

agu. The invention of any previous pseudo claims agr to agt, in which the precursor comprises hexamethylenedisiloxane (HMDSO), octamethylcyclotetrasiloxane (OMCTS), tetramethyldisiloxane (TMDSO), or a combination of these.

agv. The invention of any previous pseudo claims agr to agu, in which the precursor comprises Parylene N or poly(paraxylylene); Parylene C or poly-chloroparaxylylene); Parylene D or poly,5-dichloropara-xylylene); Parylene HT® or poly(tetrafluoropara-xylylene), or their dimers, or a combination of two or more of these.

agw. The invention of any previous pseudo claims agr to agv, in which the precursor comprises
 dimeric tetrafluoroparaxylylene,
 difluorocarbene,
 monomeric tetrafluoroethylene,
 oligomeric tetrafluoroethylene having the formula $F_2C=CF(CF_xF$ in which x is from 1 to 100, optionally 2 to 50, optionally 2-20, optionally 2-10,
 sodium chlorodifluoroacetate,
 chlorodifluoromethane,
 bromodifluoromethane,
 hexafluoropropylene oxide,
 1H,1H,2H,2H-perfluorodecyl acrylate (FDA),
 a bromofluoroalkane in which the alkane moiety has from 1 to 6 carbon atoms,
 an iodofluoroalkane in which the alkane moiety has from 1 to 6 carbon atoms, or
 a combination of any two or more of these.

agx. The invention of any previous pseudo claims agr to agw, in which the oxidizing gas comprises oxygen, nitrous oxide, water vapor, or a combination of two or more of these.

agy. The invention of any previous pseudo claims agr to agx, in which the diluent gas comprises helium, argon, krypton, xenon, neon, or a combination of two or more of these.

Apparatus—Coating or Layer Limitations agz. The invention of any previous pseudo claim ael to agy, in which the plasma modification comprises application of a coating or layer to the surface of the medical barrel.

aha. The invention of any previous pseudo claim ael to agz, in which the plasma modification comprises application of a barrier coating or layer to the surface of the medical barrel.

ahb. The invention of pseudo claim aha, in which the barrier coating or layer consists essentially of $SiO_x$, in which x is from 1.5 to 2.9.

ahc. The invention of pseudo claim aha, in which the plasma modification comprises application of a pH protective coating or layer to the surface of the medical barrel.

ahd. The invention of pseudo claim ahc, in which the pH protective coating or layer consists essentially of $SiO_xC_y$, in which x is from about 0.5 to about 2.4, optionally from about 0.5 to 1, and y is from about 0.6 to about 3, optionally from about 2 to about 3.

ahe. The invention of pseudo claim aha, in which the plasma modification comprises application of a lubricity coating or layer to the surface of the medical barrel.

ahf. The invention of pseudo claim ahe, in which the lubricity coating or layer consists essentially of $SiO_xC_y$, in which x is from about 0.5 to about 2.4, optionally from about 0.5 to 1, and y is from about 0.6 to about 3, optionally from about 2 to about 3.

Apparatus—Coating or Layer Uniformity Limitations ahg. The invention of any previous pseudo claim ael to ahf, in which the apparatus is adapted to provide a uniform coating or layer having a ratio of one standard deviation of coating or layer thickness to mean coating or layer thickness of less than 0.69, alternatively from 0.69 to 0.01, alternatively from 0.69 to 0.05, alternatively from 0.66 to 0.1, alternatively from 0.66 to 0.2, alternatively from 0.66 to 0.21, alternatively less than 0.6, alternatively from 0.6 to 0.01, alternatively from 0.6 to 0.05, alternatively from 0.6 to 0.1, alternatively from 0.6 to 0.2, alternatively from 0.6 to 0.21, alternatively less than 0.5, alternatively from 0.5 to 0.01, alternatively from 0.5 to 0.05, alternatively from 0.5 to 0.1, alternatively from 0.5 to 0.2, alternatively from 0.5 to 0.21, alternatively less than 0.4, alternatively from 0.4 to 0.01, alternatively from 0.4 to 0.05, alternatively from 0.4 to 0.1, alternatively from 0.4 to 0.2, alternatively from 0.4 to 0.21, alternatively less than 0.3, alternatively from 0.3 to 0.01, alternatively from 0.3 to 0.05, alternatively from 0.3 to 0.1, alternatively from 0.3 to 0.2, alternatively from 0.3 to 0.21 ahh. The invention of any previous pseudo claim ael to ahg, in which the apparatus is adapted to provide a uniform coating or layer having a mean thickness between 1 and 1000 nm, optionally between 10 and 500 nm, and a standard deviation of less than 190 nm, alternatively from 190 to 10 nm, alternatively from 190 to 20 nm, alternatively from 190 to 30 nm, alternatively from 190 to 40 nm, alternatively from 190 to 50 nm, alternatively from 190 to 60 nm, alternatively from 190 to 70 nm, alternatively from 190 to 80 nm, alternatively less than 161 nm, alternatively from 160 to 10 nm, alternatively from 160 to 20 nm, alternatively from 160 to 30 nm, alternatively from 160 to 40 nm, alternatively from 160 to 50 nm, alternatively from 160 to 60 nm, alternatively from 160 to 70 nm, alternatively from 160 to 80 nm, alternatively less than 140 nm, alternatively from 140 to 10 nm, alternatively from 140 to 20 nm, alternatively from 140 to 30 nm, alternatively from 140 to 40 nm, alternatively from 140 to 50 nm, alternatively from 140 to 60 nm, alternatively from 140 to 70 nm, alternatively from 140 to 80 nm, alternatively less than 122 nm, alternatively from 120 to 10 nm, alternatively from 120 to 20 nm, alternatively from 120 to 30 nm, alternatively from 120 to 40 nm, alternatively from 120 to 50 nm, alternatively from 120 to 60 nm, alternatively from 120 to 70 nm, alternatively from 120 to 80 nm, alternatively less than 100 nm, alternatively from 100 to 10 nm, alternatively from 100 to 20 nm, alternatively from 100 to 30 nm, alternatively from 100 to 40 nm, alternatively from 100 to 50 nm, alternatively from 100 to 60 nm, alternatively from 100 to 70 nm, alternatively from 100 to 80 nm, alternatively less than 80 nm, alternatively from 80 to 10 nm, alternatively from 80 to 20 nm, alternatively from 80 to 30 nm, alternatively from 80 to 40 nm, alternatively from 80 to 50 nm, alternatively from 80 to 60 nm, alternatively from 80 to 70 nm, optionally a standard deviation of less than the mean thickness, alternatively a minimum standard deviation of at least 20% of the mean thickness.

ahi. The invention of any previous pseudo claimany previous pseudo claim, in which the PECVD process conditions are controlled such that the distance between the inlet tube and the wall of the medical barrel or other part undergoing PECVD is:
greater than the Debye Length,
optionally at least 2 times as great as the Debye Length,
optionally at least 3 times as great as the Debye Length,
optionally at least 4 times as great as the Debye Length,
optionally at least 5 times as great as the Debye Length,
optionally at least 6 times as great as the Debye Length,
optionally at least 7 times as great as the Debye Length,
optionally at least 8 times as great as the Debye Length,
optionally at least 9 times as great as the Debye Length,
optionally at least 10 times as great as the Debye Length,
optionally at least 20 times as great as the Debye Length,
optionally at least 30 times as great as the Debye Length,
optionally at least 40 times as great as the Debye Length,
optionally at least 50 times as great as the Debye Length,
optionally at least 60 times as great as the Debye Length,
optionally at least 70 times as great as the Debye Length,
optionally at least 80 times as great as the Debye Length,
optionally at least 90 times as great as the Debye Length,
optionally at least 100 times as great as the Debye Length.

ahj. The invention of any previous pseudo claim, in which magnetic confinement is used during PECVD if the aspect ratio between the length and inside diameter of the generally cylindrical interior surface is at least 2:1, more preferably 3:1, and more preferably 5:1 and more preferably 10:1 and more preferably 15:1 and more preferably 20:1, optionally from 2 to 10, optionally at least 4, optionally at least 6.

ahk. A vessel made according to the process of any pseudo claim ahg to ahj.

ahl. The vessel of pseudo claim ahk, comprising a medical barrel or a vial.

ahm. A pharmaceutical package comprising the medical barrel, medical barrel 4, FIG. 3, or vial of pseudo claim ahl, containing a pharmaceutical preparation, secured with a closure.

ahm1. The medical barrel of any previous pseudo claim, further comprising a fluid composition in the lumen having a pH between 4 and 9 and a closure retaining the fluid composition in the lumen, defining a fluid storage package.

ahn. The pharmaceutical package of pseudo claim ahm or ahm1, in which the pharmaceutical preparation or fluid composition comprises a member selected from the group consisting of any of the individual materials listed below in this specification.

Part 2 aho. A medical barrel, auto-injector cartridge, or similar device (14), which is the same for the present claims as a workpiece, comprising:
a dispensing end (22),
a back end (32),
a generally cylindrical interior surface 16 having an generally cylindrical interior surface 16 defining a lumen (18) extending at least part of the distance between the dispensing end (22) and the back end (32), in which the generally cylindrical interior surface 16:
is configured to receive a slidable plunger or piston (36),
has a first portion (800) extending axially from a front end at or near the dispensing end (22) to a back end (806) between and spaced from each of the dispensing end (22) and the back end (32), and
has a second portion (802) extending axially from a front end, adjacent to the first portion back end, at least part of the distance to the back end (32);
a lubricity coating or layer (34) applied by PECVD to the second portion (802) of the generally cylindrical interior surface 16, the lubricity coating or layer (34) having a mean thickness, and
either:
no lubricity coating or layer applied by PECVD to the first portion (800) of the generally cylindrical interior surface 16, or
a lubricity coating or layer (34) applied by PECVD to the first portion (800) of the generally cylindrical interior surface 16 having an mean thickness that is thinner than the mean thickness of the lubricity coating or layer (34) on the second portion (802).

ahp. A syringe (210), auto-injector (300), or similar device (14) comprising a medical barrel or cartridge (14) and a plunger or piston (36),
the medical barrel or cartridge (14) comprising:
a dispensing end (22),
a back end (32),
a generally cylindrical interior surface 16 having an generally cylindrical interior surface 16 defining a lumen (18) extending at least part of the distance between the dispensing end (22) and the back end (32), in which the generally cylindrical interior surface 16:
is configured to receive a slidable plunger or piston (36),
has a first portion (800) extending axially from a front end at or near the dispensing end (22) to a back end (806) between and spaced from each of the dispensing end (22) and the back end (32), and
has a second portion (802) extending axially, from a front end adjacent to the first portion back end (806), at least part of the distance to the back end (32);
a lubricity coating or layer (34) applied by PECVD to the second portion (802) of the generally cylindrical interior surface 16, the lubricity coating or layer (34) having an mean thickness, and
either:
no lubricity coating or layer applied by PECVD to the first portion (800) of the generally cylindrical interior surface 16, or
a lubricity coating or layer (34) applied by PECVD to the first portion (800) of the generally cylindrical interior surface 16 having an mean thickness that is thinner than the mean thickness of the lubricity coating or layer (34) on the second portion (802); and
the plunger or piston (36) disposed in the lumen (18) and slidable between a resting position contacting the second portion (802) of the generally cylindrical interior surface 16 and an advanced position contacting the first portion (800) of the generally cylindrical interior surface 16.

ahq. A prefilled syringe, auto-injector, or similar device (14) comprising a medical barrel or cartridge (14), a fluid composition (40) to be dispensed, and a plunger or piston (36);
the medical barrel or cartridge (14) comprising:
a dispensing end (22),
a back end (32),
a generally cylindrical interior surface 16 having an generally cylindrical interior surface 16 defining a lumen (18) extending at least part of the distance between the dispensing end (22) and the back end (32), in which the generally cylindrical interior surface 16:
is configured to receive a slidable plunger or piston (36),
has a first portion (800) extending axially from a front end at or near the dispensing end (22) to a back end (806) between and spaced from each of the dispensing end (22) and the back end (32), and
has a second portion (802) extending axially, from a front end adjacent to the first portion back end (806), at least part of the distance to the back end (32);
a lubricity coating or layer (34) applied by PECVD to the second portion (802) of the generally cylindrical interior surface 16, the lubricity coating or layer (34) having an mean thickness, and
either:
no lubricity coating or layer applied by PECVD to the first portion (800) of the generally cylindrical interior surface 16, or
a lubricity coating or layer (34) applied by PECVD to the first portion (800) of the generally cylindrical interior surface 16 having an mean thickness that is thinner than the mean thickness of the lubricity coating or layer (34) on the second portion (802);
the plunger or piston (36) disposed in the lumen (18) and axially slidable between a resting position contacting the second portion (802) of the generally cylindrical interior surface 16 and an advanced position contacting the first portion (800) of the generally cylindrical interior surface 16; and
the fluid composition (40) disposed in the lumen (18) between the plunger and the dispensing end (22) of the medical barrel or cartridge (14).

ahr. The invention of any previous pseudo claim, in which the lubricity coating or layer (34) has a transition of thickness between the first (800) and second (802) portions of the generally cylindrical interior surface 16.

ahs. The invention of any previous pseudo claim, in which the minimum mean thickness of the lubricity coating or layer (34) in the first portion (800) is 0 nm and the maximum mean thickness of the lubricity coating or layer (34) is 0.8 times, optionally 0.7 times, optionally 0.6 times, optionally 0.5 times, optionally 0.4 times, optionally 0.3 times, optionally 0.2 times, optionally 0.1 times, optionally 0.09 times, optionally 0.08 times, optionally 0.07 times, optionally 0.06 times, optionally 0.05 times, optionally 0.04 times, optionally 0.03 times, optionally 0.02 times, optionally 0.01 times the mean thickness of the lubricity coating or layer (34) in the second portion (802).

aht. The invention of any previous pseudo claim, further comprising a third portion of the generally cylindrical interior surface 16 between the second portion (802) of the generally cylindrical interior surface 16 and the back end (32) of the medical barrel or cartridge (14).

ahu. The invention of any previous pseudo claimsaho to aht, in which the second portion (802) of the generally cylindrical interior surface 16 has a smaller inside diameter than the rear end of the first portion (800) of the generally cylindrical interior surface 16.

ahv. The invention of any previous pseudo claims ahp to ahu, in which the break loose force (Fi) of the plunger or piston (36) from its rest position is less than 12 N, alternatively less than 10 N, alternatively less than 8 N, alternatively less than 6 N, alternatively less than 4 N, after two weeks' storage with the plunger or piston (36) in the rest position.

ahw. The invention of any previous pseudo claims ahp to ahy, in which the break loose force (Fi) of the plunger or piston (36) from its rest position is at least 3 N, after two weeks' storage with the plunger or piston (36) in the rest position.

ahx. The invention of any previous pseudo claimsahp to ahx, in which the maintenance force (Fm) of the plunger or piston (36) is between 2 and 8 N.

ahy. The invention of any previous pseudo claim, in which the dissolved Si extraction from the lubricity coating or layer (34) is less than 10, alternatively less than 5, alternatively less than 4, alternatively less than three micrograms.

ahz. The invention of any previous pseudo claim, in which the dissolved Si extraction from the lubricity coating or layer (34) is more than 2 micrograms.

aia. The invention of any previous pseudo claim, in which the linear and cyclic siloxanes extracted using aqueous media from the lubricity coating or layer (34) by gas chromatography and mass spectroscopy is less than 10, alternatively less than 1, alternatively less than 0.7, alternatively less than 0.08 microgram per gram, optionally less than the detection limit for aqueous extraction of coated plastic components.

aib. The invention of any previous pseudo claim, in which the first portion (800) of the generally cylindrical interior surface 16 is essentially free of lubricity coating or layer material.

aic. The invention of any previous pseudo claim, in which the first portion (800) of the generally cylindrical interior surface 16 is free of detectable lubricity coating or layer material.

aid. The invention of any previous pseudo claim, in which the first portion (800) of the generally cylindrical interior surface 16 has a draft angle from 0° to less than 1°, optionally from 0 to 0.5°, optionally from 0° to 0.25°, optionally from 0° to 0.16°, optionally from 0° to 0.03°, optionally from 0° to 0.014°, optionally from 0° to 0.01°.

aie. The invention of any previous pseudo claim, in which the generally cylindrical interior surface 16 has a third portion between the second portion (802) and the back end (32), the third portion having a front end adjacent to the rear end of the second portion (802) and a rear end.

aif. The invention of pseudo claim aie, in which the third portion of the generally cylindrical interior surface 16 comprises a lubricity coating or layer (34) applied by PECVD.

aig. The invention of any previous pseudo claim, in which the medical barrel wall comprises a polycarbonate, an olefin polymer (for example polypropylene (PP) or polyethylene (PE)), a cyclic olefin copolymer (COC), a cyclic olefin polymer (COP), polymethylpentene, a polyester (for example polyethylene terephthalate, polyethylene naphthalate, or polybutylene terephthalate (PBT)), polymethylmethacrylate, PVdC (polyvinylidene chloride), polyvinyl chloride (PVC), polylactic acid, polystyrene, hydrogenated polystyrene, poly(cyclohexylethylene) (PCHE), epoxy resin, nylon, polyurethane polyacrylonitrile (PAN), polyacrylonitrile (PAN), an ionomeric resin (for example Surlyn®), glass (for example borosilicate glass), or a combination of any two or more of these; preferably comprises a cyclic olefin polymer, a polyethylene terephthalate or a polypropylene; and more preferably comprises COP.

aig1. The invention of any previous pseudo claim, in which the barrel wall is made of electrically non-conductive material.

aig3. The invention of any previous pseudo claim, in which the barrel wall is made of transparent material.

aig4. The invention of any previous pseudo claim, in which the barrel wall is made of injection moldable thermoplastic material.

aih. The invention of any previous pseudo claim, in which the lubricity coating or layer (34) has an atomic ratio $SiO_xC_y$ or $SiN_xC_y$ as measured by XPS, in which x is from about 0.5 to about 2.4, y is from about 0.6 to about 3.

aii. The invention of any previous pseudo claim, in which the lubricity coating or layer (34) comprises a graded composite of $SiO_xC_y$ to $SiO_x$ or vice versa.

aij. The invention of any previous pseudo claim, in which the lubricity coating or layer (34) has an mean thickness of from 1 to 5000 nm, preferably of from 30 to 1000 nm, more preferably of from 100 to 500 nm.

aik. The method of any previous pseudo claim, in which mean thickness of a coating or layer is determined by spectral reflectance.

ail. The invention of any previous pseudo claim, in which the lubricity coating or layer (34):
  (i) has a lower wetting tension than the uncoated surface, preferably a wetting tension of from 20 to 72 dyne/cm, more preferably a wetting tension of from 30 to 60 dynes/cm, more preferably a wetting tension of from 30 to 40 dynes/cm, preferably 34 dyne/cm; and/or
  (ii) is more hydrophobic than the uncoated surface.

aim. The invention of any previous pseudo claim, in which the pharmaceutical composition comprises a biologically active compound or composition or a biological fluid, preferably (i) citrate or a citrate containing composition, (ii) a medicament, in particular insulin or an insulin containing composition, or (iii) blood or blood cells.

ain. The invention of any previous pseudo claim, in which the plunger initiation force, $F_i$, is from 2.5 to 15 N and the plunger maintenance force Fm is from 2.5 to 25 N after 1 week.

aio. The invention of any previous pseudo claim, further comprising a barrier coating or layer on at least the first portion (800) of the generally cylindrical interior surface 16.

aip. The invention of pseudo claim aio, in which the barrier coating or layer comprises $SiO_x$, in which x is from 1.5 to 2.9 as measured by XPS.

aiq. The invention of pseudo claims aio or aip, in which the barrier coating or layer is from 2 to 1000 nm thick, optionally from 20 to 300 nm thick.

air. The invention of any previous pseudo claims aio to aiq, in which the organosilicon precursor for the barrier coating or layer is a linear siloxane, preferably HMDSO or TMDSO.

ais. The invention of any previous pseudo claim, further comprising a tie coating or layer on at least the first portion (800) of the generally cylindrical interior surface 16.

ais1. The medical barrel of pseudo claim ais, in which the tie coating or layer is between the barrier coating or layer and the generally cylindrical interior surface, ais2. The medical barrel of pseudo claim ais or ais1, in which the tie coating or layer has a mean thickness from greater than 0 to 10 nm.

ait. The invention of any previous pseudo claim ais, ais1, or ais2 in which the tie coating or layer comprises $SiO_xC_y$ or $SiN_xC_y$, in which x is from about 0.5 to about 2.4 and y is from about 0.6 to about 3 as measured by XPS.

ait1. The invention of pseudo claim ais or ait, in which the tie coating or layer consists essentially of the following atomic ratios of silicon, oxygen, and carbon as determined by X-ray photoelectron spectroscopy, and atomic ratio of hydrogen as determined by Rutherford backscattering spectrometry:

| ATOMIC RATIOS | | | |
|---|---|---|---|
| Si | O | C | H |
| 1 | 0.5 to 2.4 | 0.6 to 3 | 2 to 9 | ait2. The invention of any previous pseudo claim ais or ait, in which the tie coating or layer consists essentially of the following atomic ratios of silicon, oxygen, and carbon as determined by X-ray photoelectron spectroscopy, and atomic ratio of hydrogen as determined by Rutherford backscattering spectrometry:

| ATOMIC RATIOS | | | |
|---|---|---|---|
| Si | O | C | H |
| 1 | 0.5 to 1 | 2 to 3 | 6 to 9 | ait3. The invention of pseudo claim ais or ait, in which the tie coating or layer between the barrier coating or layer and the lumen consists essentially of the following atomic ratios of silicon, nitrogen, and carbon as determined by X-ray photoelectron spectroscopy, and atomic ratio of hydrogen as determined by Rutherford backscattering spectrometry:

| ATOMIC RATIOS | | | |
|---|---|---|---|
| Si | N | C | H |
| 1 | 0.5 to 2.4 | 0.6 to 3 | 2 to 9 | ait4. The invention of pseudo claim ais or ait, in which the tie coating or layer between the barrier coating or layer and the lumen consists essentially of the following atomic ratios of silicon, nitrogen, and carbon as determined by X-ray photoelectron spectroscopy, and atomic ratio of hydrogen as determined by Rutherford backscattering spectrometry:

| ATOMIC RATIOS | | | |
|---|---|---|---|
| Si | N | C | H |
| 1 | 0.5 to 1 | 2 to 3 | 6 to 9 | aiu. The invention of pseudo claim 37 or 38, in which the tie coating or layer is from 2 to 1000 nm thick.

aiv. The invention of any previous pseudo claimsais to aiu, in which the organosilicon precursor for the tie coating or layer is a siloxane, preferably OMCTS or TMDSO.

aiw. The invention of any previous pseudo claim, further comprising a pH protective coating or layer on at least the first portion of the generally cylindrical interior surface 16.

aix. The invention of pseudo claim aiw, in which the pH protective coating or layer comprises $SiO_xC_y$ or $SiN_xC_y$, in which x is from about 0.5 to about 2.4 and y is from about 0.6 to about 3 as measured by XPS.

aiy. The invention of pseudo claim aiw or aix, in which the pH protective coating or layer is from 2 to 1000 nm thick.
coating or layer, the barrier coating or layer, and the pH protective coating or layer.

Method Claims ajg. A method of making the medical barrel, auto-injector cartridge, or similar device (14) of any previous pseudo claim, comprising:
A. providing a medical barrel, auto-injector cartridge, or similar device (14) comprising:
 a dispensing end (22),
 a back end (32),
 a generally cylindrical interior surface 16 having an generally cylindrical interior surface 16 defining a lumen (18) extending at least part of the distance between the dispensing end (22) and the back end (32), in which the generally cylindrical interior surface 16:
 is configured to receive a slidable plunger or piston (36),
 has a first portion (800) extending axially from a front end at or near the dispensing end (22) to a back end (806) between and spaced from each of the first portion dispensing end (22) and the back end (32), and
 has a second portion (802) extending axially from a front end, adjacent to the first portion back end, at least part of the distance to the back end (32);
B. applying a lubricity coating or layer (34) by PECVD to the second portion (802) of the generally cylindrical interior surface 16, the lubricity coating or layer (34) having an mean thickness, and
C. applying by PECVD either:
 no lubricity coating or layer to the first portion (800) of the generally cylindrical interior surface 16, or
 a lubricity coating or layer (34) on the first portion (800) of the generally cylindrical interior surface 16 having an mean thickness that is less than the mean thickness of the lubricity coating or layer (34) on the second portion (802).

ajh. The invention of any previous pseudo claim, in which the lubricity coating or layer (34) is applied by:
 providing a medical barrel, auto-injector cartridge, or similar device (14) having an open back end (32);
 introducing a flow of a precursor gas (588), optionally an oxidizing gas (594), and optionally a diluent gas (602) into the lumen (18) of the medical barrel, auto-injector cartridge, or similar device (14) from a gas delivery port adjacent to the open back end (32);
 applying electromagnetic energy to the lumen (18) under conditions effective to form plasma in the lumen (18);
 the method being carried out under conditions effective to deposit a lubricity coating or layer (34) on the second portion (802) of the generally cylindrical interior surface 16 having a greater mean thickness than the lubricity coating or layer (34), if any, deposited on the first portion (800) of the generally cylindrical interior surface 16.

aji. The invention of pseudo claim ajh, in which the conditions effective to deposit a lubricity coating or layer (34) on the second portion (802) of the generally cylindrical interior surface 16 having a greater mean thickness include applying the electromagnetic energy at a sufficiently low power level to reduce the thickness of the lubricity coating or layer (34) applied to the first portion (800) of the generally cylindrical interior surface 16, relative to the thickness of the lubricity coating or layer (34) applied to the second portion (802) of the generally cylindrical interior surface 16.

ajj. The invention of pseudo claim ajh or aji, in which a portion of the precursor gas (588) undergoes a chemical reaction in the plasma, forming a reaction product, and the conditions effective to deposit a lubricity coating or layer (34) on the second portion (802) of the generally cylindrical interior surface 16 having a greater mean thickness include exhausting the reaction product through the back end (32) of the medical barrel, auto-injector cartridge, or similar device (14).

ajk. The invention of any previous pseudo claims ajh to ajj, in which the precursor gas (588) comprises a linear siloxane, a monocyclic siloxane, a polycyclic siloxane, a polysilsesquioxane, a linear silazane, a monocyclic silazane, a polycyclic silazane, a polysilsesquiazane, a silatrane, a silquasilatrane, a silproatrane, an azasilatrane, an azasilquasiatrane, an azasilproatrane, or a combination of any two or more of these precursors; optionally a monocyclic siloxane, optionally octamethylcyclotetrasiloxane; optionally a linear siloxane, optionally tetramethyldisiloxane.

ajl. The invention of any previous pseudo claims ajg to ajk, in which the nominal capacity of the medical barrel, auto-injector cartridge, or similar device (14) is from 0.1 to 5 mL, optionally from 0.5 to 3 mL, optionally from 0.7 to 2 mL, optionally 1 mL.

ajm. The invention of any previous pseudo claims ajh to ajl, in which the electromagnetic energy is applied at a minimum power level of 0.5 Watts to a maximum power level of 15 Watts.

ajn. The invention of any previous pseudo claims ajh to ajm, in which the electromagnetic energy is applied at a minimum power level of 0.6 Watts, optionally 0.7 Watts, optionally 0.8 Watts, optionally 0.9 Watts, optionally 1 Watt, optionally 2 Watts.

ajo. The invention of any previous pseudo claims ajh to ajn, in which the electromagnetic energy is applied at a maximum power of 3 Watts, optionally 4 Watts, optionally 5 Watts, optionally 6 Watts, optionally 7 Watts, optionally 8 Watts, optionally 9 Watts, optionally 10 Watts.

ajp. The invention of any previous pseudo claim in which, while applying a lubricity coating or layer (34) to the generally cylindrical interior surface 16 by PECVD, a magnetic field is applied at the second portion (802) of the generally cylindrical interior surface 16, such that the net mean magnetic field strength present at the second portion (802) of the generally cylindrical interior surface 16 when depositing the lubricity coating or layer (34) is greater, optionally at least 2 times as great, optionally at least 5 times as great, optionally at least 10 times as great, optionally at least 20 times as great, optionally at least 30 times as great, optionally at least 40 times as great, optionally 50 times as great, optionally 100 times as great, optionally 200 times as great, optionally 500 times as great, as the mean magnetic field strength at the first portion (800) of the generally cylindrical interior surface 16.

ajq. The invention of any previous pseudo claim, in which, while applying a lubricity coating or layer (34) to the generally cylindrical interior surface 16 by PECVD, the minimum mean magnetic field strength when depositing the lubricity coating or layer (34), in Gauss, at the second portion (802) of the generally cylindrical interior surface 16 is greater than 1 Gauss (100 µT, microTesla), optionally at least 2 Gauss, optionally at least 5 Gauss, optionally at least 10 Gauss, optionally at least 15 Gauss, optionally at least 20 Gauss, optionally at least 25 Gauss, optionally at least 30 Gauss, optionally at least 35 Gauss, optionally at least 40 Gauss.

ajr. The invention of pseudo claim ajg, in which, while applying a lubricity coating or layer (34) to the generally cylindrical interior surface 16 by PECVD, the maximum mean magnetic field strength when depositing the lubricity coating or layer (34), in Gauss, at the second portion (802) of the generally cylindrical interior surface 16 is 100 Gauss (10,000 µT, microTesla), optionally 80 Gauss, optionally 60 Gauss, optionally 50 Gauss, optionally 45 Gauss.

ajs. The invention of any previous pseudo claims ajp to ajr, in which the magnetic field has a position, orientation, and field strength effective to improve the uniformity, density, or both of plasma modification of the surface of the medical barrel, auto-injector cartridge, or similar device.

ajt. The invention of pseudo claim ajs, in which providing the magnetic field improves the axial uniformity, density, or both of plasma distribution along at least a portion of the surface.

aju. The invention of pseudo claim ajs, in which providing the magnetic field improves the radial uniformity, density, or both of plasma distribution along at least a portion of the surface.

ajv. The invention of any previous pseudo claim, in which the plasma comprises plasma electrons and the magnetic field is effective to improve confinement of the plasma electrons in the lumen (18).

ajw. The invention of any previous pseudo claims ajp to ajv, in which the magnetic field is provided by providing a magnetic field generator (for example any of 61-78, 86, 88, 90, or 820), alternatively at least two magnetic field generators, optionally at least three magnetic field generators, optionally at least four magnetic field generators, optionally at least five magnetic field generators, optionally at least six magnetic field generators, optionally at least seven magnetic field generators, optionally at least eight magnetic field generators near the surface, each magnetic field generator having a first pole and a second pole defining a polar axis (80).

ajx. The invention of pseudo claim ajw, in which at least part of the time while providing the magnetic field, a magnetic field generator (for example any of 61-78, 86, 88, 90, or 820), alternatively at least two of the magnetic field generators, alternatively at least three of the magnetic field generators, alternatively at least four of the magnetic field generators, alternatively at least five of the magnetic field generators, alternatively at least six of the magnetic field generators, alternatively at least seven of the magnetic field generators, alternatively at least eight of the magnetic field generators, alternatively all of the magnetic field generators, have their polar axes generally parallel to the axis of the surface.

ajy. The invention of pseudo claim ajw or ajx, in which at least part of the time while providing the magnetic field, at least two of the magnetic field generators, alternatively at least three of the magnetic field generators, alternatively at least four of the magnetic field generators, alternatively at least five of the magnetic field generators, alternatively at least six of the magnetic field generators, alternatively at least seven of the magnetic field generators, alternatively at least eight of the magnetic field generators, alternatively all of the magnetic field generators, are circumferentially distributed around the surface in the operative position.

ajz. The invention of pseudo claim ajy, in which the magnetic field generators (for example any of 61-78, 86, 88, 90, or 820) have their polar axes extending axially with respect to the surface.

aka. The invention of pseudo claim ajz, in which the magnetic field generators (for example any of 61-78, 86, 88, 90, or 820) are kept stationary during PECVD.

akb. The invention of any pseudo claim ajw to aka, in which at least part of the time while providing the magnetic field, at least two of the magnetic field generators (for example any of 61-78, 86, 88, 90, or 820), alternatively at least three of the magnetic field generators, alternatively at least four of the magnetic field generators, alternatively at least five of the magnetic field generators, alternatively at least six of the magnetic field generators, alternatively at least seven of the magnetic field generators, alternatively at least eight of the magnetic field generators, alternatively all of the magnetic field generators, are substantially circumferentially equidistant from the adjacent magnetic field generators.

akc. The invention of any previous pseudo claims ajw to akb, in which at least part of the time while providing the magnetic field, a magnetic field generator (for example any of 61-78, 86, 88, 90, or 820), alternatively at least two of the magnetic field generators (for example any of 61-78, 86, 88, 90, or 820), alternatively at least three of the magnetic field generators, alternatively at least four of the magnetic field generators, alternatively at least five of the magnetic field generators, alternatively at least six of the magnetic field generators, alternatively at least seven of the magnetic field generators, alternatively at least eight of the magnetic field generators, alternatively all of the magnetic field generators, are rotated about the surface, or the surface rotates with respect to the magnetic field generators, or both, during at least a portion of the plasma treatment.

akd. The invention of any previous pseudo claims ajw to akc, in which at least one magnetic field generator (for example any of 61-78, 86, 88, 90, or 820) is a permanent magnet or a coil or a combination of at least one permanent magnet and at least one coil.

ake. The invention of any previous pseudo claims ajw to akd, in which two or more magnetic field generators (for example any of 61-78, 86, 88, 90, or 820) are spaced to define a recess between them, within which at least a portion of the surface of the medical barrel, auto-injector cartridge, or similar device is positioned.

akf. The invention of any previous pseudo claims ajw to ake, in which at least part of the time while providing the magnetic field, at least one magnetic field generator (for example any of 61-78, 86, 88, 90, or 820), the medical barrel, auto-injector cartridge, or similar device surface, or both, is rotated at a rate effective to improve the uniformity, density, or both of the mean magnetic field strength about a circumference of the medical barrel, auto-injector cartridge, or similar device surface.

akg. The invention of any previous pseudo claims ajw to akf, in which at least part of the time while providing the magnetic field, at least one magnetic field generator (for example any of 61-78, 86, 88, 90, or 820), the medical barrel, auto-injector cartridge, or similar device surface, or both, is rotated at a rate effective to improve the uniformity, reduce the intensity, or both of medical barrel, auto-injector cartridge, or similar device heating about a circumference of the medical barrel, auto-injector cartridge, or similar device surface.

akh. The invention of any previous pseudo claims ajw to akg, further comprising at least part of the time while providing the magnetic field, translating at least one of the magnetic field generators (for example any of 61-78, 86, 88, 90, or 820) axially along the medical barrel, auto-injector cartridge, or similar device surface, or translating the medical barrel, auto-injector cartridge, or similar device surface with respect to the magnetic field generator (for example any of 61-78, 86, 88, 90, or 820), or both, at a rate effective to improve the uniformity of medical barrel, auto-injector cartridge, or similar device heating along the axis of the medical barrel, auto-injector cartridge, or similar device surface.

aki. The invention of any previous pseudo claims ajw to akh, in which at least part of the time while providing the magnetic field, at least two of the magnetic field generators (for example any of 61-78, 86, 88, 90, or 820), alternatively at least three of the magnetic field generators, alternatively at least four of the magnetic field generators, alternatively at least five of the magnetic field generators, alternatively at least six of the magnetic field generators, alternatively at least seven of the magnetic field generators, alternatively at least eight of the magnetic field generators, alternatively all of the magnetic field generators, are axially stacked with respect to the generally cylindrical surface.

akj. The invention of any previous pseudo claims ajw to aki, in which at least part of the time while providing the magnetic field, at least two of the axially stacked magnetic field generators (for example any of 61-78, 86, 88, 90, or 820), alternatively at least three of the axially stacked magnetic field generators, alternatively at least four of the axially stacked magnetic field generators, alternatively at least five of the axially stacked magnetic field generators, alternatively at least six of the axially stacked magnetic field generators, alternatively at least seven of the axially stacked magnetic field generators, alternatively at least eight of the axially stacked magnetic field generators, alternatively all of the axially stacked magnetic field generators, are axially spaced from each other.

akk. The invention of any previous pseudo claims ajw to Kj, in which at least part of the time while providing the magnetic field, at least two of the axially stacked magnetic field generators (for example any of 61-78, 86, 88, 90, or 820), alternatively at least three of the axially stacked magnetic field generators, alternatively at least four of the axially stacked magnetic field generators, alternatively at least five of the axially stacked magnetic field generators, alternatively at least six of the axially stacked magnetic field generators, alternatively at least seven of the axially stacked magnetic field generators, alternatively at least eight of the axially stacked magnetic field generators, alternatively all of the axially stacked magnetic field generators, axially abut each other.

akl. The invention of any preceding pseudo claim ajw to akk, in which at least part of the time while providing the magnetic field, the magnetic field generator (any of 61-78, 86, 88, 90, or 820) is provided by positioning at least one coil near the surface and conducting an electrical current through the coil.

akm. The invention of pseudo claim akl, in which the at least one coil comprises a solenoid coil.

akn. The invention of pseudo claim akl, in which the at least one coil comprises a generally toroidal coil 8 or 9 having a central opening and a geometric axis passing through its central opening.

ako. The invention of pseudo claim akn, in which at least part of the time while providing the magnetic field, the generally toroidal coil 8 or 9 is oriented with its geometric axis at least generally parallel, optionally at least generally collinear with the axis of the surface.

akp. The invention of any of pseudo claims akn to ako, in which the generally toroidal coils 8 or 9 have at least two arc segments, optionally at least four arc segments, optionally at least 6 arc segments, optionally at least eight arc segments, optionally at least eight 45° arc segments, and alternating segments are wound in opposite directions.

akq. The invention of any of pseudo claims akn to akp, in which the generally toroidal coils have cross-sections that are substantially circular or substantially rectangular.

akr. The invention of any preceding pseudo claim ajw to akq, in which at least part of the time while providing the magnetic field, at least one magnetic field generator (any of 61-78, 86, 88, 90, or 820) is oriented with its polar axis (80) at least generally parallel to the axis of the surface.

aks. The invention of any preceding pseudo claim ajw to akr, in which at least part of the time while providing the magnetic field, at least one magnetic field generator (any of 61-78, 86, 88, 90, or 820) is oriented with its polar axis (80) at least generally collinear with the axis of the surface.

akt. The invention of any preceding pseudo claim ajw to aks, in which at least part of the time while providing the magnetic field, the magnetic field generator (any of 61-78, 86, 88, 90, or 820) has a passage extending along its polar axis (80) and the surface is located entirely within the passage.

aku. The invention of any preceding pseudo claim ajw to aku, in which the magnetic field generator (any of 61-78, 86, 88, 90, or 820) is a Helmholtz coil.

akv. The invention of pseudo claim aku, in which the Helmholtz coil comprises first and second spaced solenoid coils with a space between them providing a viewing window allowing the plasma to be viewed while the method is in progress.

akw. The invention of any preceding pseudo claim ajw to akv, in which at least part of the time while providing the magnetic field, the magnetic field generator (any of 61-78, 86, 88, 90, or 820) provides a field strength that varies along the syringe barrel, auto-injector cartridge, or similar device surface.

akx. The invention of pseudo claim akw, in which at least a portion of the syringe barrel, auto-injector cartridge, or similar device surface is generally cylindrical.

aky. The invention of pseudo claim akw or akx, in which at least part of the time while providing the magnetic field, the distance between at least one magnetic field generator (any of 61-78, 86, 88, 90, or 820) and the syringe barrel, auto-injector cartridge, or similar device surface varies along the syringe barrel, auto-injector cartridge, or similar device surface.

akz. The invention of any of pseudo claims akw, akx, or aky, in which at least part of the time while providing the magnetic field, the field strength varies along the syringe barrel, auto-injector cartridge, or similar device surface to define a profile of varying field strength.

ala. The invention of pseudo claim akz, in which at least part of the time while providing the plasma and not providing the magnetic field, the plasma modification of the surface of the syringe barrel, auto-injector cartridge, or similar device varies along the syringe barrel, auto-injector cartridge, or similar device surface to define a profile of varying plasma modification.

alb. The invention of pseudo claim ala, in which at least part of the time while providing the magnetic field, the magnetic field generators (any of 61-78, 86, 88, 90, or 820) are configured such that variations in the profile of field strength tend to counteract variations of plasma modification, improving the uniformity, density, or both of plasma modification of the surface of the syringe barrel, auto-injector cartridge, or similar device.

ald. The invention of any preceding pseudo claim ajg to alb, further comprising providing an electron mirror at or near the back end (32) of the syringe barrel, auto-injector cartridge, or similar device (14).

ale. The invention of pseudo claim ald, in which the structure providing an electron mirror comprises at least a portion of a magnetic field generator.

alf. The invention of any preceding pseudo claim ald to ale, in which the structure providing an electron mirror comprises a ferromagnetic or ferromagnetic material.

alg. The invention of any preceding pseudo claim ald to alf, in which the structure providing an electron mirror comprises a magnetic field generator.

alh. The invention of any preceding pseudo claim ald to alg, in which the structure providing an electron mirror comprises a negatively charged object or portion of an object.

ali. The invention of any preceding pseudo claim ajp to alh, in which at least part of the time while providing the magnetic field, at least a portion of the magnetic field in at least a portion of the lumen (18) is oriented with its polar axis (80) generally parallel to the axis of the surface to be treated.

alj. The invention of any preceding pseudo claim ajp to ali, in which at least part of the time while providing the magnetic field, at least a portion of the magnetic field in at least a portion of the lumen (18) is oriented with its polar axis (80) extending around the axis of the surface to be treated.

alk. The invention of any preceding pseudo claim ajp to alj, in which at least part of the time while providing the magnetic field, at least a portion of the magnetic field in at least a portion of the lumen (18) is oriented with its polar axis (80) extending generally in radial planes with respect to the surface to be treated.

all. The invention of any preceding pseudo claim ajp to alk, in which at least one magnetic field generator (any of 61-78, 86, 88, 90, or 820), alternatively at least two magnetic field generators, alternatively at least three magnetic field generators, alternatively at least four magnetic field generators, alternatively at least five magnetic field generators, alternatively at least six magnetic field generators, alternatively at least seven magnetic field generators, alternatively at least eight magnetic field generators, alternatively all of the magnetic field generators are permanent magnets (any of 61-78 or 820) having opposed first and second poles (822, 824) defining a polar axis (80) and first and second ends respectively corresponding to the first and second poles, the permanent magnets having one or more sides (820) extending from the first pole (822) to the second pole (824), in which at least one side (826) is tapered inward between the first pole (822) and the second pole (824).

alm. The invention of pseudo claim all, in which the second end (824) of at least one magnetic field generator (any of 61-78, 86, 88, 90, or 820), alternatively at least two magnetic field generators, alternatively at least three magnetic field generators, alternatively at least four magnetic field generators, alternatively at least five magnetic field generators, alternatively at least six magnetic field generators, alternatively at least seven magnetic field generators, alternatively at least eight magnetic field generators, alternatively all of the magnetic field generators is larger than the first end (822).

aln. The invention of pseudo claim alm, in which at least one magnetic field generator (any of 61-78, 86, 88, 90, or 820), alternatively at least two magnetic field generators, alternatively at least three magnetic field generators, alternatively at least four magnetic field generators, alternatively at least five magnetic field generators, alternatively at least six magnetic field generators, alternatively at least seven magnetic field generators, alternatively at least eight magnetic field generators, alternatively all of the magnetic field generators are generally conical, frustoconical, pyramidal, or frustopyramidal.

alo. The invention of pseudo claim alm or aln, in which at least one magnetic field generator (any of 61-78, 86, 88, 90, or 820), alternatively at least two magnetic field generators, alternatively at least three magnetic field generators, alternatively at least four magnetic field generators, alternatively at least five magnetic field generators, alternatively at least six magnetic field generators, alternatively at least seven magnetic field generators, alternatively at least eight magnetic field generators, alternatively all of the magnetic field generators are generally conical with a rounded smaller end (822).

alp. The invention of any pseudo claim alm to alo, in which at least one magnetic field generator (820), alternatively at least two magnetic field generators, alternatively at least three magnetic field generators, alternatively at least four magnetic field generators, alternatively at least five magnetic field generators, alternatively at least six magnetic field generators, alternatively at least seven magnetic field generators, alternatively at least eight magnetic field generators, alternatively all of the magnetic field generators are oriented in a ring-shaped array (834) with their smaller ends (822) disposed radially inward and their larger ends (824) disposed radially outward.

alq. The invention of any pseudo claim alm to alp, in which at least one magnetic field generator (any of 61-78, 86, 88, 90, or 820), alternatively at least two magnetic field generators, alternatively at least three magnetic field generators, alternatively at least four magnetic field generators, alternatively at least five magnetic field generators, alternatively at least six magnetic field generators, alternatively at least seven magnetic field generators, alternatively at least eight magnetic field generators, alternatively all of the magnetic field generators are oriented with the pole of the same sign (North or South) disposed radially inward and their first ends disposed radially outward.

alr. The invention of pseudo claim any pseudo claim alm to alq, in which at least one magnetic field generator (any of 61-78, 86, 88, 90, or 820), alternatively at least two magnetic field generators, alternatively at least three magnetic field generators, alternatively at least four magnetic field generators, alternatively at least five magnetic field generators, alternatively at least six magnetic field generators, alternatively at least seven magnetic field generators, alternatively at least eight magnetic field generators, alternatively all of the magnetic field generators are oriented with their North poles disposed radially inward.

als. The invention of any pseudo claim alm to alr, in which at least one magnetic field generator (any of 61-78, 86, 88, 90, or 820), alternatively at least two magnetic field generators, alternatively at least three magnetic field generators, alternatively at least four magnetic field generators, alternatively at least five magnetic field generators, alternatively at least six magnetic field generators, alternatively at least seven magnetic field generators, alternatively at least eight magnetic field generators, alternatively all of the magnetic field generators are oriented with their South poles disposed radially inward.

alt. The invention of any preceding pseudo claim ajp to als, in which at least one magnetic field generator (any of 61-78, 86, 88, 90, or 820), alternatively at least two magnetic field generators, alternatively at least three magnetic field generators, alternatively at least four magnetic field generators, alternatively at least five magnetic field generators, alternatively at least six magnetic field generators, alternatively at least seven magnetic field generators, alternatively at least eight magnetic field generators, alternatively all of the magnetic field generators are bar magnets.

alu. The invention of any preceding pseudo claim ajw to alt, in which at least one magnetic field generator (any of 73-78), alternatively at least two magnetic field generators, alternatively at least three magnetic field generators, alternatively at least four magnetic field generators, alternatively at least five magnetic field generators, alternatively at least six magnetic field generators, alternatively at least seven magnetic field generators, alternatively at least eight magnetic field generators, alternatively all of the magnetic field generators are ring magnets having central apertures sized to receive the syringe barrel, auto-injector cartridge, or similar device surface.

alv. The invention of pseudo claim alu, in which the north and second poles of at least one of the ring magnets (any of 73-78) are its opposed annular faces.

alw. The invention of pseudo claim alv, in which the magnetic field is provided at least in part by a stack of:
  at least one interior ring magnet (any of 73-78) having the syringe barrel, auto-injector cartridge, or similar device surface within its central recess when in its operative position,
  at least one cap magnet (any of 65-78 or 820) axially aligned with but outside the stack of interior ring magnets,
in which the interior ring magnets provide a first magnetic field strength radially adjacent to the syringe barrel, auto-injector cartridge, or similar device surface that is less than the magnetic field strength provided by the cap magnet axially adjacent to the syringe barrel, auto-injector cartridge, or similar device surface, and
  optionally one or more additional magnets, positioned between a cap magnet and the stack of interior ring magnets.

alx. The invention of any of pseudo claims alu to alw, in which the polar axis (80) of at least one of the ring magnets (73-78) is circumferential about the ring.

aly. The invention of pseudo claim alx, in which the circumference of at least one of the ring magnets (73-78) comprises plural north-second pole domains.

alz. The invention of any preceding pseudo claim ajw to aly, in which at least part of the time while providing the magnetic field, an even number of at least four magnetic field generators (61, 62) are arranged about an axis to provide a quadrupole or analogous structure between axially spaced ends.

ama. The invention of pseudo claim alz, in which the magnetic field generators are relatively movable between an effective position (834) and a non-functional position (834a).

amb. The invention of pseudo claim alz to ama, in which at least part of the time while providing the magnetic field, the quadrupole and syringe barrel, auto-injector cartridge, or similar device are relatively positioned with the axis passing through the syringe barrel, auto-injector cartridge, or similar device surface.

amc. The invention of pseudo claim alz to amb, in which at least part of the time while providing the magnetic field, the quadrupole is effective to at least partially confine the plasma at or near at least a portion of the syringe barrel, auto-injector cartridge, or similar device surface.

amd. The invention of any of pseudo claims alz to amc, in which at least part of the time while providing the magnetic field, a magnetic field generator (any of 61-78, 86, 88, 90, or 820) having an axial polar axis (80) is positioned at or near at least one of the axially spaced ends.

ame. The invention of any of pseudo claims alm to amd, in which at least part of the time while providing the magnetic field, magnetic field generators having axial polar axes are positioned at or near both of the axially spaced ends.

amf. The invention of any of pseudo claims alz to ame, in which at least one of the magnetic field generators having axial polar axes comprises a ring magnet.

amg. The invention of any of pseudo claims alz to amf, in which at least one of the magnetic field generators having axial polar axes comprises a cap magnet.

amh. The invention of any of pseudo claims alz to amh, in which at least one of the magnetic field generators having axial polar axes comprises a bar magnet.

ami. The invention of any preceding pseudo claim ajg to amh, further comprising optimizing the Fi value of a syringe barrel, auto-injector cartridge, or similar device (14) by choosing the diameter of its interior surface (16).

amj. The invention of any preceding pseudo claim ajg to ami, further comprising optimizing the $F_m$ value of a syringe barrel, auto-injector cartridge, or similar device (14) by choosing the diameter of its interior surface (16).

amk. The invention of any previous pseudo claims 3 to 180, in which the fluid composition (40) is a pharmaceutical composition suitable for parenteral administration to a human.

aml. The invention of any previous pseudo claims 3 to 181, in which the fluid composition (40) is a diagnostic composition.

amm. The invention of any previous pseudo claims 3 to 182, in which the fluid composition (40) is an anesthetic composition suitable for administration to a human.

amn. The invention of any previous pseudo claim, in which said fluid composition (40) comprises Ablavar (Gadofosveset Trisodium Injection).

amo. The invention of any previous pseudo claim, in which said fluid composition (40) comprises Abobotulinumtoxin A Injection (Dysport).

amp. The invention of any previous pseudo claim, in which said fluid composition (40) comprises Accretropin (Somatropin Injection).

amq. The invention of any previous pseudo claim, in which said fluid composition (40) comprises Acetadote (Acetylcysteine Injection).

amr. The invention of any previous pseudo claim, in which said fluid composition (40) comprises Acetazolamide Injection (Acetazolamide Injection).

ams. The invention of any previous pseudo claim, in which said fluid composition (40) comprises Acetylcysteine Injection (Acetadote).

amt. The invention of any previous pseudo claim, in which said fluid composition (40) comprises Actemra (Tocilizumab Injection).

amu. The invention of any previous pseudo claim, in which said fluid composition (40) comprises Acthrel (Corticorelin Ovine Triflutate for Injection).

amv. The invention of any previous pseudo claim, in which said fluid composition (40) comprises Acyclovir for Injection (Zovirax Injection).

amw. The invention of any previous pseudo claim, in which said fluid composition (40) comprises Adacel.

amx. The invention of any previous pseudo claim, in which said fluid composition (40) comprises Adalimumab.

amy. The invention of any previous pseudo claim, in which said fluid composition (40) comprises Adenoscan (Adenosine Injection).

amz. The invention of any previous pseudo claim, in which said fluid composition (40) comprises Adenosine Injection (Adenoscan).

ana. The invention of any previous pseudo claim, in which said fluid composition (40) comprises Adrenaclick.

anb. The invention of any previous pseudo claim, in which said fluid composition (40) comprises AdreView (lobenguane I 123 Injection for Intravenous Use).

anc. The invention of any previous pseudo claim, in which said fluid composition (40) comprises Afluria.

and. The invention of any previous pseudo claim, in which said fluid composition (40) comprises Ak-Fluor (Fluorescein Injection).

ane. The invention of any previous pseudo claim, in which said fluid composition (40) comprises Alglucerase Injection (Ceredase).

anf. The invention of any previous pseudo claim, in which said fluid composition (40) comprises Alkeran Injection (Melphalan Hcl Injection).

ang. The invention of any previous pseudo claim, in which said fluid composition (40) comprises Allopurinol Sodium for Injection (Aloprim).

anh. The invention of any previous pseudo claim, in which said fluid composition (40) comprises Aloprim (Allopurinol Sodium for Injection).

ani. The invention of any previous pseudo claim, in which said fluid composition (40) comprises Alprostadil.

anj. The invention of any previous pseudo claim, in which said fluid composition (40) comprises Alsuma (Sumatriptan Injection).

ank. The invention of any previous pseudo claim, in which said fluid composition (40) comprises Amino Acid Injections.

anl. The invention of any previous pseudo claim, in which said fluid composition (40) comprises Aminosyn.

anm. The invention of any previous pseudo claim, in which said fluid composition (40) comprises Apidra.

ann. The invention of any previous pseudo claim, in which said fluid composition (40) comprises Apremilast.

ano. The invention of any previous pseudo claim, in which said fluid composition (40) comprises Alprostadil Dual Chamber System for Injection (Caverject Impulse).

anp. The invention of any previous pseudo claim, in which said fluid composition (40) comprises AMG 108.

anq. The invention of any previous pseudo claim, in which said fluid composition (40) comprises AMG 714.

anr. The invention of any previous pseudo claim, in which said fluid composition (40) comprises Amiodarone HCl Injection (Amiodarone HCl Injection).

ans. The invention of any previous pseudo claim, in which said fluid composition (40) comprises Amobarbital Sodium Injection (Amytal Sodium).

ant. The invention of any previous pseudo claim, in which said fluid composition (40) comprises Amytal Sodium (Amobarbital Sodium Injection).

anu. The invention of any previous pseudo claim, in which said fluid composition (40) comprises Anakinra.

any. The invention of any previous pseudo claim, in which said fluid composition (40) comprises Arixtra.

anw. The invention of any previous pseudo claim, in which said fluid composition (40) comprises Amphadase (Hyaluronidase Inj).

anx. The invention of any previous pseudo claim, in which said fluid composition (40) comprises Ammonul (Sodium Phenylacetate and Sodium Benzoate Injection).

any. The invention of any previous pseudo claim, in which said fluid composition (40) comprises Anzemet Injection (Dolasetron Mesylate Injection).

anz. The invention of any previous pseudo claim, in which said fluid composition (40) comprises Apidra (Insulin Glulisine [rDNA origin] Inj).

aoa. The invention of any previous pseudo claim, in which said fluid composition (40) comprises Argatroban (Argatroban Injection).

aob. The invention of any previous pseudo claim, in which said fluid composition (40) comprises Arginine Hydrochloride Injection (R-Gene 10).

aoc. The invention of any previous pseudo claim, in which said fluid composition (40) comprises Aristocort.

aod. The invention of any previous pseudo claim, in which said fluid composition (40) comprises Aristospan.

aoe. The invention of any previous pseudo claim, in which said fluid composition (40) comprises Arsenic Trioxide Injection (Trisenox).

aof. The invention of any previous pseudo claim, in which said fluid composition (40) comprises Articane HCl and Epinephrine Injection (Septocaine).

aog. The invention of any previous pseudo claim, in which said fluid composition (40) comprises Arzerra (Ofatumumab Injection).

aoh. The invention of any previous pseudo claim, in which said fluid composition (40) comprises Asclera (Polidocanol Injection).

aoi. The invention of any previous pseudo claim, in which said fluid composition (40) comprises Atenolol Inj (Tenormin I.V. Injection).

aoj. The invention of any previous pseudo claim, in which said fluid composition (40) comprises Atracurium Besylate Injection (Atracurium Besylate Injection).

aok. The invention of any previous pseudo claim, in which said fluid composition (40) comprises Avastin.

aol. The invention of any previous pseudo claim, in which said fluid composition (40) comprises Azactam Injection (Aztreonam Injection).

aom. The invention of any previous pseudo claim, in which said fluid composition (40) comprises Azithromycin (Zithromax Injection).

aon. The invention of any previous pseudo claim, in which said fluid composition (40) comprises Aztreonam Injection (Azactam Injection).

aoo. The invention of any previous pseudo claim, in which said fluid composition (40) comprises Baclofen Injection (Lioresal Intrathecal).

aop. The invention of any previous pseudo claim, in which said fluid composition (40) comprises Bacteriostatic Water (Bacteriostatic Water for Injection).

aoq. The invention of any previous pseudo claim, in which said fluid composition (40) comprises Baclofen Injection (Lioresal Intrathecal).

aor. The invention of any previous pseudo claim, in which said fluid composition (40) comprises Bal in Oil Ampules (Dimercarprol Injection).

aos. The invention of any previous pseudo claim, in which said fluid composition (40) comprises BayHepB.

aot. The invention of any previous pseudo claim, in which said fluid composition (40) comprises BayTet.

aou. The invention of any previous pseudo claim, in which said fluid composition (40) comprises Benadryl.

aov. The invention of any previous pseudo claim, in which said fluid composition (40) comprises Bendamustine Hydrochloride Injection (Treanda).

aow. The invention of any previous pseudo claim, in which said fluid composition (40) comprises Benztropine Mesylate Injection (Cogentin).

aox. The invention of any previous pseudo claim, in which said fluid composition (40) comprises Betamethasone Injectable Suspension (Celestone Soluspan).

aoy. The invention of any previous pseudo claim, in which said fluid composition (40) comprises Bexxar.

aoz. The invention of any previous pseudo claim, in which said fluid composition (40) comprises Bicillin C-R 900/300 (Penicillin G Benzathine and Penicillin G Procaine Injection).

apa. The invention of any previous pseudo claim, in which said fluid composition (40) comprises Blenoxane (Bleomycin Sulfate Injection).

apb. The invention of any previous pseudo claim, in which said fluid composition (40) comprises Bleomycin Sulfate Injection (Blenoxane).

apc. The invention of any previous pseudo claim, in which said fluid composition (40) comprises Boniva Injection (Ibandronate Sodium Injection).

apd. The invention of any previous pseudo claim, in which said fluid composition (40) comprises Botox Cosmetic (OnabotulinumtoxinA for Injection).

ape. The invention of any previous pseudo claim, in which said fluid composition (40) comprises Bravelle (Urofollitropin Injection).

apf. The invention of any previous pseudo claim, in which said fluid composition (40) comprises Bretylium (Bretylium Tosylate Injection).

apg. The invention of any previous pseudo claim, in which said fluid composition (40) comprises Brevital Sodium (Methohexital Sodium for Injection).

aph. The invention of any previous pseudo claim, in which said fluid composition (40) comprises Brethine.

api. The invention of any previous pseudo claim, in which said fluid composition (40) comprises Briobacept.

apj. The invention of any previous pseudo claim, in which said fluid composition (40) comprises BTT-1023.

apk. The invention of any previous pseudo claim, in which said fluid composition (40) comprises Bupivacaine HCl.

apl. The invention of any previous pseudo claim, in which said fluid composition (40) comprises Byetta.

apm. The invention of any previous pseudo claim, in which said fluid composition (40) comprises Ca-DTPA (Pentetate Calcium Trisodium Inj).

apn. The invention of any previous pseudo claim, in which said fluid composition (40) comprises Cabazitaxel Injection (Jevtana).

apo. The invention of any previous pseudo claim, in which said fluid composition (40) comprises Caffeine Alkaloid (Caffeine and Sodium Benzoate Injection).

app. The invention of any previous pseudo claim, in which said fluid composition (40) comprises Calcijex Injection (Calcitrol).

apq. The invention of any previous pseudo claim, in which said fluid composition (40) comprises Calcitrol (Calcijex Injection).

apr. The invention of any previous pseudo claim, in which said fluid composition (40) comprises Calcium Chloride (Calcium Chloride Injection 10%).

aps. The invention of any previous pseudo claim, in which said fluid composition (40) comprises Calcium Disodium Versenate (Edetate Calcium Disodium Injection).

apt. The invention of any previous pseudo claim, in which said fluid composition (40) comprises Camptosar Injection (Irinotecan Hydrochloride).

apu. The invention of any previous pseudo claim, in which said fluid composition (40) comprises Canakinumab Injection (Ilaris).

apv. The invention of any previous pseudo claim, in which said fluid composition (40) comprises Capastat Sulfate (Capreomycin for Injection).

apw. The invention of any previous pseudo claim, in which said fluid composition (40) comprises Capreomycin for Injection (Capastat Sulfate).

apx. The invention of any previous pseudo claim, in which said fluid composition (40) comprises Cardiolite (Prep kit for Technetium Tc99 Sestamibi for Injection).

apy. The invention of any previous pseudo claim, in which said fluid composition (40) comprises Cefazolin and Dextrose for Injection (Cefazolin Injection).

apz. The invention of any previous pseudo claim, in which said fluid composition (40) comprises Cefepime Hydrochloride.

aqa. The invention of any previous pseudo claim, in which said fluid composition (40) comprises Cefotaxime.

aqb. The invention of any previous pseudo claim, in which said fluid composition (40) comprises Ceftriaxone.

aqc. The invention of any previous pseudo claim, in which said fluid composition (40) comprises Carnitor Injection.

aqd. The invention of any previous pseudo claim, in which said fluid composition (40) comprises Caverject.

aqe. The invention of any previous pseudo claim, in which said fluid composition (40) comprises Celestone Soluspan.

aqf. The invention of any previous pseudo claim, in which said fluid composition (40) comprises Cerebyx (Fosphenytoin Sodium Injection).

aqg. The invention of any previous pseudo claim, in which said fluid composition (40) comprises Ceredase (Alglucerase Injection).

aqh. The invention of any previous pseudo claim, in which said fluid composition (40) comprises Ceretec (Technetium Tc99m Exametazime Injection).

aqi. The invention of any previous pseudo claim, in which said fluid composition (40) comprises Certolizumab.

aqj. The invention of any previous pseudo claim, in which said fluid composition (40) comprises CF-101.

aqk. The invention of any previous pseudo claim, in which said fluid composition (40) comprises Chloramphenicol Sodium Succinate (Chloramphenicol Sodium Succinate Injection).

aql. The invention of any previous pseudo claim, in which said fluid composition (40) comprises Chloramphenicol Sodium Succinate Injection (Chloramphenicol Sodium Succinate).

aqm. The invention of any previous pseudo claim, in which said fluid composition (40) comprises Choriogonadotropin Alfa Injection (Ovidrel).

aqn. The invention of any previous pseudo claim, in which said fluid composition (40) comprises Cimzia.

aqo. The invention of any previous pseudo claim, in which said fluid composition (40) comprises Cisplatin (Cisplatin Injection).

aqp. The invention of any previous pseudo claim, in which said fluid composition (40) comprises Clomiphine Citrate.

aqq. The invention of any previous pseudo claim, in which said fluid composition (40) comprises Clonidine Injection (Duraclon).

aqr. The invention of any previous pseudo claim, in which said fluid composition (40) comprises Cogentin (Benztropine Mesylate Injection).

aqs. The invention of any previous pseudo claim, in which said fluid composition (40) comprises Colistimethate Injection (Coly-Mycin M).

aqt. The invention of any previous pseudo claim, in which said fluid composition (40) comprises Coly-Mycin M (Colistimethate Injection).

aqu. The invention of any previous pseudo claim, in which said fluid composition (40) comprises Compath.

aqv. The invention of any previous pseudo claim, in which said fluid composition (40) comprises Conivaptan Hcl Injection (Vaprisol).

aqw. The invention of any previous pseudo claim, in which said fluid composition (40) comprises Conjugated Estrogens for Injection (Premarin Injection).

aqx. The invention of any previous pseudo claim, in which said fluid composition (40) comprises Copaxone.

aqy. The invention of any previous pseudo claim, in which said fluid composition (40) comprises Corticorelin Ovine Triflutate for Injection (Acthrel).

aqz. The invention of any previous pseudo claim, in which said fluid composition (40) comprises Corvert (Ibutilide Fumarate Injection).

ara. The invention of any previous pseudo claim, in which said fluid composition (40) comprises Cubicin (Daptomycin Injection).

arb. The invention of any previous pseudo claim, in which said fluid composition (40) comprises CF-101.

arc. The invention of any previous pseudo claim, in which said fluid composition (40) comprises Cyanokit (Hydroxocobalamin for Injection).

ard. The invention of any previous pseudo claim, in which said fluid composition (40) comprises Cytarabine Liposome Injection (DepoCyt).

are. The invention of any previous pseudo claim, in which said fluid composition (40) comprises Cyanocobalamin.

arf. The invention of any previous pseudo claim, in which said fluid composition (40) comprises D.H.E. 45.

arg. The invention of any previous pseudo claim, in which said fluid composition (40) comprises Dacogen (Decitabine Injection).

arh. The invention of any previous pseudo claim, in which said fluid composition (40) comprises Dalteparin.

ari. The invention of any previous pseudo claim, in which said fluid composition (40) comprises Dantrium IV (Dantrolene Sodium for Injection).

arj. The invention of any previous pseudo claim, in which said fluid composition (40) comprises Dantrolene Sodium for Injection (Dantrium IV).

ark. The invention of any previous pseudo claim, in which said fluid composition (40) comprises Daptomycin Injection (Cubicin).

arl. The invention of any previous pseudo claim, in which said fluid composition (40) comprises Darbepoietin Alfa.

arm. The invention of any previous pseudo claim, in which said fluid composition (40) comprises DDAVP Injection (Desmopressin Acetate Injection).

arn. The invention of any previous pseudo claim, in which said fluid composition (40) comprises Decavax.

aro. The invention of any previous pseudo claim, in which said fluid composition (40) comprises Decitabine Injection (Dacogen).

arp. The invention of any previous pseudo claim, in which said fluid composition (40) comprises Dehydrated Alcohol (Dehydrated Alcohol Injection).

arq. The invention of any previous pseudo claim, in which said fluid composition (40) comprises Denosumab Injection (Prolia).

arr. The invention of any previous pseudo claim, in which said fluid composition (40) comprises Delatestryl.

ars. The invention of any previous pseudo claim, in which said fluid composition (40) comprises Delestrogen.

art. The invention of any previous pseudo claim, in which said fluid composition (40) comprises Delteparin Sodium.

aru. The invention of any previous pseudo claim, in which said fluid composition (40) comprises Depacon (Valproate Sodium Injection).

arv. The invention of any previous pseudo claim, in which said fluid composition (40) comprises Depo Medrol (Methylprednisolone Acetate Injectable Suspension).

arw. The invention of any previous pseudo claim, in which said fluid composition (40) comprises DepoCyt (Cytarabine Liposome Injection).

arx. The invention of any previous pseudo claim, in which said fluid composition (40) comprises DepoDur (Morphine Sulfate XR Liposome Injection).

ary. The invention of any previous pseudo claim, in which said fluid composition (40) comprises Desmopressin Acetate Injection (DDAVP Injection).

arz. The invention of any previous pseudo claim, in which said fluid composition (40) comprises Depo-Estradiol.

asa. The invention of any previous pseudo claim, in which said fluid composition (40) comprises Depo-Provera 104 mg/ml.

asb. The invention of any previous pseudo claim, in which said fluid composition (40) comprises Depo-Provera 150 mg/ml.

asc. The invention of any previous pseudo claim, in which said fluid composition (40) comprises Depo-Testosterone.

asd. The invention of any previous pseudo claim, in which said fluid composition (40) comprises Dexrazoxane for Injection, Intravenous Infusion Only (Totect).

ase. The invention of any previous pseudo claim, in which said fluid composition (40) comprises Dextrose/Electrolytes.

asf. The invention of any previous pseudo claim, in which said fluid composition (40) comprises Dextrose and Sodium Chloride Inj (Dextrose 5% in 0.9% Sodium Chloride).

asg. The invention of any previous pseudo claim, in which said fluid composition (40) comprises Dextrose.

ash. The invention of any previous pseudo claim, in which said fluid composition (40) comprises Diazepam Injection (Diazepam Injection).

asi. The invention of any previous pseudo claim, in which said fluid composition (40) comprises Digoxin Injection (Lanoxin Injection).

asj. The invention of any previous pseudo claim, in which said fluid composition (40) comprises Dilaudid-HP (Hydromorphone Hydrochloride Injection).

ask. The invention of any previous pseudo claim, in which said fluid composition (40) comprises Dimercarprol Injection (Bal in Oil Ampules).

asl. The invention of any previous pseudo claim, in which said fluid composition (40) comprises Diphenhydramine Injection (Benadryl Injection).

asm. The invention of any previous pseudo claim, in which said fluid composition (40) comprises Dipyridamole Injection (Dipyridamole Injection).

asn. The invention of any previous pseudo claim, in which said fluid composition (40) comprises Docetaxel for Injection (Taxotere).

aso. The invention of any previous pseudo claim, in which said fluid composition (40) comprises Dolasetron Mesylate Injection (Anzemet Injection).

asp. The invention of any previous pseudo claim, in which said fluid composition (40) comprises Doribax (Doripenem for Injection).

asq. The invention of any previous pseudo claim, in which said fluid composition (40) comprises Doripenem for Injection (Doribax).

asr. The invention of any previous pseudo claim, in which said fluid composition (40) comprises Doxercalciferol Injection (Hectorol Injection).

ass. The invention of any previous pseudo claim, in which said fluid composition (40) comprises Doxil (Doxorubicin Hcl Liposome Injection).

ast. The invention of any previous pseudo claim, in which said fluid composition (40) comprises Doxorubicin Hcl Liposome Injection (Doxil).

asu. The invention of any previous pseudo claim, in which said fluid composition (40) comprises Duraclon (Clonidine Injection).

asv The invention of any previous pseudo claim, in which said fluid composition (40) comprises Duramorph (Morphine Injection).

asw. The invention of any previous pseudo claim, in which said fluid composition (40) comprises Dysport (Abobotulinumtoxin A Injection).

asx. The invention of any previous pseudo claim, in which said fluid composition (40) comprises Ecallantide Injection (Kalbitor).

asy. The invention of any previous pseudo claim, in which said fluid composition (40) comprises Edetate Calcium Disodium Injection (Calcium Disodium Versenate).

asz. The invention of any previous pseudo claim, in which said fluid composition (40) comprises Edex (Alprostadil for Injection).

ata. The invention of any previous pseudo claim, in which said fluid composition (40) comprises Engerix.

atb. The invention of any previous pseudo claim, in which said fluid composition (40) comprises Edrophonium Injection (Enlon).

atc. The invention of any previous pseudo claim, in which said fluid composition (40) comprises Eloxatin (Oxaliplatin Injection).

atd. The invention of any previous pseudo claim, in which said fluid composition (40) comprises Emend Injection (Fosaprepitant Dimeglumine Injection).

ate. The invention of any previous pseudo claim, in which said fluid composition (40) comprises Enalaprilat Injection (Enalaprilat Injection).

atf. The invention of any previous pseudo claim, in which said fluid composition (40) comprises Enlon (Edrophonium Injection).

atg. The invention of any previous pseudo claim, in which said fluid composition (40) comprises Enoxaparin Sodium Injection (Lovenox).

ath. The invention of any previous pseudo claim, in which said fluid composition (40) comprises Eovist (Gadoxetate Disodium Injection).

ati. The invention of any previous pseudo claim, in which said fluid composition (40) comprises Enbrel.

atj. The invention of any previous pseudo claim, in which said fluid composition (40) comprises Enoxaparin.

atk. The invention of any previous pseudo claim, in which said fluid composition (40) comprises Epinepherine.

atl. The invention of any previous pseudo claim, in which said fluid composition (40) comprises Epipen.

atm. The invention of any previous pseudo claim, in which said fluid composition (40) comprises Epipen Jr.

atn. The invention of any previous pseudo claim, in which said fluid composition (40) comprises Erbitux.

ato. The invention of any previous pseudo claim, in which said fluid composition (40) comprises Ertapenem Injection (Invanz).

atp. The invention of any previous pseudo claim, in which said fluid composition (40) comprises Erythropoieten.

atq. The invention of any previous pseudo claim, in which said fluid composition (40) comprises Essential Amino Acid Injection (Nephramine).

atr. The invention of any previous pseudo claim, in which said fluid composition (40) comprises Estradiol Cypionate.

ats. The invention of any previous pseudo claim, in which said fluid composition (40) comprises Estradiol Valerate.

att. The invention of any previous pseudo claim, in which said fluid composition (40) comprises Etanercept.

atu. The invention of any previous pseudo claim, in which said fluid composition (40) comprises Exenatide Injection (Byetta).

atv. The invention of any previous pseudo claim, in which said fluid composition (40) comprises Famotidine Injection.

atw. The invention of any previous pseudo claim, in which said fluid composition (40) comprises FDG (Fludeoxyglucose F 18 Injection).

atx. The invention of any previous pseudo claim, in which said fluid composition (40) comprises Feraheme (Ferumoxytol Injection).

aty. The invention of any previous pseudo claim, in which said fluid composition (40) comprises Feridex I.V. (Ferumoxides Injectable Solution).

atz. The invention of any previous pseudo claim, in which said fluid composition (40) comprises Fertinex.

aua. The invention of any previous pseudo claim, in which said fluid composition (40) comprises Ferumoxides Injectable Solution (Feridex I.V.).

aub. The invention of any previous pseudo claim, in which said fluid composition (40) comprises Ferumoxytol Injection (Feraheme).

auc. The invention of any previous pseudo claim, in which said fluid composition (40) comprises Flagyl Injection (Metronidazole Injection).

aud. The invention of any previous pseudo claim, in which said fluid composition (40) comprises Fluarix.

aue. The invention of any previous pseudo claim, in which said fluid composition (40) comprises Fludeoxyglucose F 18 Injection (FDG).

auf. The invention of any previous pseudo claim, in which said fluid composition (40) comprises Fluorescein Injection (Ak-Fluor).

aug. The invention of any previous pseudo claim, in which said fluid composition (40) comprises Follistim AQ Cartridge (Follitropin Beta Injection).

auh. The invention of any previous pseudo claim, in which said fluid composition (40) comprises Follitropin Alfa Injection (Gonal-f RFF).

aui. The invention of any previous pseudo claim, in which said fluid composition (40) comprises Follitropin Beta Injection (Follistim AQ Cartridge).

auj. The invention of any previous pseudo claim, in which said fluid composition (40) comprises Folotyn (Pralatrexate Solution for Intravenous Injection).

auk. The invention of any previous pseudo claim, in which said fluid composition (40) comprises Fondaparinux.

aul. The invention of any previous pseudo claim, in which said fluid composition (40) comprises Forteo (Teriparatide (rDNA origin) Injection).

aum. The invention of any previous pseudo claim, in which said fluid composition (40) comprises Fostamatinib.

aun. The invention of any previous pseudo claim, in which said fluid composition (40) comprises Fosaprepitant Dimeglumine Injection (Emend Injection).

auo. The invention of any previous pseudo claim, in which said fluid composition (40) comprises Foscarnet Sodium Injection (Foscavir).

aup. The invention of any previous pseudo claim, in which said fluid composition (40) comprises Foscavir (Foscarnet Sodium Injection).

auq. The invention of any previous pseudo claim, in which said fluid composition (40) comprises Fosphenytoin Sodium Injection (Cerebyx).

aur. The invention of any previous pseudo claim, in which said fluid composition (40) comprises Fospropofol Disodium Injection (Lusedra).

aus. The invention of any previous pseudo claim, in which said fluid composition (40) comprises Fragmin.

aut. The invention of any previous pseudo claim, in which said fluid composition (40) comprises Gadobenate Dimeglumine Injection (Multihance).

auu. The invention of any previous pseudo claim, in which said fluid composition (40) comprises Gadofosveset Trisodium Injection (Ablavar).

auv. The invention of any previous pseudo claim, in which said fluid composition (40) comprises Gadoteridol Injection Solution (ProHance).

auw. The invention of any previous pseudo claim, in which said fluid composition (40) comprises Gadoversetamide Injection (OptiMARK).

aux. The invention of any previous pseudo claim, in which said fluid composition (40) comprises Gadoxetate Disodium Injection (Eovist).

auy. The invention of any previous pseudo claim, in which said fluid composition (40) comprises Ganirelix (Ganirelix Acetate Injection).

auz. The invention of any previous pseudo claim, in which said fluid composition (40) comprises Gardasil.

ava. The invention of any previous pseudo claim, in which said fluid composition (40) comprises Gemtuzumab Ozogamicin for Injection (Mylotarg).

avb. The invention of any previous pseudo claim, in which said fluid composition (40) comprises Genotropin.

avc. The invention of any previous pseudo claim, in which said fluid composition (40) comprises Gentamicin Injection.

avd. The invention of any previous pseudo claim, in which said fluid composition (40) comprises Golimumab Injection (Simponi Injection).

ave. The invention of any previous pseudo claim, in which said fluid composition (40) comprises Gonal-f RFF (Follitropin Alfa Injection).

avf. The invention of any previous pseudo claim, in which said fluid composition (40) comprises Granisetron Hydrochloride (Kytril Injection).

avg. The invention of any previous pseudo claim, in which said fluid composition (40) comprises Gentamicin Sulfate.

avh. The invention of any previous pseudo claim, in which said fluid composition (40) comprises Glatiramer Acetate.

avi. The invention of any previous pseudo claim, in which said fluid composition (40) comprises Glucagen.

avj. The invention of any previous pseudo claim, in which said fluid composition (40) comprises Glucagon.

avk The invention of any previous pseudo claim, in which said fluid composition (40) comprises Haldol (Haloperidol Injection).

avl. The invention of any previous pseudo claim, in which said fluid composition (40) comprises Havrix.

avm. The invention of any previous pseudo claim, in which said fluid composition (40) comprises Hectorol InjectiZn (Doxercalciferol Injection).

avn. The invention of any previous pseudo claim, in which said fluid composition (40) comprises Heparin.

avo. The invention of any previous pseudo claim, in which said fluid composition (40) comprises Herceptin.

avp. The invention of any previous pseudo claim, in which said fluid composition (40) comprises hG-CSF.

avq. The invention of any previous pseudo claim, in which said fluid composition (40) comprises Humalog.

avr. The invention of any previous pseudo claim, in which said fluid composition (40) comprises Human Growth Hormone.

ays. The invention of any previous pseudo claim, in which said fluid composition (40) comprises Humatrope.

avt. The invention of any previous pseudo claim, in which said fluid composition (40) comprises HuMax.

avu. The invention of any previous pseudo claim, in which said fluid composition (40) comprises Humegon.

avv. The invention of any previous pseudo claim, in which said fluid composition (40) comprises Humira.

avw. The invention of any previous pseudo claim, in which said fluid composition (40) comprises Humulin.

avx. The invention of any previous pseudo claim, in which said fluid composition (40) comprises Ibandr8nate Sodium Injection (Boniva Injection).

avy. The invention of any previous pseudo claim, in which said fluid composition (40) comprises Ibuprofen Lysine Injection (NeoProfen).

avz. The invention of any previous pseudo claim, in which said fluid composition (40) comprises Ibutilide Fumarate Injection (Corvert).

awa. The invention of any previous pseudo claim, in which said fluid composition (40) comprises Idamycin PFS (Idarubicin Hydrochloride Injection).

awb. The invention of any previous pseudo claim, in which said fluid composition (40) comprises Idarubicin Hydrochloride Injection (Idamycin PFS).

awc. The invention of any previous pseudo claim, in which said fluid composition (40) comprises Ilaris (Canakinumab Injection).

awd. The invention of any previous pseudo claim, in which said fluid composition (40) comprises Imipenem and Cilastatin for Injection (Primaxin I.V.).

awe. The invention of any previous pseudo claim, in which said fluid composition (40) comprises Imitrex.

awf. The invention of any previous pseudo claim, in which said fluid composition (40) comprises Incobotulinumtoxin A for Injection (Xeomin).

awg. The invention of any previous pseudo claim, in which said fluid composition (40) comprises Increlex (Mecasermin [rDNA origin] Injection).

awh. The invention of any previous pseudo claim, in which said fluid composition (40) comprises Indocin IV (Indomethacin Inj).

awi. The invention of any previous pseudo claim, in which said fluid composition (40) comprises Indomethacin Inj (Indocin IV).

awj. The invention of any previous pseudo claim, in which said fluid composition (40) comprises Infanrix.

awk. The invention of any previous pseudo claim, in which said fluid composition (40) comprises Innohep.

awl. The invention of any previous pseudo claim, in which said fluid composition (40) comprises Insulin/ awm. The invention of any previous pseudo claim, in which said fluid composition (40) comprises Insulin Aspart [rDNA origin] Inj (NovoLog).

awn. The invention of any previous pseudo claim, in which said fluid composition (40) comprises Insulin Glargine [rDNA origin] Injection (Lantus).

awo. The invention of any previous pseudo claim, in which said fluid composition (40) comprises Insulin Glulisine [rDNA origin] Inj (Apidra).

awp. The invention of any previous pseudo claim, in which said fluid composition (40) comprises Interferon alfa-2b, Recombinant for Injection (Intron A).

awq. The invention of any previous pseudo claim, in which said fluid composition (40) comprises Intron A (Interferon alfa-2b, Recombinant for Injection).

awr. The invention of any previous pseudo claim, in which said fluid composition (40) comprises Invanz (Ertapenem Injection).

aws. The invention of any previous pseudo claim, in which said fluid composition (40) comprises Invega Sustenna (Paliperidone Palmitate Extended-Release Injectable Suspension).

awt. The invention of any previous pseudo claim, in which said fluid composition (40) comprises lobenguane I 123 Injection for Intravenous Use (AdreView).

awu. The invention of any previous pseudo claim, in which said fluid composition (40) comprises Iopromide Injection (Ultravist).

awv. The invention of any previous pseudo claim, in which said fluid composition (40) comprises Ioversol Injection (Optiray Injection).

aww. The invention of any previous pseudo claim, in which said fluid composition (40) comprises Iplex (Mecasermin Rinfabate [rDNA origin] Injection).

awx. The invention of any previous pseudo claim, in which said fluid composition (40) comprises Iprivask.

awy. The invention of any previous pseudo claim, in which said fluid composition (40) comprises Irinotecan Hydrochloride (Camptosar Injection).

awz. The invention of any previous pseudo claim, in which said fluid composition (40) comprises Iron Sucrose Injection (Venofer).

axa. The invention of any previous pseudo claim, in which said fluid composition (40) comprises Istodax (Romidepsin for Injection).

axb. The invention of any previous pseudo claim, in which said fluid composition (40) comprises Itraconazole Injection (Sporanox Injection).

axc. The invention of any previous pseudo claim, in which said fluid composition (40) comprises Jevtana (Cabazitaxel Injection).

axd. The invention of any previous pseudo claim, in which said fluid composition (40) comprises Kalbitor (Ecallantide Injection).

axe. The invention of any previous pseudo claim, in which said fluid composition (40) comprises KCL in D5NS (Potassium Chloride in 5% Dextrose and Sodium Chloride Injection).

axf. The invention of any previous pseudo claim, in which said fluid composition (40) comprises KCL in D5W.

axg. The invention of any previous pseudo claim, in which said fluid composition (40) comprises KCL in NS.

axh. The invention of any previous pseudo claim, in which said fluid composition (40) comprises Kenalog 10 Injection (Triamcinolone Acetonide Injectable Suspension).

axi. The invention of any previous pseudo claim, in which said fluid composition (40) comprises Keppra Injection (Levetiracetam).

axj. The invention of any previous pseudo claim, in which said fluid composition (40) comprises Kineret.

axk. The invention of any previous pseudo claim, in which said fluid composition (40) comprises Kinlytic (Urokinase Injection).

axl. The invention of any previous pseudo claim, in which said fluid composition (40) comprises Kinrix.

axm. The invention of any previous pseudo claim, in which said fluid composition (40) comprises Kytril Injection (Granisetron Hydrochloride).

axn. The invention of any previous pseudo claim, in which said fluid composition (40) comprises lacosamide Tablet and Injection (Vimpat).

axo. The invention of any previous pseudo claim, in which said fluid composition (40) comprises Lactated Ringer's.

axp. The invention of any previous pseudo claim, in which said fluid composition (40) comprises Lanoxin Injection (Digoxin Injection).

axq. The invention of any previous pseudo claim, in which said fluid composition (40) comprises Lansoprazole for Injection (Prevacid I.V.).

axr. The invention of any previous pseudo claim, in which said fluid composition (40) comprises Lantus.

axs. The invention of any previous pseudo claim, in which said fluid composition (40) comprises Leucovorin Calcium (Leucovorin Calcium Injection).

axt. The invention of any previous pseudo claim, in which said fluid composition (40) comprises Lente (L).

axu The invention of any previous pseudo claim, in which said fluid composition (40) comprises Levemir.

axv. The invention of any previous pseudo claim, in which said fluid composition (40) comprises Leuproide Acetate.

axw. The invention of any previous pseudo claim, in which said fluid composition (40) comprises Levothyroxine.

axx. The invention of any previous pseudo claim, in which said fluid composition (40) comprises Levetiracetam (Keppra Injection).

axy. The invention of any previous pseudo claim, in which said fluid composition (40) comprises Lovenox.

axz. The invention of any previous pseudo claim, in which said fluid composition (40) comprises Levocarnitine Injection (Carnitor Injection).

aya. The invention of any previous pseudo claim, in which said fluid composition (40) comprises Lexiscan (Regadenoson Injection).

ayb. The invention of any previous pseudo claim, in which said fluid composition (40) comprises Lioresal Intrathecal (Baclofen Injection).

ayc. The invention of any previous pseudo claim, in which said fluid composition (40) comprises Liraglutide [rDNA] Injection (Victoza).

ayd. The invention of any previous pseudo claim, in which said fluid composition (40) comprises Lovenox (Enoxaparin Sodium Injection).

aye. The invention of any previous pseudo claim, in which said fluid composition (40) comprises Lucentis (Ranibizumab Injection).

ayf. The invention of any previous pseudo claim, in which said fluid composition (40) comprises Lupron (Leuprolide Acetate Injection).

ayg. The invention of any previous pseudo claim, in which said fluid composition (40) comprises Lusedra (Fospropofol Disodium Injection).

ayh. The invention of any previous pseudo claim, in which said fluid composition (40) comprises Magnesium Sulfate (Magnesium Sulfate Injection).

ayi. The invention of any previous pseudo claim, in which said fluid composition (40) comprises Mannitol Injection (Mannitol IV).

ayj. The invention of any previous pseudo claim, in which said fluid composition (40) comprises Marcaine (Bupivacaine Hydrochloride and Epinephrine Injection).

ayk. The invention of any previous pseudo claim, in which said fluid composition (40) comprises Maxipime (Cefepime Hydrochloride for Injection).

ayl. The invention of any previous pseudo claim, in which said fluid composition (40) comprises MDP Multidose Kit of Technetium Injection (Technetium Tc99m Medronate Injection).

aym. The invention of any previous pseudo claim, in which said fluid composition (40) comprises Mecasermin [rDNA origin] Injection (Increlex).

ayn. The invention of any previous pseudo claim, in which said fluid composition (40) comprises Mecasermin Rinfabate [rDNA origin] Injection (Iplex).

ayo. The invention of any previous pseudo claim, in which said fluid composition (40) comprises Melphalan Hcl Injection (Alkeran Injection).

ayp. The invention of any previous pseudo claim, in which said fluid composition (40) comprises Methotrexate.

ayq. The invention of any previous pseudo claim, in which said fluid composition (40) comprises Menactra.

ayr. The invention of any previous pseudo claim, in which said fluid composition (40) comprises Menopur (Menotropins Injection).

ays. The invention of any previous pseudo claim, in which said fluid composition (40) comprises Menotropins for Injection (Repronex).

ayt. The invention of any previous pseudo claim, in which said fluid composition (40) comprises Methohexital Sodium for Injection (Brevital Sodium).

ayu. The invention of any previous pseudo claim, in which said fluid composition (40) comprises Methyldopate Hydrochloride Injection, Solution (Methyldopate Hcl).

ayv. The invention of any previous pseudo claim, in which said fluid composition (40) comprises Methylene Blue (Methylene Blue Injection).

ayw. The invention of any previous pseudo claim, in which said fluid composition (40) comprises Methylprednisolone Acetate Injectable Suspension (Depo Medrol).

ayx. The invention of any previous pseudo claim, in which said fluid composition (40) comprises Metoclopramide Injection (Reglan Injection).

ayy. The invention of any previous pseudo claim, in which said fluid composition (40) comprises Metrodin (Urofollitropin for Injection).

ayz. The invention of any previous pseudo claim, in which said fluid composition (40) comprises Metronidazole Injection (Flagyl Injection).

aza. The invention of any previous pseudo claim, in which said fluid composition (40) comprises Miacalcin.

azb. The invention of any previous pseudo claim, in which said fluid composition (40) comprises Midazolam (Midazolam Injection).

azc. The invention of any previous pseudo claim, in which said fluid composition (40) comprises Minocin Injection (Minocycline Inj).

azd. The invention of any previous pseudo claim, in which said fluid composition (40) comprises Minocycline Inj (Minocin Injection).

aze. The invention of any previous pseudo claim, in which said fluid composition (40) comprises Mitoxantrone for Injection Concentrate (Novantrone).

azf. The invention of any previous pseudo claim, in which said fluid composition (40) comprises Morphine Injection (Duramorph).

azg. The invention of any previous pseudo claim, in which said fluid composition (40) comprises Morphine Sulfate XR Liposome Injection (DepoDur).

azh. The invention of any previous pseudo claim, in which said fluid composition (40) comprises Morrhuate Sodium (Morrhuate Sodium Injection).

azi. The invention of any previous pseudo claim, in which said fluid composition (40) comprises Mozobil (Plerixafor Injection).

azj. The invention of any previous pseudo claim, in which said fluid composition (40) comprises Multihance (Gadobenate Dimeglumine Injection).

azk. The invention of any previous pseudo claim, in which said fluid composition (40) comprises Multiple Electrolytes and Dextrose Injection.

azl. The invention of any previous pseudo claim, in which said fluid composition (40) comprises Multiple Electrolytes Injection.

azm. The invention of any previous pseudo claim, in which said fluid composition (40) comprises Mylotarg (Gemtuzumab Ozogamicin for Injection).

azn. The invention of any previous pseudo claim, in which said fluid composition (40) comprises Nafcillin Injection (Nafcillin Sodium).

azo. The invention of any previous pseudo claim, in which said fluid composition (40) comprises Nafcillin Sodium (Nafcillin Injection).

azp. The invention of any previous pseudo claim, in which said fluid composition (40) comprises Naltrexone XR Inj (Vivitrol).

azq. The invention of any previous pseudo claim, in which said fluid composition (40) comprises NeoProfen (Ibuprofen Lysine Injection).

azr. The invention of any previous pseudo claim, in which said fluid composition (40) comprises Nandrol Decanoate.

azs. The invention of any previous pseudo claim, in which said fluid composition (40) comprises Neostigmine Methylsulfate (Neostigmine Methylsulfate Injection).

azt. The invention of any previous pseudo claim, in which said fluid composition (40) comprises NeoTect (Technetium Tc 99m Depreotide Injection).

azu. The invention of any previous pseudo claim, in which said fluid composition (40) comprises Nephramine (Essential Amino Acid Injection).

azv. The invention of any previous pseudo claim, in which said fluid composition (40) comprises Neulasta.

azw. The invention of any previous pseudo claim, in which said fluid composition (40) comprises Neupogen.

azx. The invention of any previous pseudo claim, in which said fluid composition (40) comprises Novolin.

azy. The invention of any previous pseudo claim, in which said fluid composition (40) comprises Novolog.

azz. The invention of any previous pseudo claim, in which said fluid composition (40) comprises NeoRecormon.

baa. The invention of any previous pseudo claim, in which said fluid composition (40) comprises Neutrexin (Trimetrexate Glucuronate Inj).

bab. The invention of any previous pseudo claim, in which said fluid composition (40) comprises NPH (N).

bac. The invention of any previous pseudo claim, in which said fluid composition (40) comprises Nexterone (Amiodarone HCl Injection).

bad. The invention of any previous pseudo claim, in which said fluid composition (40) comprises Norditropin (Somatropin Injection).

bae. The invention of any previous pseudo claim, in which said fluid composition (40) comprises Normal Saline (Sodium Chloride Injection).

baf. The invention of any previous pseudo claim, in which said fluid composition (40) comprises Novantrone (Mitoxantrone for Injection Concentrate).

bag. The invention of any previous pseudo claim, in which said fluid composition (40) comprises Novolin 70/30 Innolet (70% NPH, Human Insulin Isophane Suspension and 30% Regular, Human Insulin Injection).

bah. The invention of any previous pseudo claim, in which said fluid composition (40) comprises NovoLog (Insulin Aspart [rDNA origin] Inj).

bai. The invention of any previous pseudo claim, in which said fluid composition (40) comprises Nutropin (Somatropin (rDNA origin) for Inj).

baj. The invention of any previous pseudo claim, in which said fluid composition (40) comprises Nutropin Depot (Somatropin (rDNA origin) for Inj).

bak. The invention of any previous pseudo claim, in which said fluid composition (40) comprises Octreotide Acetate Injection (Sandostatin LAR).

bal. The invention of any previous pseudo claim, in which said fluid composition (40) comprises Ocrelizumab.

bam. The invention of any previous pseudo claim, in which said fluid composition (40) comprises Ofatumumab Injection (Arzerra).

ban. The invention of any previous pseudo claim, in which said fluid composition (40) comprises Olanzapine Extended Release Injectable Suspension (Zyprexa Relprevv).

bao. The invention of any previous pseudo claim, in which said fluid composition (40) comprises Omnitrope (Somatropin [rDNA origin] Injection).

bap. The invention of any previous pseudo claim, in which said fluid composition (40) comprises Ondansetron Hydrochloride Injection (Zofran Injection).

baq. The invention of any previous pseudo claim, in which said fluid composition (40) comprises OptiMARK (Gadoversetamide Injection).

bar. The invention of any previous pseudo claim, in which said fluid composition (40) comprises Optiray Injection (Ioversol Injection).

bas. The invention of any previous pseudo claim, in which said fluid composition (40) comprises Orencia.

bat. The invention of any previous pseudo claim, in which said fluid composition (40) comprises Osmitrol Injection in Aviva (Mannitol Injection in Aviva Plastic Vessel).

bau. The invention of any previous pseudo claim, in which said fluid composition (40) comprises Osmitrol Injection in Viaflex (Mannitol Injection in Viaflex Plastic Vessel).

bav. The invention of any previous pseudo claim, in which said fluid composition (40) comprises Ovidrel (Choriogonadotropin Alfa Injection).

baw. The invention of any previous pseudo claim, in which said fluid composition (40) comprises Oxacillin (Oxacillin for Injection).

bax. The invention of any previous pseudo claim, in which said fluid composition (40) comprises Oxaliplatin Injection (Eloxatin).

bay. The invention of any previous pseudo claim, in which said fluid composition (40) comprises Oxytocin Injection (Pitocin).

baz. The invention of any previous pseudo claim, in which said fluid composition (40) comprises Paliperidone Palmitate Extended-Release Injectable Suspension (Invega Sustenna).

bba. The invention of any previous pseudo claim, in which said fluid composition (40) comprises Pamidronate Disodium Injection (Pamidronate Disodium Injection).

bbb. The invention of any previous pseudo claim, in which said fluid composition (40) comprises Panitumumab Injection for Intravenous Use (Vectibix).

bbc. The invention of any previous pseudo claim, in which said fluid composition (40) comprises Papaverine Hydrochloride Injection (Papaverine Injection).

bbd. The invention of any previous pseudo claim, in which said fluid composition (40) comprises Papaverine Injection (Papaverine Hydrochloride Injection).

bbe. The invention of any previous pseudo claim, in which said fluid composition (40) comprises Parathyroid Hormone.

bbf. The invention of any previous pseudo claim, in which said fluid composition (40) comprises Paricalcitol Injection Fliptop Vial (Zemplar Injection).

bbg. The invention of any previous pseudo claim, in which said fluid composition (40) comprises Pediarix.

bbh. The invention of any previous pseudo claim, in which said fluid composition (40) comprises PEGIntron.

bbi. The invention of any previous pseudo claim, in which said fluid composition (40) comprises Peginterferon.

bbk. The invention of any previous pseudo claim, in which said fluid composition (40) comprises Pegfilgrastim.

bbl. The invention of any previous pseudo claim, in which said fluid composition (40) comprises Penicillin G Benzathine and Penicillin G Procaine.

bbm The invention of any previous pseudo claim, in which said fluid composition (40) comprises Pentetate Calcium Trisodium Inj (Ca-DTPA).

bbn. The invention of any previous pseudo claim, in which said fluid composition (40) comprises Pentetate Zinc Trisodium Injection (Zn-DTPA).

bbo. The invention of any previous pseudo claim, in which said fluid composition (40) comprises Pepcid Injection (Famotidine Injection).

bbp. The invention of any previous pseudo claim, in which said fluid composition (40) comprises Pergonal.

bbq. The invention of any previous pseudo claim, in which said fluid composition (40) comprises Phentolamine Mesylate (Phentolamine Mesylate for Injection).

bbr. The invention of any previous pseudo claim, in which said fluid composition (40) comprises Physostigmine Salicylate (Physostigmine Salicylate (injection)).

bbs. The invention of any previous pseudo claim, in which said fluid composition (40) comprises Physostigmine Salicylate (injection) (Physostigmine Salicylate).

bbt. The invention of any previous pseudo claim, in which said fluid composition (40) comprises Piperacillin and Tazobactam Injection (Zosyn).

bbu. The invention of any previous pseudo claim, in which said fluid composition (40) comprises Pitocin (Oxytocin Injection).

bbv. The invention of any previous pseudo claim, in which said fluid composition (40) comprises Plasma-Lyte 148 (Multiple Electrolytes Inj).

bbw. The invention of any previous pseudo claim, in which said fluid composition (40) comprises Plasma-Lyte 56 and Dextrose (Multiple Electrolytes and Dextrose Injection in Viaflex Plastic Vessel).

bbx. The invention of any previous pseudo claim, in which said fluid composition (40) comprises PlasmaLyte.

bby. The invention of any previous pseudo claim, in which said fluid composition (40) comprises Plerixafor Injection (Mozobil).

bbz. The invention of any previous pseudo claim, in which said fluid composition (40) comprises Polidocanol Injection (Asclera).

bca. The invention of any previous pseudo claim, in which said fluid composition (40) comprises Potassium Chloride.

bcb. The invention of any previous pseudo claim, in which said fluid composition (40) comprises Pralatrexate Solution for Intravenous Injection (Folotyn).

bcc. The invention of any previous pseudo claim, in which said fluid composition (40) comprises Pramlintide Acetate Injection (Symlin).

bcd. The invention of any previous pseudo claim, in which said fluid composition (40) comprises Premarin Injection (Conjugated Estrogens for Injection).

bce. The invention of any previous pseudo claim, in which said fluid composition (40) comprises Prep kit for Technetium Tc99 Sestamibi for Injection (Cardiolite).

bcf. The invention of any previous pseudo claim, in which said fluid composition (40) comprises Prevacid I.V. (Lansoprazole for Injection).

bcg. The invention of any previous pseudo claim, in which said fluid composition (40) comprises Primaxin I.V. (Imipenem and Cilastatin for Injection).

bch. The invention of any previous pseudo claim, in which said fluid composition (40) comprises Progesterone.

bci. The invention of any previous pseudo claim, in which said fluid composition (40) comprises ProHance (Gadoteridol Injection Solution).

bcj. The invention of any previous pseudo claim, in which said fluid composition (40) comprises Prolia (Denosumab Injection).

bck. The invention of any previous pseudo claim, in which said fluid composition (40) comprises Promethazine HCl Injection (Promethazine Hydrochloride Injection).

bcl. The invention of any previous pseudo claim, in which said fluid composition (40) comprises Propranolol Hydrochloride Injection (Propranolol Hydrochloride Injection).

bcm. The invention of any previous pseudo claim, in which said fluid composition (40) comprises Quinidine Gluconate Injection (Quinidine Injection).

bcn. The invention of any previous pseudo claim, in which said fluid composition (40) comprises Quinidine Injection (Quinidine Gluconate Injection).

bco. The invention of any previous pseudo claim, in which said fluid composition (40) comprises R-Gene 10 (Arginine Hydrochloride Injection).

bcp. The invention of any previous pseudo claim, in which said fluid composition (40) comprises Ranibizumab Injection (Lucentis).

bcq. The invention of any previous pseudo claim, in which said fluid composition (40) comprises Ranitidine Hydrochloride Injection (Zantac Injection).

bcr. The invention of any previous pseudo claim, in which said fluid composition (40) comprises Reclast (Zoledronic Acid Injection).

bcs. The invention of any previous pseudo claim, in which said fluid composition (40) comprises Recombivarix HB.

bct. The invention of any previous pseudo claim, in which said fluid composition (40) comprises Regadenoson Injection (Lexiscan).

bcu. The invention of any previous pseudo claim, in which said fluid composition (40) comprises Reglan Injection (Metoclopramide Injection).

bcv. The invention of any previous pseudo claim, in which said fluid composition (40) comprises Remicade.

bcw. The invention of any previous pseudo claim, in which said fluid composition (40) comprises Repronex (Menotropins for Injection).

bcx. The invention of any previous pseudo claim, in which said fluid composition (40) comprises Retrovir IV (Zidovudine Injection).

bcy. The invention of any previous pseudo claim, in which said fluid composition (40) comprises Ringer's and 5% Dextrose Injection (Ringers in Dextrose).

bcz. The invention of any previous pseudo claim, in which said fluid composition (40) comprises Ringer's Injection (Ringers Injection).

bda. The invention of any previous pseudo claim, in which said fluid composition (40) comprises Rituxan.

bdb. The invention of any previous pseudo claim, in which said fluid composition (40) comprises Rituximab.

bdc. The invention of any previous pseudo claim, in which said fluid composition (40) comprises Rocuronium Bromide Injection (Zemuron).

bdd. The invention of any previous pseudo claim, in which said fluid composition (40) comprises Romidepsin for Injection (Istodax).

bde. The invention of any previous pseudo claim, in which said fluid composition (40) comprises Saizen (Somatropin Injection).

bdf. The invention of any previous pseudo claim, in which said fluid composition (40) comprises Sandostatin LAR (Octreotide Acetate Injection).

bdg. The invention of any previous pseudo claim, in which said fluid composition (40) comprises Sensorcaine (Bupivacaine HCl Injections).

bdh. The invention of any previous pseudo claim, in which said fluid composition (40) comprises Septocaine (Articane HCl and Epinephrine Injection).

bdi. The invention of any previous pseudo claim, in which said fluid composition (40) comprises Serostim LQ (Somatropin (rDNA origin) Injection).

bdj. The invention of any previous pseudo claim, in which said fluid composition (40) comprises Simponi Injection (Golimumab Injection).

bdk. The invention of any previous pseudo claim, in which said fluid composition (40) comprises Sodium Acetate (Sodium Acetate Injection).

bdl. The invention of any previous pseudo claim, in which said fluid composition (40) comprises Sodium Bicarbonate (Sodium Bicarbonate 5% Injection).

bdm. The invention of any previous pseudo claim, in which said fluid composition (40) comprises Sodium Lactate (Sodium Lactate Injection in AVIVA).

bdn. The invention of any previous pseudo claim, in which said fluid composition (40) comprises Sodium Phenylacetate and Sodium Benzoate Injection (Ammonul).

bdo. The invention of any previous pseudo claim, in which said fluid composition (40) comprises Somatropin (rDNA origin) for Inj (Nutropin).

bdp. The invention of any previous pseudo claim, in which said fluid composition (40) comprises Sporanox Injection (Itraconazole Injection).

bdq. The invention of any previous pseudo claim, in which said fluid composition (40) comprises Stelara Injection (Ustekinumab).

bdr. The invention of any previous pseudo claim, in which said fluid composition (40) comprises Sufenta (Sufentanil Citrate Injection).

bds. The invention of any previous pseudo claim, in which said fluid composition (40) comprises Sufentanil Citrate Injection (Sufenta).

bdt. The invention of any previous pseudo claim, in which said fluid composition (40) comprises Sumavel.

bdu. The invention of any previous pseudo claim, in which said fluid composition (40) comprises Sumatriptan Injection (Alsuma).

bdv. The invention of any previous pseudo claim, in which said fluid composition (40) comprises Symlin.

bdw. The invention of any previous pseudo claim, in which said fluid composition (40) comprises Symlin Pen.

bdx. The invention of any previous pseudo claim, in which said fluid composition (40) comprises Synvisc-One (Hylan G-F 20 Single Intra-articular Injection).

bdy. The invention of any previous pseudo claim, in which said fluid composition (40) comprises Taxotere (Docetaxel for Injection).

bdz. The invention of any previous pseudo claim, in which said fluid composition (40) comprises vvTechnetium Tc 99m.

bea. The invention of any previous pseudo claim, in which said fluid composition (40) comprises Telavancin for Injection (Vibativ).

beb. The invention of any previous pseudo claim, in which said fluid composition (40) comprises Temsirolimus Injection (Torisel).

bec. The invention of any previous pseudo claim, in which said fluid composition (40) comprises Tenormin I.V. Injection (Atenolol Inj).

bed. The invention of any previous pseudo claim, in which said fluid composition (40) comprises Teriparatide (rDNA origin) Injection (Forteo).

bee. The invention of any previous pseudo claim, in which said fluid composition (40) comprises Testosterone Cypionate.

bef. The invention of any previous pseudo claim, in which said fluid composition (40) comprises Testosterone Enanthate.

beg. The invention of any previous pseudo claim, in which said fluid composition (40) comprises Testosterone Propionate.

beh. The invention of any previous pseudo claim, in which said fluid composition (40) comprises Tev-Tropin (Somatropin, rDNA Origin, for Injection).

bei. The invention of any previous pseudo claim, in which said fluid composition (40) comprises tgAAC94.

bej. The invention of any previous pseudo claim, in which said fluid composition (40) comprises Thallous Chloride.

bek. The invention of any previous pseudo claim, in which said fluid composition (40) comprises Theophylline.

bel. The invention of any previous pseudo claim, in which said fluid composition (40) comprises Thiotepa (Thiotepa Injection).

bem. The invention of any previous pseudo claim, in which said fluid composition (40) comprises Thyrogen (Thyrotropin Alfa for Injection).

ben. The invention of any previous pseudo claim, in which said fluid composition (40) comprises Ticarcillin Disodium and Clavulanate Potassium Galaxy (Timentin Injection).

beo. The invention of any previous pseudo claim, in which said fluid composition (40) comprises Tigan Injection (Trimethobenzamide Hydrochloride Injectable).

bep. The invention of any previous pseudo claim, in which said fluid composition (40) comprises Timentin Injection (Ticarcillin Disodium and Clavulanate Potassium Galaxy).

beq. The invention of any previous pseudo claim, in which said fluid composition (40) comprises Tobramycin Injection (Tobramycin Injection).

ber. The invention of any previous pseudo claim, in which said fluid composition (40) comprises Tocilizumab Injection (Actemra).

bes. The invention of any previous pseudo claim, in which said fluid composition (40) comprises Torisel (Temsirolimus Injection).

bet. The invention of any previous pseudo claim, in which said fluid composition (40) comprises Totect (Dexrazoxane for Injection, Intravenous Infusion Only).

beu. The invention of any previous pseudo claim, in which said fluid composition (40) comprises Travasol (Amino Acids (Injection)).

bev. The invention of any previous pseudo claim, in which said fluid composition (40) comprises Treanda (Bendamustine Hydrochloride Injection).

bew. The invention of any previous pseudo claim, in which said fluid composition (40) comprises Trelstar (Triptorelin Pamoate for Injectable Suspension).

bex. The invention of any previous pseudo claim, in which said fluid composition (40) comprises Triamcinolone Acetonide.

bey. The invention of any previous pseudo claim, in which said fluid composition (40) comprises Triamcinolone Diacetate.

bez. The invention of any previous pseudo claim, in which said fluid composition (40) comprises Triamcinolone Hexacetonide Injectable Suspension (Aristospan Injection 20 mg).

bfa. The invention of any previous pseudo claim, in which said fluid composition (40) comprises Triesence (Triamcinolone Acetonide Injectable Suspension).

bfb. The invention of any previous pseudo claim, in which said fluid composition (40) comprises Trimethobenzamide Hydrochloride Injectable (Tigan Injection).

bfc. The invention of any previous pseudo claim, in which said fluid composition (40) comprises Trimetrexate Glucuronate Inj (Neutrexin).

bfd. The invention of any previous pseudo claim, in which said fluid composition (40) comprises Triptorelin Pamoate for Injectable Suspension (Trelstar).

bfe. The invention of any previous pseudo claim, in which said fluid composition (40) comprises Twinject.

bff. The invention of any previous pseudo claim, in which said fluid composition (40) comprises Trivaris (Triamcinolone Acetonide Injectable Suspension).

bfg. The invention of any previous pseudo claim, in which said fluid composition (40) comprises Trisenox (Arsenic Trioxide Injection).

bfh. The invention of any previous pseudo claim, in which said fluid composition (40) comprises Twinrix.

bfi. The invention of any previous pseudo claim, in which said fluid composition (40) comprises Typhoid Vi.

bfj. The invention of any previous pseudo claim, in which said fluid composition (40) comprises Ultravist (Iopromide Injection).

bfk. The invention of any previous pseudo claim, in which said fluid composition (40) comprises Urofollitropin for Injection (Metrodin).

bfl. The invention of any previous pseudo claim, in which said fluid composition (40) comprises Urokinase Injection (Kinlytic).

bfm. The invention of any previous pseudo claim, in which said fluid composition (40) comprises Ustekinumab (Stelara Injection).

bfn. The invention of any previous pseudo claim, in which said fluid composition (40) comprises Ultralente (U).

bfo. The invention of any previous pseudo claim, in which said fluid composition (40) comprises Valproate Sodium Injection (Depacon).

bfp. The invention of any previous pseudo claim, in which said fluid composition (40) comprises Valtropin (Somatropin Injection).

bfq. The invention of any previous pseudo claim, in which said fluid composition (40) comprises Vancomycin Hydrochloride (Vancomycin Hydrochloride Injection).

bfr. The invention of any previous pseudo claim, in which said fluid composition (40) comprises Vancomycin Hydrochloride Injection (Vancomycin Hydrochloride).

bfs. The invention of any previous pseudo claim, in which said fluid composition (40) comprises Vaprisol (Conivaptan Hcl Injection).

bft. The invention of any previous pseudo claim, in which said fluid composition (40) comprises VAQTA.

bfu. The invention of any previous pseudo claim, in which said fluid composition (40) comprises Vasovist (Gadofosveset Trisodium Injection for Intravenous Use).

bfv. The invention of any previous pseudo claim, in which said fluid composition (40) comprises Vectibix (Panitumumab Injection for Intravenous Use).

bfw. The invention of any previous pseudo claim, in which said fluid composition (40) comprises Venofer (Iron Sucrose Injection).

bfx. The invention of any previous pseudo claim, in which said fluid composition (40) comprises Verteporfin Inj (Visudyne).

bfy. The invention of any previous pseudo claim, in which said fluid composition (40) comprises Vibativ (Telavancin for Injection).

bfz. The invention of any previous pseudo claim, in which said fluid composition (40) comprises Victoza (Liraglutide [rDNA] Injection).

bga. The invention of any previous pseudo claim, in which said fluid composition (40) comprises Vimpat (lacosamide Tablet and Injection).

bgb. The invention of any previous pseudo claim, in which said fluid composition (40) comprises Vinblastine Sulfate (Vinblastine Sulfate Injection).

bgc. The invention of any previous pseudo claim, in which said fluid composition (40) comprises Vincasar PFS (Vincristine Sulfate Injection).

bgd. The invention of any previous pseudo claim, in which said fluid composition (40) comprises Victoza.

bge. The invention of any previous pseudo claim, in which said fluid composition (40) comprises Vincristine Sulfate (Vincristine Sulfate Injection).

bgf. The invention of any previous pseudo claim, in which said fluid composition (40) comprises Visudyne (Verteporfin Inj).

bgg. The invention of any previous pseudo claim, in which said fluid composition (40) comprises Vitamin B-12.

bgh. The invention of any previous pseudo claim, in which said fluid composition (40) comprises Vivitrol (Naltrexone XR Inj).

bgi. The invention of any previous pseudo claim, in which said fluid composition (40) comprises Voluven (Hydroxyethyl Starch in Sodium Chloride Injection).

bgj. The invention of any previous pseudo claim, in which said fluid composition (40) comprises Xeomin (Incobotulinumtoxin A for Injection).

bgk. The invention of any previous pseudo claim, in which said fluid composition (40) comprises Zantac Injection (Ranitidine Hydrochloride Injection).

bgl. The invention of any previous pseudo claim, in which said fluid composition (40) comprises Zemplar Injection (Paricalcitol Injection Fliptop Vial).

bgm. The invention of any previous pseudo claim, in which said fluid composition (40) comprises Zemuron (Rocuronium Bromide Injection).

bgn. The invention of any previous pseudo claim, in which said fluid composition (40) comprises Zevalin.

bgo. The invention of any previous pseudo claim, in which said fluid composition (40) comprises Zidovudine Injection (Retrovir IV).

bgp. The invention of any previous pseudo claim, in which said fluid composition (40) comprises Zithromax Injection (Azithromycin).

bgq. The invention of any previous pseudo claim, in which said fluid composition (40) comprises Zn-DTPA (Pentetate Zinc Trisodium Injection).

bgr. The invention of any previous pseudo claim, in which said fluid composition (40) comprises Zofran Injection (Ondansetron Hydrochloride Injection).

bgs. The invention of any previous pseudo claim, in which said fluid composition (40) comprises Zingo.

bgt. The invention of any previous pseudo claim, in which said fluid composition (40) comprises Zoledronic Acid for Inj (Zometa).

bgu. The invention of any previous pseudo claim, in which said fluid composition (40) comprises Zoledronic Acid Injection (Reclast).

bgv. The invention of any previous pseudo claim, in which said fluid composition (40) comprises Zometa (Zoledronic Acid for Inj).

bgw. The invention of any previous pseudo claim, in which said fluid composition (40) comprises Zosyn (Piperacillin and Tazobactam Injection).

bgx. The invention of any previous pseudo claim, in which said fluid composition (40) comprises Zyprexa Relprevv (Olanzapine Extended Release Injectable Suspension).

bgy. The invention of any previous pseudo claim, in which said fluid composition (40) comprises Abilify.

bgz. The invention of any previous pseudo claim, in which said fluid composition (40) comprises AccuNeb (Albuterol Sulfate Inhalation Solution).

bha. The invention of any previous pseudo claim, in which said fluid composition (40) comprises Actidose Aqua (Activated Charcoal Suspension).

bhb. The invention of any previous pseudo claim, in which said fluid composition (40) comprises Activated Charcoal Suspension (Actidose Aqua).

bhc. The invention of any previous pseudo claim, in which said fluid composition (40) comprises Advair.

bhd. The invention of any previous pseudo claim, in which said fluid composition (40) comprises Agenerase Oral Solution (Amprenavir Oral Solution).

bhe. The invention of any previous pseudo claim, in which said fluid composition (40) comprises Akten (Lidocaine Hydrochloride Ophthalmic Gel).

bhf. The invention of any previous pseudo claim, in which said fluid composition (40) comprises Alamast (Pemirolast Potassium Ophthalmic Solution).

bhg. The invention of any previous pseudo claim, in which said fluid composition (40) comprises Albumin (Human) 5% Solution (Buminate 5%).

bhh. The invention of any previous pseudo claim, in which said fluid composition (40) comprises Albuterol Sulfate Inhalation Solution.

bhi. The invention of any previous pseudo claim, in which said fluid composition (40) comprises Alinia.

bhj. The invention of any previous pseudo claim, in which said fluid composition (40) comprises Alocril.

bhk. The invention of any previous pseudo claim, in which said fluid composition (40) comprises Alphagan.

bhl. The invention of any previous pseudo claim, in which said fluid composition (40) comprises Alrex.

bhm. The invention of any previous pseudo claim, in which said fluid composition (40) comprises Alvesco.

bhn. The invention of any previous pseudo claim, in which said fluid composition (40) comprises Amprenavir Oral Solution.

bho. The invention of any previous pseudo claim, in which said fluid composition (40) comprises Analpram-HC.

bhp. The invention of any previous pseudo claim, in which said fluid composition (40) comprises Arformoterol Tartrate Inhalation Solution (Brovana).

bhq. The invention of any previous pseudo claim, in which said fluid composition (40) comprises Aristospan Injection 20 mg (Triamcinolone Hexacetonide Injectable Suspension).

bhr. The invention of any previous pseudo claim, in which said fluid composition (40) comprises Asacol.

bhs. The invention of any previous pseudo claim, in which said fluid composition (40) comprises Asmanex Astepro.

bht. The invention of any previous pseudo claim, in which said fluid composition (40) comprises Astepro (Azelastine Hydrochloride Nasal Spray).

bhu. The invention of any previous pseudo claim, in which said fluid composition (40) comprises Atrovent Nasal Spray (Ipratropium Bromide Nasal Spray).

bhv. The invention of any previous pseudo claim, in which said fluid composition (40) comprises Atrovent Nasal Spray 0.06.

bhw. The invention of any previous pseudo claim, in which said fluid composition (40) comprises Augmentin ES-600.

bhx. The invention of any previous pseudo claim, in which said fluid composition (40) comprises Azasite (Azithromycin Ophthalmic Solution).

bhy. The invention of any previous pseudo claim, in which said fluid composition (40) comprises Azelaic Acid (Finacea Gel).

bhz. The invention of any previous pseudo claim, in which said fluid composition (40) comprises Azelastine Hydrochloride Nasal Spray (Astepro).

bia. The invention of any previous pseudo claim, in which said fluid composition (40) comprises Azelex (Azelaic Acid Cream).

bib. The invention of any previous pseudo claim, in which said fluid composition (40) comprises Azopt (Brinzolamide Ophthalmic Suspension).

bic. The invention of any previous pseudo claim, in which said fluid composition (40) comprises Bacteriostatic Saline.

bid. The invention of any previous pseudo claim, in which said fluid composition (40) comprises Balanced Salt.

bie. The invention of any previous pseudo claim, in which said fluid composition (40) comprises Bepotastine.

bif. The invention of any previous pseudo claim, in which said fluid composition (40) comprises Bactroban Nasal.

big. The invention of any previous pseudo claim, in which said fluid composition (40) comprises Bactroban.

bih. The invention of any previous pseudo claim, in which said fluid composition (40) comprises Beclovent.

bii. The invention of any previous pseudo claim, in which said fluid composition (40) comprises Benzac W.

bij. The invention of any previous pseudo claim, in which said fluid composition (40) comprises Betimol.

bik. The invention of any previous pseudo claim, in which said fluid composition (40) comprises Betoptic S.

bil. The invention of any previous pseudo claim, in which said fluid composition (40) comprises Bepreve.

bim The invention of any previous pseudo claim, in which said fluid composition (40) comprises Bimatoprost Ophthalmic Solution.

bin. The invention of any previous pseudo claim, in which said fluid composition (40) comprises Bleph 10 (Sulfacetamide.Sodium Ophthalmic Solution 10%).

bio. The invention of any previous pseudo claim, in which said fluid composition (40) comprises Brinzolamide Ophthalmic Suspension (Azopt).

bip. The invention of any previous pseudo claim, in which said fluid composition (40) comprises Bromfenac Ophthalmic Solution (Xibrom).

biq. The invention of any previous pseudo claim, in which said fluid composition (40) comprises Bromhist.

bir. The invention of any previous pseudo claim, in which said fluid composition (40) comprises Brovana (Arformoterol Tartrate Inhalation Solution).

bis. The invention of any previous pseudo claim, in which said fluid composition (40) comprises Budesonide Inhalation Suspension (Pulmicort Respules).

bit. The invention of any previous pseudo claim, in which said fluid composition (40) comprises Cambia (Diclofenac Potassium for Oral Solution).

biu. The invention of any previous pseudo claim, in which said fluid composition (40) comprises Capex.

biv. The invention of any previous pseudo claim, in which said fluid composition (40) comprises Carac.

biw. The invention of any previous pseudo claim, in which said fluid composition (40) comprises Carboxine-PSE.

bix. The invention of any previous pseudo claim, in which said fluid composition (40) comprises Carnitor.

biy. The invention of any previous pseudo claim, in which said fluid composition (40) comprises Cayston (Aztreonam for Inhalation Solution).

biz. The invention of any previous pseudo claim, in which said fluid composition (40) comprises Cellcept.

bja. The invention of any previous pseudo claim, in which said fluid composition (40) comprises Centany.

bjb. The invention of any previous pseudo claim, in which said fluid composition (40) comprises Cerumenex.

bjc. The invention of any previous pseudo claim, in which said fluid composition (40) comprises Ciloxan Ophthalmic Solution (Ciprofloxacin HCL Ophthalmic Solution).

bjd. The invention of any previous pseudo claim, in which said fluid composition (40) comprises Ciprodex.

bje. The invention of any previous pseudo claim, in which said fluid composition (40) comprises Ciprofloxacin HCL Ophthalmic Solution (Ciloxan Ophthalmic Solution).

bjf. The invention of any previous pseudo claim, in which said fluid composition (40) comprises Clemastine Fumarate Syrup (Clemastine Fumarate Syrup).

bjg. The invention of any previous pseudo claim, in which said fluid composition (40) comprises CoLyte (PEG Electrolytes Solution).

bjh. The invention of any previous pseudo claim, in which said fluid composition (40) comprises Combiven.

bji. The invention of any previous pseudo claim, in which said fluid composition (40) comprises Comtan.

bjj. The invention of any previous pseudo claim, in which said fluid composition (40) comprises Condylox.

bjk. The invention of any previous pseudo claim, in which said fluid composition (40) comprises Cordran.

bjl. The invention of any previous pseudo claim, in which said fluid composition (40) comprises Cortisporin Ophthalmic Suspension.

bjm. The invention of any previous pseudo claim, in which said fluid composition (40) comprises Cortisporin Otic Suspension.

bjn. The invention of any previous pseudo claim, in which said fluid composition (40) comprises Cromolyn Sodium Inhalation Solution (Intal Nebulizer Solution).

bjo. The invention of any previous pseudo claim, in which said fluid composition (40) comprises Cromolyn Sodium Ophthalmic Solution (Opticrom).

bjp. The invention of any previous pseudo claim, in which said fluid composition (40) comprises Crystalline Amino Acid Solution with Electrolytes (Aminosyn Electrolytes).

bjq. The invention of any previous pseudo claim, in which said fluid composition (40) comprises Cutivate.

bjr. The invention of any previous pseudo claim, in which said fluid composition (40) comprises Cuvposa (Glycopyrrolate Oral Solution).

bjs. The invention of any previous pseudo claim, in which said fluid composition (40) comprises Cyanocobalamin (CaloMist Nasal Spray).

bjt. The invention of any previous pseudo claim, in which said fluid composition (40) comprises Cyclosporine Oral Solution (Gengraf Oral Solution).

bju. The invention of any previous pseudo claim, in which said fluid composition (40) comprises Cyclogyl.

bjv. The invention of any previous pseudo claim, in which said fluid composition (40) comprises Cysview (Hexaminolevulinate Hydrochloride Intravesical Solution).

bjw. The invention of any previous pseudo claim, in which said fluid composition (40) comprises DermOtic Oil (Fluocinolone Acetonide Oil Ear Drops).

bjx. The invention of any previous pseudo claim, in which said fluid composition (40) comprises Desmopressin Acetate Nasal Spray.

bjy. The invention of any previous pseudo claim, in which said fluid composition (40) comprises DDAVP.

bjz. The invention of any previous pseudo claim, in which said fluid composition (40) comprises Derma-Smoothe/FS.

bka. The invention of any previous pseudo claim, in which said fluid composition (40) comprises Dexamethasone Intensol.

bkb. The invention of any previous pseudo claim, in which said fluid composition (40) comprises Dianeal Low Calcium.

bkc. The invention of any previous pseudo claim, in which said fluid composition (40) comprises Dianeal PD.

bkd. The invention of any previous pseudo claim, in which said fluid composition (40) comprises Diclofenac Potassium for Oral Solution (Cambia).

bke. The invention of any previous pseudo claim, in which said fluid composition (40) comprises Didanosine Pediatric Powder for Oral Solution (Videx).

bkf. The invention of any previous pseudo claim, in which said fluid composition (40) comprises Differin.

bkg. The invention of any previous pseudo claim, in which said fluid composition (40) comprises Dilantin 125 (Phenytoin Oral Suspension).

bkh. The invention of any previous pseudo claim, in which said fluid composition (40) comprises Ditropan.

bki. The invention of any previous pseudo claim, in which said fluid composition (40) comprises Dorzolamide Hydrochloride Ophthalmic Solution (Trusopt).

bkj. The invention of any previous pseudo claim, in which said fluid composition (40) comprises Dorzolamide Hydrochloride-Timolol Maleate Ophthalmic Solution (Cosopt).

bkk. The invention of any previous pseudo claim, in which said fluid composition (40) comprises Dovonex Scalp (Calcipotriene Solution).

bkl. The invention of any previous pseudo claim, in which said fluid composition (40) comprises Doxycycline Calcium Oral Suspension (Vibramycin Oral).

bkm. The invention of any previous pseudo claim, in which said fluid composition (40) comprises Efudex.

bkn. The invention of any previous pseudo claim, in which said fluid composition (40) comprises Elaprase (Idursulfase Solution).

bko. The invention of any previous pseudo claim, in which said fluid composition (40) comprises Elestat (Epinastine HCl Ophthalmic Solution).

bkp. The invention of any previous pseudo claim, in which said fluid composition (40) comprises Elocon.

bkq. The invention of any previous pseudo claim, in which said fluid composition (40) comprises Epinastine HCl Ophthalmic Solution (Elestat).

bkr. The invention of any previous pseudo claim, in which said fluid composition (40) comprises Epivir HBV.

bks. The invention of any previous pseudo claim, in which said fluid composition (40) comprises Epogen.

bkt. The invention of any previous pseudo claim, in which said fluid composition (40) comprises Erythromycin Topical Solution 1.5% (Staticin).

bku. The invention of any previous pseudo claim, in which said fluid composition (40) comprises Ethiodol (Ethiodized Oil).

bkv. The invention of any previous pseudo claim, in which said fluid composition (40) comprises Ethosuximide Oral Solution (Zarontin Oral Solution).

bkw. The invention of any previous pseudo claim, in which said fluid composition (40) comprises Eurax.

bkx. The invention of any previous pseudo claim, in which said fluid composition (40) comprises Extraneal (Icodextrin Peritoneal Dialysis Solution).

bky. The invention of any previous pseudo claim, in which said fluid composition (40) comprises Felbatol.

bkz. The invention of any previous pseudo claim, in which said fluid composition (40) comprises Feridex I.V. (Ferumoxides Injectable Solution).

bla. The invention of any previous pseudo claim, in which said fluid composition (40) comprises Flovent.

blb. The invention of any previous pseudo claim, in which said fluid composition (40) comprises Floxin Otic (Ofloxacin Otic Solution).

blc. The invention of any previous pseudo claim, in which said fluid composition (40) comprises Flo-Pred (Prednisolone Acetate Oral Suspension).

bld. The invention of any previous pseudo claim, in which said fluid composition (40) comprises Fluoroplex.

ble. The invention of any previous pseudo claim, in which said fluid composition (40) comprises Flunisolide Nasal Solution (Flunisolide Nasal Spray 0.025%).

blf. The invention of any previous pseudo claim, in which said fluid composition (40) comprises Fluorometholone Ophthalmic Suspension (FML).

blg. The invention of any previous pseudo claim, in which said fluid composition (40) comprises Flurbiprofen Sodium Ophthalmic Solution (Ocufen).

blh. The invention of any previous pseudo claim, in which said fluid composition (40) comprises FML.

bli. The invention of any previous pseudo claim, in which said fluid composition (40) comprises Foradil.

blj. The invention of any previous pseudo claim, in which said fluid composition (40) comprises Formoterol Fumarate Inhalation Solution (Perforomist).

blk. The invention of any previous pseudo claim, in which said fluid composition (40) comprises Fosamax.

bll. The invention of any previous pseudo claim, in which said fluid composition (40) comprises Furadantin (Nitrofurantoin Oral Suspension).

blm. The invention of any previous pseudo claim, in which said fluid composition (40) comprises Furoxone.

bln. The invention of any previous pseudo claim, in which said fluid composition (40) comprises Gammagard Liquid (Immune Globulin Intravenous (Human) 10%).

blo. The invention of any previous pseudo claim, in which said fluid composition (40) comprises Gantrisin (Acetyl Sulfisoxazole Pediatric Suspension).

blp. The invention of any previous pseudo claim, in which said fluid composition (40) comprises Gatifloxacin Ophthalmic Solution (Zymar).

blq. The invention of any previous pseudo claim, in which said fluid composition (40) comprises Gengraf Oral Solution (Cyclosporine Oral Solution).

blr The invention of any previous pseudo claim, in which said fluid composition (40) comprises Glycopyrrolate Oral Solution (Cuvposa).

bls. The invention of any previous pseudo claim, in which said fluid composition (40) comprises Halcinonide Topical Solution (Halog Solution).

blt. The invention of any previous pseudo claim, in which said fluid composition (40) comprises Halog Solution (Halcinonide Topical Solution).

blu. The invention of any previous pseudo claim, in which said fluid composition (40) comprises HEP-LOCK U/P (Preservative-Free Heparin Lock Flush Solution).

blv. The invention of any previous pseudo claim, in which said fluid composition (40) comprises Heparin Lock Flush Solution (Hepflush 10).

blw. The invention of any previous pseudo claim, in which said fluid composition (40) comprises Hexaminolevulinate Hydrochloride Intravesical Solution (Cysview).

blx. The invention of any previous pseudo claim, in which said fluid composition (40) comprises Hydrocodone Bitartrate and Acetaminophen Oral Solution (Lortab Elixir).

bly. The invention of any previous pseudo claim, in which said fluid composition (40) comprises Hydroquinone 3% Topical Solution (Melquin-3 Topical Solution).

blz. The invention of any previous pseudo claim, in which said fluid composition (40) comprises Isopto.

bma. The invention of any previous pseudo claim, in which said fluid composition (40) comprises Ipratropium Bromide Nasal Spray (Atrovent Nasal Spray).

bmb. The invention of any previous pseudo claim, in which said fluid composition (40) comprises Itraconazole Oral Solution (Sporanox Oral Solution).

bmc. The invention of any previous pseudo claim, in which said fluid composition (40) comprises Ketorolac Tromethamine Ophthalmic Solution (Acular LS).

bmd. The invention of any previous pseudo claim, in which said fluid composition (40) comprises Kaletra.

bme. The invention of any previous pseudo claim, in which said fluid composition (40) comprises Lanoxin.

bmf. The invention of any previous pseudo claim, in which said fluid composition (40) comprises Lexiva.

bmg. The invention of any previous pseudo claim, in which said fluid composition (40) comprises Leuprolide Acetate for Depot Suspension (Lupron Depot 11.25 mg).

bmh. The invention of any previous pseudo claim, in which said fluid composition (40) comprises Levobetaxolol Hydrochloride Ophthalmic Suspension (Betaxon).

bmi. The invention of any previous pseudo claim, in which said fluid composition (40) comprises Levocarnitine Tablets, Oral Solution, Sugar-Free (Carnitor).

bmj. The invention of any previous pseudo claim, in which said fluid composition (40) comprises Levofloxacin Ophthalmic Solution 0.5% (Quixin).

bmk. The invention of any previous pseudo claim, in which said fluid composition (40) comprises Lidocaine HCl Sterile Solution (Xylocaine MPF Sterile Solution).

bml. The invention of any previous pseudo claim, in which said fluid composition (40) comprises Lok Pak (Heparin Lock Flush Solution).

bmm. The invention of any previous pseudo claim, in which said fluid composition (40) comprises Lorazepam Intensol.

bmn. The invention of any previous pseudo claim, in which said fluid composition (40) comprises Lortab Elixir (Hydrocodone Bitartrate and Acetaminophen Oral Solution).

bmo. The invention of any previous pseudo claim, in which said fluid composition (40) comprises Lotemax (Loteprednol Etabonate Ophthalmic Suspension).

bmp. The invention of any previous pseudo claim, in which said fluid composition (40) comprises Loteprednol Etabonate Ophthalmic Suspension (Alrex).

bmq. The invention of any previous pseudo claim, in which said fluid composition (40) comprises Low Calcium Peritoneal Dialysis Solutions (Dianeal Low Calcium).

bmr. The invention of any previous pseudo claim, in which said fluid composition (40) comprises Lumigan (Bimatoprost Ophthalmic Solution 0.03% for Glaucoma).

bms. The invention of any previous pseudo claim, in which said fluid composition (40) comprises Lupron Depot 11.25 mg (Leuprolide Acetate for Depot Suspension).

bmt. The invention of any previous pseudo claim, in which said fluid composition (40) comprises Megestrol Acetate Oral Suspension (Megestrol Acetate Oral Suspension).

bmu. The invention of any previous pseudo claim, in which said fluid composition (40) comprises Mepron.

bmv. The invention of any previous pseudo claim, in which said fluid composition (40) comprises Mesnex.

bmw. The invention of any previous pseudo claim, in which said fluid composition (40) comprises Mestinon.

bmx. The invention of any previous pseudo claim, in which said fluid composition (40) comprises Mesalamine Rectal Suspension Enema (Rowasa).

bmy. The invention of any previous pseudo claim, in which said fluid composition (40) comprises Melquin-3 Topical Solution (Hydroquinone 3% Topical Solution).

bmz. The invention of any previous pseudo claim, in which said fluid composition (40) comprises Methyldopate Hcl (Methyldopate Hydrochloride Injection, Solution).

bna. The invention of any previous pseudo claim, in which said fluid composition (40) comprises Methylin Oral Solution (Methylphenidate HCl Oral Solution 5 mg/5 mL and 10 mg/5 mL).

bnb. The invention of any previous pseudo claim, in which said fluid composition (40) comprises Methylprednisolone Acetate Injectable Suspension (Depo Medrol).

bnc. The invention of any previous pseudo claim, in which said fluid composition (40) comprises Methylphenidate HCl Oral Solution 5 mg/5 mL and 10 mg/5 mL (Methylin Oral Solution).

bnd. The invention of any previous pseudo claim, in which said fluid composition (40) comprises Methylprednisolone sodium succinate (Solu Medrol).

bne. The invention of any previous pseudo claim, in which said fluid composition (40) comprises Metipranolol Ophthalmic Solution (Optipranolol).

bnf. The invention of any previous pseudo claim, in which said fluid composition (40) comprises Migranal.

bng. The invention of any previous pseudo claim, in which said fluid composition (40) comprises Miochol-E (Acetylcholine Chloride Intraocular Solution).

bnh. The invention of any previous pseudo claim, in which said fluid composition (40) comprises Micro-K for Liquid Suspension (Potassium Chloride Extended Release Formulation for Liquid Suspension).

bni. The invention of any previous pseudo claim, in which said fluid composition (40) comprises Minocin (Minocycline Hydrochloride Oral Suspension).

bnj. The invention of any previous pseudo claim, in which said fluid composition (40) comprises Nasacort.

bnk. The invention of any previous pseudo claim, in which said fluid composition (40) comprises Neomycin and Polymyxin B Sulfates and Hydrocortisone.

bnl. The invention of any previous pseudo claim, in which said fluid composition (40) comprises Nepafenac Ophthalmic Suspension (Nevanac).

bnm. The invention of any previous pseudo claim, in which said fluid composition (40) comprises Nevanac (Nepafenac Ophthalmic Suspension).

bnn. The invention of any previous pseudo claim, in which said fluid composition (40) comprises Nitrofurantoin Oral Suspension (Furadantin).

bno. The invention of any previous pseudo claim, in which said fluid composition (40) comprises Noxafil (Posaconazole Oral Suspension).

bnp. The invention of any previous pseudo claim, in which said fluid composition (40) comprises Nystatin (oral) (Nystatin Oral Suspension).

bnq. The invention of any previous pseudo claim, in which said fluid composition (40) comprises Nystatin Oral Suspension (Nystatin (oral)).

bnr. The invention of any previous pseudo claim, in which said fluid composition (40) comprises Ocufen (Flurbiprofen Sodium Ophthalmic Solution).

bns. The invention of any previous pseudo claim, in which said fluid composition (40) comprises Ofloxacin Ophthalmic Solution (Ofloxacin Ophthalmic Solution).

bnt. The invention of any previous pseudo claim, in which said fluid composition (40) comprises Ofloxacin Otic Solution (Floxin Otic).

bnu. The invention of any previous pseudo claim, in which said fluid composition (40) comprises Olopatadine Hydrochloride Ophthalmic Solution (Pataday).

bnv. The invention of any previous pseudo claim, in which said fluid composition (40) comprises Opticrom (Cromolyn Sodium Ophthalmic Solution).

bnw. The invention of any previous pseudo claim, in which said fluid composition (40) comprises Optipranolol (Metipranolol Ophthalmic Solution).

bnx. The invention of any previous pseudo claim, in which said fluid composition (40) comprises Patanol.

bny. The invention of any previous pseudo claim, in which said fluid composition (40) comprises Pediapred.

bnz. The invention of any previous pseudo claim, in which said fluid composition (40) comprises PerioGard.

boa. The invention of any previous pseudo claim, in which said fluid composition (40) comprises Phenytoin Oral Suspension (Dilantin 125).

bob. The invention of any previous pseudo claim, in which said fluid composition (40) comprises Phisohex.

boc. The invention of any previous pseudo claim, in which said fluid composition (40) comprises Posaconazole Oral Suspension (Noxafil).

bod. The invention of any previous pseudo claim, in which said fluid composition (40) comprises Potassium Chloride Extended Release Formulation for Liquid Suspension (Micro-K for Liquid Suspension).

boe. The invention of any previous pseudo claim, in which said fluid composition (40) comprises Pataday (Olopatadine Hydrochloride Ophthalmic Solution).

bof. The invention of any previous pseudo claim, in which said fluid composition (40) comprises Patanase Nasal Spray (Olopatadine Hydrochloride Nasal Spray).

bog. The invention of any previous pseudo claim, in which said fluid composition (40) comprises PEG Electrolytes Solution (CoLyte).

boh. The invention of any previous pseudo claim, in which said fluid composition (40) comprises Pemirolast Potassium Ophthalmic Solution (Alamast).

boi. The invention of any previous pseudo claim, in which said fluid composition (40) comprises Penlac (Ciclopirox Topical Solution).

boj. The invention of any previous pseudo claim, in which said fluid composition (40) comprises PENNSAID (Diclofenac Sodium Topical Solution).

bok. The invention of any previous pseudo claim, in which said fluid composition (40) comprises Perforomist (Formoterol Fumarate Inhalation Solution).

bol. The invention of any previous pseudo claim, in which said fluid composition (40) comprises Peritoneal Dialysis Solution.

bom. The invention of any previous pseudo claim, in which said fluid composition (40) comprises Phenylephrine Hydrochloride Ophthalmic Solution (Neo-Synephrine).

bon. The invention of any previous pseudo claim, in which said fluid composition (40) comprises Phospholine Iodide (Echothiophate Iodide for Ophthalmic Solution).

boo. The invention of any previous pseudo claim, in which said fluid composition (40) comprises Podofilox (Podofilox Topical Solution).

bop. The invention of any previous pseudo claim, in which said fluid composition (40) comprises Pred Forte (Prednisolone Acetate Ophthalmic Suspension).

boq. The invention of any previous pseudo claim, in which said fluid composition (40) comprises Pralatrexate Solution for Intravenous Injection (Folotyn).

bor. The invention of any previous pseudo claim, in which said fluid composition (40) comprises Pred Mild.

bos. The invention of any previous pseudo claim, in which said fluid composition (40) comprises Prednisone Intensol.

bot. The invention of any previous pseudo claim, in which said fluid composition (40) comprises Prednisolone Acetate Ophthalmic Suspension (Pred Forte).

bou. The invention of any previous pseudo claim, in which said fluid composition (40) comprises Prevacid.

bov. The invention of any previous pseudo claim, in which said fluid composition (40) comprises PrismaSol Solution (Sterile Hemofiltration Hemodiafiltration Solution).

bow. The invention of any previous pseudo claim, in which said fluid composition (40) comprises ProAir.

box. The invention of any previous pseudo claim, in which said fluid composition (40) comprises Proglycem.

boy. The invention of any previous pseudo claim, in which said fluid composition (40) comprises ProHance (Gadoteridol Injection Solution).

boz. The invention of any previous pseudo claim, in which said fluid composition (40) comprises Proparacaine Hydrochloride Ophthalmic Solution (Alcaine).

bpa. The invention of any previous pseudo claim, in which said fluid composition (40) comprises Propine.

bpb. The invention of any previous pseudo claim, in which said fluid composition (40) comprises Pulmicort.

bpc. The invention of any previous pseudo claim, in which said fluid composition (40) comprises Pulmozyme.

bpd. The invention of any previous pseudo claim, in which said fluid composition (40) comprises Quixin (Levofloxacin Ophthalmic Solution 0.5%).

bpe. The invention of any previous pseudo claim, in which said fluid composition (40) comprises QVAR.

bpf. The invention of any previous pseudo claim, in which said fluid composition (40) comprises Rapamune.

bpg. The invention of any previous pseudo claim, in which said fluid composition (40) comprises Rebetol.

bph. The invention of any previous pseudo claim, in which said fluid composition (40) comprises Relacon-HC.

bpi. The invention of any previous pseudo claim, in which said fluid composition (40) comprises Rotarix (Rotavirus Vaccine, Live, Oral Suspension).

bpj. The invention of any previous pseudo claim, in which said fluid composition (40) comprises Rotavirus Vaccine, Live, Oral Suspension (Rotarix).

bpk. The invention of any previous pseudo claim, in which said fluid composition (40) comprises Rowasa (Mesalamine Rectal Suspension Enema).

bpl. The invention of any previous pseudo claim, in which said fluid composition (40) comprises Sabril (Vigabatrin Oral Solution).

bpm. The invention of any previous pseudo claim, in which said fluid composition (40) comprises Sacrosidase Oral Solution (Sucraid).

bpn. The invention of any previous pseudo claim, in which said fluid composition (40) comprises Sandimmune.

bpo. The invention of any previous pseudo claim, in which said fluid composition (40) comprises Serevent Diskus.

bpp. The invention of any previous pseudo claim, in which said fluid composition (40) comprises Solu Cortef (Hydrocortisone Sodium Succinate).

bpq. The invention of any previous pseudo claim, in which said fluid composition (40) comprises Solu Medrol (Methylprednisolone sodium succinate).

bpr. The invention of any previous pseudo claim, in which said fluid composition (40) comprises Spiriva.

bps. The invention of any previous pseudo claim, in which said fluid composition (40) comprises Sporanox Oral Solution (Itraconazole Oral Solution).

bpt. The invention of any previous pseudo claim, in which said fluid composition (40) comprises Staticin (Erythromycin Topical Solution 1.5%).

bpu. The invention of any previous pseudo claim, in which said fluid composition (40) comprises Stalevo.

bpv. The invention of any previous pseudo claim, in which said fluid composition (40) comprises Starlix.

bpw. The invention of any previous pseudo claim, in which said fluid composition (40) comprises Sterile Hemofiltration Hemodiafiltration Solution (PrismaSol Solution).

bpx. The invention of any previous pseudo claim, in which said fluid composition (40) comprises Stimate.

bpy. The invention of any previous pseudo claim, in which said fluid composition (40) comprises Sucralfate (Carafate Suspension).

bpz. The invention of any previous pseudo claim, in which said fluid composition (40) comprises Sulfacetamide Sodium Ophthalmic Solution 10% (Bleph 10).

bqa. The invention of any previous pseudo claim, in which said fluid composition (40) comprises Synarel Nasal Solution (Nafarelin Acetate Nasal Solution for Endometriosis).

bqb. The invention of any previous pseudo claim, in which said fluid composition (40) comprises Taclonex Scalp (Calcipotriene and Betamethasone Dipropionate Topical Suspension).

bqc. The invention of any previous pseudo claim, in which said fluid composition (40) comprises Tamiflu.

bqd. The invention of any previous pseudo claim, in which said fluid composition (40) comprises Tobi.

bqe. The invention of any previous pseudo claim, in which said fluid composition (40) comprises TobraDex.

bqf. The invention of any previous pseudo claim, in which said fluid composition (40) comprises Tobradex ST (Tobramycin/Dexamethasone Ophthalmic Suspension 0.3%/0.05%).

bqg. The invention of any previous pseudo claim, in which said fluid composition (40) comprises Tobramycin/Dexamethasone Ophthalmic Suspension 0.3%/0.05% (Tobradex ST).

bqh. The invention of any previous pseudo claim, in which said fluid composition (40) comprises Timolol.

bqi. The invention of any previous pseudo claim, in which said fluid composition (40) comprises Timoptic.

bqj. The invention of any previous pseudo claim, in which said fluid composition (40) comprises Travatan Z.

bqk. The invention of any previous pseudo claim, in which said fluid composition (40) comprises Treprostinil Inhalation Solution (Tyvaso).

bql. The invention of any previous pseudo claim, in which said fluid composition (40) comprises Trusopt (Dorzolamide Hydrochloride Ophthalmic Solution).

bqm. The invention of any previous pseudo claim, in which said fluid composition (40) comprises Tyvaso (Treprostinil Inhalation Solution).

bqn. The invention of any previous pseudo claim, in which said fluid composition (40) comprises Ventolin.

bqo. The invention of any previous pseudo claim, in which said fluid composition (40) comprises Vfend.

bqp. The invention of any previous pseudo claim, in which said fluid composition (40) comprises Vibramycin Oral (Doxycycline Calcium Oral Suspension).

bqq. The invention of any previous pseudo claim, in which said fluid composition (40) comprises Videx (Didanosine Pediatric Powder for Oral Solution).

bqr. The invention of any previous pseudo claim, in which said fluid composition (40) comprises Vigabatrin Oral Solution (Sabril).

bqs. The invention of any previous pseudo claim, in which said fluid composition (40) comprises Viokase.

bqt. The invention of any previous pseudo claim, in which said fluid composition (40) comprises Viracept.

bqu. The invention of any previous pseudo claim, in which said fluid composition (40) comprises Viramune.

bqv. The invention of any previous pseudo claim, in which said fluid composition (40) comprises Vitamin K1 (Aqueous Colloidal Solution of Vitamin K1).

bqw. The invention of any previous pseudo claim, in which said fluid composition (40) comprises Voltaren Ophthalmic (Diclofenac Sodium Ophthalmic Solution).

bqx. The invention of any previous pseudo claim, in which said fluid composition (40) comprises Zarontin Oral Solution (Ethosuximide Oral Solution).

bqy. The invention of any previous pseudo claim, in which said fluid composition (40) comprises Ziagen.

bqz. The invention of any previous pseudo claim, in which said fluid composition (40) comprises Zyvox.

bra. The invention of any previous pseudo claim, in which said fluid composition (40) comprises Zymar (Gatifloxacin Ophthalmic Solution).

brb. The invention of any previous pseudo claim, in which said fluid composition (40) comprises Zymaxid (Gatifloxacin Ophthalmic Solution)

brc. The invention of any previous pseudo claim, in which said fluid composition (40) comprises 17-Hydroxyprogesterone.

brd. The invention of any previous pseudo claim, in which said fluid composition (40) comprises ACE (Angiotensin I converting enzyme)

bre. The invention of any previous pseudo claim, in which said fluid composition (40) comprises Acetaminophen.

brf. The invention of any previous pseudo claim, in which said fluid composition (40) comprises Acid phosphatase.

brg. The invention of any previous pseudo claim, in which said fluid composition (40) comprises ACTH.

brh. The invention of any previous pseudo claim, in which said fluid composition (40) comprises Activated clotting time.

bri. The invention of any previous pseudo claim, in which said fluid composition (40) comprises Activated protein C resistance.

brj. The invention of any previous pseudo claim, in which said fluid composition (40) comprises Adrenocorticotropic hormone (ACTH).

brk. The invention of any previous pseudo claim, in which said fluid composition (40) comprises Alanine aminotransferase (ALT).

brl. The invention of any previous pseudo claim, in which said fluid composition (40) comprises Albumin.

brm. The invention of any previous pseudo claim, in which said fluid composition (40) comprises Aldolase.

brn. The invention of any previous pseudo claim, in which said fluid composition (40) comprises Aldosterone.

bro. The invention of any previous pseudo claim, in which said fluid composition (40) comprises Alkaline phosphatase.

brp. The invention of any previous pseudo claim, in which said fluid composition (40) comprises Alkaline phosphatase (ALP).

brq. The invention of any previous pseudo claim, in which said fluid composition (40) comprises Alpha1-antitrypsin.

brr. The invention of any previous pseudo claim, in which said fluid composition (40) comprises Alpha-fetoprotein.

brs. The invention of any previous pseudo claim, in which said fluid composition (40) comprises Alpha-fetoprotien.

brt. The invention of any previous pseudo claim, in which said fluid composition (40) comprises Ammonia levels.

bru. The invention of any previous pseudo claim, in which said fluid composition (40) comprises Amylase.

brv. The invention of any previous pseudo claim, in which said fluid composition (40) comprises ANA (antinuclear antbodies).

brw. The invention of any previous pseudo claim, in which said fluid composition (40) comprises ANA (antinuclear antibodies).

brx. The invention of any previous pseudo claim, in which said fluid composition (40) comprises Angiotensin-converting enzyme (ACE).

bry. The invention of any previous pseudo claim, in which said fluid composition (40) comprises Anion gap.

brz. The invention of any previous pseudo claim, in which said fluid composition (40) comprises Anticardiolipin antibody.

bsa. The invention of any previous pseudo claim, in which said fluid composition (40) comprises Anticardiolipin antivbodies (ACA).

bsb. The invention of any previous pseudo claim, in which said fluid composition (40) comprises Anti-centromere antibody.

bsc. The invention of any previous pseudo claim, in which said fluid composition (40) comprises Antidiuretic hormone.

bsd. The invention of any previous pseudo claim, in which said fluid composition (40) comprises Anti-DNA.

bse The invention of any previous pseudo claim, in which said fluid composition (40) comprises Anti-Dnase-B.

bsf. The invention of any previous pseudo claim, in which said fluid composition (40) comprises Anti-Gliadin antibody.

bsg. The invention of any previous pseudo claim, in which said fluid composition (40) comprises Anti-glomerular basement membrane antibody.

bsh. The invention of any previous pseudo claim, in which said fluid composition (40) comprises Anti-HBc (Hepatitis B core antibodies.

bsi. The invention of any previous pseudo claim, in which said fluid composition (40) comprises Anti-HBs (Hepatitis B surface antibody.

bsj. The invention of any previous pseudo claim, in which said fluid composition (40) comprises Antiphospholipid antibody.

bsk. The invention of any previous pseudo claim, in which said fluid composition (40) comprises Anti-RNA polymerase.

bsl. The invention of any previous pseudo claim, in which said fluid composition (40) comprises Anti-Smith (Sm) antibodies.

bsm. The invention of any previous pseudo claim, in which said fluid composition (40) comprises Anti-Smooth Muscle antibody.

bsn. The invention of any previous pseudo claim, in which said fluid composition (40) comprises Antistreptolysin O (ASO).

bso. The invention of any previous pseudo claim, in which said fluid composition (40) comprises Antithrombin III.

bsp. The invention of any previous pseudo claim, in which said fluid composition (40) comprises Anti-Xa activity.

bsq. The invention of any previous pseudo claim, in which said fluid composition (40) comprises Anti-Xa assay.

bsr. The invention of any previous pseudo claim, in which said fluid composition (40) comprises Apolipoproteins.

bss. The invention of any previous pseudo claim, in which said fluid composition (40) comprises Arsenic.

bst. The invention of any previous pseudo claim, in which said fluid composition (40) comprises Aspartate aminotransferase (AST).

bsu. The invention of any previous pseudo claim, in which said fluid composition (40) comprises B12.

bsv. The invention of any previous pseudo claim, in which said fluid composition (40) comprises Basophil.

bsw. The invention of any previous pseudo claim, in which said fluid composition (40) comprises Beta-2-.Microglobulin bsx. The invention of any previous pseudo claim, in which said fluid composition (40) comprises Beta-hydroxybutyrate.

bsy. The invention of any previous pseudo claim, in which said fluid composition (40) comprises B-HCG.

bsz. The invention of any previous pseudo claim, in which said fluid composition (40) comprises Bilirubin.

bta. The invention of any previous pseudo claim, in which said fluid composition (40) comprises Bilirubin, direct.

btb. The invention of any previous pseudo claim, in which said fluid composition (40) comprises Bilirubin, indirect.

btc. The invention of any previous pseudo claim, in which said fluid composition (40) comprises Bilirubin, total.

btd. The invention of any previous pseudo claim, in which said fluid composition (40) comprises Bleeding time.

bte. The invention of any previous pseudo claim, in which said fluid composition (40) comprises Blood gases (arterial).

btf. The invention of any previous pseudo claim, in which said fluid composition (40) comprises Blood urea nitrogen (BUN).

btg. The invention of any previous pseudo claim, in which said fluid composition (40) comprises BUN.

bth. The invention of any previous pseudo claim, in which said fluid composition (40) comprises BUN (blood urea nitrogen).

bti. The invention of any previous pseudo claim, in which said fluid composition (40) comprises CA 125.

btj. The invention of any previous pseudo claim, in which said fluid composition (40) comprises CA 15-3.

btk. The invention of any previous pseudo claim, in which said fluid composition (40) comprises CA 19-9.

btl. The invention of any previous pseudo claim, in which said fluid composition (40) comprises Calcitonin.

btm. The invention of any previous pseudo claim, in which said fluid composition (40) comprises Calcium.

btn. The invention of any previous pseudo claim, in which said fluid composition (40) comprises Calcium. (ionized)

bto. The invention of any previous pseudo claim, in which said fluid composition (40) comprises Carbon monoxide (CO).

btp. The invention of any previous pseudo claim, in which said fluid composition (40) comprises Carcinoembryonic antigen (CEA).

btq. The invention of any previous pseudo claim, in which said fluid composition (40) comprises CBC.

btr. The invention of any previous pseudo claim, in which said fluid composition (40) comprises CEA.

bts. The invention of any previous pseudo claim, in which said fluid composition (40) comprises CEA (carcinoembryonic antigen).

btt. The invention of any previous pseudo claim, in which said fluid composition (40) comprises Ceruloplasmin.

btu. The invention of any previous pseudo claim, in which said fluid composition (40) comprises CH50Chloride.

btv. The invention of any previous pseudo claim, in which said fluid composition (40) comprises Cholesterol.

btw. The invention of any previous pseudo claim, in which said fluid composition (40) comprises Cholesterol, HDL.

btx. The invention of any previous pseudo claim, in which said fluid composition (40) comprises Clot lysis time.

bty. Clot The invention of any previous pseudo claim, in which said fluid composition (40) comprises retraction time.

btz. The invention of any previous pseudo claim, in which said fluid composition (40) comprises CMP.

bua. The invention of any previous pseudo claim, in which said fluid composition (40) comprises CO2.

bub. The invention of any previous pseudo claim, in which said fluid composition (40) comprises Cold agglutinins.

buc. The invention of any previous pseudo claim, in which said fluid composition (40) comprises Complement C3.

bud. The invention of any previous pseudo claim, in which said fluid composition (40) comprises Copper.

bue. The invention of any previous pseudo claim, in which said fluid composition (40) comprises Corticotrophin releasing hormone (CRH) stimulation test.

buf. The invention of any previous pseudo claim, in which said fluid composition (40) comprises Cortisol.

bug. The invention of any previous pseudo claim, in which said fluid composition (40) comprises Cortrosyn stimulation test.

buh. The invention of any previous pseudo claim, in which said fluid composition (40) comprises C-peptide.

bui. The invention of any previous pseudo claim, in which said fluid composition (40) comprises CPK (Total).

buj. The invention of any previous pseudo claim, in which said fluid composition (40) comprises CPK-MB.

buk. The invention of any previous pseudo claim, in which said fluid composition (40) comprises C-reactive protein.

bul. The invention of any previous pseudo claim, in which said fluid composition (40) comprises Creatinine.

bum. The invention of any previous pseudo claim, in which said fluid composition (40) comprises Creatinine kinase (CK).

bun. The invention of any previous pseudo claim, in which said fluid composition (40) comprises Cryoglobulins.

buo. The invention of any previous pseudo claim, in which said fluid composition (40) comprises DAT (Direct antiglobulin test).

bup. The invention of any previous pseudo claim, in which said fluid composition (40) comprises D-Dimer.

buq. The invention of any previous pseudo claim, in which said fluid composition (40) comprises Dexamethasone suppression test/ bur. The invention of any previous pseudo claim, in which said fluid composition (40) comprises DHEA-S.

bus. The invention of any previous pseudo claim, in which said fluid composition (40) comprises Dilute Russell viper venom.

but. The invention of any previous pseudo claim, in which said fluid composition (40) comprises Elliptocytes.

buu. The invention of any previous pseudo claim, in which said fluid composition (40) comprises Eosinophil.

buv. The invention of any previous pseudo claim, in which said fluid composition (40) comprises Erythrocyte sedimentation rate (ESR).

buw. The invention of any previous pseudo claim, in which said fluid composition (40) comprises Estradiol.

bux. The invention of any previous pseudo claim, in which said fluid composition (40) comprises Estriol.

buy. The invention of any previous pseudo claim, in which said fluid composition (40) comprises Ethanol.

buz. The invention of any previous pseudo claim, in which said fluid composition (40) comprises Ethylene glycol.

bva. The invention of any previous pseudo claim, in which said fluid composition (40) comprises Euglobulin lysis.

bvb. The invention of any previous pseudo claim, in which said fluid composition (40) comprises Factor V Leiden.

bvc. The invention of any previous pseudo claim, in which said fluid composition (40) comprises Factor VIII inhibitor.

bvd. The invention of any previous pseudo claim, in which said fluid composition (40) comprises Factor VIII level.

bve. The invention of any previous pseudo claim, in which said fluid composition (40) comprises Ferritin.

bvf. The invention of any previous pseudo claim, in which said fluid composition (40) comprises Fibrin split products.

bvg. The invention of any previous pseudo claim, in which said fluid composition (40) comprises Fibrinogen.

bvh. The invention of any previous pseudo claim, in which said fluid composition (40) comprises Folate.

bvi. The invention of any previous pseudo claim, in which said fluid composition (40) comprises Folate (serum).

bvj. The invention of any previous pseudo claim, in which said fluid composition (40) comprises Fractional excretion of sodium (FENA).

bvk. The invention of any previous pseudo claim, in which said fluid composition (40) comprises FSH (follicle stimulating factor).

bvl. The invention of any previous pseudo claim, in which said fluid composition (40) comprises FTA-ABS.

bvm. The invention of any previous pseudo claim, in which said fluid composition (40) comprises Gamma glutamyl transferase (GGT).

bvn. The invention of any previous pseudo claim, in which said fluid composition (40) comprises Gastrin.

bvo. The invention of any previous pseudo claim, in which said fluid composition (40) comprises GGTP (Gamma glutamyl transferase).

bvp. The invention of any previous pseudo claim, in which said fluid composition (40) comprises Glucose.

bvq. The invention of any previous pseudo claim, in which said fluid composition (40) comprises Growth hormone.

bvr. The invention of any previous pseudo claim, in which said fluid composition (40) comprises Haptoglobin.

bvs. The invention of any previous pseudo claim, in which said fluid composition (40) comprises HBeAg (Hepatitis Be antigen).

bvt. The invention of any previous pseudo claim, in which said fluid composition (40) comprises HBs-Ag (Hepatitis B surface antigen).

bvu. The invention of any previous pseudo claim, in which said fluid composition (40) comprises *Helicobacter pylori*.

bvv. The invention of any previous pseudo claim, in which said fluid composition (40) comprises Hematocrit.

bvw. The invention of any previous pseudo claim, in which said fluid composition (40) comprises Hematocrit (HCT).

bvx. The invention of any previous pseudo claim, in which said fluid composition (40) comprises Hemoglobin.

bvy. The invention of any previous pseudo claim, in which said fluid composition (40) comprises Hemoglobin A1C.

bvz. The invention of any previous pseudo claim, in which said fluid composition (40) comprises Hemoglobin electrophoresis.

bwa. The invention of any previous pseudo claim, in which said fluid composition (40) comprises Hepatitis A antibodies.

bwb. The invention of any previous pseudo claim, in which said fluid composition (40) comprises Hepatitis C antibodies.

bwc. The invention of any previous pseudo claim, in which said fluid composition (40) comprises IAT (Indirect antiglobulin test).

bwd. The invention of any previous pseudo claim, in which said fluid composition (40) comprises Immunofixation (IFE).

bwe. The invention of any previous pseudo claim, in which said fluid composition (40) comprises Iron.

bwf. The invention of any previous pseudo claim, in which said fluid composition (40) comprises Lactate dehydrogenase (LDH).

bwg. The invention of any previous pseudo claim, in which said fluid composition (40) comprises Lactic acid (lactate).

bwh. The invention of any previous pseudo claim, in which said fluid composition (40) comprises LDH.

bwi. The invention of any previous pseudo claim, in which said fluid composition (40) comprises LH (Leutinizing hormone.

bwj. The invention of any previous pseudo claim, in which said fluid composition (40) comprises Lipase.

bwk. The invention of any previous pseudo claim, in which said fluid composition (40) comprises Lupus anticoagulant.

bwl. The invention of any previous pseudo claim, in which said fluid composition (40) comprises Lymphocyte.

bwm. The invention of any previous pseudo claim, in which said fluid composition (40) comprises Magnesium.

bwn. The invention of any previous pseudo claim, in which said fluid composition (40) comprises MCH (mean corpuscular hemoglobin.

bwo. The invention of any previous pseudo claim, in which said fluid composition (40) comprises MCHC (mean corpuscular hemoglobin concentration).

bwp. The invention of any previous pseudo claim, in which said fluid composition (40) comprises MCV (mean corpuscular volume).

bwq. The invention of any previous pseudo claim, in which said fluid composition (40) comprises Methylmalonate.

bwr. The invention of any previous pseudo claim, in which said fluid composition (40) comprises Monocyte.

bws. The invention of any previous pseudo claim, in which said fluid composition (40) comprises MPV (mean platelet volume).

bwt. The invention of any previous pseudo claim, in which said fluid composition (40) comprises Myoglobin.

bwu. The invention of any previous pseudo claim, in which said fluid composition (40) comprises Neutrophil.

bwv. The invention of any previous pseudo claim, in which said fluid composition (40) comprises Parathyroid hormone (PTH).

bww. The invention of any previous pseudo claim, in which said fluid composition (40) comprises Phosphorus.

bwx. The invention of any previous pseudo claim, in which said fluid composition (40) comprises Platelets (plt).

bwy. The invention of any previous pseudo claim, in which said fluid composition (40) comprises Potassium.

bwz. The invention of any previous pseudo claim, in which said fluid composition (40) comprises Prealbumin.

bwa. The invention of any previous pseudo claim, in which said fluid composition (40) comprises Prolactin.

bwb. The invention of any previous pseudo claim, in which said fluid composition (40) comprises Prostate specific antigen (PSA).

bwc. The invention of any previous pseudo claim, in which said fluid composition (40) comprises Protein C.

bwd. The invention of any previous pseudo claim, in which said fluid composition (40) comprises Protein S.

bwe. The invention of any previous pseudo claim, in which said fluid composition (40) comprises PSA (prostate specific antigen).

bwf. The invention of any previous pseudo claim, in which said fluid composition (40) comprises PT (Prothrombin time).

bwg. The invention of any previous pseudo claim, in which said fluid composition (40) comprises PTT (Partial thromboplastin time).

bwh. The invention of any previous pseudo claim, in which said fluid composition (40) comprises RDW (red cell distribution width).

bwi. The invention of any previous pseudo claim, in which said fluid composition (40) comprises Renin.

bwj. The invention of any previous pseudo claim, in which said fluid composition (40) comprises Rennin.

bwk. The invention of any previous pseudo claim, in which said fluid composition (40) comprises Reticulocyte count.

bwl. The invention of any previous pseudo claim, in which said fluid composition (40) comprises reticulocytes.

bwm. The invention of any previous pseudo claim, in which said fluid composition (40) comprises Rheumatoid factor (RF).

bwm. The invention of any previous pseudo claim, in which said fluid composition (40) comprises Sed Rate.

bwo. The invention of any previous pseudo claim, in which said fluid composition (40) comprises Serum glutamic-pyruvic transaminase (SGPT).

bwp. The invention of any previous pseudo claim, in which said fluid composition (40) comprises Serum protein electrophoresis (SPEP).

bwq. The invention of any previous pseudo claim, in which said fluid composition (40) comprises Sodium.

bwr. The invention of any previous pseudo claim, in which said fluid composition (40) comprises T3-resin uptake (T3RU).

bwr. The invention of any previous pseudo claim, in which said fluid composition (40) comprises T4, Free.

bws. The invention of any previous pseudo claim, in which said fluid composition (40) comprises Thrombin time.

bwt. The invention of any previous pseudo claim, in which said fluid composition (40) comprises Thyroid stimulating hormone (TSH).

bwu. The invention of any previous pseudo claim, in which said fluid composition (40) comprises Thyroxine (T4).

bwv. The invention of any previous pseudo claim, in which said fluid composition (40) comprises Total iron binding capacity (TIBC).

bww. The invention of any previous pseudo claim, in which said fluid composition (40) comprises Total protein.

bwx. The invention of any previous pseudo claim, in which said fluid composition (40) comprises Transferrin.

bwy. The invention of any previous pseudo claim, in which said fluid composition (40) comprises Transferrin saturation.

bwz. The invention of any previous pseudo claim, in which said fluid composition (40) comprises Triglyceride (TG).

bxa. The invention of any previous pseudo claim, in which said fluid composition (40) comprises Troponin.

bxb. The invention of any previous pseudo claim, in which said fluid composition (40) comprises Uric acid.

bxc. The invention of any previous pseudo claim, in which said fluid composition (40) comprises Vitamin B12.

bxd. The invention of any previous pseudo claim, in which said fluid composition (40) comprises White blood cells (WBC).

bxe. The invention of any previous pseudo claim, in which said fluid composition (40) comprises Widal test.

Medical Barrel Pseudo Claims bxf. A medical syringe barrel or medical cartridge barrel comprising:
- a wall having a generally cylindrical interior surface defining at least a portion of a lumen, optionally the entire lumen, the generally cylindrical interior surface having an inside diameter of 4 to 15 mm; and
- a PECVD set of one or more plasma enhanced chemical vapor deposition coatings or layers on at least a portion of the generally cylindrical interior surface optionally the entire generally cylindrical interior surface, at least one coating or layer of the PECVD set comprising a barrier coating or layer having a mean thickness from 10 to 500 nm with a standard deviation less than the mean thickness.

bxg. The medical barrel of pseudo claim bxf, in which the barrier coating or layer has a thickness range from 10 to 500 nm.

bxh. The medical barrel of any previous pseudo claim, in which the standard deviation is at least 20% of the mean thickness.

bxi. The medical barrel of any previous pseudo claim, made of electrically non-conductive material.

bxj. The medical barrel of any previous pseudo claim, made of transparent material.

bxk. The medical barrel of any previous pseudo claim, made of injection moldable thermoplastic material.

bxl. The medical barrel of any previous pseudo claim, made of COC (cyclic olefin copolymer), COP (cyclic olefin polymer), PET (polyethylene terephthalate), polypropylene, polycarbonate, polystyrene, polymethylmethacrylate, glass, or a combination of two or more of these.

bxm. The medical barrel of any previous pseudo claim, in which the aspect ratio between the length and inside diameter of the generally cylindrical interior surface subjected to PECVD is from 2 to 10.

bxn. The medical barrel of any previous pseudo claim, in which the barrier coating or layer consists essentially of $SiO_x$, in which x is from 1.5 to 2.9 as determined by XPS.

bxo. The medical barrel of any previous pseudo claim, in which the oxygen barrier improvement factor of the wall and PECVD set, compared to the wall without the PECVD set, is from 5 to 12.

bxp. The medical barrel of any previous pseudo claim, further comprising a closure seated to the medical barrel to form a closed lumen, in which the lumen has a volume between 0.5 and 50 ml and the inward oxygen transmission rate through the wall and the PECVD set is from 0.0012 to 0.00048 cubic cm per package per day, at 20° C., at atmospheric pressure outside the wall.

bxq. The medical barrel of any previous pseudo claim, in which the PECVD set further comprises a pH protective coating or layer between the barrier coating or layer and the lumen.

bxr. The medical barrel of pseudo claim bxq, in which the pH protective coating or layer consists essentially of $SiO_xC_y$ or $SiN_xC_y$, in which x is from about 0.5 to about 2.4 and y is from about 0.6 to about 3, each as measured by XPS.

bxs. The medical barrel of pseudo claim bxq or bxr, in which the pH protective coating or layer consists essentially of the following atomic ratios of silicon, oxygen, and carbon as determined by X-ray photoelectron spectroscopy, and atomic ratio of hydrogen as determined by Rutherford backscattering spectrometry:

| ATOMIC RATIOS | | | |
|---|---|---|---|
| Si | O | C | H |
| 1 | 0.5 to 2.4 | 0.6 to 3 | 2 to 9 | bxt. The medical barrel of any previous pseudo claims bxq to bxs, in which the pH protective coating or layer has a mean thickness from 50 to 500 nm.

bxu. The medical barrel of any previous pseudo claims bxq to bxt, in which an FTIR absorbance spectrum of the pH protective coating or layer has a ratio greater than 0.75 between:

the maximum amplitude of the Si—O—Si symmetrical stretch peak between about 1000 and 1040 cm$^{-1}$, and the maximum amplitude of the Si—O—Si asymmetric stretch peak between about 1060 and about 1100 cm$^{-1}$.

bxv. The medical barrel of any previous pseudo claim, in which the PECVD set further comprises a tie coating or layer between the barrier coating or layer and the generally cylindrical interior surface, in which the tie coating or layer has a mean thickness from greater than 0 to 10 nm.

bxw. The medical barrel of pseudo claim bxv, in which the tie coating or layer consists essentially of $SiO_xC_y$ or $SiN_xC_y$, in which x is from about 0.5 to about 2.4 and y is from about 0.6 to about 3, each as measured by XPS.

bxx. The medical barrel of any previous pseudo claims bxv to bxw, in which the tie coating or layer consists essentially of the following atomic ratios of silicon, oxygen, and carbon as determined by X-ray photoelectron spectroscopy, and atomic ratio of hydrogen as determined by Rutherford backscattering spectrometry:

| ATOMIC RATIOS | | | |
|---|---|---|---|
| Si | O | C | H |
| 1 | 0.5 to 2.4 | 0.6 to 3 | 2 to 9 | bxy. The medical barrel of any previous pseudo claim, in which the PECVD set is effective to maintain an oxygen barrier improvement factor, versus a barrel without the PECVD set, of at least 5 after the PECVD set is stored in contact with U.S. Pharmacopeia Water for Injection having a pH of 7.0 for a period of three months at a temperature of 25° C.

bxz. The medical barrel of any previous pseudo claim, in which the PECVD set is effective to maintain an oxygen barrier improvement factor, versus a barrel without the PECVD set, of at most 31 after the PECVD set is stored in contact with U.S. Pharmacopeia Water for Injection having a pH of 7.0 for a period of three months at a temperature of 25° C.

bya. The medical barrel of any previous pseudo claim, further comprising a fluid composition in the lumen having a pH between 4 and 9 and a closure retaining the fluid composition in the lumen, defining a fluid storage package.

byb. The medical barrel of any previous pseudo claim, in which the barrier coating or layer is applied by PECVD using as a precursor a linear siloxane, a monocyclic siloxane, a polycyclic siloxane, a polysilsesquioxane, a linear silazane, a monocyclic silazane, a polycyclic silazane, a polysilsesquiazane, a silatrane, a silquasilatrane, a silproatrane, an azasilatrane, an azasilquasiatrane, an azasilproatrane, or a combination of any two or more of these precursors.

byc. The medical barrel of any previous pseudo claim, in which the barrier coating or layer is applied by PECVD using as a precursor hexamethylenedisiloxane (HMDSO), tetramethylenedisiloxane (TMDSO), or a combination of these.

byd. The medical barrel of any previous pseudo claim, in which the PECVD set comprises:

a tie coating or layer applied by PECVD using as a precursor tetramethylenedisiloxane (TMDSO);

a barrier coating or layer applied by PECVD using as a precursor hexamethylenedisiloxane (HMDSO); and a pH protective coating or layer applied by PECVD using as a precursor tetramethylenedisiloxane (TMDSO)

bye. A syringe comprising a medical barrel of any previous pseudo claim.

byf. A cartridge comprising a medical barrel of any previous pseudo claim.

Magnet Process Pseudo Claims byg. A method of making a medical barrel for a medical cartridge or syringe, the method comprising:
providing a medical barrel comprising a wall having a generally cylindrical inner surface defining at least a portion of a lumen, the generally cylindrical inner surface having a diameter in the range from 4 to 15 mm;
providing an inner electrode having an outer surface including a portion located within the lumen and coaxial with and radially spaced from 1.2 to 6.9 mm. from the generally cylindrical inner surface, the inner electrode having an internal passage having at least one outlet;
providing an outer electrode;
introducing a gaseous PECVD precursor into the lumen via at least one outlet of the internal passage;
applying electromagnetic energy to the outer electrode under conditions effective to form a plasma enhanced chemical vapor deposition (PECVD) gas barrier coating on at least a portion of the generally cylindrical inner surface, the barrier coating or layer having a mean thickness; and
applying a magnetic field adjacent to the medical barrel while applying the electromagnetic energy, optionally for the entire applying step, under conditions effective to reduce the standard deviation of the mean thickness of the gas barrier coating on the generally cylindrical inner surface.

byh. The method of pseudo claim byg, in which the plasma comprises plasma electrons and the magnetic field is effective to improve confinement of the plasma electrons in the lumen during PECVD.

byi. The method of any previous pseudo claim, in which the magnetic field is provided by one or more magnetic field generators near and extending axially along the length of the generally cylindrical surface, each magnetic field generator having a north pole and a south pole defining a polar axis.

byj. The method of pseudo claim byi, in which at least one of the magnetic field generators extends at least the substantial length of the medical barrel.

byk. The method of pseudo claim byi or byj, in which a condition effective to reduce the standard deviation of the mean thickness of the gas barrier coating on the generally cylindrical inner surface is that at least part of the time while providing the magnetic field, one or more of the magnetic field generators have their polar axes generally parallel to the axis of the generally cylindrical surface.

byl. The method of any previous pseudo claims byi to byk, in which at least part of the time while providing the magnetic field, at least two of the magnetic field generators are circumferentially distributed around the generally cylindrical surface in the operative position.

bym. The method of any previous pseudo claims byi to byl, in which at least part of the time while providing the magnetic field, at least one magnetic field generator comprises an annular cylinder having an internal passage extending along its polar axis and the generally cylindrical surface is located entirely within the internal passage.

byn. The method of any previous pseudo claims byi to bym, in which a condition effective to reduce the standard deviation of the mean thickness of the gas barrier coating on the generally cylindrical inner surface is that at least part of the time while providing the magnetic field, at least a portion of the magnetic field in at least a portion of the lumen is oriented with its polar axis extending generally in radial planes with respect to the generally cylindrical surface to be treated.

byo. The method of any previous pseudo claims byi to byn, in which at least two magnetic field generators are distributed circumferentially about the axis of the generally cylindrical surface with alternating magnetic field generators oriented with their polar axes reversed.

byp. The method of any previous pseudo claims byi to byo, in which at least one of the magnetic field generators or the generally cylindrical surface is rotated relative to the other.

byq. The method of any previous pseudo claim, in which the medical barrel, before conducting PECVD, has an attached hypodermic needle, the generally cylindrical surface having a needle end, a back end, and a body portion between the ends.

byr. The method of any previous pseudo claim, in which at least part of the time while providing the magnetic field, at least a portion of the plasma is at least partially confined to the vicinity of the generally cylindrical surface in an electron bottle.

bys. The method of pseudo claim byr, in which the electron bottle is defined by structure providing a stronger magnetic field at or near one end of the generally cylindrical surface than between the ends of the generally cylindrical surface.

byt. The method of pseudo claim byr or bys, in which the electron bottle is defined by structure providing a stronger magnetic field at or near one end of the generally cylindrical surface than at or near at the other end of the generally cylindrical surface.

byu. The method of any previous pseudo claims byr to byt, in which the electron bottle comprises a negatively charged object or portion of an object positioned adjacent to at least one end of the generally cylindrical surface.

byv. The method of any previous pseudo claims byr to byu, in which at least one magnetic field generator is a bar magnet.

byw. The method of any previous pseudo claims byr to byv, in which at least one magnetic field generator is a ring magnet having the generally cylindrical surface within its central recess when in its operative position.

byx. The method of any previous pseudo claim, in which the electromagnetic energy is radio frequency energy.

byy. The method of any previous pseudo claim, in which the outer electrode is generally cylindrical and the generally cylindrical surface of the medical barrel is disposed within the outer electrode.

byz. The method of any previous pseudo claim, in which the electromagnetic energy is applied at a power level of from 0.1 to 500 Watts for applying a gas barrier coating or layer.

bza. The method of any previous pseudo claim, in which the electromagnetic energy for applying a gas barrier coating or layer is applied in multiple discrete pulses.

bzb. The method of any previous pseudo claim, in which the gaseous PECVD precursor comprises a linear siloxane, a monocyclic siloxane, a polycyclic siloxane, a polysilsesquioxane, a linear silazane, a monocyclic silazane, a polycyclic silazane, a polysilsesquiazane, a silatrane, a silquasilatrane, a silproatrane, an azasilatrane, an azasilquasiatrane, an azasilproatrane, or a combination of any two or more of these precursors.

bzc. The method of any previous pseudo claim, in which the gaseous PECVD precursor comprises hexamethylenedisiloxane (HMDSO), tetramethylenedisiloxane (TMDSO), or a combination of these.

bzd. A syringe comprising a medical barrel made by the method of any previous pseudo claim.

bze. A cartridge comprising a medical barrel made by the method of any previous pseudo claim.

bzf. The apparatus for applying a magnetic field within the generally cylindrical wall of the medical barrel described in any previous pseudo claim, comprising
- a medical barrel holder comprising a seat sized and positioned for seating the medical barrel to establish the location of the axis of the generally cylindrical inner surface,
- a feeder associated with the holder configured to feed a PECVD precursor to the lumen of a medical barrel when seated on the seat; and
- one or more magnetic field generators associated with the holder for applying a magnetic field within the lumen of a medical barrel when seated on the seat.

bzg. An apparatus for coating a medical barrel for a medical cartridge or syringe, the apparatus comprising:
- a barrel holder comprising a seat sized and positioned for seating a medical barrel comprising a wall having a generally cylindrical inner surface defining at least a portion of a lumen, optionally the entire lumen, having a diameter in the range from 4 to 15 mm,
- an inner electrode having an outer surface including a portion positioned to be located within a lumen of a medical barrel when seated on the seat and coaxial with and radially spaced from 1.2 to 6.9 mm. from the generally cylindrical inner surface, the inner electrode having an internal passage having at least one outlet;
- an outer electrode;
- a feeder associated with the holder, configured to feed a PECVD precursor to the lumen of a medical barrel when seated on the seat; and
- one or more magnetic field generators associated with the holder for applying a magnetic field within the lumen of a medical barrel when seated on the seat.

The invention claimed is:

1. A medical syringe barrel or medical cartridge barrel comprising:
    - a wall having a generally cylindrical interior surface defining at least a portion of a lumen, the generally cylindrical interior surface having an inside diameter of 4 to 15 mm and the aspect ratio between the length and inside diameter of the generally cylindrical interior surface subjected to PECVD is from 2 to 10; and
    - a PECVD set of one or more plasma enhanced chemical vapor deposition coatings or layers on at least a portion of the generally cylindrical interior surface, the PECVD set comprising:
        - a barrier coating or layer having a mean thickness from 10 to 500 nm with a standard deviation less than the mean thickness; and
        - a pH protective coating or layer between the barrier coating or layer and the lumen, in which a Fourier transform infrared spectroscopy (FTIR) absorbance spectrum of the pH protective coating or layer has a ratio greater than 0.75 and at most 1.7 between:
            the maximum amplitude of the Si—O—Si symmetrical stretch peak between about 1000 and 1040 cm$^{-1}$, and
            the maximum amplitude of the Si—O—Si asymmetric stretch peak between about 1060 and about 1100 cm$^{-1}$.

2. The medical syringe barrel or medical cartridge barrel of claim 1, in which the medical syringe barrel or medical cartridge barrel has an attached hypodermic needle, the generally cylindrical surface having a needle end, a back end, and a body portion between the ends.

3. The medical syringe barrel or medical cartridge barrel of claim 1, in which the standard deviation is at least 20% of the mean thickness.

4. The medical syringe barrel or medical cartridge barrel of claim 1, made of COC (cyclic olefin copolymer), COP (cyclic olefin polymer), PET (polyethylene terephthalate), polypropylene, polycarbonate, polystyrene, polymethylmethacrylate, glass, or a combination of two or more of these.

5. The medical syringe barrel or medical cartridge barrel of claim 1, in which the barrier coating or layer consists essentially of $SiO_x$, in which x is from 1.5 to 2.9 as determined by X-ray photoelectron spectroscopy (XPS).

6. The medical syringe barrel or medical cartridge barrel of claim 1, in which the oxygen barrier improvement factor of the wall and PECVD set, compared to the wall without the PECVD set, is from 5 to 12.

7. The medical syringe barrel or medical cartridge barrel of claim 1, further comprising a closure seated to the medical barrel to form a closed lumen, in which the lumen has a volume between 0.5 and 50 ml and the inward oxygen transmission rate through the wall and the PECVD set is from 0.0012 to 0.00048 cubic cm per package per day, at 20° C., at atmospheric pressure outside the wall.

8. The medical syringe barrel or medical cartridge barrel of claim 1, in which the PECVD set is effective to maintain an oxygen barrier improvement factor, versus a barrel without the PECVD set, of at least 5 and at most 31 after the PECVD set is stored in contact with U.S. Pharmacopeia Water for Injection having a pH of 7.0 for a period of three months at a temperature of 25° C.

9. The medical syringe barrel or medical cartridge barrel of claim 1, further comprising a fluid composition in the lumen having a pH between 4 and 9 and a closure retaining the fluid composition in the lumen, defining a fluid storage package.

10. The medical syringe barrel or medical cartridge barrel of claim 1, wherein the medical syringe barrel or medical cartridge barrel is made of transparent material.

11. The medical syringe barrel or medical cartridge barrel of claim 1, wherein the medical syringe barrel or medical cartridge barrel is made of injection moldable thermoplastic material.

12. The medical syringe barrel or medical cartridge barrel of claim 1, wherein the medical syringe barrel or medical cartridge barrel is made of COC (cyclic olefin copolymer), COP (cyclic olefin polymer), PET (polyethylene terephthalate), polypropylene, polycarbonate, polystyrene, polymethylmethacrylate, glass, or a combination of two or more of these.

13. The medical syringe barrel or medical cartridge barrel of claim 1, in which the pH protective coating or layer consists essentially of $SiO_xC_y$, in which x is from about 0.5 to about 2.4 and y is from about 0.6 to about 3, each as measured by XPS.

14. The medical syringe barrel or medical cartridge barrel of claim 1, in which the pH protective coating or layer consists essentially of the following atomic ratios of silicon, oxygen, and carbon as determined by X-ray photoelectron spectroscopy, and atomic ratio of hydrogen as determined by Rutherford backscattering spectrometry:

| ATOMIC RATIOS | | | |
|---|---|---|---|
| Si | O | C | H |
| 1 | 0.5 to 2.4 | 0.6 to 3 | 2 to 9. |

15. The medical syringe barrel or medical cartridge barrel of claim 1, in which the pH protective coating or layer has a mean thickness from 50 to 500 nm.

16. The medical syringe barrel or medical cartridge barrel of claim 1, further comprising a tie coating or layer consisting essentially of $SiO_xC_y$, in which x is from about 0.5 to about 2.4 and y is from about 0.6 to about 3, each as measured by XPS.

17. The medical syringe barrel or medical cartridge barrel of claim 16, in which the tie coating or layer consists essentially of the following atomic ratios of silicon, oxygen, and carbon as determined by X-ray photoelectron spectroscopy, and atomic ratio of hydrogen as determined by Rutherford backscattering spectrometry:

| ATOMIC RATIOS | | | |
|---|---|---|---|
| Si | O | C | H |
| 1 | 0.5 to 2.4 | 0.6 to 3 | 2 to 9. |

18. The medical syringe barrel or medical cartridge barrel of claim 1, in which the PECVD set is effective to maintain an oxygen barrier improvement factor, versus a barrel without the PECVD set, of at most 31 after the PECVD set is stored in contact with U.S. Pharmacopeia Water for Injection having a pH of 7.0 for a period of three months at a temperature of 25° C.

19. The medical syringe barrel or medical cartridge barrel of claim 1, in which the PECVD set further comprises a tie coating or layer between the barrier coating or layer and the generally cylindrical interior surface, in which the tie coating or layer has a mean thickness from greater than 0 to 10 nm.

20. A syringe comprising a medical syringe barrel or medical cartridge barrel of claim 1.

21. A medical syringe barrel or medical cartridge barrel comprising:
    a wall having a generally cylindrical interior surface defining at least a portion of a lumen, the generally cylindrical interior surface having an inside diameter of 4 to 15 mm; and
    a PECVD set of one or more plasma enhanced chemical vapor deposition coatings or layers on at least a portion of the generally cylindrical interior surface, the PECVD set comprising:
        a barrier coating or layer having a mean thickness from 10 to 500 nm with a standard deviation less than the mean thickness;
        a pH protective coating or layer between the barrier coating or layer and the lumen, in which a Fourier transform infrared spectroscopy (FTIR) absorbance spectrum of the pH protective coating or layer has a ratio greater than 0.75 and at most 1.7 between:
            the maximum amplitude of the Si—O—Si symmetrical stretch peak between about 1000 and 1040 cm$^{-1}$, and
            the maximum amplitude of the Si—O—Si asymmetric stretch peak between about 1060 and about 1100 cm$^{-1}$; and
        a tie coating or layer between the barrier coating or layer and the generally cylindrical interior surface, in which the tie coating or layer has a mean thickness from greater than 0 to 10 nm.

22. A cartridge comprising a medical syringe barrel or medical cartridge barrel of claim 21.

23. A medical syringe barrel or medical cartridge barrel comprising:
    a wall having a generally cylindrical interior surface defining at least a portion of a lumen, the generally cylindrical interior surface having an inside diameter of 4 to 15 mm; and
    a PECVD set of one or more plasma enhanced chemical vapor deposition coatings or layers on at least a portion of the generally cylindrical interior surface, the PECVD set comprising:
        a barrier coating or layer having a mean thickness from 10 to 500 nm with a standard deviation from 190 to 10 nm; and
        a pH protective coating or layer between the barrier coating or layer and the lumen, in which a Fourier transform infrared spectroscopy (FTIR) absorbance spectrum of the pH protective coating or layer has a ratio greater than 0.75 between:
            the maximum amplitude of the Si—O—Si symmetrical stretch peak between about 1000 and 1040 cm$^{-1}$, and
            the maximum amplitude of the Si—O—Si asymmetric stretch peak between about 1060 and about 1100 cm$^{-1}$.

24. The medical syringe barrel or medical cartridge barrel of claim 23, in which the standard deviation of the mean barrier coating or layer thickness is from 160 to 20 nm.

25. The medical syringe barrel or medical cartridge barrel of claim 23, in which the standard deviation of the mean barrier coating or layer thickness is from 140 to 20 nm.

26. The medical syringe barrel or medical cartridge barrel of claim 23, in which the standard deviation of the mean barrier coating or layer thickness is from 120 to 50 nm.

\* \* \* \* \*